United States Patent
Nam et al.

(10) Patent No.: US 11,858,937 B2
(45) Date of Patent: Jan. 2, 2024

(54) SUBSTITUTED PYRAZOLO[1,5-A]PYRIMIDINES AND PYRAZOLO[1,5-A][1,3,5]TRIAZINES AS CDK INHIBITORS

(71) Applicants: QURIENT CO., LTD., Gyeonggi-do (KR); LEAD DISCOVERY CENTER GMBH, Dortmund (DE)

(72) Inventors: Kiyean Nam, Gyeonggi-do (KR); Jaeseung Kim, Seoul (KR); Yeejin Jeon, Gyeonggi-do (KR); Donghoon Yu, Gyeonggi-do (KR); Mooyoung Seo, Gyeonggi-do (KR); Dongsik Park, Gyeonggi-do (KR); Jan Eickhoff, Herdecke (DE); Gunther Zischinsky, Dortmund (DE); Uwe Koch, Dortmund (DE)

(73) Assignees: QURIENT CO., LTD., Gyeonggi-Do (KR); LEAD DISCOVERY CENTER GMBH, Dortmund (DE)

(*) Notice: Subject to any disclaimer, the term of this patent is extended or adjusted under 35 U.S.C. 154(b) by 0 days.

(21) Appl. No.: 17/045,009

(22) PCT Filed: Apr. 11, 2019

(86) PCT No.: PCT/EP2019/059289
§ 371 (c)(1),
(2) Date: Oct. 2, 2020

(87) PCT Pub. No.: WO2019/197546
PCT Pub. Date: Oct. 17, 2019

(65) Prior Publication Data
US 2021/0139483 A1    May 13, 2021

Related U.S. Application Data

(60) Provisional application No. 62/656,041, filed on Apr. 11, 2018.

(51) Int. Cl.
A61K 31/519    (2006.01)
A61K 31/53     (2006.01)
C07D 487/04    (2006.01)

(52) U.S. Cl.
CPC .................. *C07D 487/04* (2013.01)

(58) Field of Classification Search
CPC ..... A61K 31/519; A61K 31/53; C07D 487/04
USPC ..................... 514/246, 259.31; 544/184, 281
See application file for complete search history.

(56) References Cited

U.S. PATENT DOCUMENTS

2018/0057497 A1*  3/2018  Samajdar ............... A61P 35/02

FOREIGN PATENT DOCUMENTS

| WO | 2013128028 A1 | 9/2013 |
| WO | 2013128029 A1 | 9/2013 |
| WO | 2015154022 A1 | 10/2015 |
| WO | 2016142855 A2 | 9/2016 |

OTHER PUBLICATIONS

Patel, Hetal, et al., "ICEC0942, An Orally Bioavailable Selective Inhibitor of CDK7 for Cancer Treatment", Molecular Cancer Therapeutics, vol. 17, No. 6, Mar. 15, 2018, pp. 1156-1166.

* cited by examiner

*Primary Examiner* — Douglas M Willis
(74) *Attorney, Agent, or Firm* — SALIWANCHIK, LLOYD & EISENSCHENK

(57) ABSTRACT

The present invention relates to pyrazolo [1,5-a][1,3,5] triazine and pyrazolo [1,5-a]pyrimidine derivatives having Formula I:

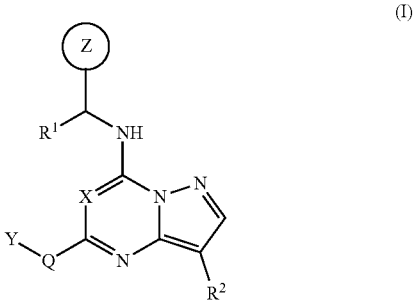

and/or pharmaceutically acceptable salts thereof, the use of these derivatives as pharmaceutically active agents, especially for the prophylaxis and/or treatment of cell proliferative diseases, inflammatory diseases, immunological diseases, cardiovascular diseases and infectious diseases. Furthermore, the present invention is directed towards pharmaceutical compositions containing at least one of the pyrazolo[1,5-a][1,3,5]triazine and pyrazolo[1,5-a]pyrimidine derivatives and/or pharmaceutically acceptable salts thereof.

47 Claims, No Drawings

SUBSTITUTED PYRAZOLO[1,5-A]PYRIMIDINES AND PYRAZOLO[1,5-A][1,3,5]TRIAZINES AS CDK INHIBITORS

CROSS REFERENCE TO RELATED APPLICATIONS

This application is a National Stage Application of International Application Number PCT/EP2019/059289, filed Apr. 11, 2019; which claims the benefit of U.S. Provisional Application Ser. No. 62/656,041, filed Apr. 11, 2018, in their entirety.

FIELD OF THE INVENTION

The Present invention relates to pyrazolo[1,5-a][1,3,5]triazine and pyrazolo[1,5-a]pyrimidine derivatives and/or pharmaceutically acceptable salts thereof, the use of these derivatives as pharmaceutically active agents, especially for the prophylaxis and/or treatment of cell proliferative diseases, inflammatory diseases, immunological diseases, cardiovascular diseases and infectious diseases. Furthermore, the present invention is directed towards pharmaceutical compositions containing at least one of the pyrazolo[1,5-a][1,3,5]triazine and pyrazolo[1,5-a]pyrimidine derivatives and/or pharmaceutically acceptable salts thereof.

BACKGROUND OF THE INVENTION

Cyclin-dependent kinase (CDK) family members that trigger passage through the cell cycle are being considered as attractive therapeutic targets, especially for cancer. CDK family members that control other processes such as transcription and RNA processing have caught less attention so far, although experimental evidence for their involvement in different pathological processes is emerging. Together with cell cycle control, CDK/cyclin complexes also have been identified as conserved components of the RNA polymerase II (Pol II) transcriptional machinery (Bregman et al., 2000, *Front Biosci.* 5:244-257). There are currently 20 known mammalian CDKs. While CDK7-13 have been linked to transcription, only CDK 1, 2, 4, and 6 show demonstrable association with cell cycle. Unique among the mammalian CDKs, CDK7 has consolidated kinase activities, regulating both the cell cycle progression and transcription (Desai et al., 1995, Mol. Cell Biol. 15, 345-350).

The general transcription factor TFIIH purified from mammalian cells consists of ten subunits, seven of which (p62, p52, p44, p34, XPD, XPB, and TTDA) form the core complex. Three subunits (cyclin H, MAT1, and CDK7) from the CDK-activating kinase (CAK), which is linked to TFIIH's core via the XPD (ATP-dependent helicase) subunit of complex. During the process of transcription initiation, the helicase activity of TFIIH opens the core promoter DNA, while CDK7 phosphorylates the C-terminal domain (CTD) of Pol II at serine 5 and 7 (Akhtar et al., 2009, Mol. Cell 34, 387-393) as well as other transcription factors controlling the initiation-to-elongation transition (Larochelle et al., 2012, Nat. Strut. Mol. Biol. 19, 1108-1115 Therefore CDK7 is essential factor for transcription process, which suggests that CDK7 is a target for cancer therapy, especially transcription addicted cancer.

CDK7 has long been asserted as having an essential role in cellular metabolism and viability. Transcriptional CDK inhibitors down-regulate a large number of short-lived anti-apoptotic proteins, such as the anti-apoptotic proteins myeloid cell leukemia-1 (Mcl-1), B-cell lymphoma extra-long (Bcl-xL) and XIAP (X-linked IAP), D-cyclins, c-Myc, Mdm-2 (leading to p53 stabilization), $p21^{waf1}$ proteins whose transcription is mediated by nuclear factor-kappa B (NF-kB) and hypoxia-induced VEGF (Shapiro G I. 2006, *J Clin Oncol;* 24(11):1770-83). The transcriptional non-selective cyclin-dependent kinase inhibitor flavopiridol induces apoptosis in multiple myeloma cells through transcriptional repression and down-regulation of Mcl-1. These findings supported previous postulates that CDK7 might be a valuable target for drugs directed toward the treatment of malignancies and cell cycle-associated diseases (Lolli G and Johnson L N. 2005. *Cell Cycle* 4:572-577).

The function of CDK7 as regulator of general transcription and CDK7 is a therapeutic target for treatment of many diseases and syndromes are associated with mutations in regulatory regions and in transcription factors, cofactors, chromatin regulators and noncoding RNAs. These mutations can contribute to cancer, autoimmunity, neurological disorders, developmental syndromes, diabetes, cardiovascular disease, and obesity, among others. Some transcription factors control RNA polymerase II pause release and elongation and, when their expression or function is altered, can produce aggressive tumor cells (c-Myc) or some forms of autoimmunity (AIRE) (Tong Ihn Lee and Richard A. Young, *Cell,* 2013, 152:1237-1251). Therefore, inhibition of human CDK7 kinase activity is likely to result in anti-proliferative activity through the function in cell cycle progression and transcriptional regulation by inhibition of some transcription factor related to oncogene through inhibition of general transcription process. More important thing is that CDK7 has been shown to regulate exponential expression of oncogenic transcription factors more dramatically than it does to other housekeeping genes in cancer cells. Thus Inhibition of CDK7 can differentially affect transcription of certain oncogenes and housekeeping gene, therefore therapeutic window can be secured. For this reason, transcriptional regulation and pharmacological inhibition through appropriate general transcription inhibition by CDK7 could be applied to treat proliferative disorder, including cancer. As a general regulator of transcription, CDK7 is a therapeutic target for treatment of disease like inflammation, virus replication such as HIV, EBV, cancer and cardiac hypertrophy. HIV-1 gene expression is regulatory by a viral transactivator protein (Tat) which induces transcriptional elongation of HIV-1 long tandem repeat. This induction requires hyperphosphorylation of the C-terminal domain repeat of RNA polymerase II. To archives said hyperphosphorylation, Tat stimulates CTD kinases associated with general transcription factors of the promoter complex, specifically TFIIH-associated CDK7 (Nekhai et al.; Biochem J. (2002) 364, 649-657). The inventors of US 615968 also described that Tat binds to CDK7 and that this interaction increase the ability of CAK to phosphorylate CTD. The authors of US 615968 further disclose that the transcriptional activation by Tat is dependent upon the kinase activity of CDK7. Additionally, Young Kyeung Kim and colleagues conclude that the recruitment and activation of TFIIH represents a rate-limiting step for the emergence of HIV from latency (Young Kyeung Kim, EMBO (2006) 25, 3596-3604).

Levels of CDK7 and CDK9, as well as other components of the kinase complexes, MAT-1/cyclin H are upregulated during Human cytomegalovirus infection. In addition, there is an increase in the kinase activities of CDK7 and CDK9 (Tamrakar et al., Journal of Virology, 2005, 79; 15477-15493).

Many antiviral drugs target viral proteins. These have the disadvantage that viruses often develop resistance against these drugs. Antiviral drugs targeting cellular proteins essential for viral process, like CDK7, could bypass this disadvantage. These drugs may further be effective in treating several unrelated viruses and their effects should be additive to traditional antiviral agents. Inhibitors of CDK7, which has its dual function of CDK-activating kinase and transcription regulation is very effective in the treatment of several viruses.

BRIEF SUMMARY OF THE INVENTION

It is an object of the present invention to provide compounds and/or pharmaceutically acceptable salts thereof which can be used as pharmaceutically active agents, especially for prophylaxis and/or treatment of cell proliferative diseases, inflammatory diseases, immunological diseases, cardiovascular diseases and infectious diseases, as well as compositions comprising at least one of those compounds and/or pharmaceutically acceptable salts thereof as pharmaceutically active ingredients.

DETAILED DESCRIPTION OF THE INVENTION

In one aspect, the present invention relates to pyrazolo-triazine or pyrazolo-pyrimidine compounds which are defined by general formula I

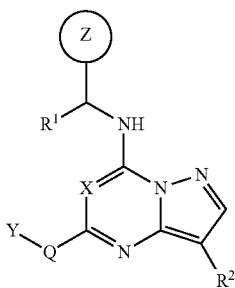

Formula I wherein

X is, independently at each occurrence, selected from CH and N;

Q is either absent or independently, at each occurrence, selected from the group consisting of —NH—, —NH(CH$_2$)—, —NH(CH$_2$)$_2$—, —NH(C=O)—, —NHSO$_2$—, —O—, —O(CH$_2$)—, —(C=O)—, —(C=O)NH— and —(C=O)(CH$_2$)—;

Y is, independently at each occurrence, selected from the group consisting of C3-C8 cycloalkyl, aryl, heteroaryl, heterocyclyl, and C1-C6 alkyl, wherein C1-C6 alkyl is substituted with one or two of —OR$^5$, —N(R$^5$)R$^5$, aryl, heteroaryl and heterocyclyl, C3-C8 cycloalkyl can be substituted with one or two of R$^3$, R$^4$ and —(C=O)R$^5$, heterocyclyl can be substituted with one or two of R$^3$, R$^4$ and —(C=O)R$^5$, and aryl or heteroaryl can be substituted with one or two of R$^3$, C1-C6 alkyl, —OR$^5$, —N(R$^5$)R$^5$, —(C=O)R$^5$, halogen, heteroaryl and heterocyclyl;

R$^1$ is, at each occurrence, independently selected from the group consisting of hydrogen and methyl;

R$^2$ is, at each occurrence, independently selected from the group consisting of halogen, C1-C6 alkyl, C3-C10 cycloalkyl, —CN, —(C=O)CH$_3$ and C1-C3 haloalkyl, any of which is optionally substituted;

R$^3$ is either absent or independently, at each occurrence, selected from the group consisting of hydrogen, —OR$^5$, halogen, —N(R$^5$)R$^5$, —NH(C=)R$^5$, —(C=O)NH$_2$, aryl, heteroaryl, heterocyclyl, C1-C6 alkyl and C1-C6 alkyl substituted with —OH or —NH$_2$;

R$^4$ is, independently, at each occurrence, selected from the group consisting of hydrogen, halogen, —OR$^5$, —N(R$^5$)R$^5$, (=O), aryl, heteroaryl, heterocyclyl, C1-C6 alkyl and C1-C6 alkyl substituted with —OH or —NH$_2$';

R$^5$ is, at each occurrence, independently selected from the group consisting of hydrogen, C1-C6 alkyl, C3-C6 cycloalkyl, C1-C3 haloalkyl, heteroaryl, heterocyclyl, heteroaryl substituted with one or two of halogen, —OR$^{11}$, —N(R$^{11}$)R$^{11}$, C1-C6 alkyl and C1-C6 alkyl substituted with —OH, —NH$_2$, heterocyclyl substituted with one or two of halogen, —OR$^{11}$, —N(R$^{11}$)R$^{11}$, C1-C6 alkyl and C1-C6 alkyl substituted with —OH or —NH$_2$;

Z is any structure of the following group A;

Group A

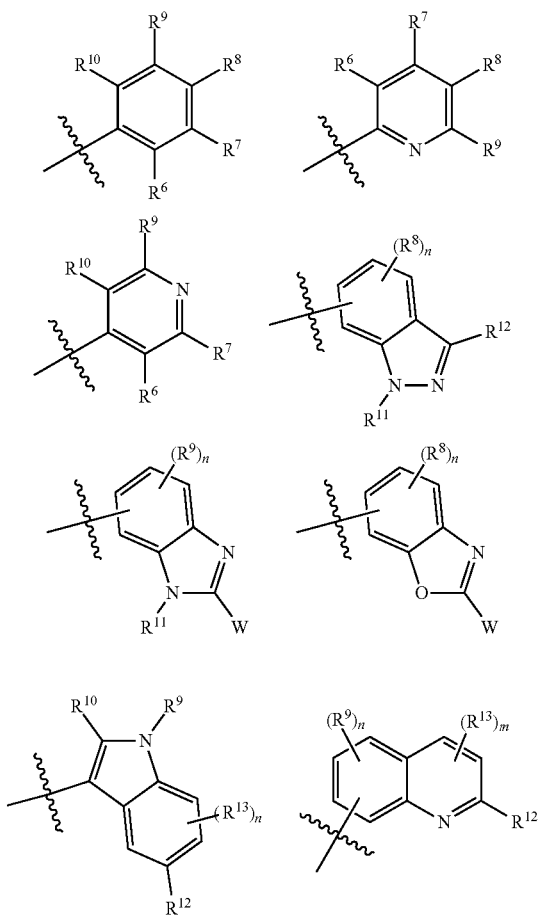

-continued
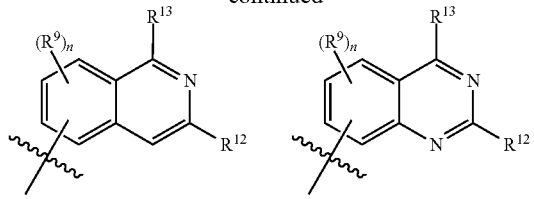
Wherein n=1, 2, or 3; m=1, or 2;
R⁶ and R⁷ are, at each occurrence, independently selected from the group consisting of hydrogen, —NH(C═O)R¹⁴, —NHR¹⁴, —OR¹⁴ and any structure of the following group B, with the proviso that, when Z is
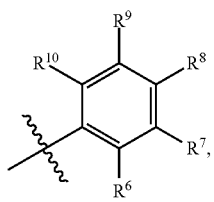
one of R⁶ and R⁷ is not H;
Group B
-continued
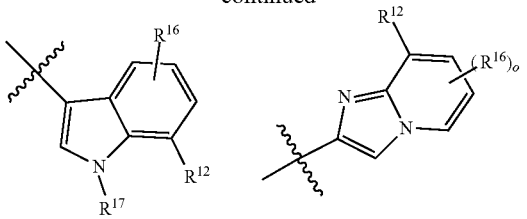
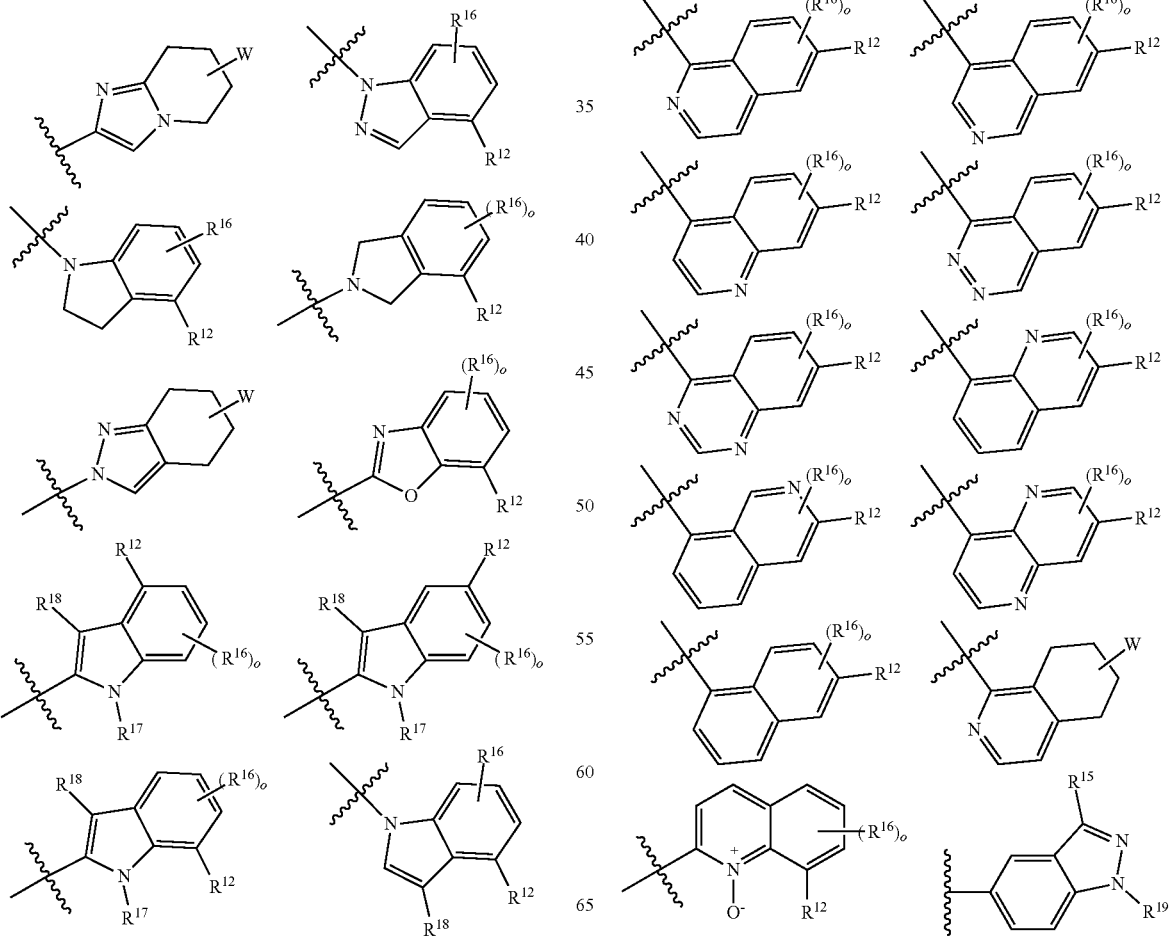

-continued

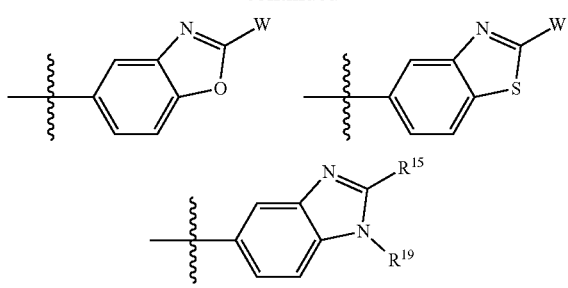

wherein o is, independently at each occurrence, selected from 1, 2 and 3;

W is any structure of the following group C;

Group C (c-1)

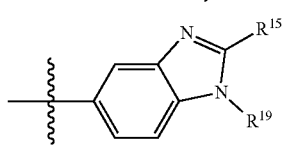

(c-2)

(c-3)

(c-4)

(c-5)

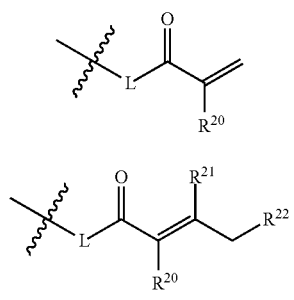

(c-6)

(c-7)

(c-8)

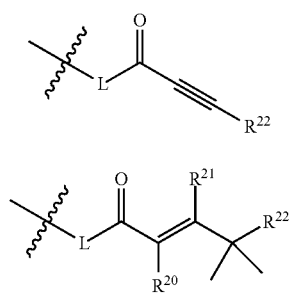

-continued (c-9)

(c-10)

(c-11)

(c-12)

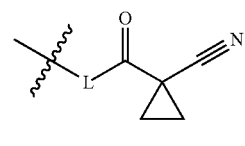

(c-13)

(c-14)

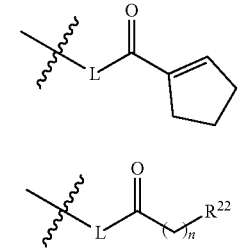

L is absent or, at each occurrence, independently selected from the group consisting of —O— and —NH—;

wherein n is, independently at each occurrence, selected from 1, 2 and 3;

$R^8$, $R^9$ and $R^{10}$ are, at each occurrence, independently selected from the group consisting of hydrogen, halogen, C1-C6 alkyl, C1-C3 haloalkyl, —$OR^5$, —CN and C1-C6 alkyl substituted with —OH, —$OR^5$ or —$NHR^5$;

$R^{11}$ is, at each occurrence, independently selected from the group consisting of hydrogen, C1-C6 alkyl, C3-C10 cycloalkyl and W, as defined above;

$R^{12}$ is, at each occurrence, independently selected from hydrogen and W, as defined above; Wherein if $R^{11}$ is W, $R^{12}$ is hydrogen;

$R^{13}$ is, at each occurrence, independently selected from the group consisting of hydrogen, halogen, C1-C6 alkyl, C1-C3 haloalkyl, —$NH_2$, —$OR^5$, —CN and W, as defined above;

Wherein if $R^{13}$ is W, $R^{12}$ is hydrogen;

$R^{14}$ is any structure of group D;

Group D

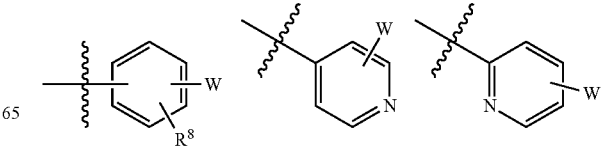

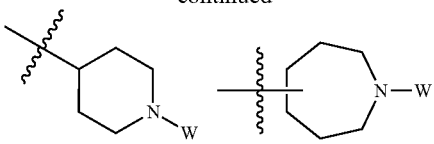

$R^{15}$ is, at each occurrence, independently selected from hydrogen and W, as defined above;

$R^{16}$ is, at each occurrence, independently selected from the group consisting of hydrogen, halogen, C1-C6 alkyl, C1-C3 haloalkyl, —NH$_2$, —OR$^5$, —CN and W, as defined above;

Wherein if $R^{16}$ is W, $R^{12}$ is hydrogen;

$R^{17}$ is, at each occurrence, independently selected from the group consisting of hydrogen, C1-C6 alkyl and C1-C3 haloalkyl;

$R^{18}$ is, at each occurrence, independently selected from the group consisting of hydrogen, halogen, C1-C6 alkyl, C1-C3 haloalkyl, —NH$_2$, —OR$^5$ and —CN;

$R^{19}$ is, at each occurrence, independently selected from the group consisting of hydrogen, C1-C6 alkyl, C3-C10 cycloalkyl and W, as defined above;

Wherein if $R^{19}$ is W, $R^{15}$ is hydrogen;

$R^{20}$ and $R^{21}$ are, at each occurrence, independently selected from the group consisting of hydrogen, halogen, C1-C6 alkyl, C1-C3 haloalkyl, —OR$^5$, heterocyclyl and —CN;

$R^{22}$ is, at each occurrence, independently selected from the group consisting of hydrogen, halogen, C1-C6 alkyl, C3-C10 cycloalkyl, —N(R$^5$)$_2$, —NR$^{19}$R$^{20}$, —NR$^{19}$CH$_2$(CO)NH$_2$, heterocyclyl, —OR$^5$ and —CN;

or an enantiomer, stereoisomeric form, mixture of enantiomers, diastereomer, mixture of diastereomer, racemate of the above mentioned compounds or a pharmaceutically acceptable salt thereof.

The present invention also relates to enantiomers, stereoisomeric forms, mixtures of enantiomers, diastereomers, mixtures of diastereomers, racemates of the above mentioned compounds and to pharmaceutically acceptable salts thereof.

In one embodiment of the compounds of general formula I above, the compounds have the general formula Ia Formula Ia

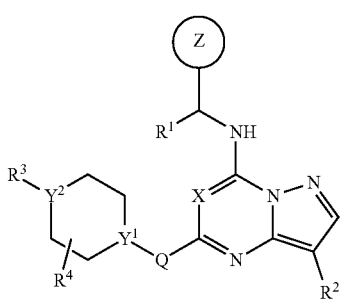

wherein

X is, independently at each occurrence, selected from CH and N;

Y$^1$ is, independently at each occurrence, selected from CH, C(OH) and N;

Y$^2$ is, independently at each occurrence, selected from CH, C(OH) and N;

Q is absent or, at each occurrence, independently selected from the group consisting of —NH—, —NH(CH$_2$)—, —NH(C═O)—, —NHSO$_2$—, —O—, —O(CH$_2$)—, —(C═O)— and —(C═O)(CH$_2$)—;

$R^1$ is, at each occurrence, independently selected from the group consisting of hydrogen and methyl;

$R^2$ is, at each occurrence, independently selected from the group consisting of halogen, C1-C6 alkyl, C3-C10 cycloalkyl, —CN, —(C═O)CH$_3$ and C1-C3 haloalkyl, any of which is optionally substituted;

$R^3$ is, at each occurrence, independently selected from the group consisting of hydrogen, —OH, halogen, —N(R$^5$)$_2$, —NH(C═O)R$^5$, —(C═O)NH$_2$, C1-C6 alkyl and C1-C6 alkyl substituted with —OH or —NH$_2$;

$R^4$ is, at each occurrence, absent or independently selected from the group consisting of hydrogen, halogen, —OH, —OR$^5$, —NH$_2$, C1-C6 alkyl and C1-C6 alkyl substituted with —OH or —NH$_2$;

$R^5$ is, at each occurrence, independently selected from the group consisting of hydrogen, C1-C6 alkyl and C1-C3 haloalkyl;

Z is any structure of the following group A;

Group A

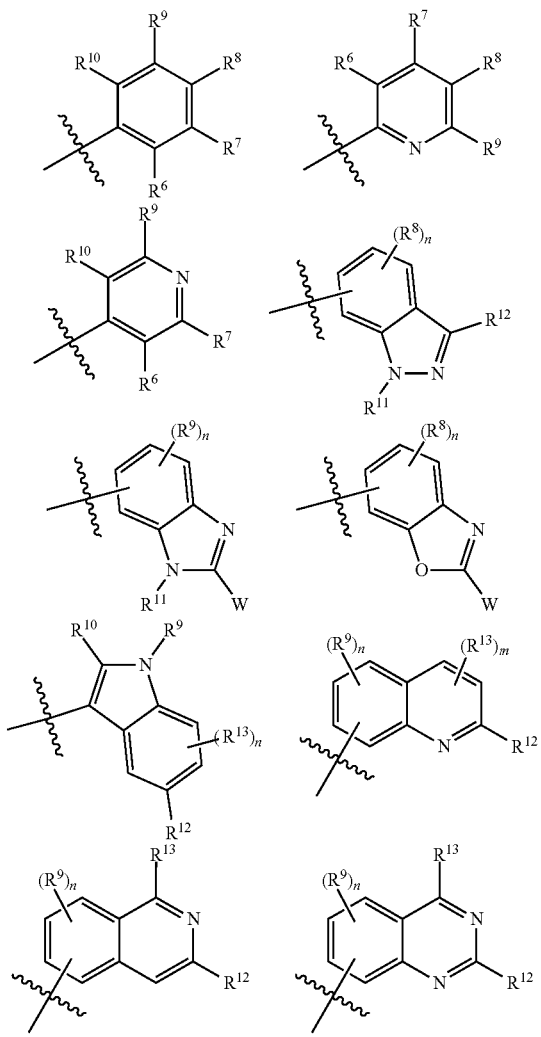

wherein n=1, 2, or 3; m=1, or 2;

R⁶ and R⁷ are, at each occurrence, independently selected from the group consisting of hydrogen, —NH(C=O)R¹⁴, —NHR¹⁴, —OR¹⁴ and any structure of the following group B, with the proviso that, when Z is
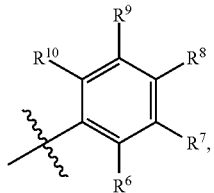
one of R6 and R7 is not H;
Group B
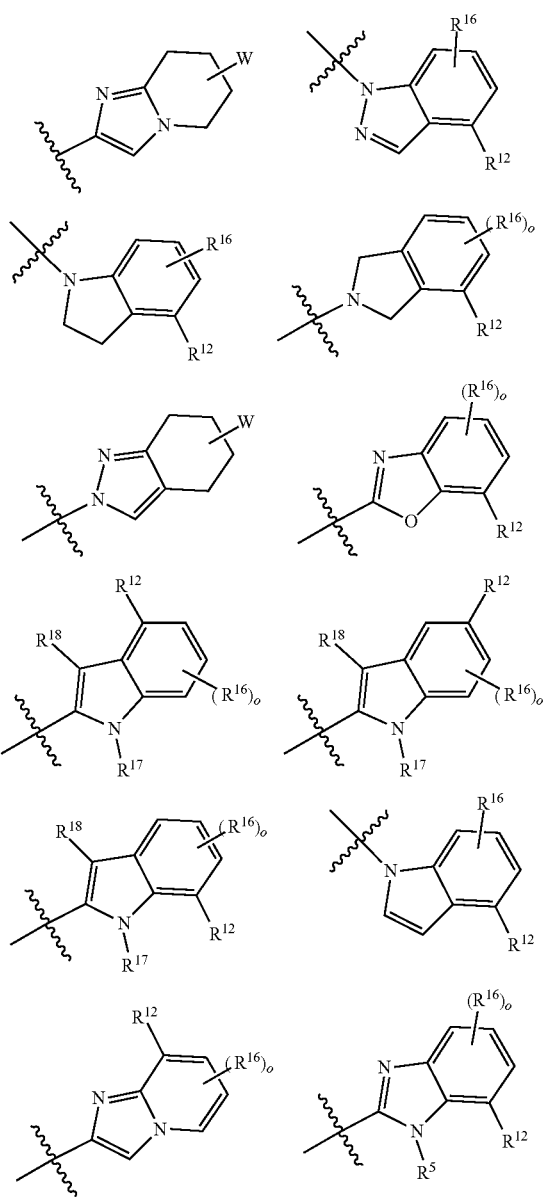
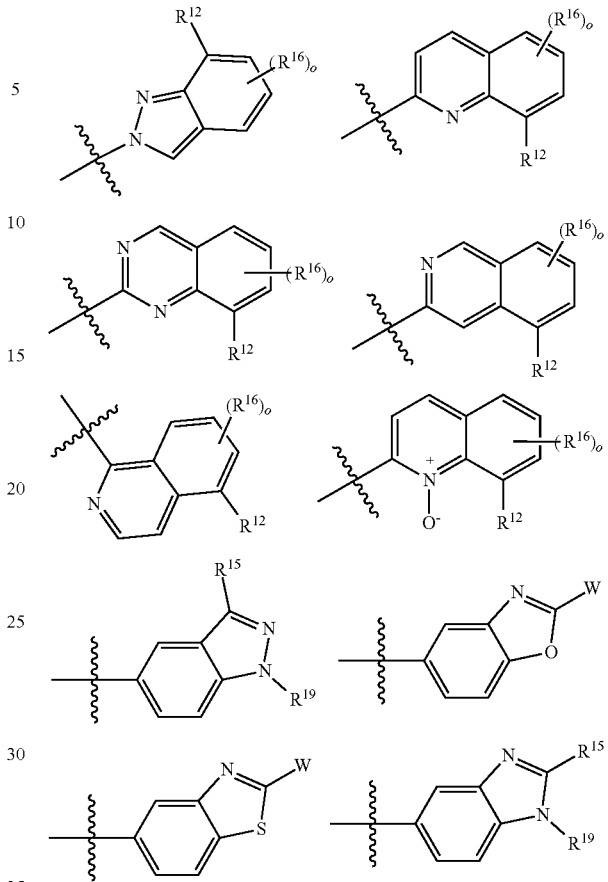
wherein o=1, 2 or 3;
W is any structure of the following group C;
Group C
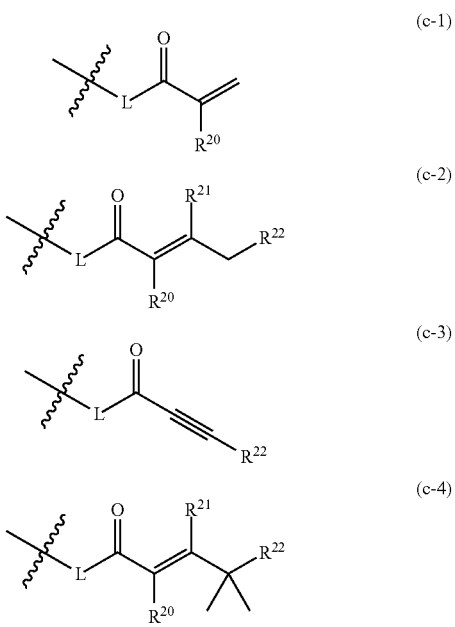

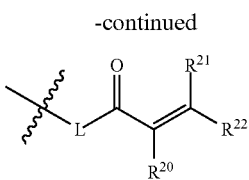

(c-5)

L is absent or, at each occurrence, independently selected from the group consisting of —O— and —NH—;

$R^8$, $R^9$ and $R^{10}$ are, at each occurrence, independently selected from the group consisting of hydrogen, halogen, C1-C6 alkyl, C1-C3 haloalkyl, —$OR^5$, —CN and C1-C6 alkyl substituted with —OH, —$OR^5$ or —$NHR^5$;

$R^{11}$ is, at each occurrence, independently selected from the group consisting of hydrogen, C1-C6 alkyl, C3-C10 cycloalkyl and W, as defined above;

$R^{12}$ is, at each occurrence, independently selected from hydrogen and W, as defined above;

Wherein if $R^{11}$ is W, $R^{12}$ is hydrogen;

$R^{13}$ is, at each occurrence, independently selected from the group consisting of hydrogen, halogen, C1-C6 alkyl, C1-C3 haloalkyl, —$NH_2$, —$OR^5$, —CN and W, as defined above;

Wherein if $R^{13}$ is W, $R^{12}$ is hydrogen;

$R^{14}$ is any structure of group D;

Group D

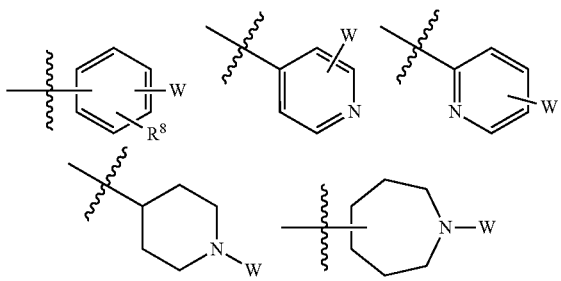

$R^{15}$ is, at each occurrence, independently selected from hydrogen and W, as defined above;

$R^{16}$ is, at each occurrence, independently selected from the group consisting of hydrogen, halogen, C1-C6 alkyl, C1-C3 haloalkyl, —$NH_2$, —$OR^5$, —CN and W, as defined above;

Wherein if $R^{16}$ is W, $R^{12}$ is hydrogen;

$R^{17}$ is, at each occurrence, independently selected from the group consisting of hydrogen, C1-C6 alkyl and C1-C3 haloalkyl;

$R^{18}$ is, at each occurrence, independently selected from the group consisting of hydrogen, halogen, C1-C6 alkyl, C1-C3 haloalkyl, —$NH_2$, —$OR^5$ and —CN;

$R^{19}$ is, at each occurrence, independently selected from the group consisting of hydrogen, C1-C6 alkyl, C3-C10 cycloalkyl and W, as defined above;

Wherein if $R^{19}$ is W, $R^{15}$ is hydrogen;

$R^{20}$ and $R^{21}$ are, at each occurrence, independently selected from the group consisting of hydrogen, halogen, C1-C6 alkyl, C1-C3 haloalkyl, —$OR^5$, heterocycle and —CN;

$R^{22}$ is, at each occurrence, independently selected from the group consisting of hydrogen, C1-C6 alkyl, C3-C10 cycloalkyl, —$N(R^5)_2$, —$NR^{19}R^{20}$, heterocycle, —$OR^5$ and —CN.

In one embodiment of the compounds of general formula I or formula Ia above, at least one of Z, $R^6$, $R^7$, $R^{11}$, $R^{12}$, $R^{13}$, $R^{15}$, $R^{16}$ and $R^{19}$ is W, as defined above for general formula I, or is a structure containing W, as defined above for general formula I.

In one embodiment of the compounds of general formula I or formula Ia above exactly one of Z, $R^6$, $R^7$, $R^{11}$, $R^{12}$, $R^{13}$, $R^{15}$, $R^{16}$ and $R^{19}$ is W, as defined above for general formula I, or is a structure containing W, as defined above for general formula I.

In one embodiment, at least one of Z, $R^6$, $R^7$, $R^{11}$, $R^{12}$, $R^{13}$, $R^{15}$, $R^{16}$ and $R^{19}$ is W, as defined above, or is a structure containing W, as defined above for general formula Ia.

In one embodiment, exactly one of Z, $R^6$, $R^7$, $R^{11}$, $R^{12}$, $R^{13}$, $R^{15}$, $R^{16}$ and $R^{19}$ is W, as defined above, or is a structure containing W, as defined above for general formula Ia.

In one embodiment of the compounds of general formula I above, $R^1$ is hydrogen and the compound has the general formula II

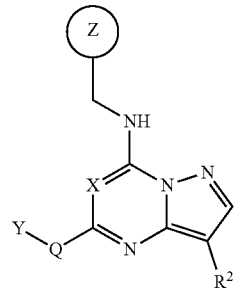

Formula II wherein X, Y, Z, $R^2$ and Q are as defined above for general formula I.

In one embodiment of the compounds of general formula I above, the compounds have the general formula III

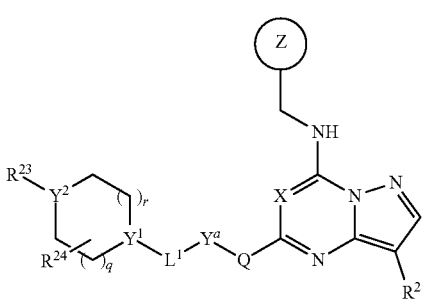

Formula III wherein X, Z, $R^2$ and Q are as defined above for general formula I, and $Y^a$ is either absent or independently, at each occurrence, selected from the group consisting of aryl, heteroaryl, heterocyclyl, aryl substituted with one or two of C1-C6 alkyl, —$OR^5$, —$N(R^5)R^5$, and halogen, heteroaryl substituted with one or two of C1-C6 alkyl, —$OR^5$, —N(R⁵)R⁵ and halogen, heterocyclyl substituted with one or two of R²³ and R²⁴;

R²³ is either absent or independently, at each occurrence, selected from the group consisting of hydrogen, —OR⁵, halogen, —N(R⁵)R⁵, —NH(C═O)R⁵, —(C═O)NH₂, aryl, heteroaryl, heterocyclyl, C1-C6 alkyl and C1-C6 alkyl substituted with —OH or —NH₂;

R²⁴ is, independently, at each occurrence, selected from the group consisting of hydrogen, halogen, —OR⁵, —N(R⁵)R⁵, (═O), aryl, heteroaryl, heterocyclyl, C1-C6 alkyl and C1-C6 alkyl substituted with —OH or —NH₂';

wherein R⁵ is as defined in claim 1;

L' is either absent or independently, at each occurrence, selected from the group consisting of —NH—, —NH(CH₂)—, —NH(C═O)—, —NHSO₂—, —O—, —O(CH₂)—, —(C═O)—, —(C═O)NH— and —(C═O)(CH₂)—;

Y¹ is, independently at each occurrence, selected from CH, C(OH) and N;

Y² is, independently at each occurrence, selected from CH, C(OH), O and N;

q is, independently at each occurrence, selected from 0, 1 and 2;

r is, independently at each occurrence, selected from 0, 1, 2 and 3;

In one embodiment of the compounds of general formula I or general formula Ia above Z is Z¹, and Z¹ is any structure of the following group E;

Group E

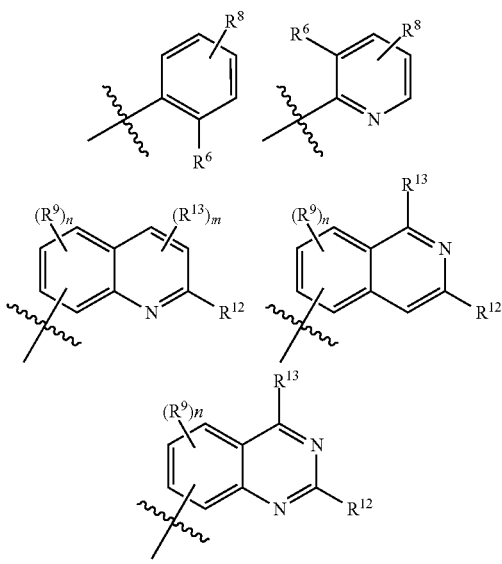

wherein m is, independently at each occurrence, selected from 1 and 2; and n is as defined above for general formula I;

R⁸, R⁹, R¹² and R¹³ are as defined above for general formula I;

R⁶ is any structure of group B as defined above for general formula I.

In one embodiment of the compounds of general formula Ia above,

Z is Z¹, and Z¹ is any structure of the following group E;

Group E

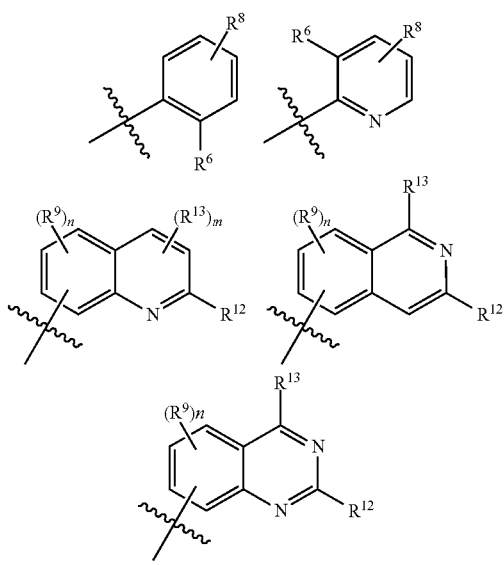

wherein n=1, 2, or 3; m=1 or 2;

R⁸, R⁹, R¹² and R¹³ are as defined above; and

R⁶ is any structure of group B as defined above.

In one embodiment of the compounds of general formula I or general formula Ia above, Z is

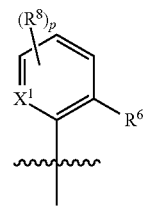

p is, independently at each occurrence, selected from 0, 1, 2 and 3;

X¹ is, independently at each occurrence, selected from CR⁸ and N;

R⁶ is any structure of group B, as defined above for general formula I; and

R⁸ is as defined above for general formula I.

In one embodiment of the compounds of general formula Ia above,

Z is

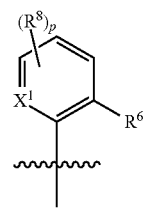

p is 0, 1, 2 or 3

$X^1$ is, independently at each occurrence, selected from $CR^8$ and N;

$R^6$ is any structure of group B, as defined above; and $R^8$ is as defined above.

In one embodiment of the compounds of general formula I or general formula Ia above, Z is

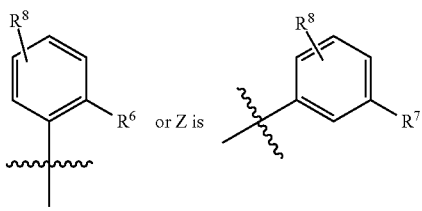

wherein $R^6$-$R^8$ are as defined above for general formula I.

In one embodiment of the compounds of general formula Ia above,

Z is

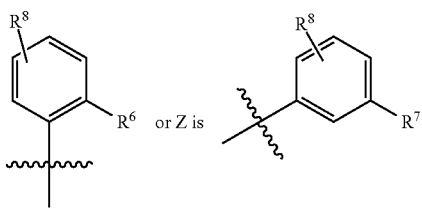

wherein $R^6$-$R^8$ are as defined above.

In one embodiment of the compounds of general formula I above,

Z is

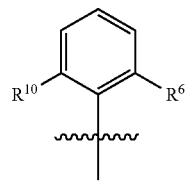

wherein $R^6$ and $R^{10}$ are as defined above for general formula I.

In one embodiment of the compounds of general formula I above, the compounds have the general formula IV

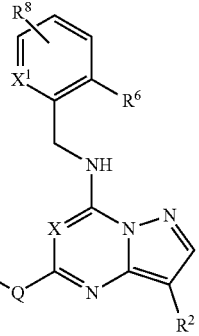

Formula IV wherein X, $X^1$, $R^6$, $R^8$ and Q are as defined above for general formula I, and $X^1$ is as defined above;

wherein $Y^b$ is any structure of the following group F;

Group F

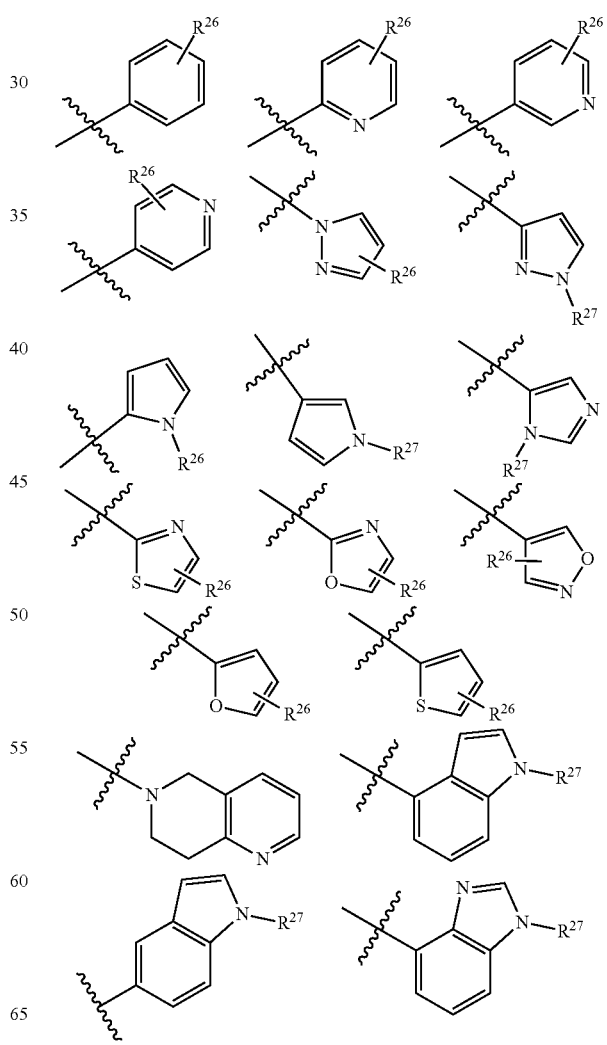

-continued

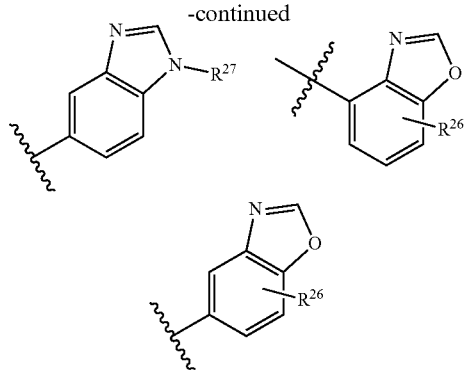

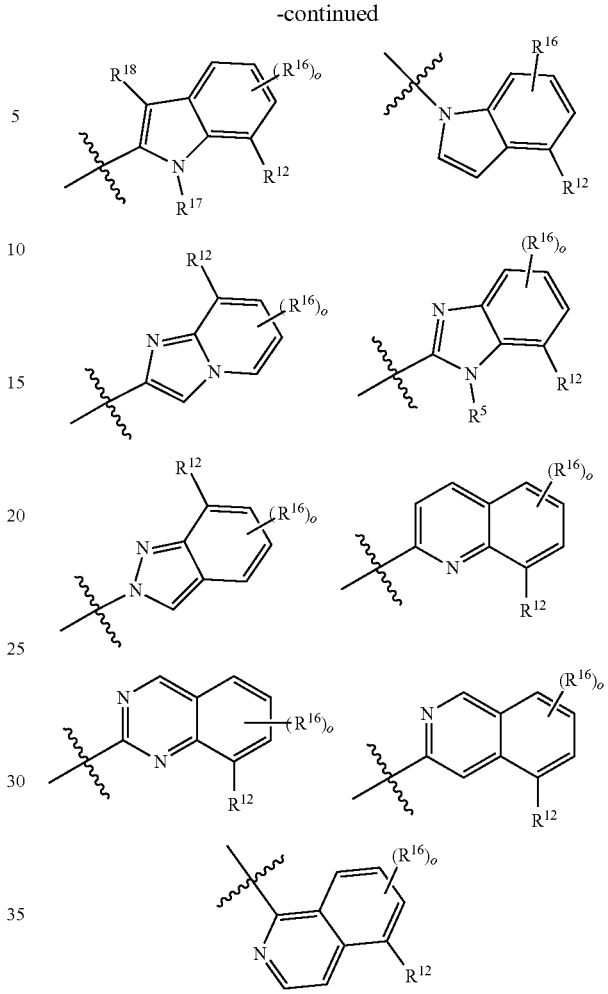

$R^{26}$ and $R^{27}$ is either absent or independently, at each occurrence, selected from the group consisting of hydrogen, —$OR^5$, halogen, —$N(R^5)R^5$, —$NH(C\!=\!O)R^5$, —$(C\!=\!O)NH_2$, aryl, heteroaryl, heterocyclyl, C1-C6 alkyl and C1-C6 alkyl substituted with —OH or —$NH_2$;

wherein $R^5$ is as defined above for general formula I.

In one embodiment of the compounds of general formula I above, $R^2$ is C1-C6 alkyl.

In one embodiment of the compounds of general formula Ia above, $R^2$ is C1-C6 alkyl.

In one embodiment of the compounds of general formula I above or of general formula Ia above, $R^6$ and $R^7$ are, at each occurrence, independently selected from —$NH(C\!=\!O)R^{14}$, —$NHR^{14}$, —$OR^{14}$, any structure of the following group B'

Group B'

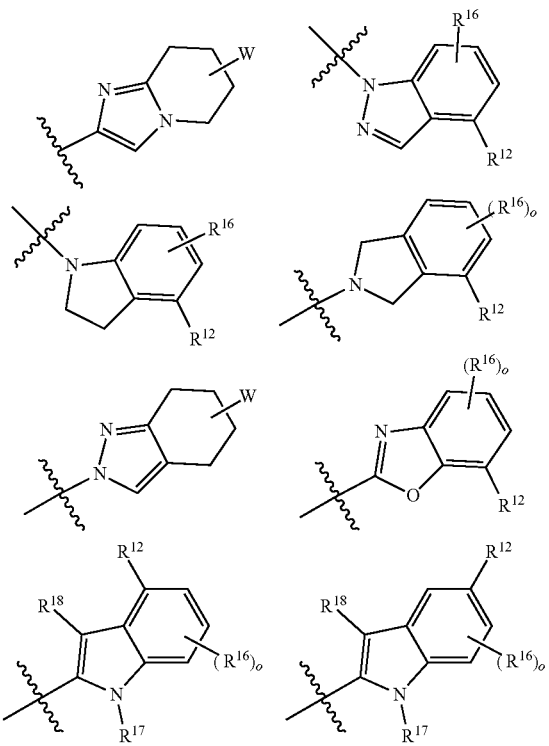

wherein $R^N$ is selected from the group consisting of

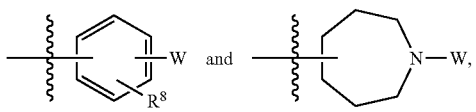

wherein $R^5$, $R^8$, $R^{12}$, $R^{16}$, $R^{17}$, $R^{18}$ and W are as defined above.

In one embodiment of the compounds of general formula I above or of general formula Ia above, W is selected from the group consisting of

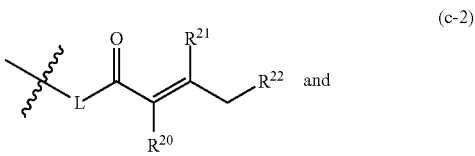

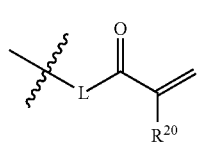

(c-1)

$R^{20}$-$R^{22}$ and L being as defined above.

In one embodiment of the compounds of general formula Ia above or of general formula III above, $Y^1$ is N, $Y^2$ is CH, and $R^3$ is —$N(R^5)_2$, $R^5$ being as defined above.

In one embodiment, the present invention also relates to pharmaceutically acceptable salts of the compounds according to the present invention, as defined herein.

In one embodiment, the compound according to the present invention is a compound selected from structures 1-88, as listed further below in table 7.

In a further aspect, the present invention also relates to a pharmaceutical composition comprising a compound according to the present invention as defined herein, as an active ingredient, together with at least one pharmaceutically acceptable carrier, excipient and/or diluent.

In one aspect, the present invention also relates to a compound according to the present invention as defined herein, for use as a pharmaceutical or pharmaceutically active agent, wherein said pharmaceutical or pharmaceutically active agent preferably has an inhibitory activity on cyclin-dependent kinase 7 (CDK7).

In one aspect, the present invention also relates to a compound according to the present invention, as defined herein, for use in a method of prevention and/or treatment of a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases.

In one embodiment, the disease associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), is a disease associated with, accompanied by, caused by and/or induced by CDK7 dysfunction and/or hyperfunction. In one embodiment, the disease associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), is a proliferative disease. In one embodiment said proliferative disease is a cancer.

In one embodiment said cancer is selected from adenocarcinoma, choroidal melanoma, acute leukemia, acoustic neurinoma, ampullary carcinoma, anal carcinoma, astrocytoma, basal cell carcinoma, pancreatic cancer, Desmoid tumor, bladder cancer, bronchial carcinoma, estrogen dependent and independent breast cancer, Burkitt's lymphoma, corpus cancer, Carcinoma unknown primary tumor (CUP-syndrome), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic tumor, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymphomas, stomach cancer, malignant melanoma, malignant neoplasia, malignant tumors gastrointestinal tract, breast carcinoma, rectal cancer, medulloblastomas, melanoma, meningiomas, Hodgkin's/Non-Hodgkin's lymphoma, mycosis fungoides, nasal cancer, neurinoma, neuroblastoma, kidney cancer, renal cell carcinomas, oligodendroglioma, esophageal carcinoma, osteolytic carcinomas and osteoplastic carcinomas, osteosarcomas, ovarian carcinoma, pancreatic carcinoma, penile cancer, plasmacytoma, prostate cancer, pharyngeal cancer, rectal carcinoma, retinoblastoma, vaginal cancer, thyroid carcinoma, esophageal cancer, T-cell lymphoma, thymoma, tube carcinoma, eye tumors, urethral cancer, urologic tumors, urothelial carcinoma, vulva cancer, wart appearance, soft tissue tumors, soft tissue sarcoma, Nephroblastoma, cervical carcinoma, tongue cancer, invasive ductal carcinoma, invasive lobular carcinoma, ductal carcinoma in situ, lobular carcinoma in situ, small-cell lung carcinoma, non-small-cell lung carcinoma, bronchial adenoma, pleuropulmonary blastoma, mesothelioma, brain stem glioma, hypothalamic glioma, cerebellar astrocytoma, cerebral astrocytoma, neuroectodermal tumor, pineal tumors, sarcoma of the uterus, salivary gland cancers, anal gland adenocarcinomas, mast cell tumors, pelvis tumor, ureter tumor, hereditary papillary renal cancers, sporadic papillary renal cancers, intraocular melanoma, hepatocellular carcinoma, cholangiocarcinoma, mixed hepatocellular cholangiocarcinoma, squamous cell carcinoma, malignant melanoma, Merkel cell skin cancer, non-melanoma skin cancer, hypopharyngeal cancer, nasopharyngeal cancer, oropharyngeal cancer, oral cavity cancer, squamous cell cancer, oral melanoma, AIDS-related lymphoma, cutaneous T-cell lymphoma, lymphoma of the central nervous system, malignant fibrous histiocytoma, lymph sarcoma, rhabdomyo sarcoma, malignant histiocytosis, fibroblastic sarcoma, hemangio sarcoma, hemangiopericytoma, leiomyosarcoma (LMS), canine mammary carcinoma, and feline mammary carcinoma.

In one embodiment, said infectious disease, including opportunistic diseases, is selected from AIDS, Adenovirus Infection, Alveolar Hydatid Disease (AHD), Amoebiasis, Angiostrongyliasis, Anisakiasis, Anthrax, Babesiosis, Balantidiasis, *Baylisascaris* Infection, *Bilharzia* (Schistosomiasis), *Blastocystis hominis* Infection, Lyme Borreliosis, Botulism, Brainerd Diarrhea, Brucellosis, Bovine Spongiform Encephalopathy (BSE), Candidiasis, Capillariasis, Chronic Fatigue Syndrome (CFS), Chagas Disease, Chickenpox, *Chlamydia pneumoniae* Infection, Cholera, Chronic Fatigue Syndrome, Creutzfeldt-Jakob Disease (CJD), Clonorchiasis, Cutaneous Larva migrans (CLM), Coccidioidomycosis, Conjunctivitis, Coxsackievirus A16 (Cox A16), Cryptococcal disease, Cryptosporidiosis, West Nile fever, Cyclosporiasis, Neurocysticercosis, Cytomegalovirus Infection, Dengue Fever, *Dipylidium caninum* Infection, Ebola Hemorrhagic Fever (EHF), Alveolar Echinococcosis (AE), Encephalitis, *Entamoeba coli* Infection, *Entamoeba dispar* Infection, *Entamoeba hartmanni* Infection, *Entamoeba*

*polecki* Infection, Pinworm Infection, Enterovirus Infection (Polio/Non-Polio), Epstein Barr Virus Infection, *Escherichia coli* Infection, Foodborne Infection, Aphthae epizooticae, Fungal Dermatitis, Fungal Infections, Gastroenteritis, Group A streptococcal Disease, Group B streptococcal Disease, Hansen's Disease (Leprosy), Hantavirus Pulmonary Syndrome, Head Lice Infestation (Pediculosis), *Helicobacter pylori* Infection, Hematologic Disease, Hendra Virus Infection, Hepatitis (HCV, HBV), Herpes Zoster (Shingles), HIV Infection, Human Ehrlichiosis, Human Parainfluenza Virus Infection, Influenza, Isosporiasis, Lassa Fever, Leishmaniasis, Visceral leishmaniasis (VL), Malaria, Marburg Hemorrhagic Fever, Measles, Meningitis, *Mycobacterium avium* Complex (MAC) Infection, *Naegleria* Infection, Nosocomial Infections, Nonpathogenic Intestinal Amebae Infection, Onchocerciasis, Opisthorchiasis, Papilloma virus Infection, Parvovirus Infection, Plague, *Pneumocystis* Pneumonia (PCP), Polyomavirus Infection, Q Fever, Rabies, Respiratory Syncytial Virus (RSV) Infection, Rheumatic Fever, Rift Valley Fever, Rotavirus Infection, Roundworms Infection, *Salmonellosis*, Scabies, Shigellosis, Shingles, Sleeping Sickness, Smallpox, Streptococcal Infection, Tapeworm Infection, Tetanus, Toxic Shock Syndrome, Tuberculosis, duodenum, *Vibrio parahaemolyticus* Infection, *Vibrio* septicemia, Viral Hemorrhagic Fever, Warts, Waterborne infectious Diseases, Varicella-Zoster Virus infection, Pertussis and Yellow Fever.

In one embodiment, the immunological disease and/or autoimmune disease is selected from asthma, diabetes, rheumatic diseases, rejection of transplanted organs and tissues, rhinitis, chronic obstructive pulmonary diseases, osteoporosis, ulcerative colitis, sinusitis, lupus erythematosus, recurrent infections, atopic dermatitis/eczema and occupational allergies, food allergies, drug allergies, severe anaphylactic reactions, anaphylaxis, manifestations of allergic diseases, primary immunodeficiencies, antibody deficiency states, cell mediated immunodeficiencies, severe combined immunodeficiency, DiGeorge syndrome, Hyper IgE syndrome (HIES), Wiskott-Aldrich syndrome (WAS), ataxia-telangiectasia, immune mediated cancers, white cell defects, autoimmune diseases, systemic lupus erythematosus (SLE), rheumatoid arthritis (RA), multiple sclerosis (MS), immune-mediated or Type 1 Diabetes Mellitus, immune mediated glomerulonephritis, scleroderma, pernicious anemia, alopecia, pemphigus, pemphigus vulgaris, myasthenia gravis, inflammatory bowel diseases, Crohn's disease, psoriasis, autoimmune thyroid diseases, Hashimoto's disease, dermatomyositis, Goodpasture syndrome (GPS), myasthenia gravis (MG), Sympathetic ophthalmia, Phakogene Uveitis, chronical aggressive hepatitis, primary biliary cirrhosis, autoimmune hemolytic anemia, and Werlhof's disease.

In one embodiment, the inflammatory disease is caused, induced, initiated and/or enhanced by bacteria, viruses, prions, parasites, fungi, and/or caused by irritative, traumatic, metabolic, allergic, autoimmune, or idiopathic agents.

In one embodiment, the inflammatory disease is selected from the group comprising or consisting of inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, and inflammatory diseases of the larynx.

In one embodiment, the inflammatory disease is selected from inflammatory diseases of the central nervous system (CNS), inflammatory rheumatic diseases, inflammatory diseases of blood vessels, inflammatory diseases of the middle ear, inflammatory bowel diseases, inflammatory diseases of the skin, inflammatory disease uveitis, inflammatory diseases of the larynx, wherein preferably said inflammatory diseases are selected from the group comprising abscessation, *acanthamoeba* infection, acne vulgaris, actinomycosis, acute inflammatory dermatoses, acute laryngeal infections of adults, acute multifocal placoid pigment epitheliopathy, acute (thermal) injury, acute retinal necrosis, acute suppurative otitis media, algal disorders, allergic contact dermatitis, amyloidosis angioedema, ankylosing spondylitis, aspergillosis, atopic dermatitis, pseudorabies, autoantibodies in vasculitis, bacterial disorders, bacterial laryngitis, bacterial meningitis, Behçet's disease (BD), birdshot choroidopathy, Gilchrist's disease, Borna disease, brucellosis, bullous myringitis, bursitis, candidiasis, canine distemper encephalomyelitis, canine distemper encephalomyelitis in immature animals, canine hemorrhagic fever, canine herpes virus encephalomyelitis, cholesteatoma, chronic granulomatous diseases (CGD), chronic inflammatory dermatoses, chronic relapsing encephalomyelitis, chronic suppurative otitis media, Ocular Cicatricial pemphigoid (OCP), common upper respiratory infection, granuloma, Crohn's disease, cryptococcal disease, dermatomyositis, diphtheria, discoid lupus erythematosus (DLE), drug-induced vasculitis, drug or hypersensitivity reaction, encephalitozoonosis, eosinophilic meningoencephalitis, Erythema multiforme (EM), feline leukemia virus, feline immunodeficiency virus, feline infectious peritonitis, feline Polioencephalitis, feline spongiform encephalopathy, fibromyalgia, Fuchs Heterochromic Uveitis, gastroesophageal (laryngopharyngeal) reflux disease, giant cell arteritis, glanders, glaucomatocyclitic crisis, gonorrhea granular myringitis, Granulomatous meningoencephalitis (GME), herpes simplex, histoplasmosis, idiopathic diseases, idiopathic inflammatory disorders, immune and idiopathic disorders, infections of the immunocompromised host, infectious canine hepatitis, inhalation laryngitis, interstitial nephritis, irritant contact dermatitis, juvenile rheumatoid arthritis, Kawasaki's disease, La Crosse virus encephalitis, laryngeal abscess, laryngotracheobronchitis, leishmaniasis, lens-induced uveitis, leprosy, leptospirosis, leukemia, lichen planus, lupus, lymphoma, meningitis, meningoencephalitis in greyhounds, miscellaneous meningitis/meningoencephalitis, microscopic polyangiitis, multifocal choroiditis, multifocal distemper encephalomyelitis in mature animals, multiple sclerosis, Muscle Tension Dysphonia (MTD), mycotic (fungal) diseases, mycotic diseases of the CNS, necrotizing encephalitis, neosporosis, old dog encephalitis, onchocerciasis, parasitic encephalomyelitis, parasitic infections, Pars planitis, parvovirus encephalitis, pediatric laryngitis, pollution and inhalant allergy, polymyositis, post-vaccinal canine distemper encephalitis, prion protein induced diseases, protothecosis, protozoal encephalitis-encephalomyelitis, psoriasis, psoriatic arthritis, pug dog encephalitis, radiation injury, radiation laryngitis, radionecrosis, relapsing polychondritis, Reiter's syndrome, retinitis pigmentosa, retinoblastoma, rheumatoid arthritis, Rickettsial disorders, rocky mountain spotted fever, salmon poisoning disease (SPD), Sarcocystosis, sarcoidosis, schistosomiasis, scleroderma, Rhinoscleroma, serpiginous choroiditis, shaker dog disease, Sjogren's syndrome, spasmodic croup, spirochetal (syphilis) diseases, spongiotic dermatitis, sporotrichosis, steroid responsive meningitis-arteritis, Stevens-Johnson syndrome (SJS, EM major), epiglottitis, sympathetic ophthalmia, Syngamosis, syphilis, systemic vasculitis in sarcoidosis, Takayasu's arteritis, tendinitis (tendonitis), Thromboangiitis obliterans (Buerger Disease), tick-borne encephalitis in dogs, toxic epidermal necrolysis (TEN), toxocariasis, toxoplasmosis, trauma, traumatic laryngitis, trichinosis, trypanosomiasis, tuberculosis, tularemia, ulcerative colitis, urticaria (hives), vasculitis, vasculitis and malignancy, vasculitis and rheumatoid arthritis, vasculitis in the idiopathic inflammatory myopathies, vasculitis of the central nervous system, vasculitis secondary to bacterial, fungal, and parasitic infection, viral disorders, viral laryngitis, vitiligo, vocal abuse, vocal-cord hemorrhage, Vogt-Koyanagi-Harada syndrome (VKH), Wegener's granulomatosis, and Whipple's disease.

The present invention also relates to a method of treatment and/or prevention of a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases, wherein said method of treatment and/or prevention comprises administering a compound according to the present invention as defined herein, to a patient in need thereof.

In one embodiment, the patient in need thereof is a mammal. In one embodiment, the patient in need thereof is a human being. In another embodiment, the patient in need thereof is a non-human animal.

In one embodiment, the disease which is prevented or treated in said method is as defined herein.

The present invention also relates to the use of a compound according to the present invention as defined herein in the manufacture of a medicament for the prevention and/or treatment of a disease which is associated with inhibition of apoptosis, abnormal transcriptional activity and/or cell cycle arrest by aberrant activity and/or overexpression of one or several cyclin-dependent kinases (CDKs), in particular cyclin-dependent kinase 7 (CDK7), wherein the disease is selected from proliferative diseases, infectious diseases, including opportunistic diseases, immunological diseases, autoimmune diseases, and inflammatory diseases, as defined herein.

Further advantageous features, aspects and details of the invention are evident from the dependent claims, the description, the examples and the drawings.

The compounds of the present invention are highly efficient inhibitors of CDK7 threonine/serine kinase and/or its complex, CDK7/MAT1/CycH. The inventive compounds are suitable for the use as a pharmaceutically active agent. The inventive compounds are suitable for the treatment of disorders associated with, accompanied by, caused by and/or induced by CDK7 and its complex, in particular a hyperfunction or dysfunction thereof. The inventive compounds are thus suitable for the treatment of CDK7-associated diseases or disorders and CDK7 complex induced disorders.

The inventive compounds are also useful in the manufacture of a medicament or of a pharmaceutical composition for the treatment of disorders associated with, accompanied by, caused by and/or induced by CDK7 and its complex, in particular a hyperfunction or dysfunction thereof. The inventive compounds are further used in the manufacture of a medicament or of a pharmaceutical composition for the treatment and/or prevention of CDK7 and its complex induced disorders.

The present inventors have found that in particular in those embodiments of the present invention wherein the compounds according to the present invention contain a W-group, as defined above, they are able to bind covalently to —SH-groups of cysteine residues within cyclin-dependent kinase(s), especially CDK7, thus forming a covalent bond and an adduct between the compound and the kinase and thus inhibiting the kinase(s). This concerns in particular those embodiments wherein at least one of Z, $R^6$, $R^7$, $R^{11}$, $R^{12}$, $R^{13}$, $R^{15}$, $R^{16}$ and $R^{19}$ is W, as defined above, or is a structure containing W, as defined above.

Furthermore it concerns those embodiments wherein exactly one of Z, $R^6$, $R^7$, $R^{11}$, $R^{12}$, $R^{13}$, $R^{15}$, $R^{16}$ and $R^{19}$ is W, as defined above, or is a structure containing W, as defined above. This is because all W-structures as defined above contain a double or triple bond allowing a reaction with a sulfhydryl group within the kinase and allowing the formation of an adduct between the compound and the kinase. Through the covalent binding of a compound in accordance with the present invention, the kinase is inhibited. The term "exactly one", as used in this context, means that it is only one (and no more) of the recited groups/residues which is W or a structure containing W, as defined above.

The term "optionally substituted" as used herein is meant to indicate that a hydrogen atom where present and attached to a member atom within a group, or several such hydrogen atoms, may be replaced by a suitable group, such as halogen including fluorine, $C_1$-$C_3$ alkyl, $C_1$-$C_3$ haloalkyl, methylhydroxyl, COOMe, C(O)H, COOH, OMe, or $OCF_3$;

The term "alkyl" refers to a monovalent straight, branched or cyclic chain, saturated aliphatic hydrocarbon radical having a number of carbon atoms in the specified range. Thus, for example, "$C_1$-$C_6$ alkyl" refers to any of the hexyl alkyl and pentyl alkyl isomers as well as n-, iso-, sec-, and t-butyl, n- and isopropyl, cyclic propyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" refers to all of the hexenyl and pentenyl isomers as well as 1-butenyl, 2-butenyl, 3-butenyl, isobutenyl, 1-propenyl, 2-propenyl, and ethenyl (or vinyl).

The term "cycloalkyl", alone or in combination with any other term, refers to a group, such as optionally substituted or non-substituted cyclic hydrocarbon, having from three to eight carbon atoms, unless otherwise defined. Thus, for example, "$C_3$-$C_8$ cycloalkyl" refers to cyclopropyl, cyclobutyl, cyclopentyl, cyclohexyl, cycloheptyl, and cyclooctyl.

The term "haloalkyl" refers to an alkyl group, as defined herein that is substituted with at least one halogen. Examples of straight or branched chained "haloalkyl" groups useful in the present invention include, but are not limited to, methyl, ethyl, propyl, isopropyl, n-butyl, and t-butyl substituted independently with one or more halogens. The term "haloalkyl" should be interpreted to include such substituents such as —$CHF_2$, —$CF_3$, —$CH_2$—$CH_2$—F, —$CH_2$—$CF_3$, and the like.

The term "heteroalkyl" refers to an alkyl group where one or more carbon atoms have been replaced with a heteroatom, such as, O, N, or S. For example, if the carbon atom of alkyl group which is attached to the parent molecule is replaced with a heteroatom (e.g., O, N, or S) the resulting heteroalkyl groups are, respectively, an alkoxy group (e.g., —$OCH_3$, etc.), an amine (e.g., —$NHCH_3$, —$N(CH_3)_2$, etc.), or thioalkyl group (e.g., —SCH$_3$, etc.). If a non-terminal carbon atom of the alkyl group which is not attached to the parent molecule is replaced with a heteroatom (e.g., O, N, or S) and the resulting heteroalkyl groups are, respectively, an alkyl ether (e.g., —CH$_2$CH$_2$—O—CH$_3$, etc.), alkyl amine (e.g., —CH$_2$NHCH$_3$, —CH$_2$N(CH$_3$)$_2$, etc.), or thioalkyl ether (e.g., —CH$_2$—S—CH$_3$).

The term "halogen" refers to fluorine, chlorine, bromine, or iodine.

The term "phenyl" as used herein is meant to indicate that optionally substituted or non-substituted phenyl group.

The term "benzyl" as used herein is meant to indicate that optionally substituted or non-substituted benzyl group.

The term "heteroaryl" refers to (i) optionally substituted 5- and 6-membered heteroaromatic rings and (ii) optionally substituted 9- and 10-membered bicyclic, fused ring systems in which at least one ring is aromatic, wherein the heteroaromatic ring or the bicyclic, fused ring system contains from 1 to 4 heteroatoms independently selected from N, O, and S, where each N is optionally in the form of an oxide and each S in a ring which is not aromatic is optionally S(O) or S(O)$_2$. Suitable 5- and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl, tetrazolyl, oxazolyl, isooxazolyl, oxadiazolyl, thiazolyl, isothiazolyl, and thiadiazolyl. Suitable 9- and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl, benzofuranyl, imidazo[1,2-a] pyridinyl, benzotriazolyl, dihydroindolyl, dihydroisoindolyl, indazolyl, indolinyl, isoindolinyl, quinoxalinyl, quinazolinyl, 2,3-dihydrobenzo furanyl, and 2,3-dihydrobenzo-1,4-dioxinyl.

The term "heterocyclyl" refers to (i) optionally substituted 4- to 8-membered, saturated and unsaturated but non-aromatic monocyclic rings containing at least one carbon atom and from 1 to 4 heteroatoms, (ii) optionally substituted bicyclic ring systems containing from 1 to 6 heteroatoms, and (iii) optionally substituted tricyclic ring systems, wherein each ring in (ii) or (iii) is independent of fused to, or bridged with the other ring or rings and each ring is saturated or unsaturated but nonaromatic, and wherein each heteroatom in (i), (ii), and (iii) is independently selected from N, O, and S, wherein each N is optionally in the form of an oxide and each S is optionally oxidized to S(O) or S(O)$_2$. Suitable 4- to 8-membered saturated heterocyclyls include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, dioxanyl, and azacyclooctyl. Suitable unsaturated heterocyclic rings include those corresponding to the saturated heterocyclic rings listed in the above sentence in which a single bond is replaced with a double bond. It is understood that the specific rings and ring systems suitable for use in the present invention are not limited to those listed in this and the preceding paragraphs. These rings and ring systems are merely representative.

Pharmaceutically Acceptable Salts

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulfonate derived from benzensulfonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulfonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt.

In another embodiment, the compounds of the invention are used in their respective free base form according to the present invention.

Metal salts of a chemical compound of the invention include alkali metal salts, such as the sodium salt of a chemical compound of the invention containing a carboxy group.

The chemical compounds of the invention may be provided in unsolvated or solvated forms together with a pharmaceutically acceptable solvent(s) such as water, ethanol, and the like. Solvated forms may also include hydrated forms such as the monohydrate, the dihydrate, the hemihydrate, the trihydrate, the tetrahydrate, and the like. In general, solvated forms are considered equivalent to unsolvated forms for the purposes of this invention.

Further aspects of the present invention are illustrated and exemplified by the following schemes, examples, tables and procedural descriptions which are given merely to illustrate, not to limit the present invention. The scope of protection for the present invention is merely limited by the appended claims.

Tables

Reference is now made to tables, wherein

Table 1 shows activity data in CDK1, CDK2, CDK5 and CDK7 enzymatic assay for selected compounds of the invention. Inhibition is indicated as $IC_{50}$ with the following key: A=$IC_{50}$ less than 100 nM; B=$IC_{50}$ greater than 100 nM, but less than 1,000 nM; C=$IC_{50}$ greater than 1,000 nM. Also table 1 shows selectivity data in CDK1/CDK7, CDK2/CDK7 and CDK5/CDK7 for selected compounds of the invention. Selectivity is indicated as CDK1/CDK7*, CDK2/CDK7 and CDK5/CDK7* with the follow key: A=greater than 500 fold; B=less than 500 fold, but greater than 50 fold; C=less than 50 fold.

Table 2 shows activity data of cellular H460 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 3 shows activity data of cellular MV4-11 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 4 shows activity data of A2780 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 5 shows activity data of OVCAR-3 viability assay for selected compounds of the invention. Inhibition is indicated as $IC_{50}$ with the following key: A=$IC_{50}$ less than 1 uM; B=$IC_{50}$ greater than 1 uM, but less than 10 uM; C=$IC_{50}$ greater than 10 uM.

Table 6 summarizes compounds 1-88 in terms of their structures and corresponding characteristics.

EXAMPLES

The invention is now further described by reference to the following examples which are intended to illustrate, not to limit the scope of the invention.

Example 1: Enzymatic Assay for CDK1, CDK2, CDK5 and CDK7

Enzymatic Binding Assay Protocol for CDK1, CDK2, CDK5 and CDK7

Inhibition activity of the respective compound on CDK kinase under Km value of ATP was tested in FRET based The LANCE® Ultra kinase assay (Perkin Elmer), which uses a ULight™-labeled peptide substrate and an appropriate Europium-labeled anti-phospho-antibody. Test compounds were made with DMSO solutions, and then 4-fold serial dilutions for 8 doses were prepared using automated liquid handler (POD™ 810, Labcyte) and 80 nL/well of diluted compound solutions were added into the 384-well plates (Greiner, Cat #784075). And then 68 nM of ULight-MBP peptide (Perkin Elmer, Cat #TRF0109-M) and 5 ul/well of ATP (Sigma, Cat #A7699) were added to the plate. After 1 min centrifugation at 1000 rpm, purified CDKs/Cyclin complex were added with the following concentrations respectively. 24 uM for CDK1/Cyclin B (Invitrogen, Cat #PR4768C), 22 uM for CDK2/Cyclin A (Invitrogen, Cat #PV6290), 10 uM for CDK5/p25 (Invitrogen, Cat #PR8543B) and 400 uM for CDK7/Cyclin H/MNAT1 (Invitrogen, Cat #PR6749B) were added to each corresponding plate for CDK1, CDK2, CDK5 and CDK7. Incubate at 23° C. for 60 min and then Eu-labeled anti-phospho-Myelin Basic Protein (PE, Cat #TRF0201-M) and EDTA (Invitrogen, Cat #15575038) mixture in Lance Detection Buffer (Perkin Elmer, Cat #CR97100) was added in each well. After additional incubation at 23° C. for 60 min, test articles were measured the fluorescence using Envision leader (Perkin Elmer, USA) [Laser as excitation light; APC 615 nm and Europium 665 as the first and the second emission filter]. Data were analyzed using XL Fit software.

Example 2: Cellular H460, MV4-11, A2780 and OVCAR-3 Viability Assay

Cell Culture

Human T-cell acute lymphoblastic leukemia cell line, MV4-11_(ATCC, Cat #CRL-9591), NSCLC (Non-small cell lung cancer) cell line H460 (ATCC, Cat #HTB-177), A2780 (ECACC, Cat #93112519) and OVCAR-3 (ATCC, Cat #HTB-161) were obtained from ATCC. Cells were grown in RPMI-1640 media (Invitrogen, Cat #22400-089) supplemented with 10% FBS (Invitrogen, Cat #10099141) and 1% penicillin/streptomycin (Invitrogen, Cat #15070063) and cultured at 37° C., 5% $CO_2$ in a humidified chamber. All cell lines were routinely tested for *mycoplasma*.

Cell H460, MV4-11, A2780 and OVCAR-3 Viability Assay Protocol

To effect of the CDK7 inhibitor to inhibit the growth of target cancer cells, viability assay were conducted a 72 hour time period. Briefly, the candidate cell line was plated in 96 well plate at the following density of cells respectively. $1\times10^4$ cells/well for MV4-11, $5\times10^3$ for H460 and OVCAR-3, and $1\times10^3$ for A2780. After 24 hours, the cells were treated with various concentrations of the compound (ranging from 0.0015 uM to 10 uM). DMSO solvent without compound served as a control and final DMSO concentration lest than 0.1%. After 72 hours of incubation at 37° C., 5% $CO_2$ incubator, cells were analyzed for the viability using the CellTiter-Glo Luminescent Cell Viability Assay (Promega, Cat #G7570). All viability assays were performed in duplicate and Luminescence was read using an Envision (Perkin Elmer, USA). Data was analyzed using XLfit software.

Example 3: Derivatization of the Pyrazolo-Triazine General Scaffold

Presented compounds underwent derivation according to the methods outlined below (Scheme 1-37). Resulting derivatives were examined for enzymatic binding and cellular activity (H460, MV4-11, A2780 and OVCAR-3), using the assays described above (Examples 1 and 2) and the results are summarized in Table 1-5. The synthesized compounds 1-88 are shown in Table 6.

Scheme 1 General Synthetic route 1

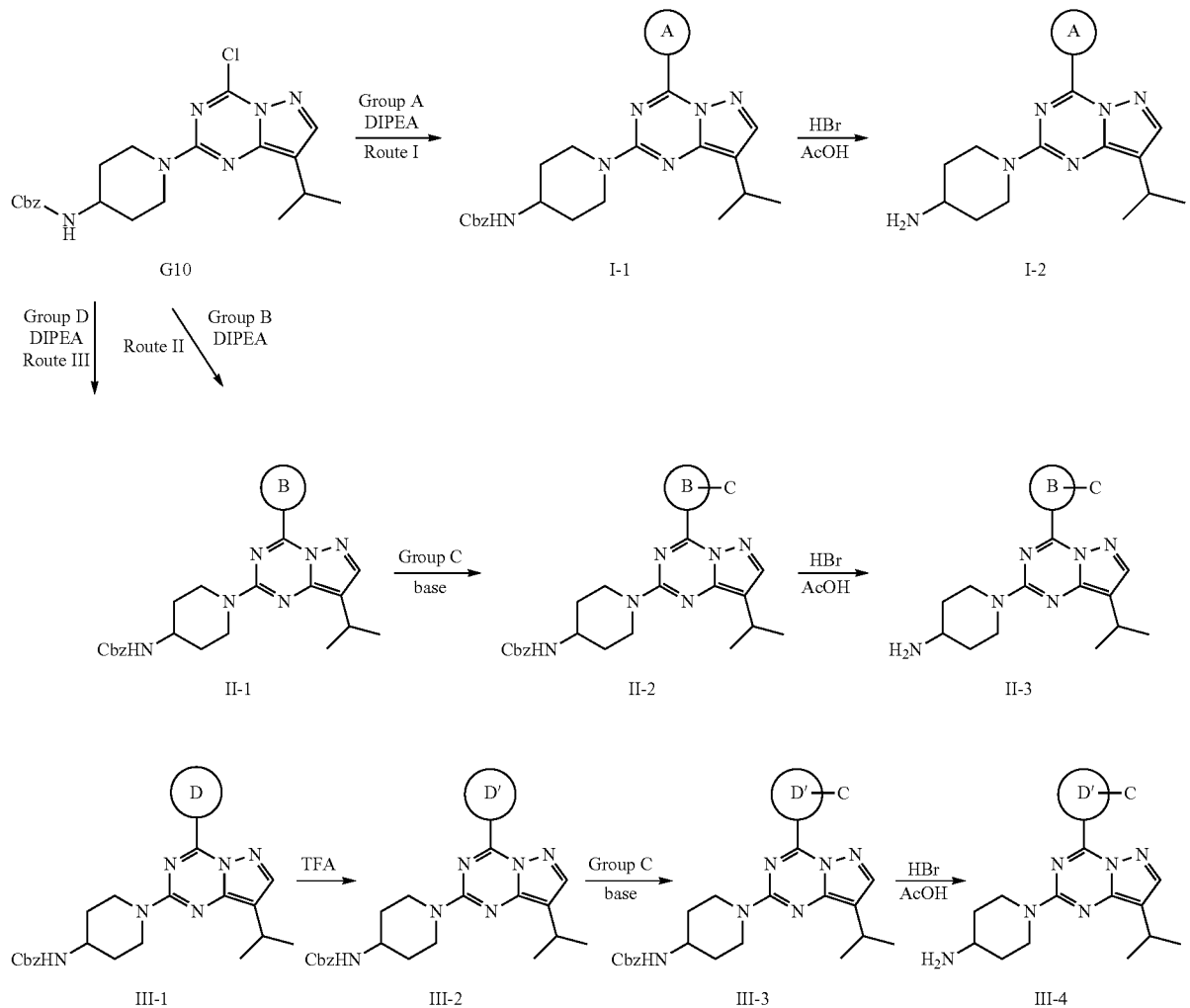

The method to prepare compounds of formula I-2, II-3 and III-4 were shown in Scheme 1.

Route I: Compound G10 can be treated with group A in presence of DIPEA to give compounds I-1. Compounds I-2 can be treated with HBr/AcOH to obtain the compounds of formula I-2.

Route II: Compound G10 can be treated with group B in presence of DIPEA to give compounds II-1. Compound II-1 can be treated with group C which is defined claim 1 in presence of DIPEA and acyl chloride to give compounds II-2. Compounds II-2 can be treated with HBr/AcOH to obtain the compounds of formula II-3.

Route III: Compound G10 can be treated with group D in presence of DIPEA to give compounds III-1. Compound III-1 can be treated with TFA to give compounds III-2. Compound III-2 can be treated with group C which was defined claim 1 in presence of DIPEA and acyl chloride to give compounds III-3. Compounds III-3 can be treated with HBr/AcOH to obtain the compounds of formula III-4.

General Schemes of Group A

Scheme 2 Synthetic route for A7

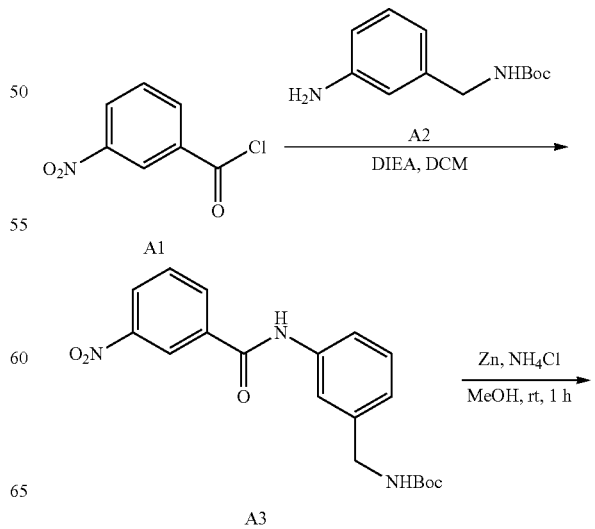

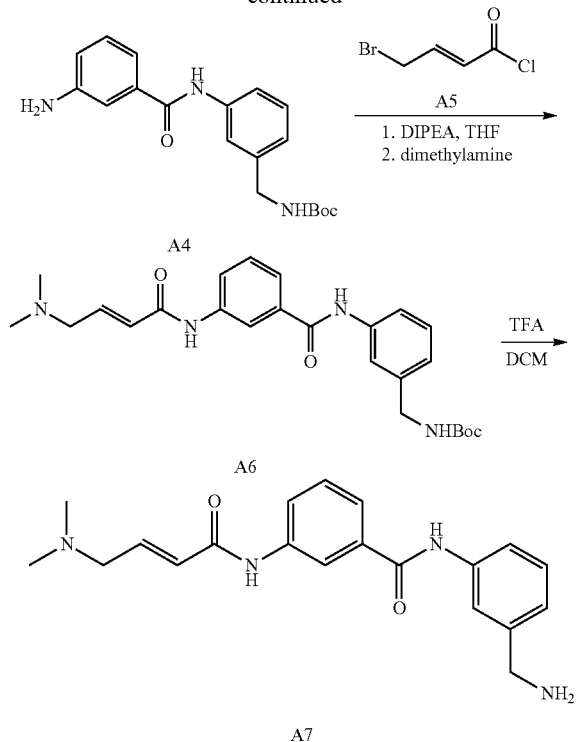

Procedure for Synthesis of A4

To a solution of compound A3 (1.76 g) in MeOH (40.0 mL) was added Zn powder (3.10 g, 47.40 mmol) and NH$_4$Cl (2.54 g, 47.4 mmol). The reaction mixture was stirred at 10° C. for 1 hour. TLC showed the reaction was completed. The reaction mixture was poured into saturated aqueous NaHCO$_3$ solution (20 mL) and extracted with EtOAc (10 mL×2). The combined extract was washed with brine (10 mL), dried over anhydrous Na$_2$SO$_4$, filtered and concentrated under reduced pressure to give a crude product. The crude product was purified by Combi flash to give compound A4 (875 mg) as a brown gum.

Procedure for Synthesis of A6

To a solution of compound A4 (775 mg, 2.27 mmol) and DIPEA (601 mg, 4.65 mmol) in anhydrous THF (10 mL) was added a solution of compound A5 (500 mg, 2.72 mmol) in anhydrous THF (1.0 mL) dropwise at 15° C. After stirred at 15° C. for 10 minutes, dimethylamine (2 M in THF, 7.57 mL) was added. The reaction solution was stirred at 15° C. for 20 minutes. TLC showed the reaction was complete. The reaction mixture was poured into water (10 mL) and then extracted with EtOAc (10 mL×2). The organic layer was washed with water (10 mL) and brine (10 mL), dried over anhydrous Na$_2$SO$_4$, filtered and concentrated under reduced pressure to give the crude product as a brown gum. The crude product was purified by Combi flash to give compound A6 (337 mg) as a light brown gum.

Procedure for Synthesis of A7

To a solution of compound A6 (168 mg) in DCM (2 mL) was added TFA (500 uL). The reaction solution was stirred at 10° C. for 2 hours. TLC showed the reaction was completed. The mixture was concentrated under reduced pressure. The residue was partitioned between DCM (10 mL) and saturated aqueous NaHCO$_3$ solution (10 mL). The organic and aqueous layer was concentrated under reduced pressure to give 130 mg of crude compound A7. The crude product was used directly in the next step without further purification.

Procedure for Synthesis of A3

To a solution of compound A2 (2.64 g), DIPEA (3.07 g, 23.7 mmol) in DCM (40.0 mL) was added 3-nitrobenzoyl chloride A1 (2.20 g, crude) at 0° C. The reaction mixture was stirred at 10° C. for 16 hours under N$_2$ atmosphere. TLC showed a new spot was formed. The reaction solution was washed with water (10 mL), dried over anhydrous Na$_2$SO$_4$, filtered, concentrated under reduced pressure. The residue was purified by Combi flash to give compound A3 (1.96 g) as an off-white powder.

Scheme 3 Synthetic route for A16 and A18

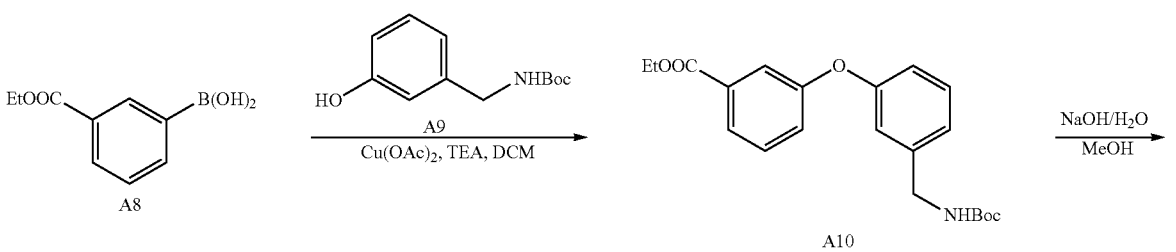

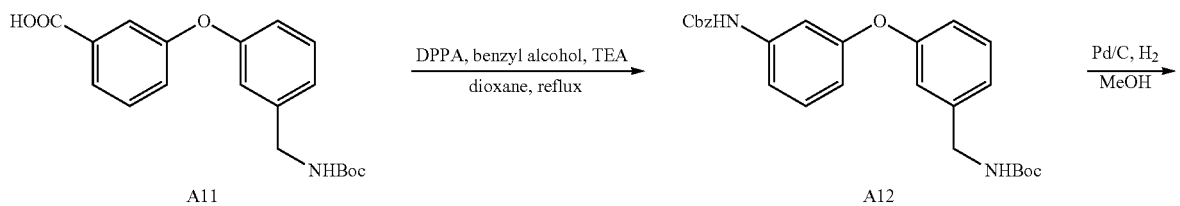

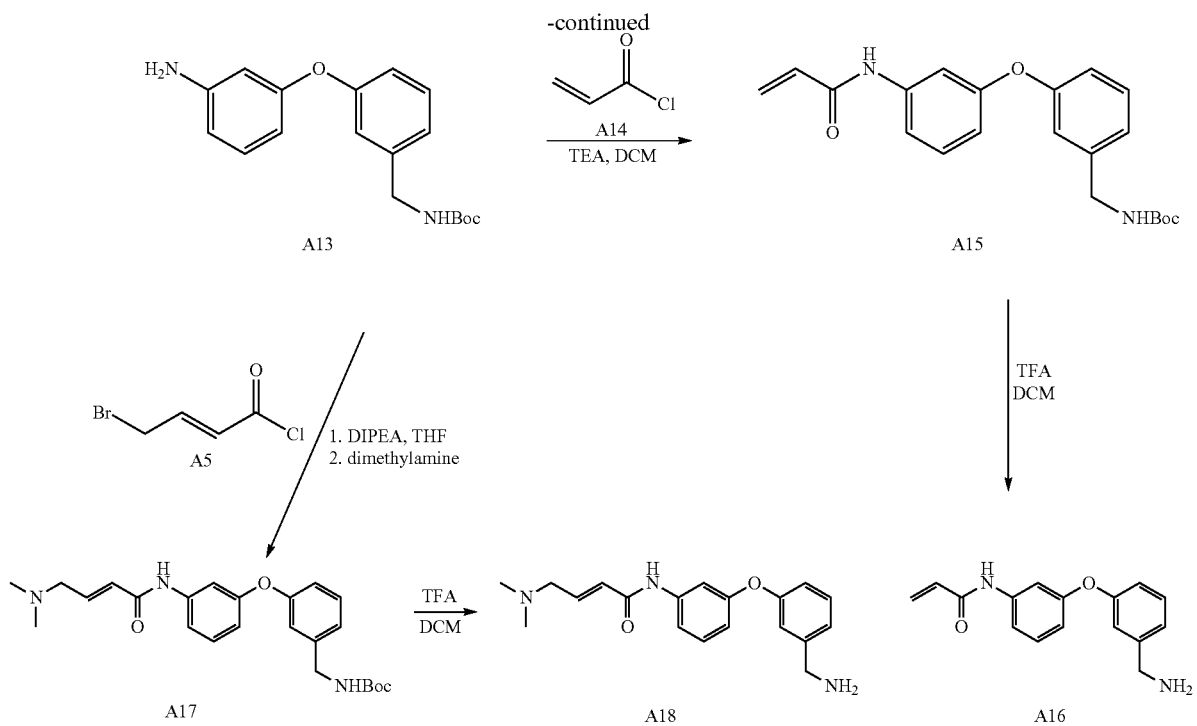

Procedure for Synthesis of A10

To a solution of compound A8 (2.80 g, 12.5 mmol) in anhydrous DCM (100 mL) was added compound A9 (3.65 g, 18.8 mmol), Cu(OAc)$_2$ (3.42 g, 18.8 mmol) and TEA (3.81 g, 37.6 mmol, 5.22 mL). The reaction mixture was stirred at 15° C. for 1 day. TLC showed compound A13 was consumed. The reaction mixture was filtered. The filtrate was washed with water (20 mL) and concentrated under reduced pressure to give a light brown gum. The crude gum was purified by Combi flash to give compound A10 (629 mg) as a white powder.

Procedure for Synthesis of A11

To a solution of compound A10 (625 mg, 1.68 mmol) in MeOH (6 mL) was added NaOH (1 M, 3.36 mL). The reaction mixture was stirred at 15° C. for 17 hour. TLC showed the reaction was completed. The reaction mixture was concentrated under reduced pressure. The residue was dissolved in water (5 mL) and neutralized by aqueous HCl solution (1 M, 3.40 mL), then extracted with DCM (10 mL×2). The organic layer was washed with water (10 mL), dried over anhydrous Na$_2$SO$_4$, filtered, concentrated under reduced pressure to give compound A11 (483 mg) as a white powder.

Procedure for Synthesis of A12

To a solution of compound A11 (383 mg, 1.12 mmol), benzyl alcohol (969 mg, 8.96 mmol, 931.67 uL), TEA (453 mg, 4.48 mmol, 621 uL) in dioxane (10 mL) was added DPPA (339 mg, 1.23 mmol, 267 uL). The reaction solution was heated to reflux for 2 hours. TLC showed the reaction was completed. The reaction mixture was partitioned between water (30 mL) and DCM (30 mL). The organic layer was washed with water (10 mL×2), brine (10 mL), dried over anhydrous Na$_2$SO$_4$, and concentrated under reduced pressure to give a residue. The crude product was purified by Combi flash to give compound A12 (1.20 g, crude) as a colorless oil. The crude product was used directly in the next step without further purification.

Procedure for Synthesis of A13

To a solution of compound A12 (1.10 g, crude) in MeOH (50 mL) was added Pd/C (100 mg, 50% wet, 10% Pd). The reaction mixture was degassed under vacuum and purged with H$_2$ for 3 times, then stirred at 15° C. for 16 hours under H$_2$ atmosphere (15 psi). TLC showed the reaction was completed. The reaction mixture was filtered through a pad of Celite. The filtrate was concentrated under reduced pressure. The residue was purified by Combi flash to give compound A13 (210 mg) as a colorless oil.

Procedure for Synthesis of A15

To a solution of compound A13 (140 mg, 0.445 mmol), TEA (64 mg, 0.63 mmol) in DCM (2 mL) was added acryl chloride A14 (61.0 mg, 0.674 mmol) dropwise at 20° C. The reaction solution was stirred at 20° C. for 2 hours under N$_2$ atmosphere. TLC showed the reaction was completed. The reaction was quenched with water (5 mL) and extracted with DCM (10 mL×2). The combined extract was washed with water (5 mL), dried over anhydrous Na$_2$SO$_4$, filtered, concentrated under reduced pressure to give the crude product as a brown gum. The crude product was purified by Combi flash to give compound A15 (131 mg) as a brown gum.

Procedure for Synthesis of A16

The compound A15 (130 mg) was followed the same procedure of A7 to obtain 90 mg of compound A16 as a brown gum.

Procedure for Synthesis of A17

To a solution of compound A13 (210 mg, 0.668 mmol) and DIPEA (177 mg, 1.37 mmol) in anhydrous THF (5 mL) was added a solution of compound A5 (147 mg, 0.801 mmol) in anhydrous THF (1.0 mL) dropwise at 15° C. After stirred at 15° C. for 30 minutes, LCMS showed the desired product. The reaction mixture was poured into water (10 mL) and then extracted with DCM (10 mL×2). The organic layer was washed with water (10 mL) and brine (10 mL), dried over anhydrous Na$_2$SO$_4$, filtered and concentrated under reduced pressure to give the crude product as a brown gum. The crude product was purified by Combi flash to give compound A17 (183 mg) as a light brown gum.

Procedure for Synthesis of A18

The compound A17 (180 mg) was followed the same procedure of A7 to obtain 133 mg of compound A18 as a brown gum.

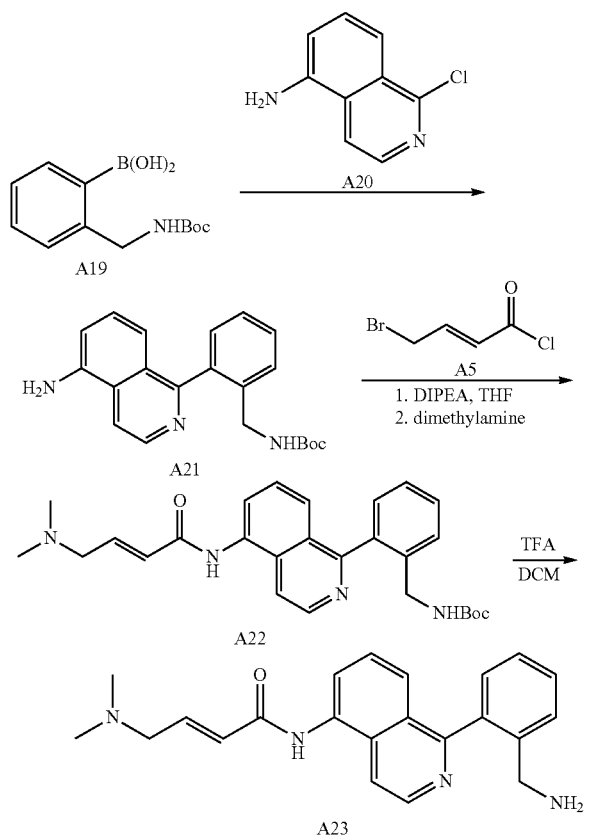

Procedure for Synthesis of 21

To a solution of compound A20 (300 mg, 1.68 mmol) and compound A19 (506 mg, 2.02 mmol) in dioxane (5 mL) and $H_2O$ (1 mL) was added $Cs_2CO_3$ (547 mg, 1.68 mmol), Pd(dppf)Cl$_2$ (123 mg, 0.168 mmol) under $N_2$. The resulting mixture was heated at 100° C. and stirred for 1.5 hours to give black suspension. LCMS and TLC showed the reaction was completed. The reaction mixture was quenched by addition $H_2O$ (50 mL) and extracted with EtOAc (50 mL×2). The combined organic layers were washed with brine (20 mL×2), dried over $Na_2SO_4$, filtered and concentrated under reduced pressure to give a residue. The residue was purified by combi flash to give compound A21 (240 mg) as a yellow solid.

Procedure for Synthesis of A22

The compound A21 (408 mg) was followed the same procedure of A6 to obtain 184 mg of compound A22 as a yellow oil.

Procedure for Synthesis of A23

The compound A22 (184 mg) was followed the same procedure of A7 to obtain 160 mg of compound A23 as a yellow oil.

General Schemes of Group B

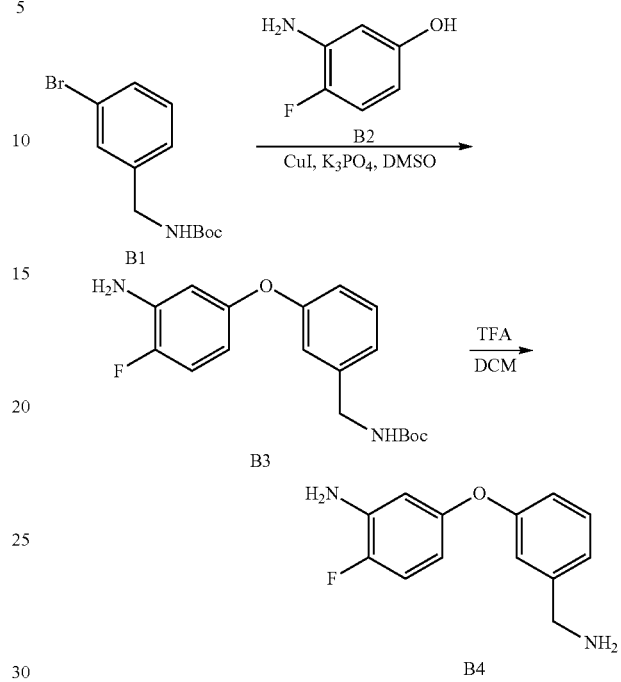

Procedure for Synthesis of B3

To a solution of compound B1 (2.48 g, 8.66 mmol), compound B2 (1.00 g, 7.87 mmol), pyridine-2-carboxylic acid (194 mg, 1.57 mmol) and $K_3PO_4$ (3.34 g, 15.7 mmol) in DMSO (15 mL) was added CuI (150 mg, 0.787 mmol), the mixture was purged with $N_2$ for three times and stirred at 90° C. for 17 hours to give a dark solution. LCMS showed the reaction was completed. TLC showed the reaction was completed. The reaction mixture was poured into water (100 mL), extracted with EtOAc (100 mL×2), the combined extracts was washed with brine (30 mL×2), dried over anhydrous $Na_2SO_4$, filtered and concentrated under reduced pressure to give a residue. The residue was purified by Combi flash to give compound B3 (860 mg) as light yellow oil.

Procedure for Synthesis of B4

To a solution of compound B3 (860 mg, 2.59 mmol) in DCM (7 mL) was added TFA (3 mL), the reaction mixture was stirred at 25° C. under $N_2$ for 1 hour to give a brown solution. TLC showed the reaction was completed. The reaction mixture was concentrated under reduced pressure to give compound B4 (800 mg) as brown oil.

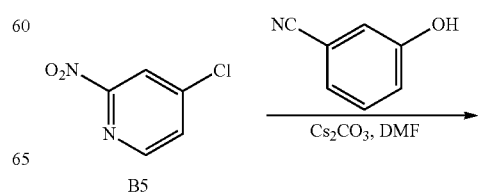

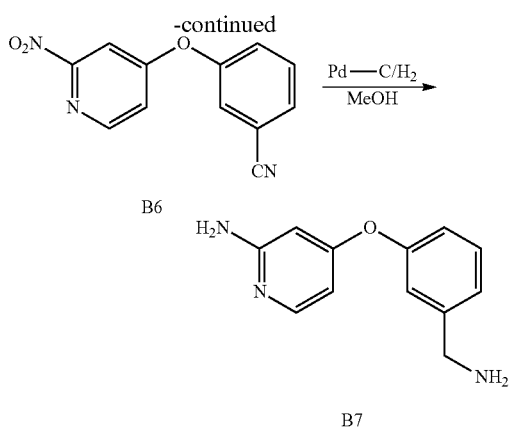

Procedure for Synthesis of B6

To a suspension of compound B5 (4.00 g, 25.2 mmol) and Cs₂CO₃ (16.4 g, 50.5 mmol) in DMF (50 mL) was added 3-cyanophenol (3.16 g, 26.5 mmol), the mixture was stirred at 60° C. for 17 hours to give a brown suspension. Crude LCMS (RT: 1.384 min) showed the reaction was completed. The mixture was poured into water (400 mL), a lot of white solid appeared, filtered, the filter cake was washed with water (30 mL×3) to give the crude product. The crude product was purified by Combi flash to give 1.00 g of compound B6 as a yellow powder.

Procedure for Synthesis of B7

To a solution of compound B6 (850 mg, 3.52 mmol) and Pd/C (170 mg, 10% Pd) in MeOH (10 mL) was added NH₃·H₂O (1.83 g, 5.21 mmol), the mixture was purged with N₂ for three times and stirred at 20° C. under H₂ balloon (15 psi) for 1 hour to give a brown suspension. The crude LCMS showed the reaction was completed. The mixture was filtered, the filtrate was concentrated under reduced pressure to give 700 mg of compound B7 as a yellow gum.

Procedure for Synthesis of B10

To a solution of NaH (1.73 g, 43.4 mmol) in DMF (100 mL) was added 7-nitro-2H-indazole B8 (5.19 g, 31.8 mmol) in several portion at 20° C., the resulting mixture was stirred for 1 hour at 20° C., then 2-fluorobenzonitrile B9 (3.50 g, 28.9 mmol) was added to the mixture, the reaction mixture was stirred for another 12 hours at 130° C. to give black suspension. TLC showed the reaction was completed. The reaction mixture was quenched by addition H₂O (500 mL) and extracted with EtOAc (500 mL×2). The combined organic layers were washed with brine (100 mL×2), dried over Na₂SO₄, filtered and concentrated under reduced pressure to give a residue. The residue was purified by triturated to obtain compound B10 (1.80 g) as a black solid.

Procedure for Synthesis of B11

To a solution of compound B10 (200 mg, 0.8 mmol) in MeOH (20 mL) and NH₃·H₂O (1.00 mL, 25%) was added Raney-Ni (64.8 mg, 0.8 mmol) under N₂. The suspension was degassed under vacuum and purged with H₂ several times. The mixture was stirred under H₂ (40 psi) at 20° C. for 2 hours to give black suspension. TLC and LCMS showed the reaction was completed. The reaction mixture was filtered by celite pad and concentrated under reduced pressure to give a residue. The residue was purified by Combi flash to obtain compound B11 (50 mg) as a yellow oil.

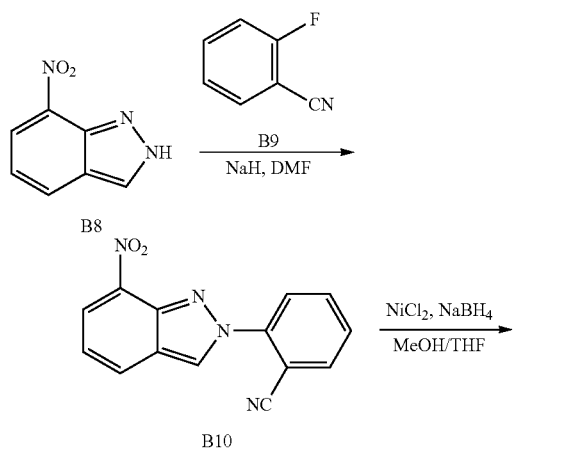

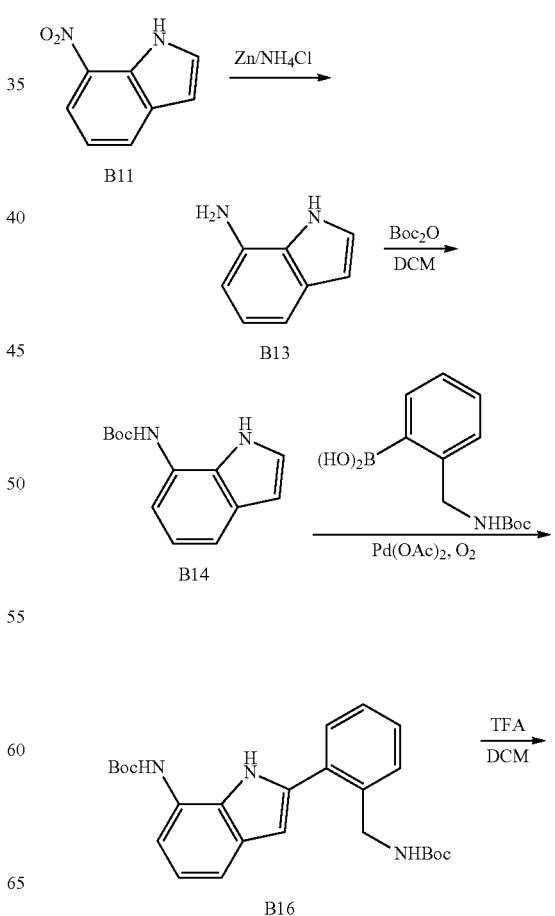

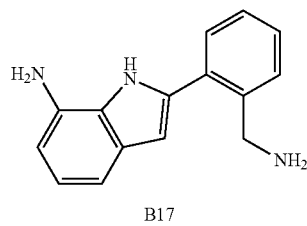

B17

Procedure for Synthesis of B13

To a solution of compound B12 (1.50 g, 9.25 mmol) in MeOH (50 mL) was added Zn (6.05 g, 92.5 mmol) and NH$_4$Cl (4.95 g, 92.5 mmol). The resulting mixture was stirred at 20° C. for 12 hours to give black suspension. TLC showed the reaction was completed, one new spot was formed. The reaction mixture was filtered and concentrated under reduced pressure to give a residue to give 1.80 g compound B13 as a black solid and used in the next step without purification.

Procedure for Synthesis of B14

To a solution of crude product compound B13 (1.80 g, 6.81 mmol) in MeOH (50 mL) was added Et$_3$N (689 mg, 6.81 mmol) and Boc$_2$O (2.23 g, 10.2 mmol). The resulting mixture was stirred at 20° C. for 12 hours to give black solution. TLC showed one new spot was formed. The reaction mixture was filtered under reduced pressure to give a residue. The residue was purified by Combi flash to obtain compound B14 (781 mg) as a white solid.

Procedure for Synthesis of B16

To a mixture of compound B14 (810 mg, 3.23 mmol), compound B15 (500 mg, 2.15 mmol) in HOAc (20 mL) was added Pd(OAc)$_2$ (241 mg, 1.08 mmol), the mixture was stirred at 40-50° C. under O$_2$ (15 psi) atmosphere for 12 hours to give a black brown suspension. LCMS (Rt=1.436 min) showed the reaction was completed. AcOH was removed under reduced pressure, and the residue was dissolved in DCM (150 mL) and washed with saturated aqueous NaHCO$_3$ (100 mL×3). The organic layer was dried over Na$_2$SO$_4$, filtered, concentrated under reduced pressure to give black brown oil. The mixture was for Combi flash to give compound B16 (380 mg) as a yellow gum.

Procedure for Synthesis of B17

To a mixture of compound B16 (380 mg, 0.869 mmol) in DCM (30 mL) was added TFA (8 mL). The mixture was stirred at 15° C. for 0.5 hour to give a yellow mixture. LCMS showed the reaction was completed. The mixture was combined and concentrated under reduced pressure to give compound B17 (350 mg) as yellow oil Scheme 9 General Synthetic route for B23

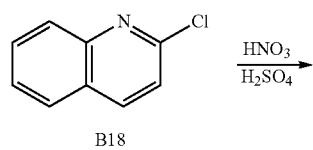

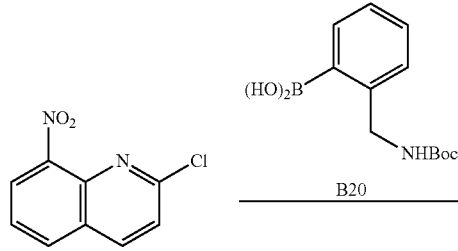

Procedure for Synthesis of B19

A solution of 2-chloroquinoline B18 (2.00 g, 12.2 mmol) in H$_2$SO$_4$ (20 mL) was cooled to 0° C. HNO$_3$ (3.55 g, 36.7 mmol) was added dropwise. The reaction solution was stirred at 25° C. for 1 hour to give a black brown solution. TLC showed the reaction was completed. The reaction solution was poured into water (50 mL), neutralized to pH=7-8 with saturated Na$_2$CO$_3$. The resulting mixture was extracted with DCM (200 mL×2). The combined organic layer was washed with brine (200 mL), dried over anhydrous Na$_2$SO$_4$ and concentrated under reduced pressure. The residue was purified by Combi Flash to give compound B19 (1.30 g) as a yellow solid.

Procedure for Synthesis of B21

To a solution of compound B19 (560 mg, 2.68 mmol) and compound B20 (2.02 g, 8.04 mmol) in dioxane (10 mL)/H$_2$O (3 mL) was added Cs$_2$CO$_3$ (1.75 g, 5.36 mmol) and Pd(dppf)Cl$_2$ (98.1 mg, 0.134 mmol) under N$_2$ atmosphere. The reaction mixture was heated to 100° C. and stirred for 16 hours under N$_2$ atmosphere to give a black mixture. TLC showed the reaction was completed. The reaction mixture was diluted with water (100 mL) and extracted with EtOAc (200 mL×2). The combined extracts were dried over anhydrous Na$_2$SO$_4$ and concentrated under reduced pressure. The residue was purified by Combi Flash to give compound B21 (1.00 g) as brown solid.

Procedure for Synthesis of B22

To a solution of compound B21 (500 mg, 1.32 mmol) and NH$_4$Cl (706 mg, 13.2 mmol) in MeOH (10 mL) was added Zn (863 mg, 13.2 mmol) slowly. The reaction mixture was stirred at 25° C. for 16 hours to give a black brown mixture. TLC showed the reaction was completed. The reaction mixture was diluted with MeOH (50 mL) and filtered. The filtrate was concentrated under reduced pressure. The residue was purified by Combi Flash to give compound B22 (500 mg) as a yellow solid.

Procedure for Synthesis of B23

To a solution of compound B22 (500 mg, 1.43 mmol) in DCM (7 mL) was added TFA (3 mL). The reaction solution was stirred at 25° C. for 1 hour to give a red solution. LCMS showed the reaction was completed. The reaction was diluted with DCM (10 mL) and concentrated under reduced pressure to give compound B23 (300 mg) as black brown oil.

Scheme 10 General Synthetic route for B31

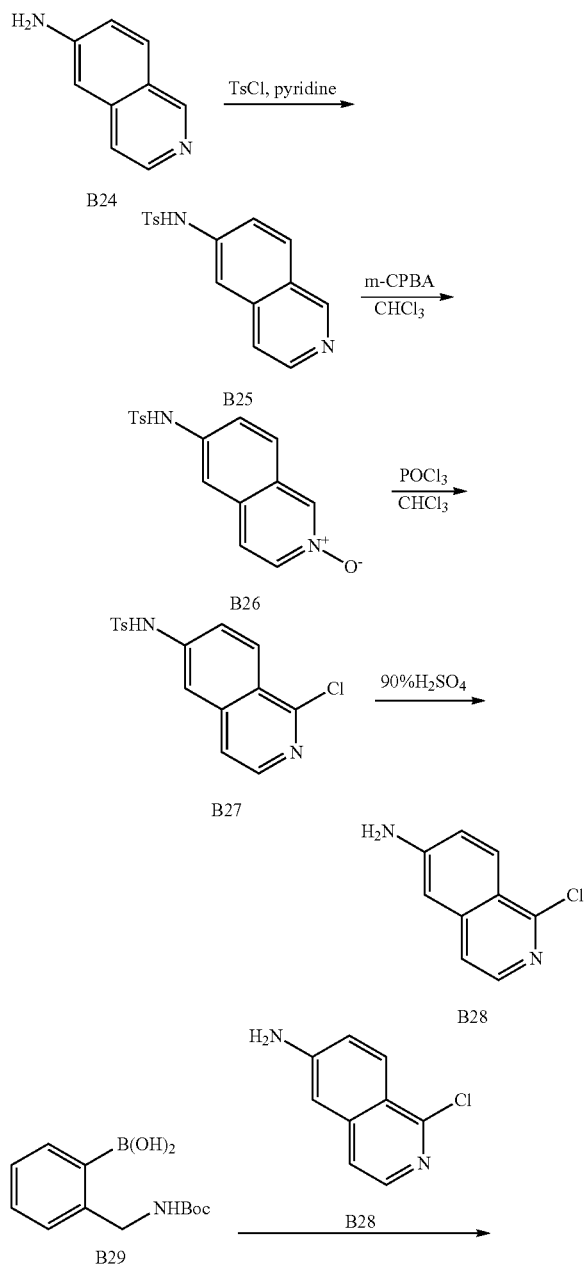

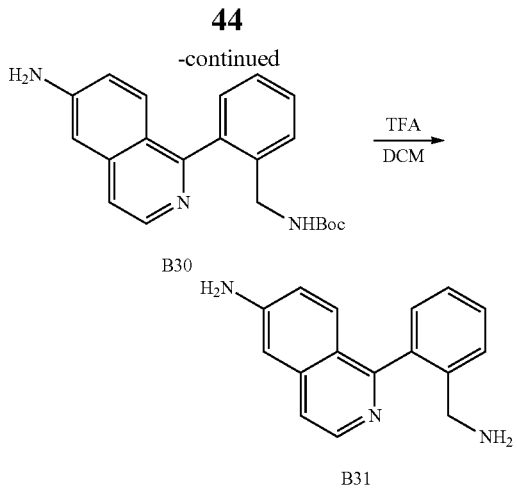

Procedure for Synthesis of B25

Isoquinolin-6-amine B24 (2.00 g, 13.87 mmol) was dissolved in pyridine (20 mL), and 4-methylbenzenesulfonyl chloride (3.17 g, 16.64 mmol) was added. The reaction mixture was stirred at 20° C. for 12 hours. LCMS showed the reaction was completed. To the reaction mixture was added water (30 mL) under good stirring, the mixture was stirred at 20° C. for 0.5 hour, pale yellow solid precipitated out. The mixture was filtered and the solid was collected and washed with water (5 mL) to give compound B25 (2.2 g) as a yellow solid.

Procedure for Synthesis of B26

Compound B25 (2.00 g, 6.70 mmol) was dissolved in $CHCl_3$ (30.00 mL). Under ice-cooling (0° C.), m-CPBA (1.71 g, 7.91 mmol) was added thereto, followed by stirring at 20° C. for 12 hours. TLC showed the reaction was completed. The solvent was evaporated and the resulting solid were washed with MTBE (50 mL). The filter cake was collected and dried in high vacuum to give compound B26 (1.96 g) as a light yellow solid.

Procedure for Synthesis of B27

To a mixture of compound B26 (4.20 g, 13.4 mmol) in $CHCl_3$ (120 mL) was added $POCl_3$ (45.1 g, 293.9 mmol). The reaction mixture was heated to 61° C. and stirred for 16 hours to give a black brown solution. TLC showed the reaction was completed. The reaction solution was cooled to 20° C. and concentrated under reduced pressure. The residue was poured into water (200 mL) and neutralized to pH=8-9 with saturated $Na_2CO_3$. 300 mL EtOAc was added and the mixture was filtered. The filtrate was collected, separated and the aqueous phase was extracted with EtOAc (200 ml×2). The combined extracts were collected, dried over anhydrous $Na_2SO_4$ and concentrated under reduced pressure to give compound B27 (4.00 g) as a yellow solid.

Procedure for Synthesis of B28

A solution of compound B27 (4.00 g, 12.0 mmol) in $H_2SO_4$ (50 mL) (90%) was stirred at 20° C. for 16 hours to give a black brown solution. LCMS showed the reaction was completed. The reaction solution was cooled to 0-10° C. with ice-water (100 mL), neutralized to pH=7-8 with $Na_2CO_3$ (solid) and extracted with EtOAc (300 mL×2). The combined extracts were collected, dried over anhydrous $Na_2SO_4$ and concentrated under reduced pressure to give compound B28 (1.80 g) as a red solid.

Procedure for Synthesis of B30

To a solution of compound B28 (1.00 g, 5.60 mmol) and compound B29 (4.22 g, 16.8 mmol) in dioxane (15 mL)/$H_2O$ (5 mL) was added $Cs_2CO_3$ (3.65 g, 11.2 mmol) and Pd(dppf)Cl$_2$ (205 mg, 0.280 mmol) under N$_2$ atmosphere. The reaction mixture was heated to 100° C. and stirred for 4 hours under N$_2$ atmosphere to give a black mixture. TLC showed the reaction was completed. The reaction mixture was diluted with water (100 mL) and extracted with EtOAc (200 mL×2). The combined extracts were dried over anhydrous Na$_2$SO$_4$ and concentrated under reduced pressure. The residue was purified by Combi Flash to give compound B30 (1.00 g) as black brown oil.

Procedure for Synthesis of B31

To a solution of compound B30 (1.00 g, 2.86 mmol) in DCM (14 mL) was added TFA (6 mL) slowly. The reaction solution was stirred at 25° C. for 1 hour to give a red solution. LCMS showed the reaction was completed. The reaction solution was concentrated under reduced pressure to give compound B31 (1.00 g) as black brown oil, used for next step without further purification.

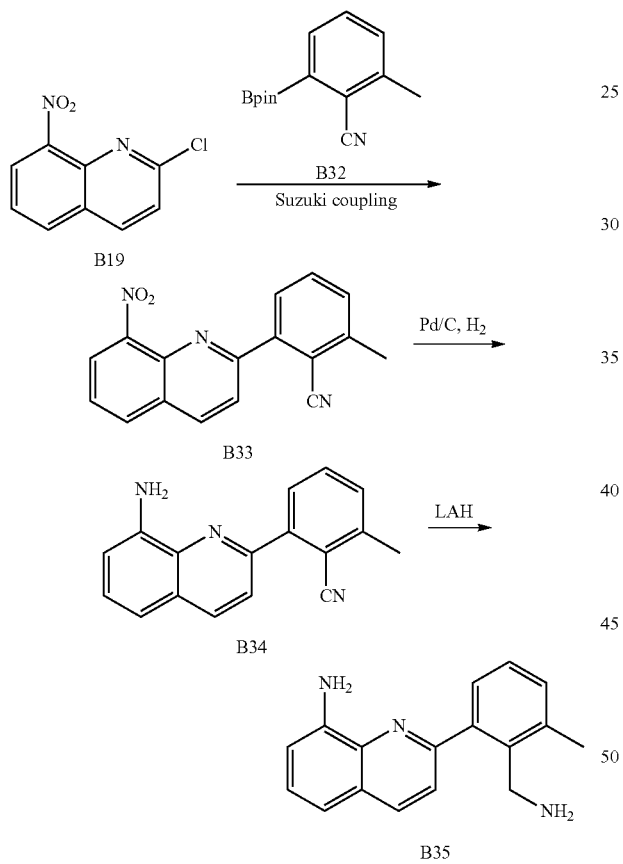

Scheme 11 General Synthetic route for B35

Procedure for Synthesis of B33

To a solution of compound B19 (2.7 g, 12.9 mmol, 1 eq) and compound 32 (3.15 g, 12.9 mmol, 1.0 eq) in dioxane (50 mL) and H$_2$O (10 mL) were added Na$_2$CO$_3$ (2.74 g, 25.9 mmol, 2 eq) and Pd(PPh$_3$)$_4$ (748 mg, 0.65 mmol, 0.05 eq) under N$_2$. The resulting mixture was heated at 80° C. and stirred for 12 hrs to give yellow suspension. TLC showed the reaction was completed. The reaction mixture was filtered to give a residue as a light yellow solid. Then the residue was dissolved in DCM (200 mL) and H$_2$O (200 mL), and extracted with DCM (200 mL). The combined organic layers were washed with brine (100 mL), dried over Na$_2$SO$_4$, filtered and concentrated under reduced pressure to give compound B33 (3.25 g) as a light yellow solid.

Procedure for Synthesis of B34

To a solution of compound B33 (2.5 g, 8.64 mmol, 1 eq) in DCM (100 mL) was added Pd/C (1.5 g, 1.75 mmol) under N$_2$. The suspension was degassed under vacuum and purged with H$_2$ several times. The mixture was stirred under H$_2$ (15 psi) at 15° C. for 12 hours to give black solution. LCMS showed the reaction was completed. The reaction mixture was filtered and concentrated under reduced pressure to give compound B34 (1.96 g) as a yellow solid.

Procedure for Synthesis of B35

To a suspension of LiAlH$_4$ (673 mg, 17.7 mmol, 2 eq) in THF (20 mL) was added a solution of compound B34 (2.3 g, 8.87 mmol, 1 eq) in THF (10 mL) at 0° C. The reaction mixture was stirred at 15° C. for 1 hour to give red solution. LCMS showed the reaction was completed. The mixture was quenched by saturated NH$_4$Cl solution. The mixture was partitioned between EtOAc and H$_2$O. The aqueous phase was extracted with EtOAc. The combined organic was washed with brine (200 mL), dried over anhydrous Na$_2$SO$_4$, filtered and concentrated under reduced pressure to afford compound B35 (1.53 g, crude) as a brown solid. The crude product was used in the next step directly.

General Schemes of Group D

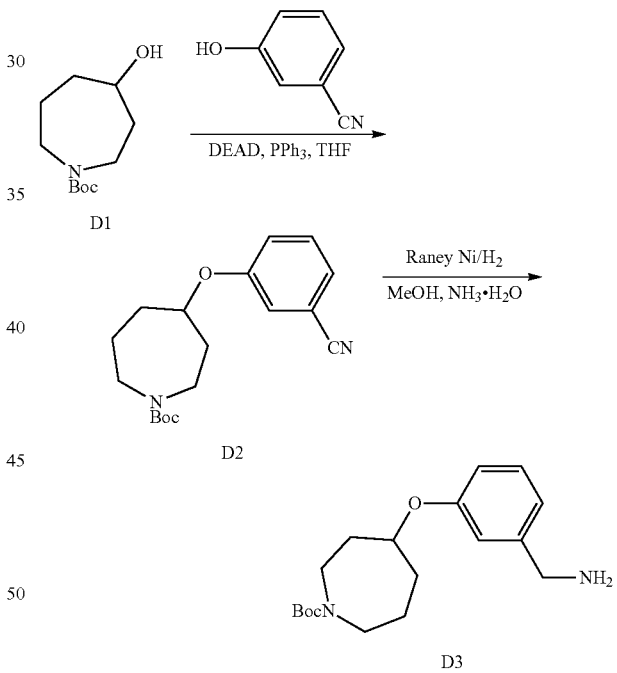

Scheme 12 General Synthetic route for D3

Procedure for Synthesis of D2

To a solution of compound D1 (500 mg, 2.32 mmol) and 3-hydroxybenzonitrile (276 mg, 2.32 mmol) in THF (20 mL) was added PPh$_3$ (730 mg, 2.78 mmol) and DEAD (485 mg, 2.78 mmol). The resulting mixture was stirred at 20° C. for 12 hour to give yellow solution. LCMS and TLC showed the reaction completed. The reaction mixture was quenched by addition H$_2$O (50 mL) and extracted with EtOAc (50 mL×2). The combined organic layers were washed with brine (30 mL×2), dried over Na$_2$SO$_4$, filtered and concentrated under reduced pressure to give a residue. The residue was purified by Combi flash to obtain compound D2 (587 mg) as a yellow oil Procedure for Synthesis of D3

To a solution of compound D2 (587 mg, 1.86 mmol) in MeOH (20 mL) and NH$_3$·H$_2$O (1 mL) (28%) was added Raney-Ni (159 mg, 1.86 mmol) under N$_2$. The suspension was degassed under vacuum and purged with H$_2$ several times. The mixture was stirred under H$_2$ (15 psi) at 20° C. for 2 hours to give black suspension. LCMS showed the reaction was completed. The reaction mixture was filtered by celite pad and concentrated under reduced pressure to give compound D3 (600 mg) as yellow oil,

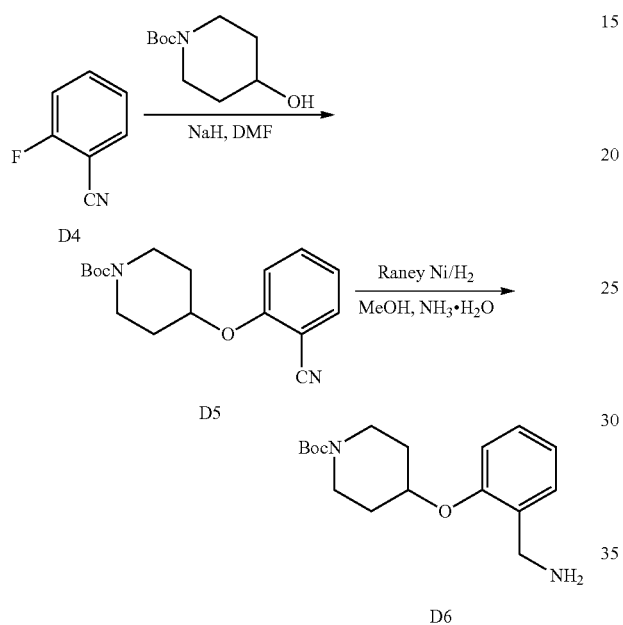

Scheme 13 General Synthetic route for D6

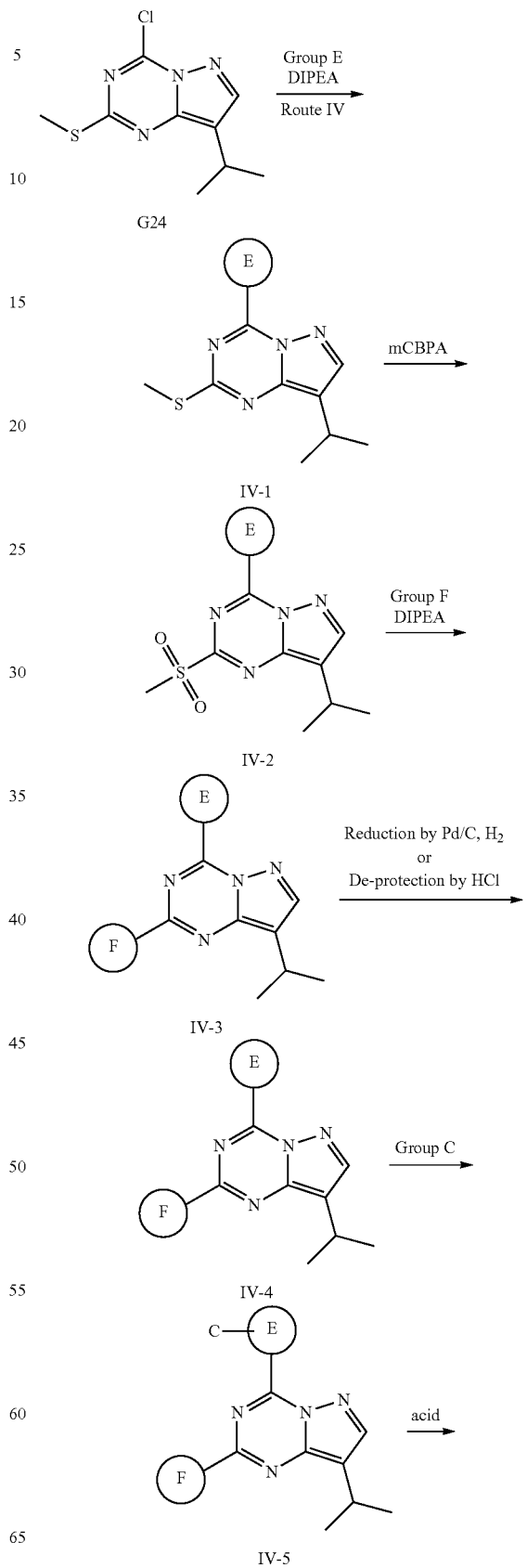

Scheme 14 General Synthetic route 2

Procedure for Synthesis of D5

To tert-butyl 4-hydroxypiperidine-1-carboxylate (4.82 g, 23.95 mmol) in DMF (50 mL) was added portionwise NaH (1.44 g, 35.92 mmol) at 0° C. The reaction mixture was stirred at 20° C. for 2 hours. Then 2-fluorobenzonitrile D4 (2.90 g, 23.95 mmol) was added the above mixture and the reaction mixture was heated to 50° C. for 1 hour. TLC showed the reaction was completed. Saturated NH$_4$Cl (100 mL) was added dropwise into the reaction mixture carefully at 0° C. to quench the reaction. The mixture was extracted with EtOAc (100 mL×2). The combined extracts were washed with water (50 mL×3), brine (100 mL), dried over anhydrous Na$_2$SO$_4$, filtered and concentrated under reduced pressure to give compound D5 (9.10 g, crude) as a light yellow oil.

Procedure for Synthesis of D6

To a mixture of Raney-Ni (425 mg, 4.96 mmol) and compound D5 (3.00 g, 9.92 mmol) in MeOH (90 mL) was added NH$_3$·H$_2$O (6 mL) under N$_2$ atmosphere. The suspension was degassed under vacuum and purged with H$_2$ three times. The mixture was stirred under H$_2$ (15 psi) at 20° C. for 4 hours. LCMS showed the reaction was completed. The reaction mixture was filtered, the filtrate was concentrated to remove most MeOH. The residue was diluted with DCM (100 mL), washed with brine (80 mL×2), dried over anhydrous Na2SO4, filtered and concentrated under reduced pressure to give compound D6 (2.90 g) as a light yellow oil.

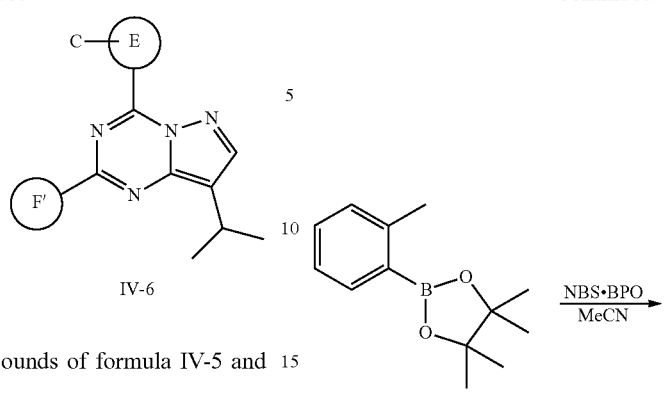

The method to prepare compounds of formula IV-5 and IV-6 is shown in Scheme 14.

Route IV: Compound G24 can be treated with group E in presence of DIPEA to give compounds IV-1. Compound IV-1 can be treated with mCPBA to give compounds IV-2. Compound IV-2 can be treated with group F in presence of DIPEA to give compounds IV-3. Compound IV-3 can be treated with Pd/C and $H_2$, or HCl to give compounds IV-4. Compound IV-4 can be treated with group C which was defined claim 1 to give compounds IV-5. Compounds IV-5 can be treated with acid such as HCl to obtain the compounds of formula IV-6.

General Schemes of Group E

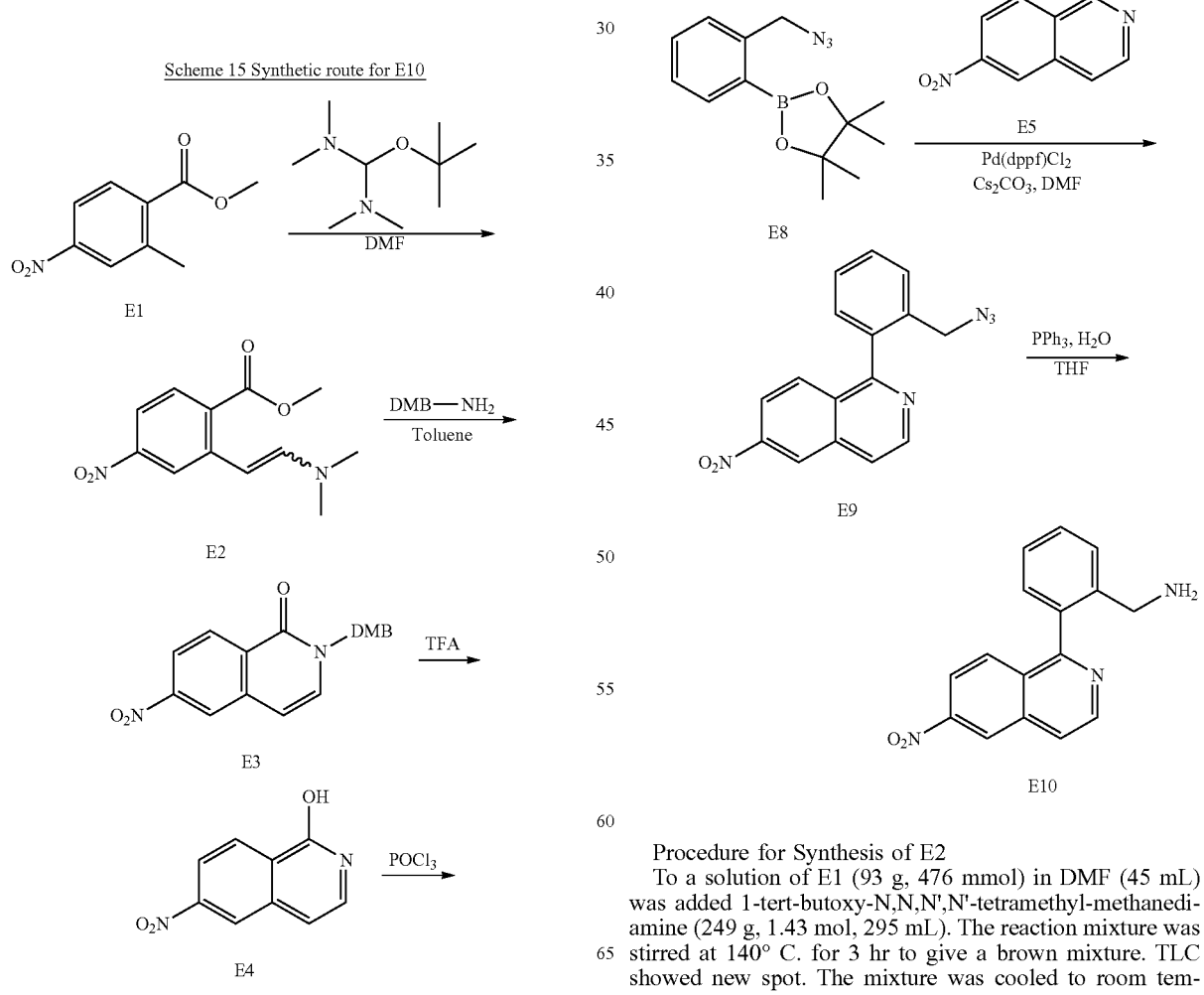

Procedure for Synthesis of E2

To a solution of E1 (93 g, 476 mmol) in DMF (45 mL) was added 1-tert-butoxy-N,N,N',N'-tetramethyl-methanediamine (249 g, 1.43 mol, 295 mL). The reaction mixture was stirred at 140° C. for 3 hr to give a brown mixture. TLC showed new spot. The mixture was cooled to room temperature and stirred at 0° C. for 30 min. Solid was precipitated out. After filtration, the filter cake was washed with EtOAc/PE and dried under reduced pressure to give compound E2 (69 g) as a purple powder.

Procedure for Synthesis of E3

A solution of E2 (63 g, 252 mmol), (2,4-dimethoxyphenyl)methanamine (63 g, 378 mmol, 57 mL) in toluene (150 mL) was stirred at 35° C. for 2 hours to give a yellow mixture. Then the reaction was stirred at 65° C. for 2 hours to give a yellow mixture. Then the reaction was stirred at 110° C. for 3 hours to give a yellow mixture. TLC showed new spot. The mixture was cooled to 20° C. The yellow solid was precipitated out. The mixture was filtered. The filter cake was washed with PE (50 mL) for twice and dried over high vacuum to give compound E3 (50 g) as yellow solid.

Procedure for Synthesis of E4

A solution of E3 (55 g, 162 mmol) in TFA (330 mL) was stirred at 70° C. for 16 hours to give a purple mixture. TLC showed new spot. The reaction mixture was concentrated under reduced pressure to give a residue. The residue was added PE (60 mL), and stirred at 25° C. for 2 hours to give a purple mixture. After filtration, the filter cake was washed with PE (50 mL), dried under reduced pressure to give compound E4 (80 g, crude) as purple solid.

Procedure for Synthesis of E5

A solution of E4 (80 g, 421 mmol) in POCl$_3$ (341 mL) was stirred at 100° C. for 2 hours to give a brown mixture. TLC showed new spot. The reaction mixture was concentrated under reduced pressure to give a residue. The residue was dissolved in DCM (1000 mL). The organic layer was washed with saturated NaHCO$_3$ solution (1000 mL), solid was precipitated out. After filtration, the filter cake was washed with DCM (300 mL×2). The organic layer was dried over anhydrous Na$_2$SO$_4$, filtered and concentrated under reduced pressure to give a crude product. The residue was purified by column chromatography to give compound E5 (35 g) as light yellow solid.

Procedure for Synthesis of E7

To a solution of E6 (40 g, 183 mmol) in MeCN (400 mL) was added NBS (35.9 g, 202 mmol), BPO (444 mg, 1.83 mmol). The reaction mixture was stirred at 90° C. for 4 hours to give a brown mixture. LCMS showed the desired MS. The reaction mixture was diluted with water (200 mL) and extracted with EtOAc (100 mL*2). The organic layer was washed with water (100 mL*4), brine (100 mL*3), dried over anhydrous Na$_2$SO$_4$, filtered and concentrated under reduced pressure to give E7 (57 g, crude) as brown oil.

Procedure for Synthesis of E8

A mixture of E7 (57 g, 192 mmol) and NaN$_3$ (18.8 g, 290 mmol) in DMSO (290 mL) was stirred at 25° C. for 16 hours to give a brown mixture. LCMS showed the desired MS. The reaction mixture was quenched with NaHCO$_3$ (500 mL) and extracted with EtOAc (200 mL*2). The organic layer was washed with water (300 mL*4), brine (300 mL*4), dried over anhydrous Na$_2$SO$_4$, filtered and concentrated under reduced pressure to give E8 (42 g, crude) as brown oil.

Procedure for Synthesis of E9

To a solution of E8 (12 g, 46.3 mmol) in dioxane (60 mL) and H$_2$O (15 mL) was added E5 (9.66 g, 46.3 mmol), Cs$_2$CO$_3$ (30.2 g, 92.6 mmol, 2 eq) and Pd(dppf)Cl$_2$ (1.69 g, 2.32 mmol, 0.05 eq). The reaction mixture was stirred at 80° C. under N$_2$ atmosphere protect for 5 hours to give a black mixture. TLC showed new spot. The reaction mixture was diluted with water (300 mL) and extracted with EtOAc (200 mL*2). The organic layer was washed with water (100 mL*4), brine (100 mL*2), dried over anhydrous Na$_2$SO$_4$, filtered and concentrated under reduced pressure to give a residue. The residue was purified by column chromatography to give E9 (8 g) as brown solid.

Procedure for Synthesis of E10

To a solution of E9 (8 g, 26.2 mmol, 1 eq) in THF (80 mL)/H$_2$O (40 mL) was added PPh$_3$ (10.3 g, 39.3 mmol, 1.5 eq). The reaction mixture was stirred at 60° C. for 16 hours to give a brown mixture. TLC showed the reaction completed. The reaction mixture was diluted with water (100 mL) and extracted with EtOAc (100 mL*2). The organic layer was washed with brine (100 mL), dried over anhydrous Na$_2$SO$_4$, filtered and concentrated under reduced pressure to give a E10 (7.32 g, crude) as brown gum.

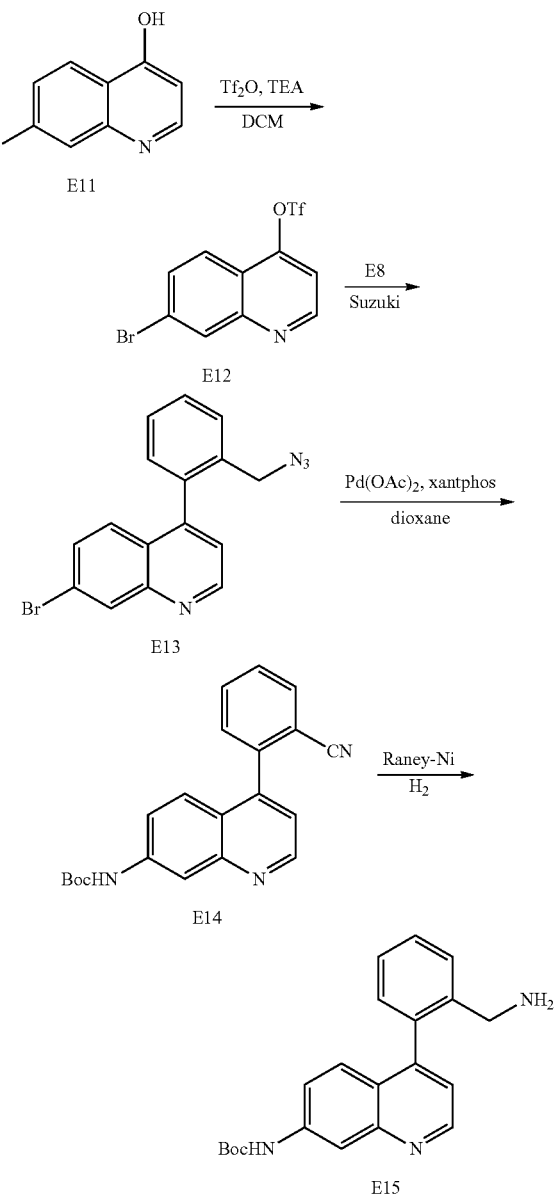

Scheme 16 Synthetic route for E15

Procedure for Synthesis of E12

To a mixture of E11 (2 g, 8.93 mmol) in pyridine (20 mL) was added Tf$_2$O (3.02 g, 10.71 mmol, 1.77 mL, 1.2 eq) at 0° C., the mixture was stirred at 0° C. for 2 hours to give a brown mixture. LCMS showed the reaction was completed.

The reaction mixture was quenched with water (20 mL) and extracted with EtOAc (20 mL×2). The organic layer was washed with water (20 mL×2), brine (30 mL×4), dried over anhydrous Na₂SO₄, filtered and concentrated under reduced pressure to give crude product. The crude product was purified by combi flash to afford E12 (2.2 g) as a white solid.

Procedure for Synthesis of E13

The compound E13 (2.2 g) was followed the same procedure of B33 to obtain 1.3 g of compound E13 as a yellow powder.

Procedure for Synthesis of E14

To a mixture of E13 (600 mg, 1.77 mmol) and NH₂Boc (248 mg, 2.12 mmol) in dioxane (10 mL) was added Pd(OAc)₂ (39.71 mg, 176.89 umol) and Xantphos (204 mg, 353.79 umol) and Cs₂CO₃ (1.15 g, 3.54 mmol), the mixture was stirred at 100° C. for 16 hours to give a black mixture. TLC showed the reactant was consumed. The reaction mixture was quenched with water (20 mL) and extracted with EtOAc (20 mL×2). The organic layer was washed with water (20 mL×2), brine (30 mL×4), dried over anhydrous Na2SO4, filtered and concentrated under reduced pressure to give crude product. The crude product was purified by combi flash to afford E14 (190 mg) as a yellow solid.

Procedure for Synthesis of E15

The compound E14 (400 mg) was followed the same procedure of B11 to obtain 385 mg of compound E15 as a yellow gum.

(chloro)stannane (10.4 g, 32 mmol, 1.2 eq) was added into the reaction at −78° C. The reaction was stirred at −78° C. for 30 min and the reaction was stirred at 15° C. for 17 hours to give a yellow mixture. TLC showed the starting material was not consumed completely. Saturated NH₄Cl (20 mL) was added into the reaction mixture. The mixture was partitioned between EtOAc (300 mL) and H₂O (300 mL). The organic extract was washed with saturated NH₄Cl (300 mL), brine (300 mL), dried over anhydrous Na₂SO₄, filtered and concentrated under reduced pressure to give yellow gum. The crude product was purified by combi flash to give compound E17 (9.8 g) as yellow oil.

Procedure for Synthesis of E19

To a suspension of compound E18 (1 g, 5.10 mmol) in THF (10 mL) was added BH₃·THF (1 M, 15.3 mL) under N₂ atmosphere at 0° C. The reaction was stirred at 15° C. for 30 min to give a yellow mixture. LCMS showed the starting material was not consumed completely. The reaction was stirred at 15° C. for 17 hours to give a yellow mixture. LCMS showed the starting material was consumed completely. Little mixture was purified by prep-TLC to give a sample. The reaction was quenched with MeOH (4 mL). The reaction mixture was concentrated under reduced pressure to give E19 (1.1 g, crude) as a yellow gum.

Procedure for Synthesis of E20

The compound B19 (1.1 g) was followed the same procedure of B14 to obtain 890 mg of compound E20 as a colorless oil.

Scheme 17 Synthetic route for E22

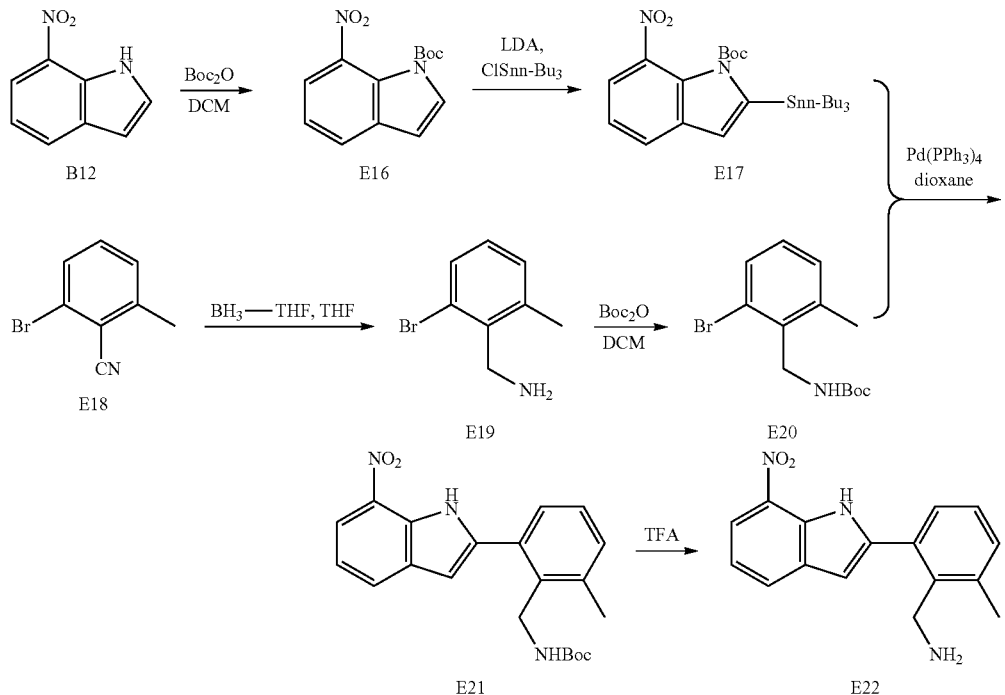

Procedure for Synthesis of E16

The compound B12 (10.2 g) was followed the same procedure of B14 to obtain 15.2 g of compound E16 as a yellow powder.

Procedure for Synthesis of E17

To a solution of compound E16 (7 g, 26.7 mmol) in THF (45 mL) was added LDA (2 M, 20 mL) at −78° C. under N₂. The reaction was stirred at −78° C. for 30 min. Tributyl Procedure for Synthesis of E21

The compound E20 (800 mg) and E17 (1.91 g) was followed the same procedure of B33 to obtain 385 mg of compound E21 as a yellow oil.

Procedure for Synthesis of E22

The compound E21 (600 mg) was followed the same procedure of A7 to obtain 450 mg of compound E22 as a yellow powder.

General Schemes of Group F

Scheme 18 Synthetic route for F5

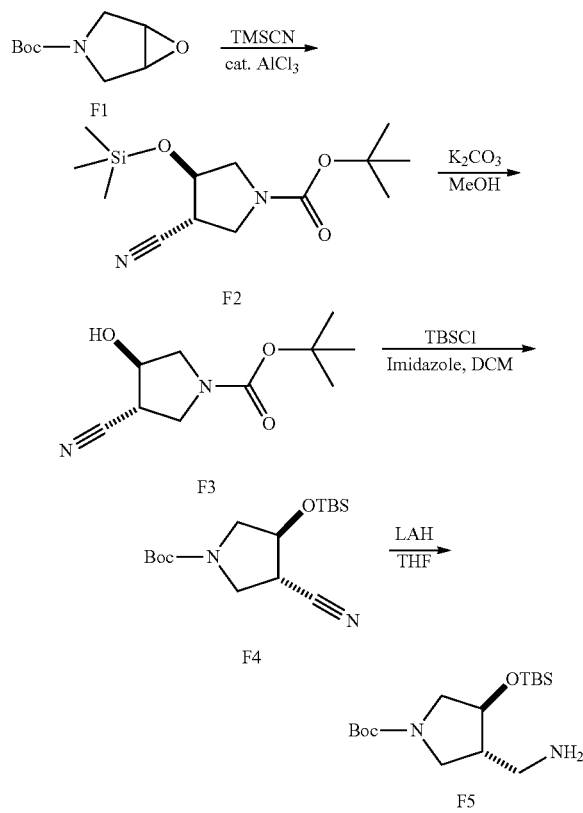

Procedure for Synthesis of F2

To a mixture of compound F1 (3 g, 16.20 mmol) and trimethylsilylformonitrile (1.61 g, 16.20 mmol, 2.03 mL) was added $AlCl_3$ (60 mg, 449.97 umol, 24.59 uL, 2.78e-2 eq), and the mixture was heated to 50° C. for 20 hours. TLC showed the reaction was completed. The reaction was quenched by water (10 mL) and then extracted with EtOAc (10 mL*2). The combined organic phase was dried over anhydrous $Na_2SO_4$, filtered and concentrated in vacuo to give the compound F2 (4.6 g) as a yellow solid.

Procedure for Synthesis of F3

To a solution of compound F2 (1 g, 3.52 mmol) in MeOH (10 mL) was added $K_2CO_3$ (52.48 mg, 379.71 umol). The mixture was stirred at 20° C. for 2 hr. TLC indicated that material was disappeared and one major new spot with larger polarity was detected. 8.75 mL of HCl (0.1 M) was added to the reaction mixture, and then it was extracted with EtOAc (2*20 mL). The combined organic layer was dried over ($Na_2SO_4$) and evaporated to dryness to give compound F3 (0.74 g) as yellow oil.

Procedure for Synthesis of F4

A mixture of compound F3 (2.42 g, 11.40 mmol), imidazole (993.59 mg, 14.59 mmol) and tert-butyl-chloro-dimethyl-silane (2.06 g, 13.68 mmol, 1.68 mL) in DMF (10 mL) was stirred at 20° C. for 14 hr. TLC indicated that material was consumed completely and new spots formed. The reaction mixture was diluted with water 50 mL and then it was extracted with EtOAc 100 mL (50 mL×2). The combined organic layers were washed with aqueous NaCl 100 mL (50 mL×2), dried over $Na_2SO_4$, filtered and concentrated under reduced pressure to give a residue. The residue was purified by silica gel chromatography eluted with (PE: EtOAc=5:1) to give compound F4 (2.44 g) as colorless oil.

Procedure for Synthesis of F5

To the solution of compound F4 (1 g, 3.06 mmol) in THF (12 mL) was added LAH (200 mg, 5.27 mmol) at 0° C., and it was stirred at 0° C. for 0.5 hr to give a white suspension. TLC indicated that material disappeared. The reaction mixture was diluted with THF (20 mL) and then quenched with water (0.2 mL), 15% aq. NaOH (0.2 mL) and water (0.6 mL) at 0° C. Then it was stirred at 0° C. for 0.5 hr. The mixture was dried over anhydrous $Na_2SO_4$ and then filtered, and the filter cake was washed with EtOAc (20 mL). The combined filtrate was concentrated under reduced pressure to give compound F5 (870 mg, mixture of 2 trans-isomer) as colorless oil.

Scheme 19 Synthetic route for F9

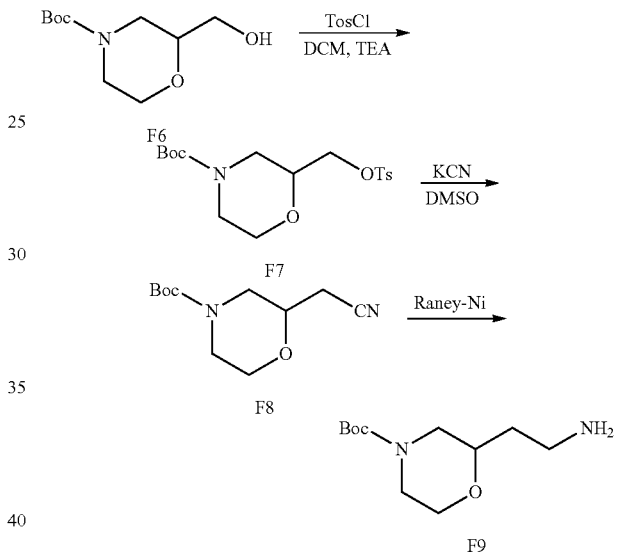

Procedure for Synthesis of F7

To a mixture of F6 (1.7 g, 7.82 mmol), TEA (1.03 g, 10.2 mmol) in DCM (10 mL) was added TosCl (1.57 g, 8.21 mmol, 1.05) at 0° C. The reaction was stirred at 20° C. for 17 hours to give a yellow solution. LCMS showed the desired MS value was observed. The reaction was concentrated under reduced pressure. The concentrate was dissolved in EtOAc (150 mL) and the resulting solution was washed with aqueous HCl (100 mL, pH=4), aqueous NaOH (1 N, 100 mL), brine (150 mL), dried over anhydrous $Na_2SO_4$, filtered and concentrated under reduced pressure to give F7 (2.49 g) as yellow oil.

Procedure for Synthesis of F8

To a mixture of F7 (2.3 g, 6.19 mmol) in DMSO (20 mL) was added KCN (443 mg, 6.81 mmol, 291 uL) and KI (1.54 g, 9.29 mmol), the mixture was stirred at 80° C. for 3 hours and 100° C. for 2 hours to give a black mixture. TLC showed the reactant was consumed. The reaction mixture was quenched with water (50 mL) and extracted with EtOAc (50 mL×2). The organic layer was washed with water (50 mL×2), brine (30 mL×4), dried over anhydrous $Na_2SO_4$, filtered and concentrated under reduced pressure to give crude product. The crude product was purified by combi flash to afford F8 (1.19 g) as a yellow oil.

Procedure for Synthesis of F9

A solution of F8 (600 mg, 2.65 mmol) in MeOH (20 mL) was added Raney-Ni (227 mg, 2.65 mmol), the suspension was degassed under vacuum and purged with $H_2$ several times, the mixture was stirred at 25° C. under $H_2$ (15 psi) for 16 hours to give a black mixture. TLC (PE/EA=1/1) showed the reaction was completed. The mixture was filtered and concentrated under reduced pressure to afford F9 (530 mg, crude) as a yellow oil.

Commercial available reagents were used for group E such as benzyl piperidin-4-ylcarbamate, tert-butyl piperidin-4-ylcarbamate, tert-butyl piperazine-1-carboxylate, tert-butyl 2-(aminomethyl)morpholine-4-carboxylate, tert-butyl 2-(hydroxymethyl)morpholine-4-carboxylate, tert-butyl 4-aminopiperidine-1-carboxylate, 4-methoxypiperidine, piperidin-4-ylmethanamine, 4-methoxycyclohexan-1-amine, (tetrahydro-2H-pyran-4-yl)methanamine, morpholine, azepan-4-ol, pyrrolidin-3-ol, 4-aminocyclohexan-1-ol, N-methylpiperidin-4-amine, (1R,4R)-4-(aminomethyl)cyclohexan-1-ol, (1S,3S)-3-aminocyclopentan-1-ol, piperidin-4-ol, 4-(aminomethyl)piperidin-2-one, piperidin-4-ylmethanol, 4-(trifluoromethoxy)piperidine, 4-ethoxypiperidine, 4-isopropoxypiperidine, 4-ethoxycyclohexan-1-amine, 4-methoxycyclohexan-1-amine, 4-isopropoxycyclohexan-1-amine and 3-aminopropan-1-ol.

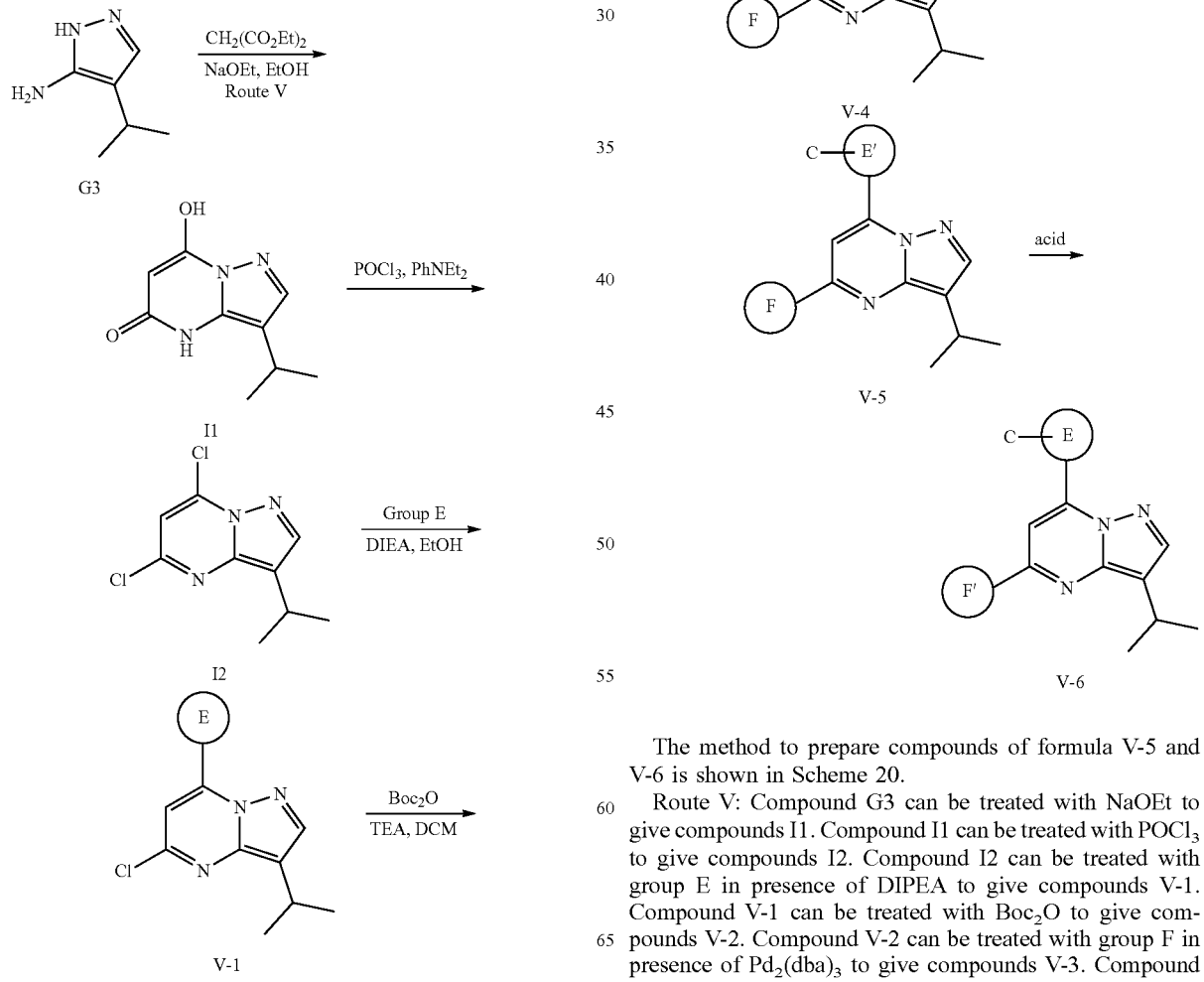

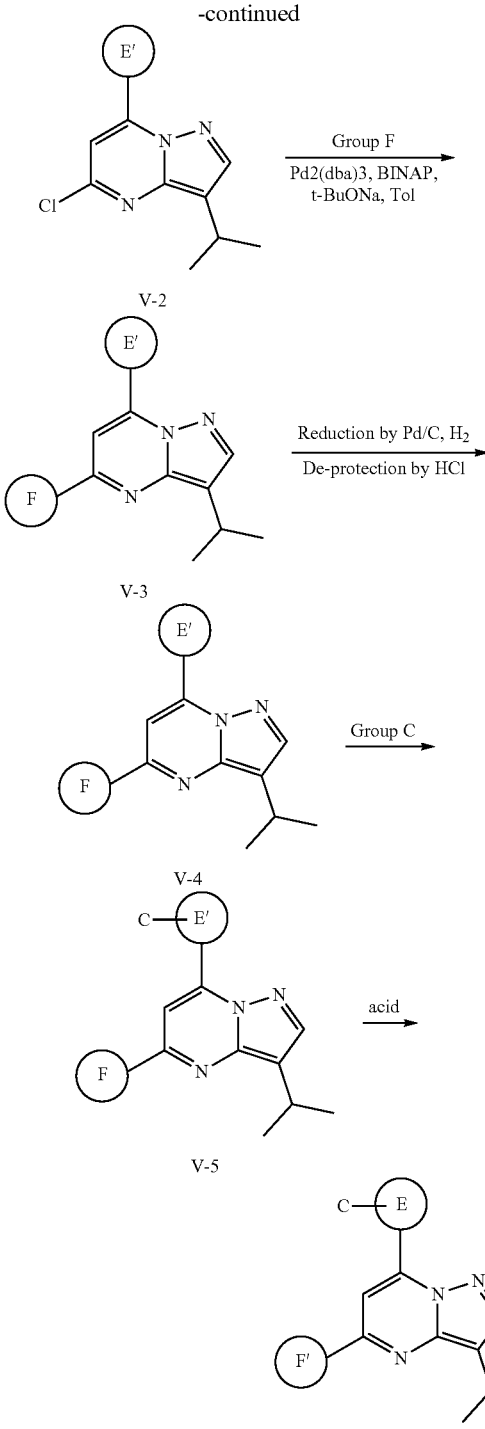

The method to prepare compounds of formula V-5 and V-6 is shown in Scheme 20.

Route V: Compound G3 can be treated with NaOEt to give compounds I1. Compound I1 can be treated with POCl₃ to give compounds I2. Compound I2 can be treated with group E in presence of DIPEA to give compounds V-1. Compound V-1 can be treated with Boc₂O to give compounds V-2. Compound V-2 can be treated with group F in presence of Pd₂(dba)₃ to give compounds V-3. Compound V-3 can be treated with Pd/C and H₂, or HCl to give compounds V-4. Compound V-4 can be treated with group C which was defined claim 1 to give compounds V-5. Compounds V-5 can be treated with acid such as HCl to obtain the compounds of formula V-6.

Procedure for Synthesis of I1

Na (790 mg, 34.3 mmol) was added into anhydrous EtOH (125 mL), the mixture was stirred at 10° C. for an hour. Compound G3 (3.50 g, 27.9 mmol) and diethyl propanedioate (5.42 g, 33.8 mmol) were added into this solution. The mixture was stirred at 78° C. for 16 hours under N$_2$ atmosphere to give a yellow solution. TLC showed the reaction was completed. The mixture was concentrated under reduced pressure. The residue was dissolved in water (60 mL) and acidified to pH=3 with 3M HCl, then filtered to give compound I1 (3.70 g) as a white powder.

Procedure for Synthesis of I2

To a mixture of compound I1 (1.30 g, 6.73 mmol) in POCl$_3$ (20.6 g, 134 mmol) was added N,N-diethylaniline (672 mg, 4.51 mmol). The mixture was stirred at 100° C. for 16 hours under N$_2$ atmosphere. TLC showed a new spot. Most of POCl$_3$ was removed under reduced pressure. Then the mixture was poured into H$_2$O (40 mL), extracted with DCM (50 mL×3). The organic layer was washed with brine (50 mL×2), dried over anhydrous Na$_2$SO$_4$, then filtered, and concentrated under reduced pressure to give compound I2 (3.11 g, crude) as a yellow oil, without further purification for next step.

Scheme 21 Synthetic route of compound 1 through Route I in General synthetic route 1

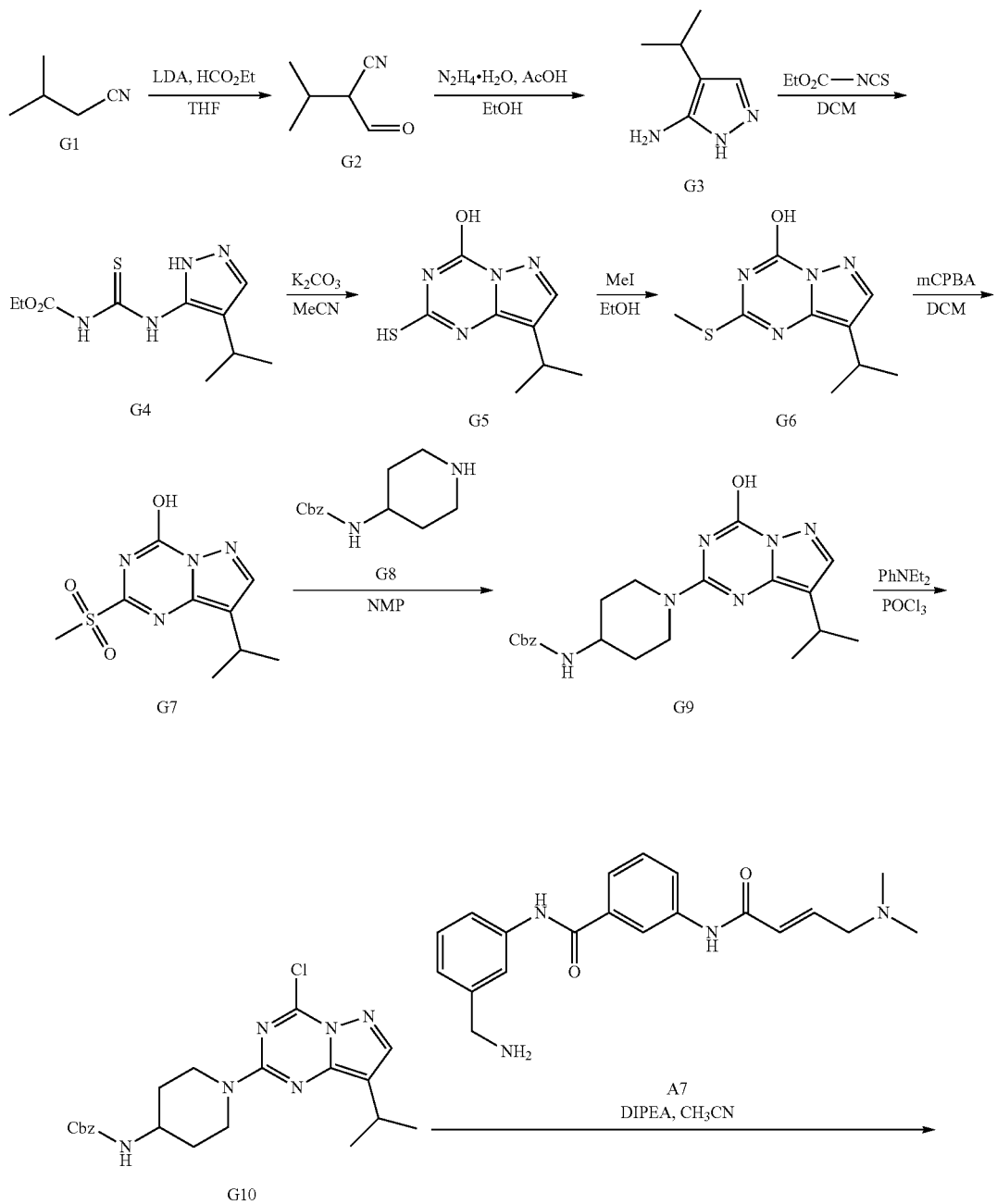

-continued

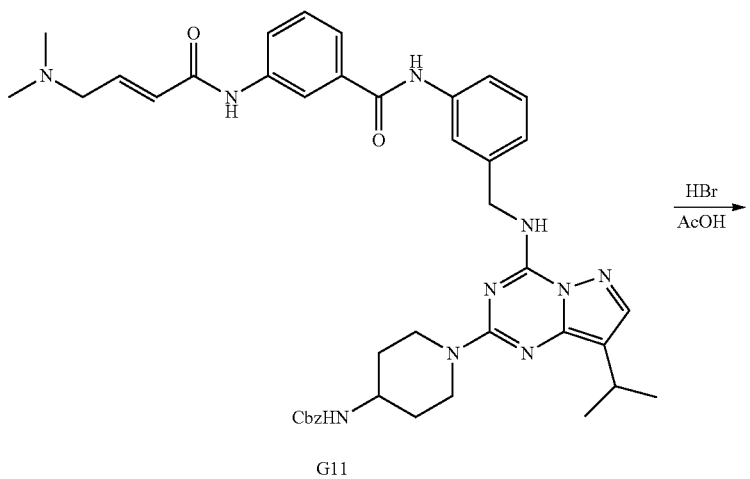

G11

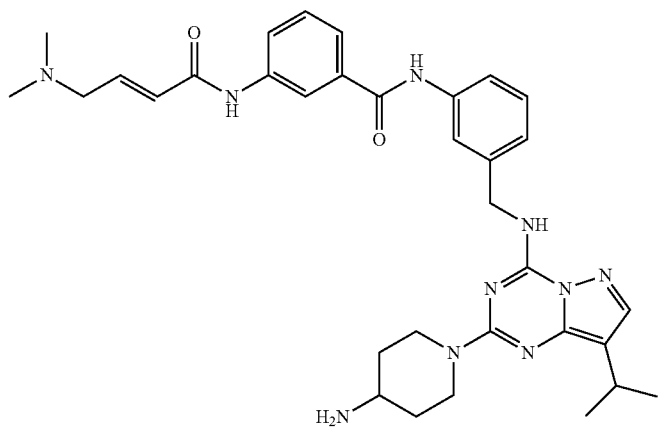

Compound 1

Procedure for Synthesis of G2

To a mixture of diisopropylamine (6.69 g, 66.2 mmol) in anhydrous THF (20 mL) was added n-BuLi (2.5 M, 27.7 mL) at 0° C. and stirred at 0° C. for 0.5 hour, then the mixture was cooled to −70° C. and G1 (5.00 g, 60.2 mmol) in THF (20 mL) was added into the mixture at −70° C. and stirred at −70° C. for 0.5 hour, then the mixture was poured into a mixture of ethyl formate (4.90 g, 66.2 mmol) in THF (20 mL) at −70° C. under $N_2$ atmosphere and the resulting mixture was stirred at −70° C. for 0.5 hours, then warmed to 15° C. and stirred at 15° C. for 17 hours. TLC (silica gel, PE/EtOAc=2/1) showed the reaction was completed. The reaction mixture was poured into aqueous HCl (150 mL, 1M) at 0° C. and stirred at 0° C. for 0.5 hours, then the mixture was extracted with EtOAc (150 mL×3). The organic layer was washed with brine (250 ml), dried over anhydrous $Na_2SO_4$, filtered, the filtrate was concentrated under reduced pressure to give compound G2 (5.0 g) as a yellow oil. The crude product was used directly in next step without further purification.

Procedure for Synthesis of G3

To a solution of compound G2 (8.82 g, 67.5 mmol) and AcOH (7.09 g, 118 mmol) in EtOH (5 mL) was added $NH_2$—$NH_2$·$H_2O$ (4.39 g, 87.7 mmol), the resulting mixture was stirred at 78° C. for 17 hours to give a pale yellow solution. TLC showed the reaction was completed. The reaction mixture was concentrated under reduced pressure to give a residue, then the pH value of the residue was adjusted to 9 with aqueous NaOH (1M), diluted with water (50 mL) and extracted with EtOAc (100 mL×3). The organic layer was washed with brine (150 mL), dried over anhydrous $Na_2SO_4$, filtered and the filtrate was concentrated under reduced pressure to give compound G3 (10.0 g, crude) as a yellow gum. The crude product was used directly in next step without further purification.

Procedure for Synthesis of G4

To a mixture of compound G3 (5.00 g, 40.0 mmol) in anhydrous DCM (25 mL) was added a mixture of ethoxycarbonyl isothiocyanate (4.72 g, 36.0 mmol) in anhydrous DCM (25 mL) at −70° C. and stirred at −70° C. for 1 hour, a lot of white solid appeared. TLC showed the reaction was completed. Then the mixture was allowed to warm to −10° C. and filtered, and the filter cake was washed with DCM (15 mL) to give 4.50 g of desired compound as a white solid, the structure was confirmed by HNMR. The filtrate was purified by silica gel column to give compound G4 (1.80 g) as a white solid.

Procedure for Synthesis of G5

To a mixture of compound G4 (6.30 g, 24.6 mmol) in MeCN (50 mL) was added $K_2CO_3$ (6.79 g, 49.2 mmol), the mixture was stirred at 80° C. for 8 hours. Crude LCMS showed the reaction was completed. The mixture was cooled to room temperature, then AcOH (15 mL) was added into the mixture and stirred at 15° C. for 20 minutes, then the resulting mixture was concentrated under reduced pressure to give a residue, which was washed with water (50 mL×3) to give compound G5 (4.20 g) as a white solid.

Procedure for Synthesis of G6

To a mixture of compound G5 (4.20 g, 20.0 mmol) in EtOH (40 mL) was added NaOH (2.00 g, 50.0 mmol) in $H_2O$ (20 mL) at 15° C., then MeI (2.84 g, 20.0 mmol) was added into above mixture and the resulting mixture was stirred at 15° C. for 2 hours. Crude LCMS showed the reaction was completed. The mixture was concentrated under reduced to give a residue, which was treated with ice cold water (50 mL) and aqueous HCl (20 mL, 6M) for 30 minutes, a lot of white solid appeared, filtered to give the crude product. The crude product was poured into MeCN (50 mL) to give a suspension, then the suspension was concentrated under reduced pressure to give compound G6 (3.60 g) as a white solid.

Procedure for Synthesis of G7

To a mixture of compound G6 (1.00 g, 4.46 mmol) in DCM (30 mL) was added m-CPBA (3.07 g, 14.2 mmol) in portions at 20° C. The reaction mixture was stirred at 20° C. for 2 hours. LCMS showed the reaction was complete. The reaction mixture was diluted with a mixture solution of brine (20 mL) and $NaOH/H_2O$ (3M, 10 mL). The aqueous layer was separated and brought pH to 1 with HCl (3M). A lot of white powder was precipitated. The mixture was then extracted with EtOAc (50 mL×2). The organic layer was washed with brine (20 mL), dried over anhydrous $Na_2SO_4$, filtered, concentrated under reduced pressure to give a residue. The residue was purified by Combi Flash to give compound G7 (1.03 g) as light brown gum.

Procedure for Synthesis of G9

To a solution of compound G7 (6.62 g, 25.83 mmol) in NMP (100 mL) was added compound G8 (18.15 g, 77.5 mmol). The reaction mixture was stirred at 140° C. for 16 hours. TLC showed the reaction was complete. The reaction mixture was partitioned between brine (500 mL) and EtOAc (400 mL). The organic layer was washed with water (100 mL×2), brine (100 mL), dried over anhydrous $Na_2SO_4$, and concentrated under reduced pressure to give a residue. The residue was purified by Combi Flash to give a brown gum, which was triturated with $CH_3CN$ (50 mL) to give compound G9 (2.06 g) as an off-white powder.

Procedure for Synthesis of G10

To a mixture of compound G9 (89 mg, 0.22 mmol) in $POCl_3$ (4.41 g, 28.7 mmol) was added N,N-diethylaniline (97 mg, 0.65 mmol) at 20° C. The reaction mixture was stirred at 80° C. for 2 hours. The reaction mixture was concentrated under reduced pressure to give compound G10 (93 mg) as an brown gum as the crude product. The crude product was used directly in next step without further purification.

Procedure for Synthesis of G11

To a solution of compound G10 (127 mg, 0.297 mmol), DIPEA (95.9 mg, 0.742 mmol) in DMF (2 mL) was added compound A7 (131 mg, 0.371 mmol). The reaction solution was stirred at 10° C. for 1 hour. LCMS showed the desired MS value. The reaction mixture was partitioned between EtOAc (20 mL) and saturated aqueous $NaHCO_3$ solution (20 mL). The organic layer was washed with brine (10 mL), dried over anhydrous $Na_2SO_4$, filtered, concentrated under reduced pressure. The residue was purified by Combi flash to give compound G11 (103 mg) as a brown gum Procedure for Synthesis of Compound 1

To a solution of compound G11 (70 mg, 0.094 mmol) in AcOH (0.5 mL) was added HBr/AcOH (0.5 mL, 35% purity) at 15° C. This reaction solution was stirred at 15° C. for 1 hour to give a light brown solution. LCMS showed the reaction was complete. The reaction was diluted with 5 mL of MTBE to precipitate a grey powder, which was collected by filtration. The solid was dissolved in MeOH (4 mL), and then a drop of ammonia water (28%) was added to basify the solution. The crude product dissolved in MeOH was purified by prep-HPLC. The eluent containing the desired product was concentrated under reduced pressure and the residual solution was lyophilized to give compound 1 (9.9 mg) as a white powder.

Scheme 22 Synthetic route for compound 9 through Route I in General synthetic route 1

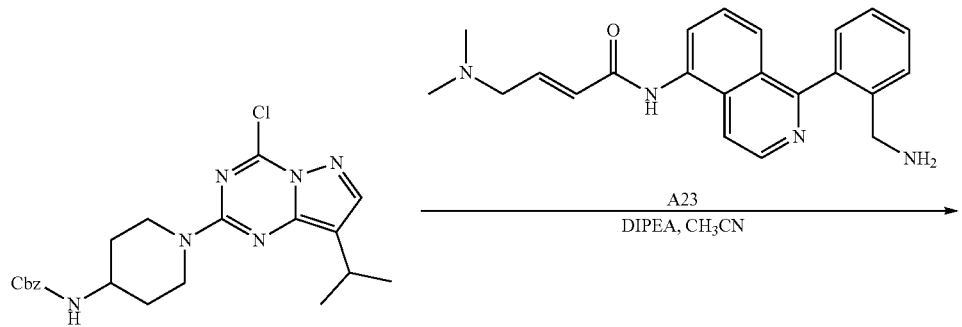

G10

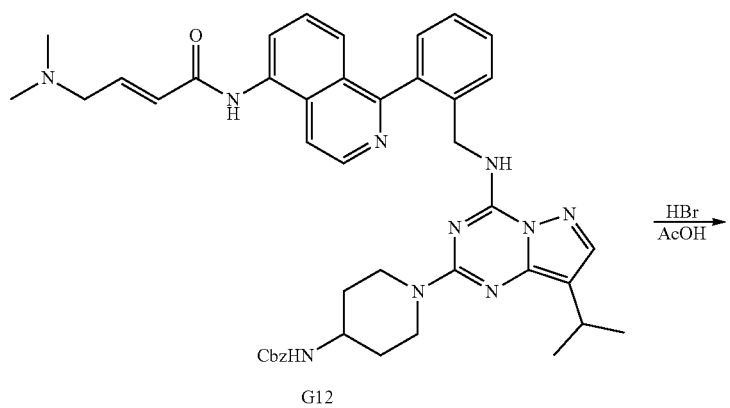

G12

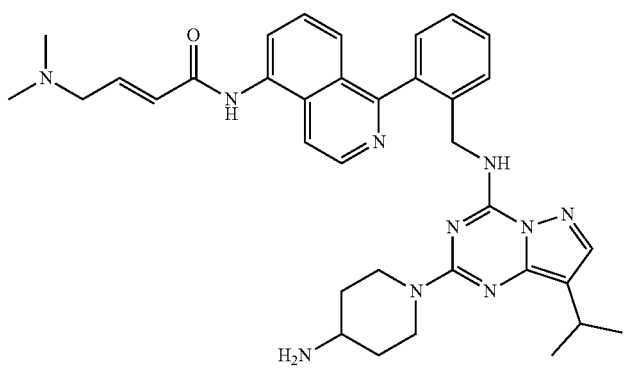

Compound 9

Procedure for Synthesis of G12

To a solution of compound A23 (183 mg, 0.385 mmol) in CH₃CN (10 mL) was added DIPEA (226 mg, 1.75 mmol) and compound G10 (150 mg, 0.35 mmol). The resulting mixture was stirred at 20° C. for 1 hour to give white suspension. TLC showed the reaction was completed. The reaction mixture was quenched by addition H₂O (50 mL) and extracted with EtOAc (50 mL×2). The combined organic layers were washed with brine (10 mL×2), dried over Na₂SO₄, filtered and concentrated under reduced pressure to give a residue. The residue was purified by Combi flash to obtain compound G12 (75 mg) as an off-white solid.

Procedure for Synthesis of Compound 9

A solution of compound G12 (30 mg, 0.4 mmol) in HBr/HOAC (35%) (1 mL) was stirred at 20° C. for 1 hour to give yellow solution. TLC showed the reaction was completed. The reaction was addition MTBE (50 mL) and lots of solid was precipitated, filtered under reduced pressure to give filter cake as an off-white solid. The filter cake was purified by prep-HPLC. The residue was concentrated most of solvent and lyophilized to obtain compound 9 (7.8 mg) as a white powder.

Scheme 23 Synthetic route for compound 16 through Route II in General synthetic route 1

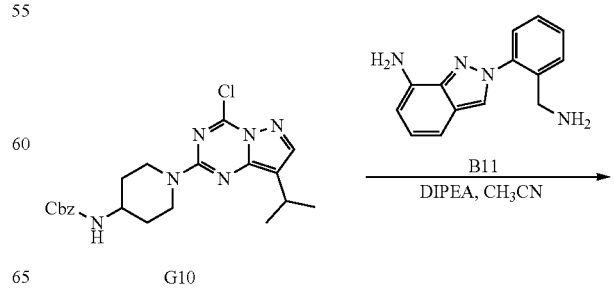

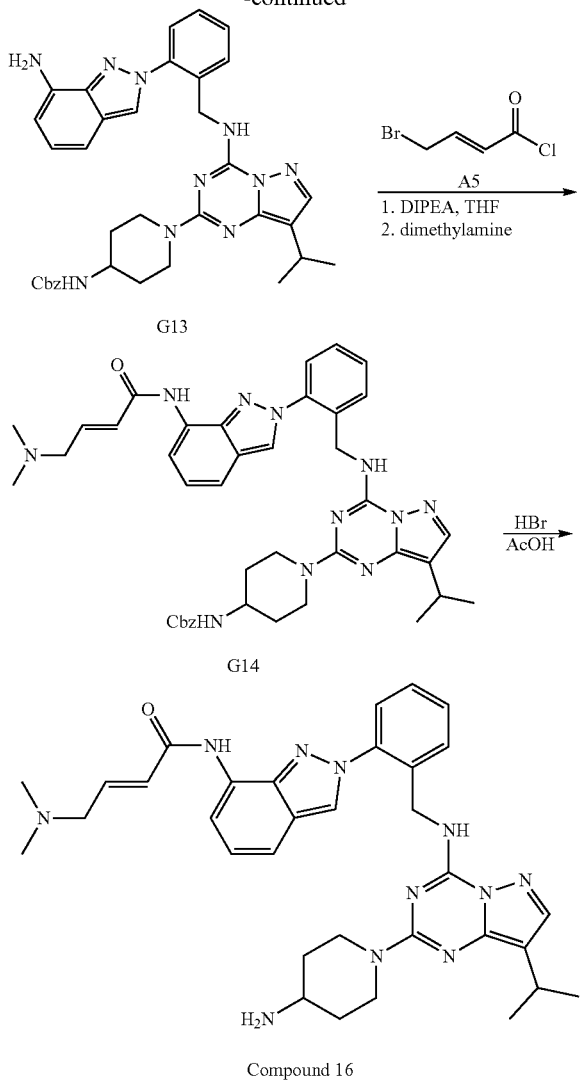

G13

G14

Compound 16

Procedure for Synthesis of G13

A solution of compound B11 (50 mg, 0.2 mmol) and compound G10 (90 mg, 0.2 mmol) in CH$_3$CN (5 mL) was added DIPEA (27.1 mg, 0.2 mmol). The resulting mixture was stirred at 0° C. for 30 min to give red solution. TLC showed the reaction was completed. The reaction mixture was concentrated under reduced pressure to give a residue. The residue was purified by Combi flash to obtain compound G13 (100 mg) as a yellowish solid.

Procedure for Synthesis of G14

To a solution of compound G13 (100 mg, 0.158 mmol) in THF (5 mL) was added compound A5 (58.2 mg, 0.317 mmol) and DIPEA (82 mg, 0.634 mmol), the resulting mixture was stirred at 20° C. for 1 hour to give red solution, LCMS showed the reaction was completed, dimethylamine (71.5 mg, 1.59 mmol) was added to the mixture, then stirred for another 3 hours at 20° C. to give red solution. TLC showed the reaction was completed. The reaction mixture was quenched by addition H$_2$O (50 mL) and extracted with EtOAc (50 mL×2). The combined organic layers were washed with brine (20 mL×2), dried over Na$_2$SO$_4$, filtered and concentrated under reduced pressure to give a residue. The residue was purified by Combi flash to give 100 mg (impure), which was purified by prep-TLC to obtain compound G14 (50 mg) as a yellow solid.

Procedure for Synthesis of Compound 16

A solution of compound G14 (50 mg, 67.4 umol) in HBr/HOAc (35%) (1 mL) was stirred at 20° C. for 30 min to give red solution. LCMS showed the reaction was completed. To the reaction mixture was added MTBE (3 mL) to precipitate a yellow gum. The yellow gum was collected by filtration and washed with MTBE (3 mL×2). The yellow gum was dissolved in MeOH (2 mL) and purified by cation exchange resin eluting with 5% NH$_3$·H$_2$O/MeOH, then lyophilized to obtain compound 16 (29.9 mg) as a yellow solid.

Scheme 24 Synthetic route for compound 25 through Route II in General synthetic route 1

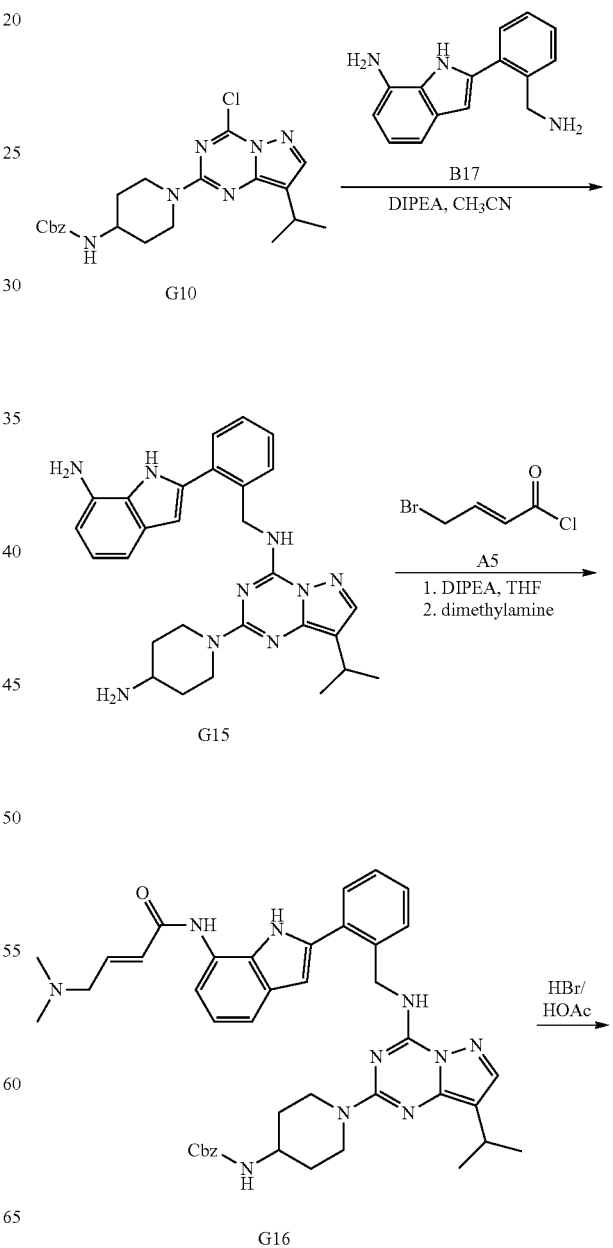

G10

G15

G16

Scheme 25 Synthetic route for compound 20 through Route II in General synthetic route 1

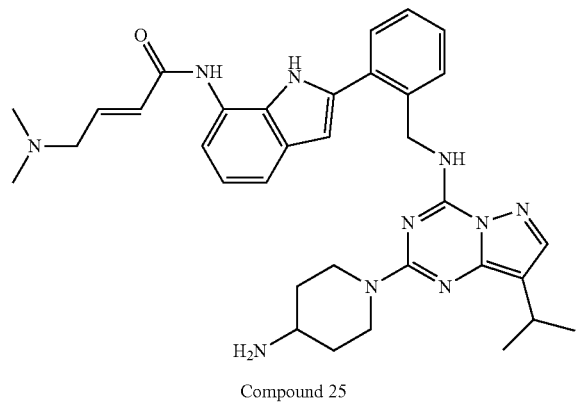

Compound 25

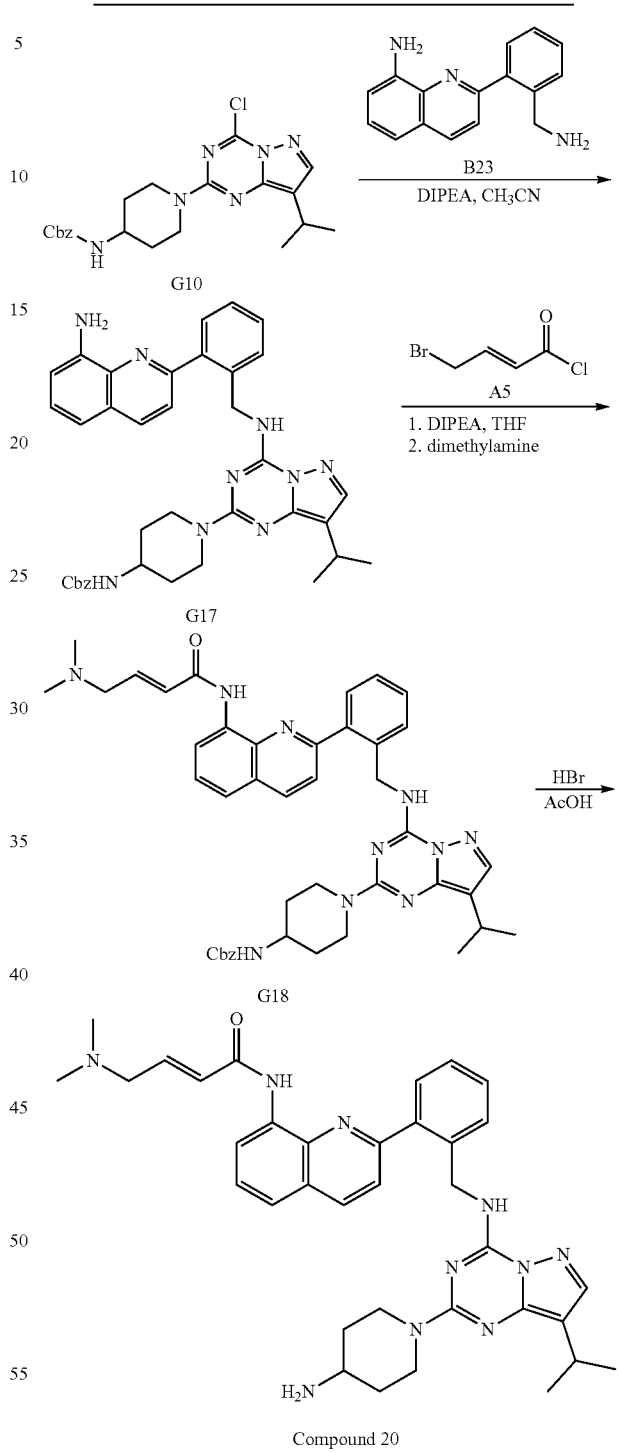

Compound 20

Procedure for Synthesis of G15

To a mixture of compound B17 (403 mg, 0.866 mmol) in MeCN (5 mL) was added DIPEA (976 uL), compound G10 (338 mg, 0.787 mmol). The mixture was stirred at 15° C. for 0.5 hour to give a yellow mixture. TLC showed the reaction was completed. The mixture was partitioned between DCM (50 mL) and water (50 mL), the mixture was extracted with DCM (50 mL×2), the combined extracted was washed with brine (50 mL), dried over $Na_2SO_4$, filtered, concentrated under reduced pressure to give a yellow oil, which was purified by Combi flash to give compound G15 (250 mg) as yellow oil.

Procedure for Synthesis of G16

To a mixture of compound G15 (250 mg, 0.397 mmol) in THF (5 mL) was added DIPEA (0.257 mg, 1.98 mmol), compound A5 (218 mg, 1.19 mmol). The yellow mixture was stirred at 15° C. for 1 hour. The color of mixture was become black. LCMS showed the reaction was completed. Dimethylamine (2 M, 992 uL) was added to the mixture and stirred at 15° C. for 1 hour to give a black brown mixture. LCMS showed the reaction was completed. The mixture was partitioned between DCM (50 mL) and water (30 mL), The aqueous was extracted with DCM (50 mL×2), the combined extracted phase was washed with brine (30 mL), dried over anhydrous $Na_2SO_4$, filtered, concentrated under reduced pressure to give a brown oil, which was purified by Combi flash to give compound G16 (250 mg) as a brown gum.

Procedure for Synthesis of Compound 25

A mixture of compound G16 (250 mg, 0.337 mmol) in HBr/HOAc (3 mL) was stirred at 15° C. for 0.5 hour to give a yellow mixture. LCMS showed the reaction was complete. To the reaction mixture was added MTBE (10 mL) to precipitate yellow powder. The white powder was collected by filtration and washed with MTBE (5 mL×2), basified by saturated $Na_2CO_3$ to pH=9-10, and extracted with DCM (50 mL×2), the combined organic phase was washed with water (50 mL), dried over anhydrous $Na_2SO_4$, filtered and concentrated under reduced pressure to give yellow oil, which was purified by prep-HPLC (0.1% TFA), basified by saturated $Na_2CO_3$ to pH=9-10, and extracted with DCM (50 mL×3), dried over anhydrous $Na_2SO_4$, filtered and concentrated under reduced pressure to give compound 25 (30 mg) as a white powder.

Procedure for Synthesis of G17

To a solution of compound B23 (230 mg, 0.633 mmol) in $CH_3CN$ (5 mL) was added DIPEA (818 mg, 6.33 mmol) and compound G10 (299 mg, 0.696 mmol) at 0-5° C. The reaction was stirred at 25° C. for 1 hour to give a black brown solution. LCMS showed desired MS value. The reaction was diluted with DCM (30 mL) and concentrated under reduced pressure. The residue was partitioned between water (50 mL) and DCM (100 mL). The separated organic layer was washed with water (80 mL), brine (80 mL), dried over anhydrous Na$_2$SO$_4$ and concentrated under reduced pressure. The residue was purified by Combi Flash to give compound G17 (150 mg) as yellow oil.

Procedure for Synthesis of G18

To a solution of compound G17 (200 mg, 0.312 mmol) in THF (5 mL) was added DIPEA (201 mg, 1.56 mmol) and compound A5 (172 mg, 0.935 mmol). The reaction solution was stirred at 25° C. for 30 minutes to give a black brown solution. Then, dimetnylamine (2 M, 1.56 mL) was added and stirred for another 16 hours to give a black brown solution LCMS and TLC showed the reaction was completed. The reaction mixture was concentrated under reduced pressure. The residue was partitioned between DCM (150 mL) and water (100 mL). The organic layer was washed with water (100 mL), brine (100 mL) and concentrated under reduced pressure. The residue was purified by Combi Flash to give compound G18 (100 mg) as a yellow oil.

Procedure for Synthesis of Compound 20

A solution of compound G18 (150 mg, 0.199 mmol) in HBr/HOAc (2 mL, 35%) was stirred at 25° C. for 0.5 hour to give a red solution. LCMS showed the reaction was completed. 10 mL MTBE was added and the resulting white mixture was filtered. The filter cake was collected, washed with MTBE (20 mL), dissolved in MeOH (3 mL) and basified by cation exchange resin to give compound 20 (46.6 mg) as a yellow powder.

Scheme 26 Synthetic route for compound 11 through Route II in General synthetic route 1

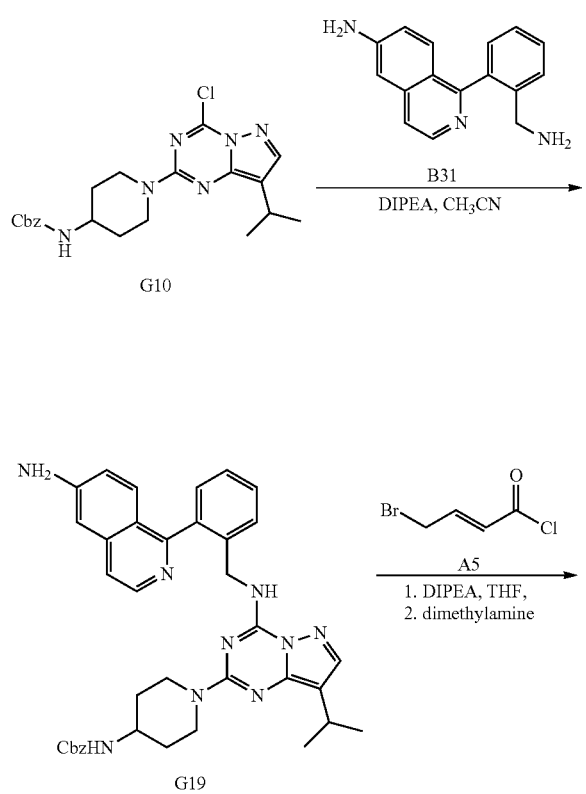

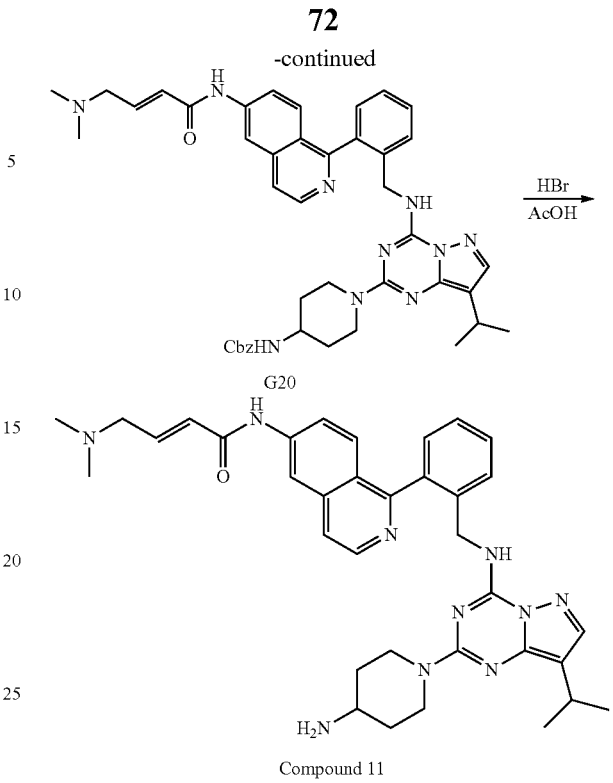

Compound 11

Procedure for Synthesis of G19

To a solution of compound B31 (400 mg, 0.933 mmol) in CH$_3$CN (10 mL) was added DIPEA (362 mg, 2.80 mmol) and compound G10 (500 mg, 1.38 mmol) at 0-10° C. The reaction was stirred for 1 hour at 25° C. to give a brown solution. Crude LCMS showed the reaction was completed. TLC showed new spot formed. The reaction solution was concentrated under reduced pressure. The residue was purified by Combi Flash to give compound F19 (380 mg) as a yellow gum.

Procedure for Synthesis of G20

To a solution of compound G19 (380 mg, 0.600 mmol) in THF (5 mL) was added a solution of compound A5 (330 mg, 1.80 mmol) in THF (2 mL) at 0-5° C. in an ice-bath. The reaction solution was stirred at 0-25° C. for 0.5 hour. Dimethylamine (2M, 3 mL, 10 eq) was added and stirred for another 2 hours to give a black brown solution. Crude LCMS showed the reaction was completed. TLC showed the reaction was completed. The reaction solution was concentrated under reduced pressure. The residue was dissolved in DCM (200 mL), washed with saturated NH$_4$Cl (100 mL), water (100 mL) and brine (100 mL), the organic layer was dried over anhydrous Na$_2$SO$_4$ and concentrated under reduced pressure. The residue was purified by Combi Flash to give compound G20 (130 mg) as a yellow solid.

Procedure for Synthesis of Compound 11

A solution of compound G20 (70 mg, 0.093 mmol) in HBr/HOAc (1 mL, 35%) was stirred at 25° C. for 0.5 hour to give a yellow solution. LCMS showed desired MS value. 10 mL MTBE was added and the resulting mixture was filtered to give a white solid. The solid was dissolved in MeOH (2 mL), purified by cation exchange resin and lyophilized to give a white powder which was further purified by prep-HPLC. The fraction was concentrated under reduced pressure. The residue was neutralized to pH=7-8 with K$_2$CO$_3$ (solid). The resulting white mixture was extracted with EtOAc (50 mL×2). The organic layer was Scheme 27 Synthetic route for compound 18 through Route III in General synthetic route 1

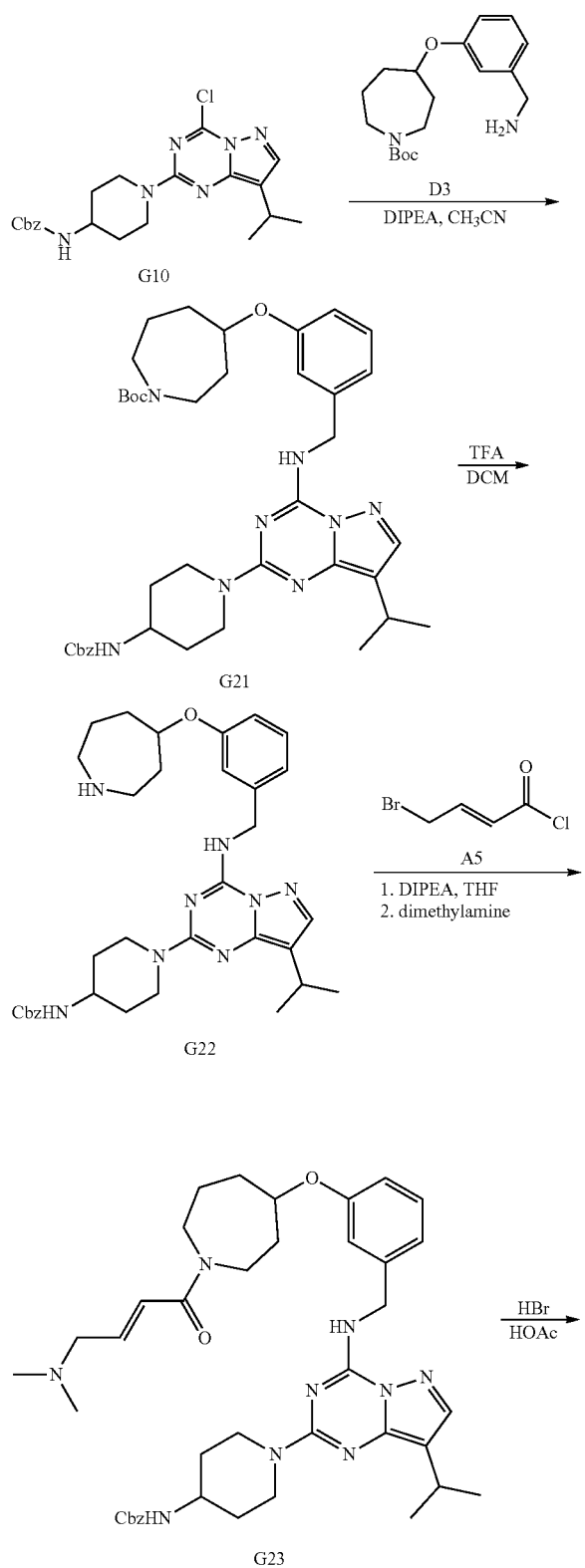

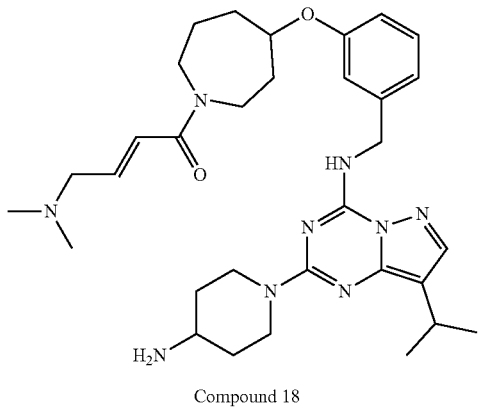 [SMILES: CC(C)c1cnn2c(NCc3cccc(OC4CCCN(C(=O)/C=C/CN(C)C)CC4)c3)nc(N3CCC(N)CC3)nc12]

Compound 18

Procedure for Synthesis of G21

To a solution of compound D3 (300 mg, 0.7 mmol) and compound G10 (448 mg, 1.40 mmol) in CH$_3$CN (20 mL) was added DIPEA (181 mg, 1.40 mmol). The resulting mixture was stirred at 20° C. for 1 hour to give yellow solution. LCMS showed the reaction was completed. The reaction mixture was concentrated under reduced pressure to give a residue, TLC. The residue was purified by Combi flash to compound G21 (240 mg) as a yellow oil.

Procedure for Synthesis of G22

To a solution of compound G21 (240 mg, 0.34 mmol) in DCM (7 mL) was added TFA (4.62 g, 40.5 mmol). The resulting mixture was stirred at 20° C. for 1 hour to give yellow solution. TLC and LCMS showed the reaction was completed. The reaction mixture was concentrated under reduced pressure to give compound G22 (268 mg) as a yellow oil.

Procedure for Synthesis of G23

To a solution of compound G22 (268 mg, 0.37 mmol) in THF (20 mL) was added DIPEA (143 mg) and compound A5 (67.6 mg, 0.37 mmol), the resulting mixture was stirred at 20° C. for 1 hour, LCMS showed the reaction was completed, then dimethylamine (83.1 mg, 1.84 mmol) was added to the mixture and stirred for another 2 hours to give yellow suspension. TLC showed the reaction was completed. The reaction mixture was quenched by addition H$_2$O (50 mL), extracted with EtOAc (50 mL). The organic layers were washed with brine (20 mL), dried over Na$_2$SO$_4$, filtered and concentrated under reduced pressure to give a residue. The residue was purified by Combi flash to give compound G23 (74 mg) as a yellow oil.

Procedure for Synthesis of Compound 18

A solution of compound G23 (74.0 mg, 0.1 mmol) in HBr/HOAc (35%) (1 mL) was stirred at 20° C. for 1 hour to give yellow solution. LCMS showed the reaction was completed. To the reaction mixture was added MTBE (3 mL) to precipitate a white gum. The gum solid was collected by filtration and washed with MTBE (3 mL×2). The white gum was dissolved in MeOH (2 mL) and purified by cation exchange resin (PCX-SPE) eluting with 5% NH$_3$·H$_2$O/MeOH, the flows was concentrated and lyophilized to obtain compound 18 (42.9 mg) as a white powder.

dried over anhydrous Na$_2$SO$_4$, concentrated and lyophilized to give compound 11 (23.1 mg) as a white powder Scheme 28 Synthetic route for compound 44 through Route IV in General synthetic route 2

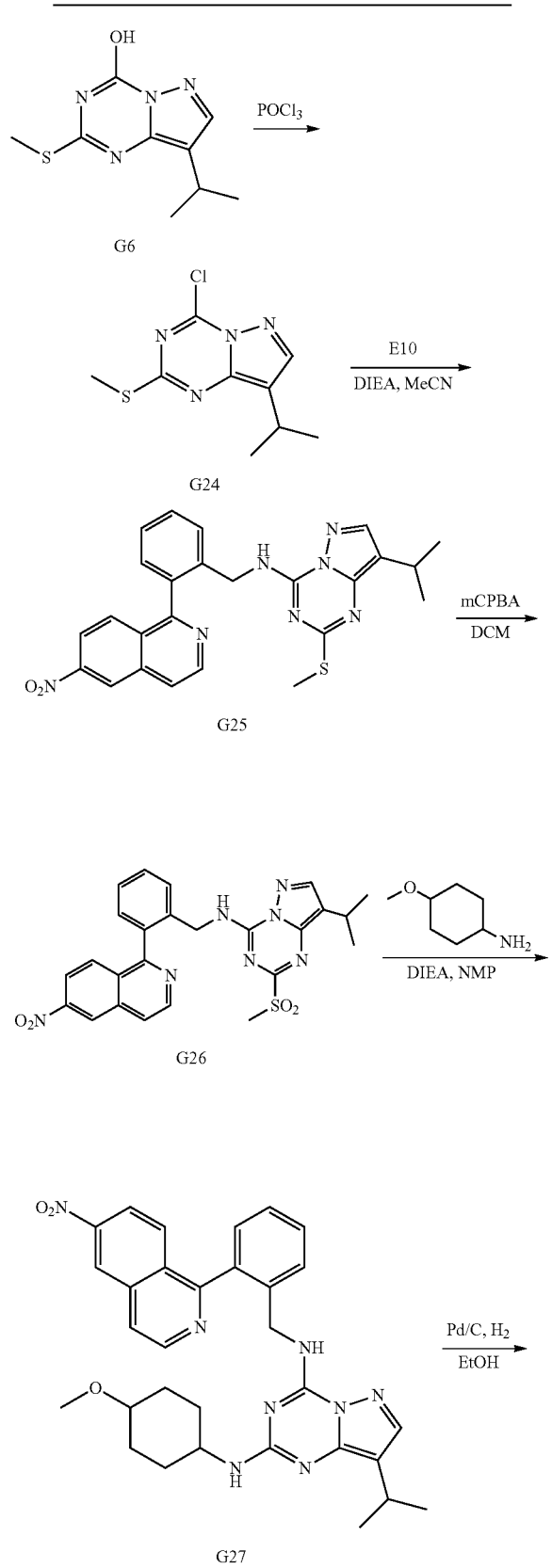

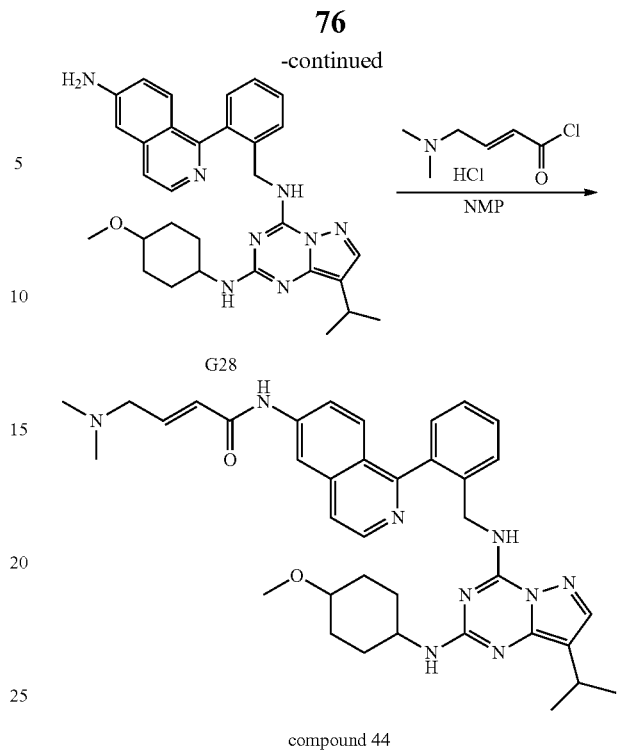

compound 44

Procedure for Synthesis of G24

To a mixture of compound G6 (1.00 g, 4.46 mmol) in POCl$_3$ (14 mL) was added N,N-diethylaniline (2.00 g, 13.4 mmol) at 15° C., the mixture was stirred at 90° C. for 3 hours. The mixture was concentrated under reduced pressure to give compound G24 (3.20 g, crude) as a brown gum, which was used to next step without purification.

Procedure for Synthesis of G25

To a solution of E10 (7.32 g, 26.2 mmol) in MeCN (70 mL) was added DIEA (6.77 g, 52.4 mmol, 9.13 mL), G24 (6.36 g, 26.2 mmol). The reaction mixture was stirred at 25° C. for 16 hours to give brown mixture. TLC showed new spot. The reaction mixture was diluted with water (100 mL) and extracted with EtOAc (100 mL*2). The organic layer was dried over anhydrous Na$_2$SO$_4$, filtered and concentrated under reduced pressure to give a residue. The residue was purified by column chromatography to give G25 (11.3 g) as yellow solid.

Procedure for Synthesis of G26

To a mixture of G25 (11.3 g, 23.2 mmol) in DCM (110 mL) was added m-CPBA (10.0 g, 46.5 mmol, 80% purity) at 0-10° C., the mixture was stirred at 0-10° C. for 2 hours to give a yellow mixture. LCMS showed the reaction was not completed. The mixture was stirred at 0-10° C. for another 1 hour to give a yellow mixture. LCMS showed the desired product was observed. The mixture was partitioned between DCM (100 mL) and saturated aqueous Na$_2$SO$_3$ (100 mL). The aqueous phase was extracted with DCM (100 mL×2). The combined organic extract was dried over anhydrous Na$_2$SO$_4$, filtered and concentrated under reduced pressure to give crude product. The crude product was purified by combi flash to afford G26 (6.6 g) as a yellow solid.

Procedure for Synthesis of G27

To a solution of 4-methoxycyclohexanamine (71.9 mg, 0.556 mmol) and G26 (180 mg, 0.348 mmol) in NMP (1 mL) was added DIEA (135 mg, 1.04 mmol). The resulting mixture was heated at 110° C. and stirred for 12 hrs to give brown solution. LCMS and TLC showed the reaction was completed. The reaction mixture was quenched by addition H₂O (50 mL) and extracted with EtOAc (50 mL×2). The combined organic layers were washed with brine (30 mL×2), dried over Na₂SO₄, filtered and concentrated under reduced pressure to give a residue. The residue was purified by column chromatography (SiO₂, Petroleum ether/Ethyl acetate=1:1) to obtain compound G27 (105 mg) as an orange yellow solid.

Procedure for Synthesis of G28

The compound G27 (105 mg) was followed the same procedure of B7 to obtain 110 mg of compound G28 as a yellow solid.

Procedure for Synthesis of Compound 44

To a solution of G28 (110 mg, 0.172 mmol) in NMP (2 mL) was added (E)-4-(dimethylamino)but-2-enoyl chloride (3 M, 172 uL) at 0° C., the resulting mixture was stirred at 15° C. for 12 hour to give yellow solution, LCMS showed most of the starting material consumed. The reaction mixture was quenched by addition H₂O (50 mL) and extracted with EtOAc (50 mL×2). The combined organic layers were washed with brine (20 mL×2), dried over Na₂SO₄, filtered and concentrated under reduced pressure to give a residue. The residue was purified by prep-HPLC, then concentrated to obtain compound 44 (21 mg) as a light yellow solid.

Scheme 29 Synthetic route for compound 79 through Route IV in General synthetic route 2

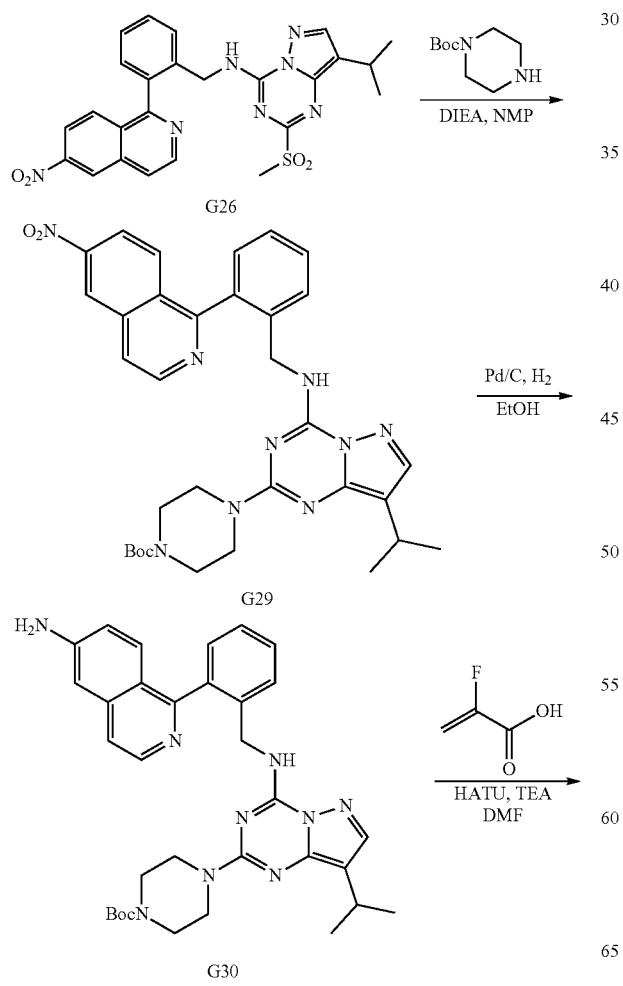

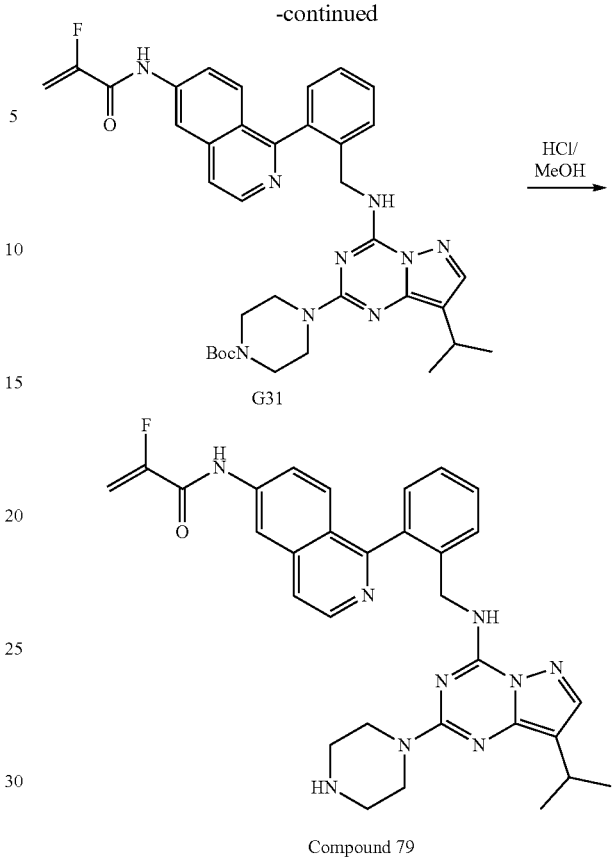

Compound 79

Procedure for Synthesis of G29

To a solution of compound G26 (300 mg, 0.58 mmol) and tert-butyl piperazine-1-carboxylate (323.88 mg, 1.74 mmol) in NMP (3 mL) was added DIPEA (149.83 mg, 1.16 mmol, 201.93 uL). The resulting mixture was heated at 110° C. and stirred for 2 hrs to give yellow solution. LCMS and TLC showed the reaction was completed. The reaction mixture was quenched by addition H₂O (50 mL) and extracted with EtOAc (50 mL×2). The combined organic layers were washed with brine (30 mL×3), dried over Na₂SO₄, filtered and concentrated under reduced pressure to give a residue. The residue was purified by column chromatography to obtain compound G29 (285 mg) as a yellow solid.

Procedure for Synthesis of G30

The compound G29 (285 mg) was followed the same procedure of B7 to obtain 258 mg of compound G30 as a yellow solid.

Procedure for Synthesis of G31

To a solution of 2-fluoroprop-2-enoic acid (16.38 mg, 181.90 umol) in DMF (2 mL) were added TEA (46.02 mg, 454.76 umol, 63.30 uL) and HATU (69.17 mg, 181.90 umol), and then compound G30 (90 mg, 151.59 umol) was added to the mixture and stirred at 15° C. for 2 hours to give brown solution. LCMS showed part of the starting material remained, the reaction was stirred at 15° C. for another 2 hours to give brown solution. LCMS indicated that the reaction was almost complete. The reaction mixture was poured into water (15 mL), and the yellow suspension was filtered. The filter cake was washed with PE (10 mL) and dried to give compound G31 (100 mg) as a yellow solid.

Procedure for Synthesis of Compound 79

A mixture of compound G31 (100 mg) in 4M HCl/MeOH (2 mL) was stirred at 15° C. for 1 hr to give a yellow solution. LCMS and HPLC indicated that the reaction worked well. The solvent was removed under reduced pressure to give the crude product. It was purified by prep-HPLC most of solvent was removed under reduced pressure, and the remaining solvent was removed by lyophilization to give compound 79 (34.7 mg) as a yellow solid.

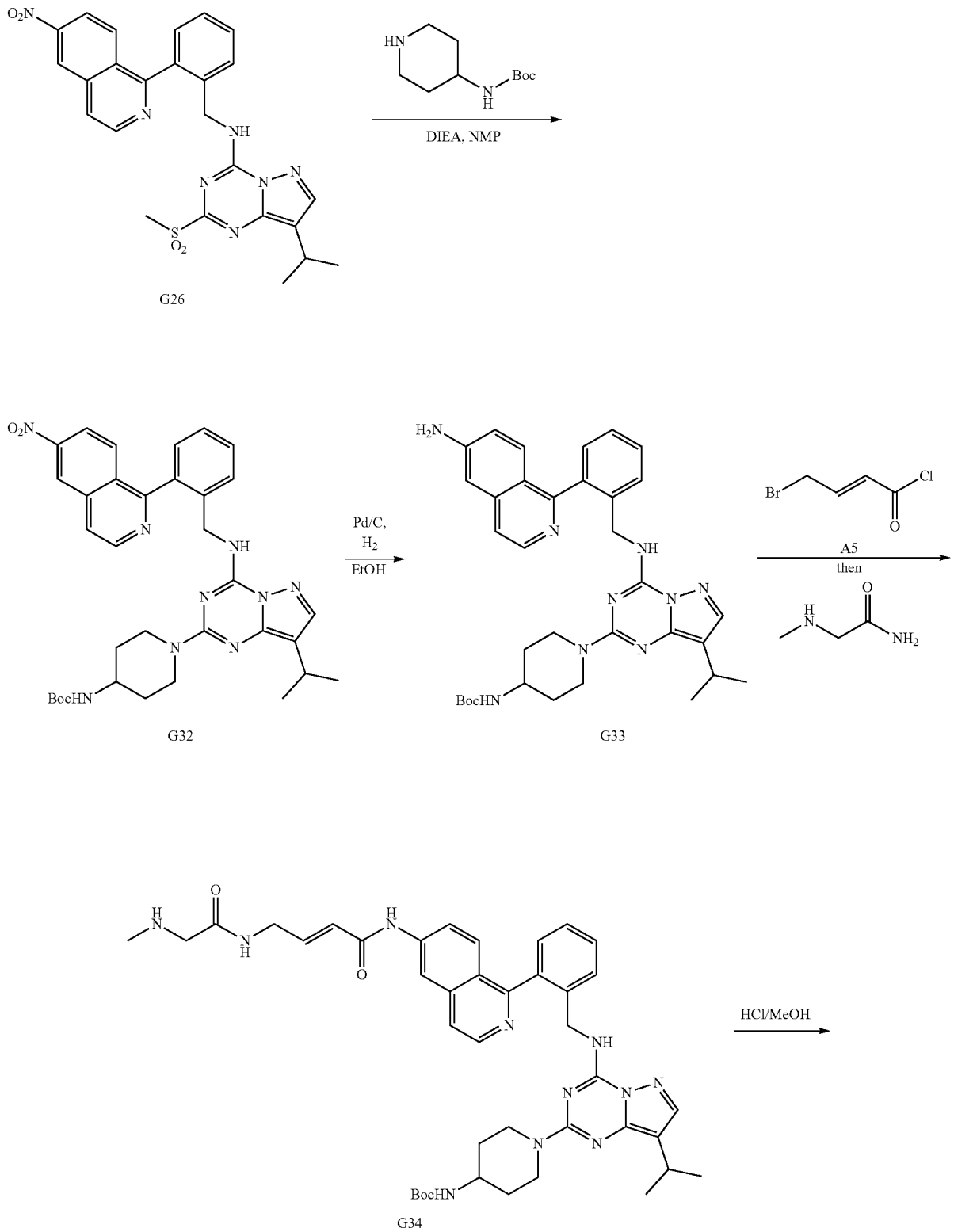

Scheme 30 Synthetic route for compound 58 through Route IV in General synthetic route 2

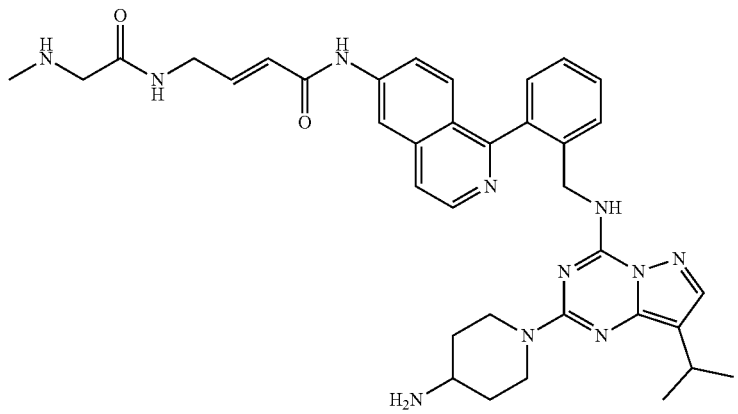

Compound 58

Procedure for Synthesis of G32

To a mixture of compound G26 (500 mg, 0.96 mmol) and tert-butyl N-(4-piperidyl)carbamate (386 mg, 1.93 mmol) in NMP (5 mL) was added DIEA (249 mg, 1.93 mmol, 336 uL), and the mixture was stirred at 110° C. for 16 hours to give a brown mixture. LCMS showed the reaction was completed. The reaction mixture was quenched with water (20 mL) and extracted with EtOAc (20 mL×2). The organic layer was washed with water (20 mL×2), brine (30 mL×4), dried over anhydrous $Na_2SO_4$, filtered and concentrated under reduced pressure to give crude product. The crude product was purified by combi flash to afford compound G32 (520 mg) as a red solid.

Procedure for Synthesis of G33

The compound G32 (520 mg) was followed the same procedure of B7 to obtain 450 mg of compound G33 as a yellow solid.

Procedure for Synthesis of G34

To a solution of compound G33 (50 mg, 82 umol, 1 eq) in THF (2 mL) was added a solution of A5 (30 mg, 164 umol, 2 eq) in THF (2 mL) at 0-5° C. in an ice-bath. The reaction solution was stirred at 0-25° C. for 1.5 hours. 2-(methylamino)acetamide (21 mg, 246 umol, 3 eq) and DIEA (10 mg, 82 umol, 14 uL, 1 eq) were added and it was stirred for another 16 hours to give a black brown solution. LCMS showed the desired product was observed. The reaction mixture was quenched with water (20 mL) and extracted with EtOAc (20 mL×2). The organic layer was washed with water (20 mL×2), brine (30 mL×4), dried over anhydrous $Na_2SO_4$, filtered and concentrated under reduced pressure to give crude product. The crude product was purified by prep-TLC to afford compound G34 (22 mg) as a white powder.

Procedure for Synthesis of Compound 58

The compound G34 (22 mg) was followed the same procedure of compound 79 to obtain 3 mg of compound 58 as a yellow solid.

Scheme 31 Synthetic route for compound 81 through Route V in General synthetic route 3

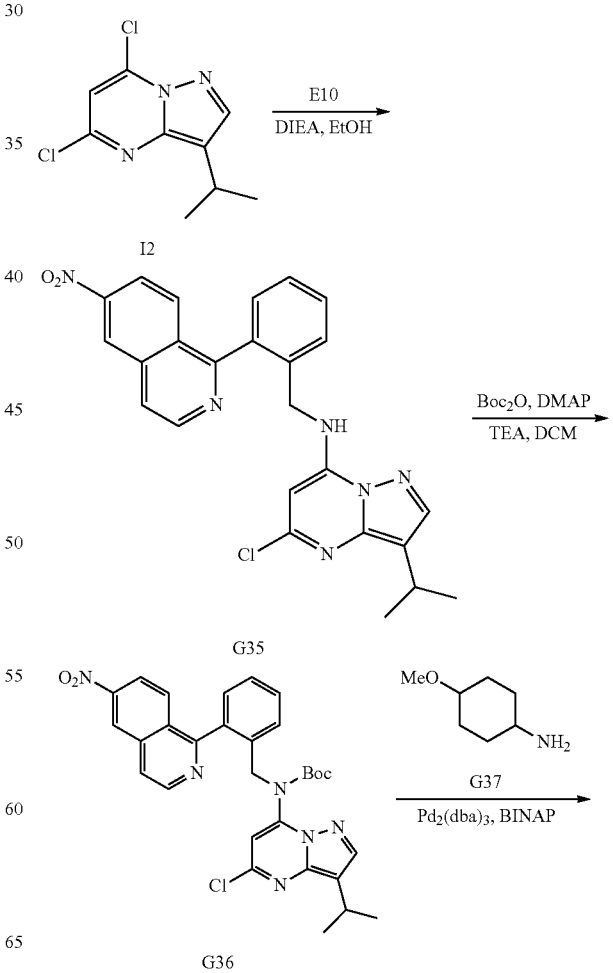

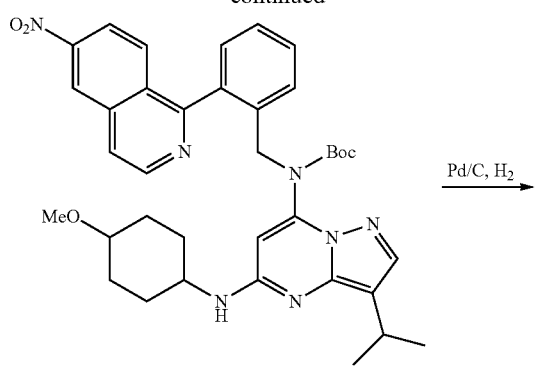

G38

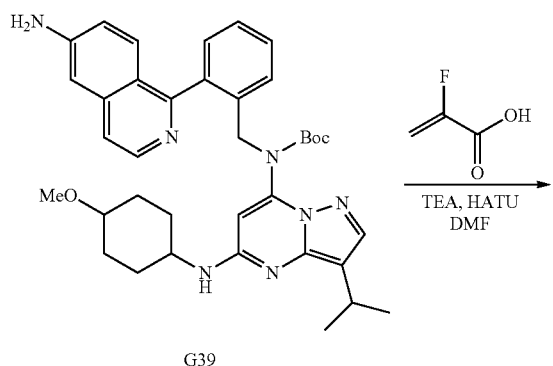

G39

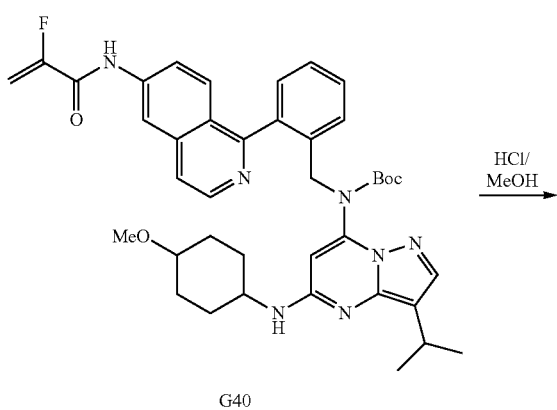

G40

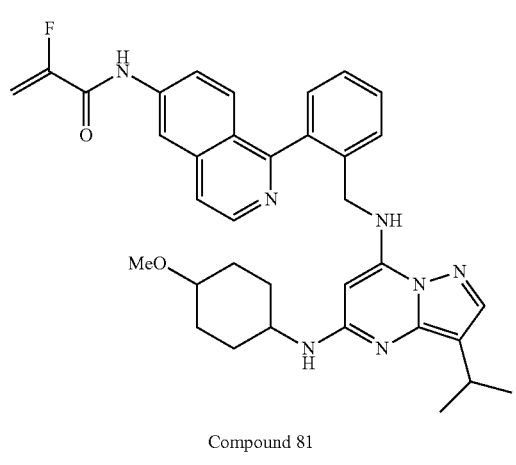

Compound 81

Procedure for Synthesis of G35

To a solution of compound E10 (728 mg, 2.61 mmol) and compound 12 (500 mg, 2.17 mmol) in EtOH (10 mL) was added DIPEA (561 mg, 4.35 mmol, 0.757 mL, 2 eq). The resulting mixture was stirred at 75° C. for 12 hrs to give brown solution. TLC showed the reaction was completed. The reaction mixture was concentrated under reduced pressure to give a residue. Then diluted with $H_2O$ (50 mL) and extracted with EtOAc (50 mL×2). The combined organic layers were washed with brine (20 mL×2), dried over $Na_2SO_4$, filtered and concentrated under reduced pressure to give a residue. The residue was purified by column chromatography to obtain compound G35 (948 mg) as a brown gum.

Procedure for Synthesis of G36

The compound G35 (948 mg) was followed the same procedure of compound B14 to obtain 930 mg of compound G36 as a yellow solid.

Procedure for Synthesis of G38

To a mixture of compound G36 (200 mg, 349 umol) and compound G37 (90.19 mg, 698 umol) in toluene (5 mL) were added $Pd_2(dba)_3$ (31.9 mg, 34.9 umol), t-BuONa (50.3 mg, 523 umol, 1.5 eq) and BINAP (21.7 mg, 34.9 umol), and the mixture was stirred at 95° C. for 4 hours to give a yellow mixture. LCMS showed the reaction was not completed. The mixture was stirred at 95° C. for another 6 hours to give a red mixture. TLC showed the reaction was completed. The mixture was partitioned between EtOAc (15 ml) and water (10 mL). The aqueous phase was extracted with EtOAc (10 mL×2). The combined organic extract was washed with brine (130 mL), dried over $Na_2SO_4$, filtered, concentrated under reduced pressure to give crude product. The crude product was purified by combi flash to afford compound G38 (130 mg) as a yellow solid.

Procedure for Synthesis of G39

The compound G38 (130 mg) was followed the same procedure of compound B7 to obtain 110 mg of compound G39 as a yellow solid.

Procedure for Synthesis of G40

The compound G39 (100 mg) was followed the same procedure of compound G31 to obtain 70 mg of compound G40 as a yellow solid.

Procedure for Synthesis of Compound 81

The compound G40 (70 mg) was followed the same procedure of compound 79 to obtain 18 mg of compound 81 as a yellow solid.

Exceptional Synthetic Route

Scheme 32 Synthetic route for compound 22

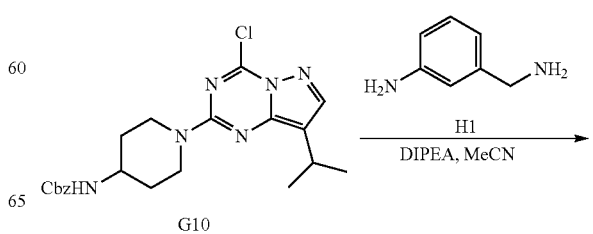

G10

-continued

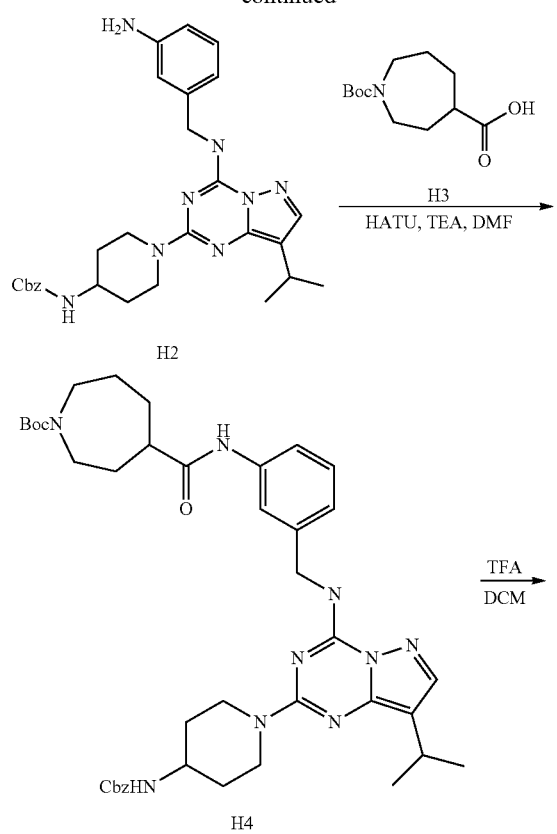

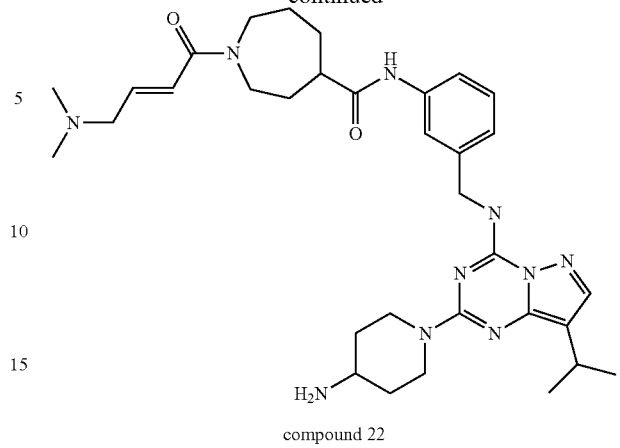

compound 22

Procedure for Synthesis of H2

To a mixture of compound H1 (214 mg, 1.75 mmol), DIPEA (1 mL) in MeCN (10 mL) was added compound G10 (500 mg, 1.17 mmol). The reaction solution was stirred at 20° C. for 1 hour to give a yellow mixture. LCMS showed the reaction was completed. The reaction mixture was partitioned with DCM (100 mL) and water (80 mL). The aqueous phase was extracted with DCM (80 mL×2). The combined extract was washed with brine (80 mL×2), dried over anhydrous $Na_2SO_4$ and filtrated, then concentrated under reduced pressure to give crude product as yellow oil, which was purified by Combi flash to give compound H2 (500 mg) as a yellow gum.

Procedure for Synthesis of H4

To a mixture of compound H2 (200 mg, 0.822 mmol) in DMF (5 mL) was added HATU (391 mg, 1.03 mmol), TEA (139 mg, 1.37 mmol), and stirred at 20° C. for 30 minutes. Then compound H3 (352 mg, 0.685 mmol) was added to the mixture, and stirred at 60° C. under $N_2$ atmosphere for 5 hours to give a yellow mixture. LCMS showed the reaction was completed. The mixture cooled to temperature and poured into water (50 mL). The yellow solid precipitated out from the mixture. The mixture was filtered and the filter cake was washed with water (50 mL) to give a crude product as a yellow powder, which was purified by Combi flash to give compound H4 (302 mg) as a yellow gum.

Procedure for Synthesis of H5

The compound H4 (300 mg) was followed the same procedure of A7 to obtain 290 mg of compound H5 as a yellow gum.

Procedure for Synthesis of H6

The compound H5 (200 mg) was followed the same procedure of A6 to obtain 101 mg of compound H6 as a yellow oil.

Procedure for Synthesis of Compound 22

To a mixture of compound H6 (100 mg, 0.133 mmol) in HBr/HOAc (2 mL, 35%) was stirred at 20° C. for 1 hour to give a yellow mixture. LCMS showed the reaction was completed. To the reaction mixture was added MTBE (10 mL) to precipitate an off-white powder. The white powder was collected by filtration and washed with MTBE (5 mL×2), which was purified by prep-HPLC (0.1% TFA) and then basified by cation exchange resin eluting with 5% $NH_3·H_2O$/MeOH to give compound 22 (15 mg) as a white powder.

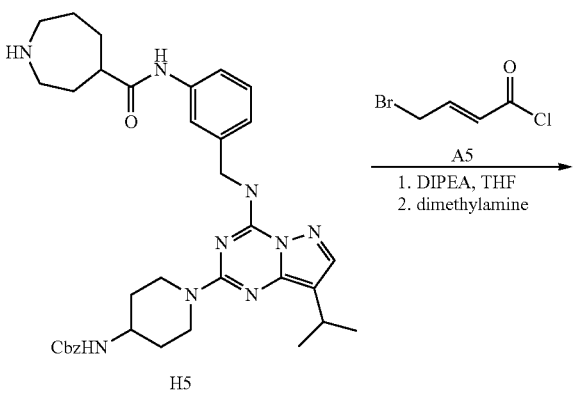

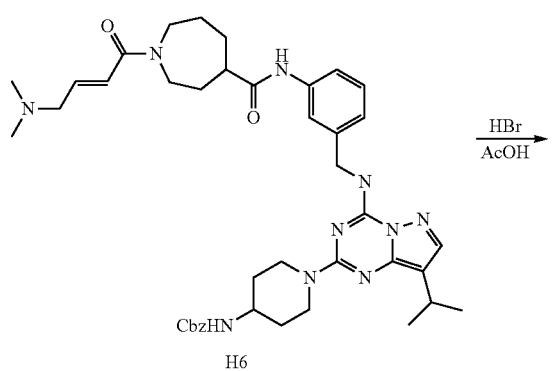

Scheme 33 Synthetic route for compound 21

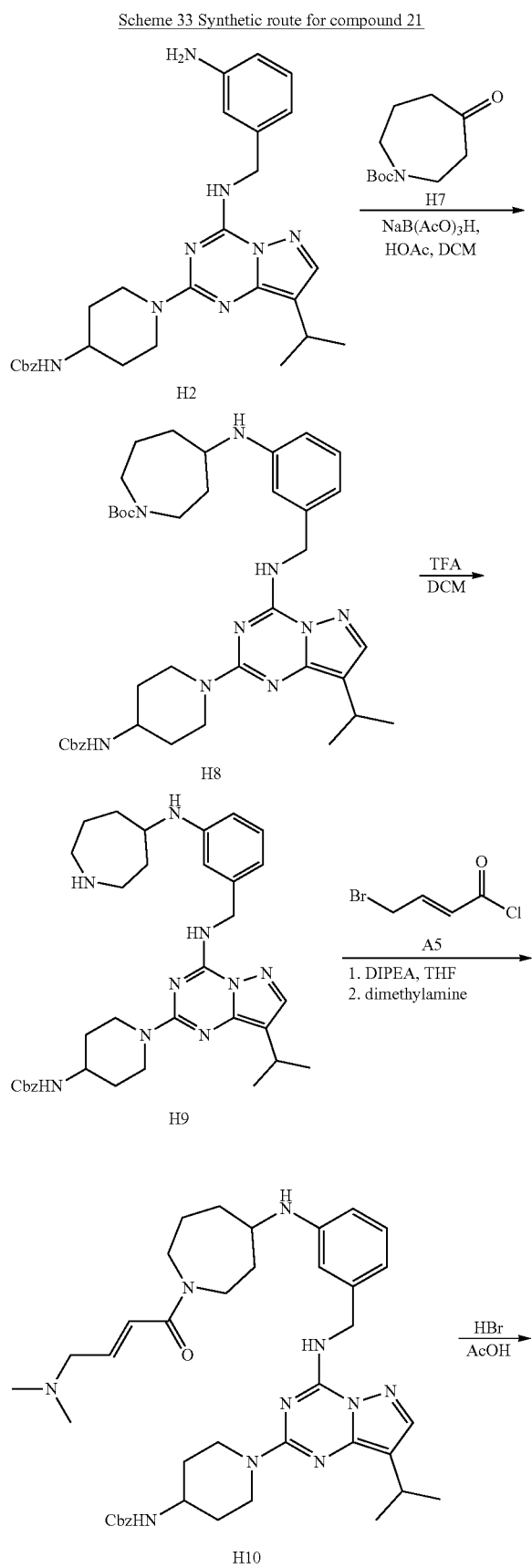

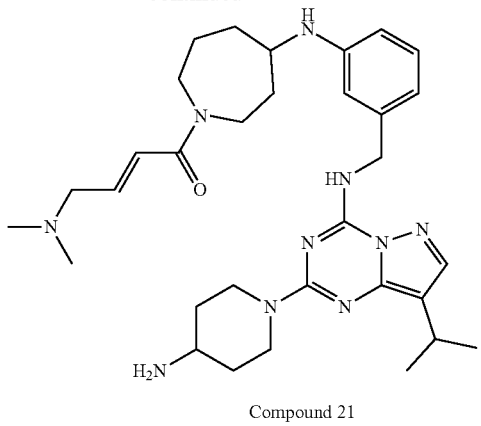

Compound 21

Procedure for Synthesis of H8

To a mixture of compound H2 (207 mg, 0.972 mmol), compound H7 (500 mg, 0.972 mmol) in DCM (8 mL) was added AcOH (58.3 mg, 0.972 mmol). The mixture was stirred at 20° C. for 1 hour and then added NaBH(OAc)$_3$ (309 mg, 1.46 mmol) to the mixture, and stirred at 20° C. for 24 hours. LCMS show desired MS value. The mixture was partitioned between DCM (50 mL) and saturated NaHCO$_3$ (50 mL). The DCM phase was washed with NaHCO$_3$ (50 mL×2), and dried over anhydrous Na$_2$SO$_4$, filtered, concentrated under reduced pressure to give yellow oil, which was purified by Combi flash to give compound H8 (200 mg) as a yellow oil.

Procedure for Synthesis of H9

To a mixture of compound H8 (200 mg, 0.281 mmol) in DCM (5 mL) was added TFA (1 mL). The mixture was stirred at 20° C. for 2 hours to give a yellow mixture. LCMS showed the reaction was completed. The mixture was combined and concentrated under reduced pressure to give compound H9 (200 mg) as a yellow oil

Procedure for Synthesis of H10

To a mixture of compound H9 (200 mg, 0.276 mmol) in THF (5 mL) was added DIPEA (178 mg, 1.38 mmol), compound A5 (152 mg, 0.827 mmol). The yellow mixture was stirred at 25° C. for 1 hour and become black. LCMS showed the reaction was completed. Dimethylamine (2 M, 689 uL) was added to the mixture and stirred at 25° C. for 1 hour to give a brown mixture. LCMS showed desired MS value. The mixture was partitioned between DCM (50 mL) and water (30 mL). The aqueous phase was extracted with DCM (50 mL×2). The combined extracted phase was washed with brine (30 mL), dried over anhydrous Na$_2$SO$_4$, filtered, concentrated under reduced pressure to give brown oil, which was purified by Combi flash to give compound H10 (180 mg) as brown oil.

Procedure for Synthesis of Compound 21

To a mixture of compound H10 (180 mg, 0.249 mmol) in HBr/HOAc (2.00 mL, 35% purity) was stirred at 20° C. for 1 hour to give a yellow mixture. TLC showed the reaction was completed. To the reaction mixture was added MTBE (10 mL) to precipitate an off-white powder. The white powder was collected by filtration and washed with MTBE (5 mL×2). The crude product was purified by prep-HPLC to give compound 21 (16.2 mg) as a white powder.

Scheme 34 Synthetic route for compound 12

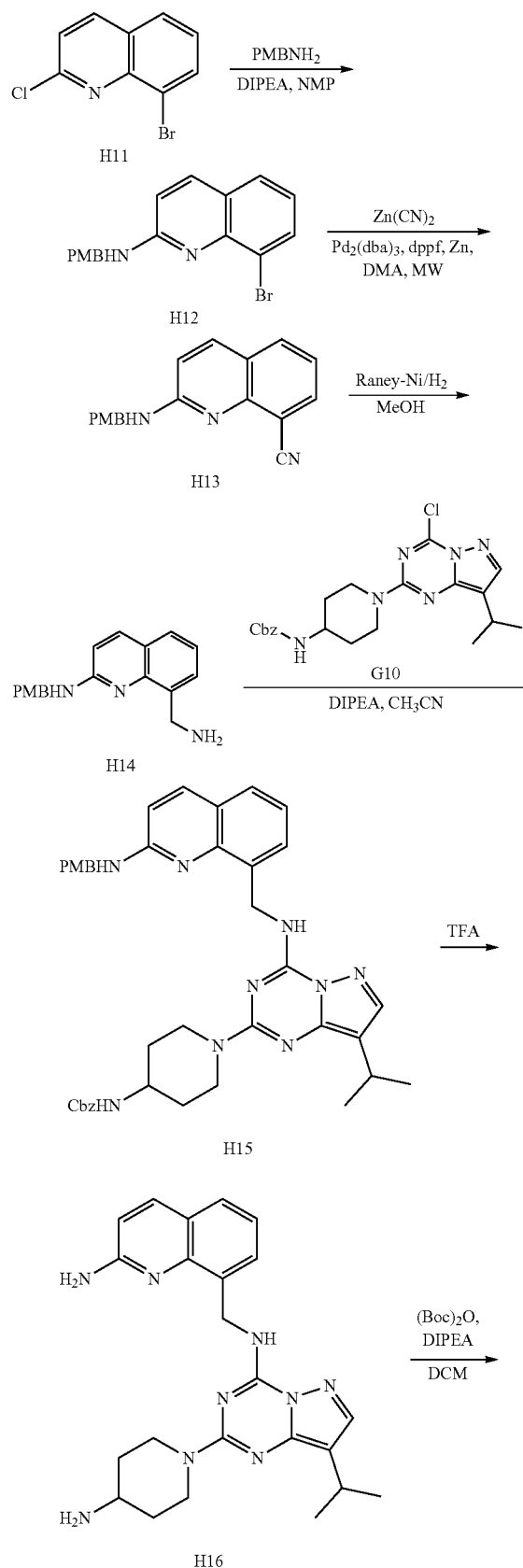

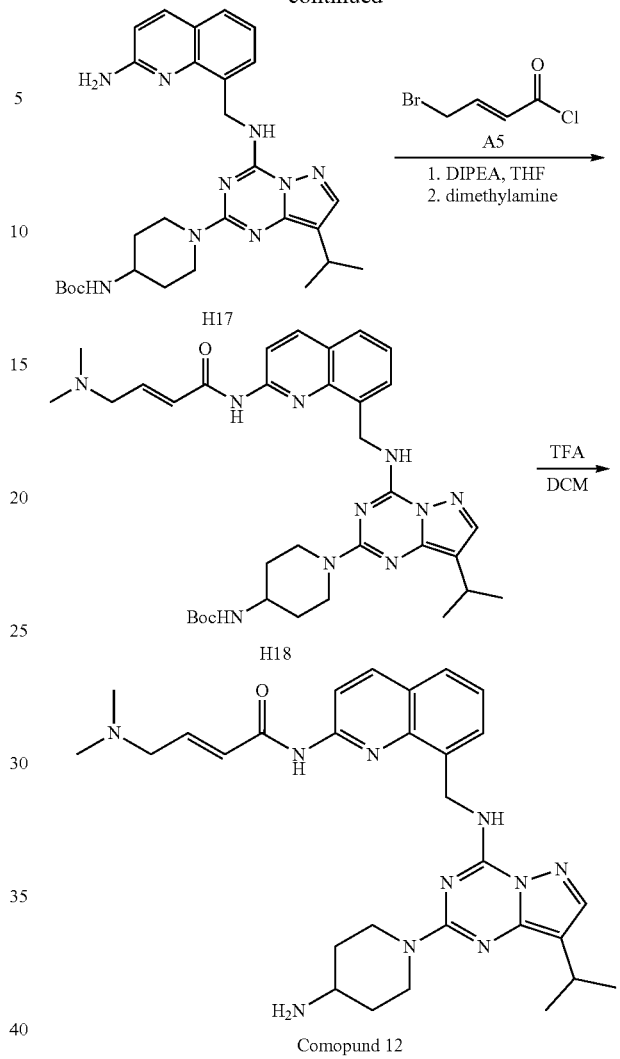

Procedure for Synthesis of H12

A mixture of compound H11 (500 mg, 2.06 mmol) and DIPEA (400 mg, 3.09 mmol) in NMP (5 mL) was added (4-methoxyphenyl)methanamine (475 mg, 3.46 mmol). The reaction mixture was stirred at 135° C. for 24 hours under $N_2$ atmosphere. The mixture was cooled to room temperature, water (50 mL) was added to the reaction mixture and extracted with MTBE (30 mL×3), the combined organic phase was washed with water (20 mL) and brine (20 mL), dried with anhydrous $Na_2SO_4$ and concentrated under reduced pressure to give the residue. The residue was purified by silica gel column to give compound H12 (910 mg) as a red solid.

Procedure for Synthesis of H13

To a solution of compound H12 (500 mg, 1.46 mmol) in DMA (5 mL) was added $Zn(CN)_2$ (103 mg, 0.876 mmol), $Pd_2(dba)_3$ (134 mg, 0.146 mmol), DPPF (162 mg, 0.292 mmol) and Zn (15.28 mg, 0.234 mmol). The reaction was stirred at 150° C. under microwave condition for 0.5 hour under $N_2$ atmosphere. LCMS showed the reaction was completed. The mixture was partitioned between with water (30 mL) and EtOAc (30 mL). The aqueous phase was extracted with EtOAc (20 mL). The combined extracts were washed with bine (50 mL), dried over anhydrous $Na_2SO_4$, filtered and concentrated under reduced pressure to give compound, which was purified by Combi flash to give compound H13 (300 mg) as a red gum.

Procedure for Synthesis of H14

To a mixture of Raney-Ni (100 mg) in MeOH (30 mL) was added compound H13 (500 mg, 1.73 mmol) and $NH_3 \cdot H_2O$ (2.5 mL, 25%). The suspension was degassed under vacuum and purged with $H_2$ several times, the mixture was stirred at 25° C. under $H_2$ (15 psi) for 3 hours to give a black mixture. TLC showed the reaction was completed. The mixture was filtered, the filtrate was concentrated under reduced pressure to give compound H14 (400 mg) as a yellow gum.

Procedure for Synthesis of H15

To a mixture of compound H14 (90.0 mg, 0.307 mmol), DIPEA (165 mg, 1.28 mmol) in MeCN (1 mL) was added compound G10 (110 mg, 256 mmol). The reaction solution was stirred at 25° C. for 1 hour to give a yellow mixture. LCMS showed the reaction was completed. The mixture was partitioned with DCM (30 mL) and water (20 mL). The aqueous phase was extracted with DCM (30 mL×2). The combined extract was washed with brine (30 mL×2), dried over anhydrous $Na_2SO_4$ and filtrated, then concentrated under reduced pressure to give crude product as yellow oil. The crude product was purified by Combi flash to give compound H15 (100 mg) as a yellow gum.

Procedure for Synthesis of H16

To a mixture of compound H15 (100 mg, 0.146 mmol) in TFA (1 mL) was stirred at 25° C. for 3 hours, LCMS showed a lot of starting material was still remained, and heated to 60° C. for 12 hours LCMS showed desired MS value, then heated to 80° C. for 14 hours to give a yellow mixture. LCMS showed the reaction was completed. The mixture was partitioned with DCM (50 mL) and saturated solution of $NaHCO_3$ (30 mL). The aqueous phase was extracted with DCM (50 mL×2). The combined extract was washed with brine (30 mL×2), dried over anhydrous $Na_2SO_4$ and filtrated, then concentrated under reduced pressure to give compound H16 (100 mg) as a yellow gum.

Procedure for Synthesis of H17

To a solution of compound H16 (100 mg, crude) and di-tert-butyl dicarbonate (55.6 mg, 0.255 mmol) in DCM (1 mL) was added DIPEA (32.9 mg, 0.255 mmol). The resulting mixture was stirred at 25° C. for 2 hours to give colorless solution. LCMS showed the reaction was completed. The mixture was concentrated under reduced pressure to give compound H17 (102 mg) as a yellow gum.

Procedure for Synthesis of H18

To a mixture of compound H17 (102 mg) in THF (2 mL) was added DIPEA (248 mg, 1.92 mmol) and compound A5 (106 mg, 0.576 mmol), the mixture was stirred at 25° C. for 1 hour. LCMS showed the reaction was completed, dimethylamine (2M, 383 uL) was added to the mixture. The mixture was stirred at 25° C. for 30 hours to give a brown mixture. LCMS showed the reaction was completed. The mixture was partitioned between DCM (50 mL) and water (30 mL), The aqueous was extracted with DCM (50 mL×2), the combined extracted phase was washed with brine (30 mL), dried over anhydrous $Na_2SO_4$, filtered, concentrated under reduced pressure to give a brown oil, which was purified by Combi flash to give compound H18 (80 mg) as a yellow oil.

Procedure for Synthesis of Compound 12

To a mixture of compound H18 (80 mg, 0.083 mmol) in DCM (2 mL) was added TFA (770 mg, 0.5 mL), the mixture was stirred at 25° C. for 1 hour to give a yellow mixture. LCMS showed the reaction was completed. The mixture was concentrated under reduced pressure to give yellow oil, which was purified by prep-HPLC to give compound 12 (6.4 mg) as a white powder.

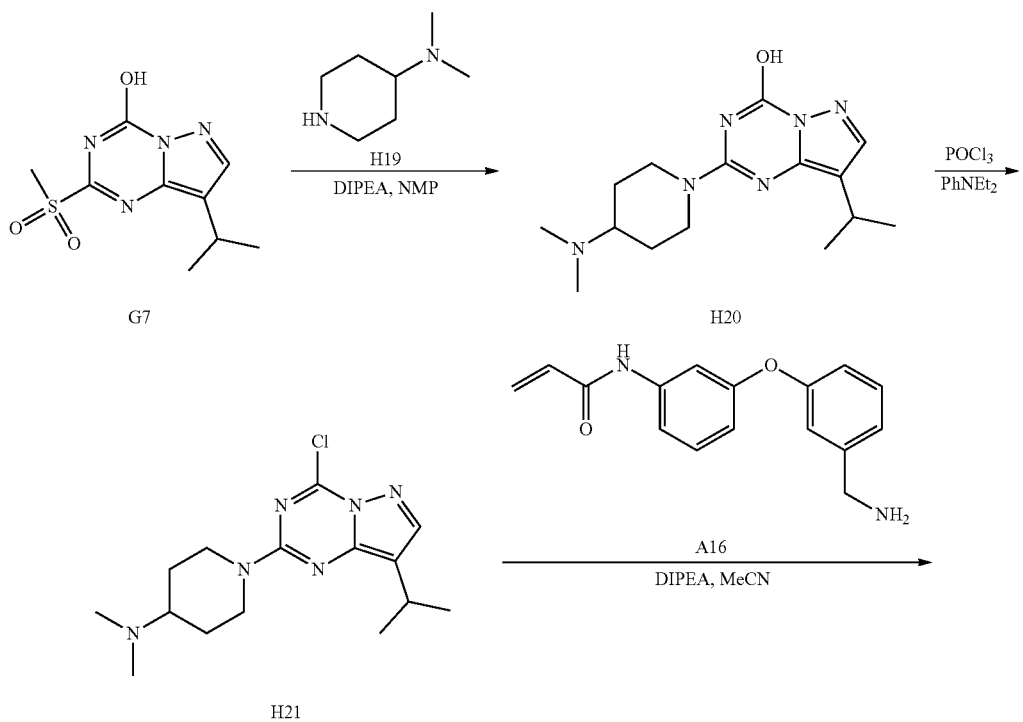

Scheme 35 Synthetic route for compound 14

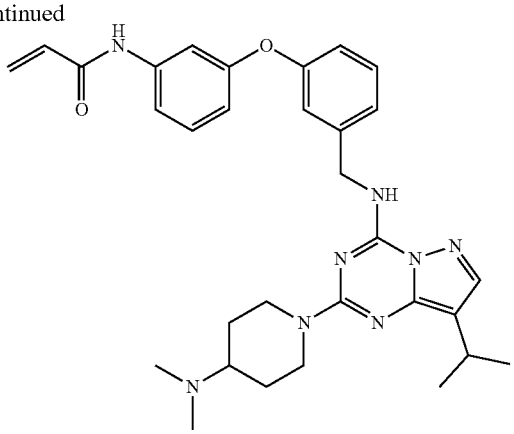

Compound 14

Procedure for Synthesis of H20

To a mixture of compound G7 (650 mg, 2.54 mmol) and DIPEA (1.64 g, 12.7 mmol) in NMP (12 mL) was added compound H19 (488 mg, 3.80 mmol). The reaction mixture was stirred at 140° C. for 28 hours under $N_2$ atmosphere to give a brown solution. LCMS showed the reaction was completed. The reaction was conducted two pots in parallel. The reaction mixture was combined and concentrated under reduced pressure to give crude product as a brown gum, which was washed with MeOH (15 mL) to give compound H20 (1.09 g) as a yellow powder.

Procedure for Synthesis of H21

To a mixture of compound H20 (400 mg, 1.31 mmol) in $POCl_3$ (5 mL) was added N, N-diethylaniline (588 mg, 3.94 mmol). The mixture was stirred at 90° C. for 1 hour to give a yellow mixture. The mixture was concentrated under reduced pressure to give compound H21 (420 mg) as a brown oil.

Procedure for Synthesis of Compound 14

To a mixture of compound H21 (300 mg, 0.929 mmol), DIPEA (2.40 g, 18.6 mmol) in $CH_3CN$ (5 mL) was added compound A16 (533 mg, 1.39 mmol). The reaction solution was stirred at 25° C. for 1 hour to give a yellow mixture. LCMS showed the reaction was completed. The mixture was portioned between DCM (80 mL) and water (50 mL), the aqueous phase was extracted by DCM (80 mL×2), the combined extracted phase was washed with brine (80 mL×2), dried over anhydrous $Na_2SO_4$, filtered, concentrated under reduced pressure to give a yellow oil. Crude product was purified by Combi flash and then by prep-TLC. The product was lyophilized to give compound 14 (45.5 mg) as a yellow powder.

Scheme 36 Synthetic route for compound 41

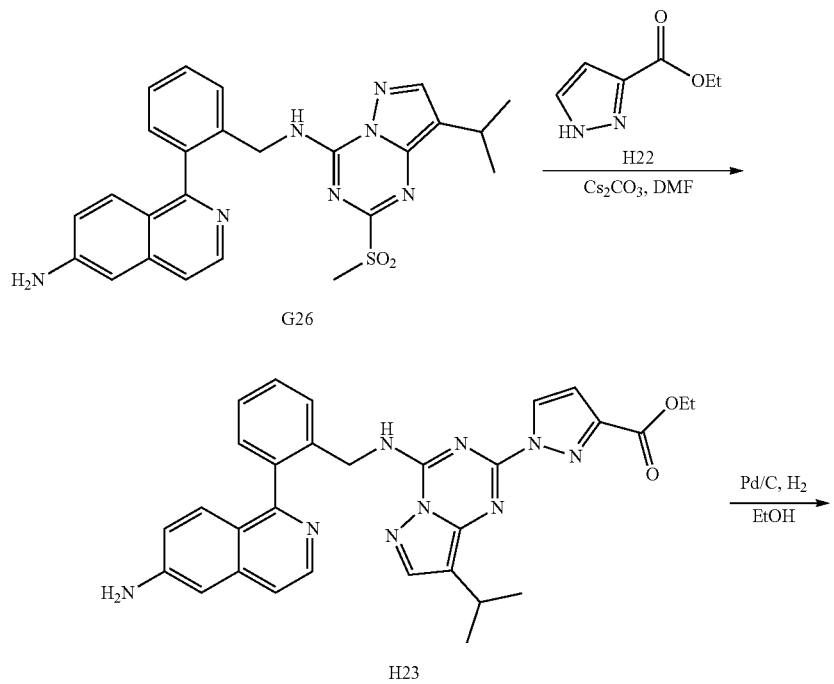

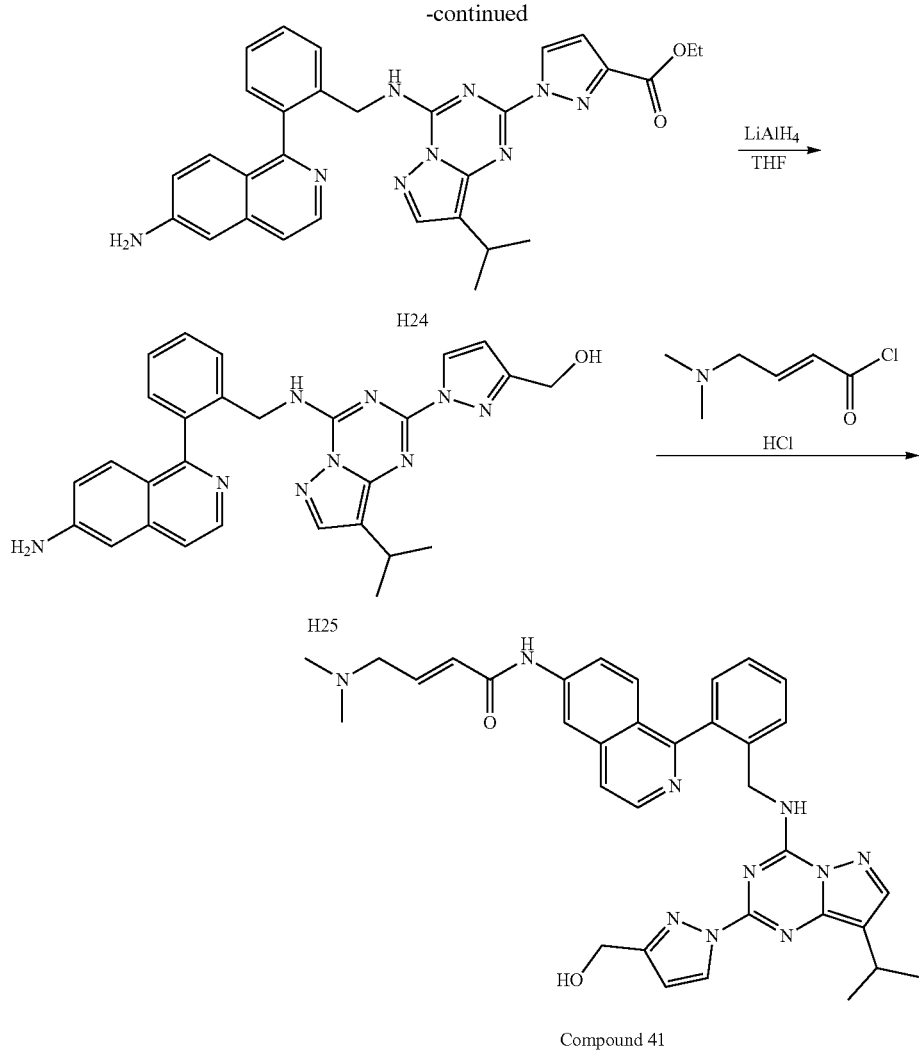

Procedure for Synthesis of H23

To a solution of compound G26 (500 mg, 966.07 umol) and compound H22 (271 mg, 1.93 mmol) in DMF (10 mL) was added Cs$_2$CO$_3$ (630 mg, 1.93 mmol). The resulting mixture was heated at 30-40° C. and stirred for 16 hr to give yellow solution. LCMS showed the reaction was completed. The mixture was filtered and was partitioned between EtOAc (50 mL). The aqueous layer was extracted with EtOAc (50 mL*3). The organic layer was washed with saturated brine (50 mL), dried over anhydrous Na$_2$SO$_4$, filtered, and concentrated under reduced pressure to give the crude product as a yellow oil. The crude product was purified by combi flash to give compound H23 (490 mg) as a yellow oil.

Procedure for Synthesis of H24

The compound H23 (490 mg) was followed the same procedure of B7 to obtain 440 mg of compound H24 as a yellow powder.

Procedure for Synthesis of H25

The compound H24 (390 mg) was followed the same procedure of E3 to obtain 310 mg of compound H25 as a yellow powder.

Procedure for Synthesis of Compound 41

The compound H25 (150 mg) was followed the same procedure of compound 44 to obtain 23 mg of compound 41 as a yellow powder.

Scheme 37 Synthetic route for compound 41

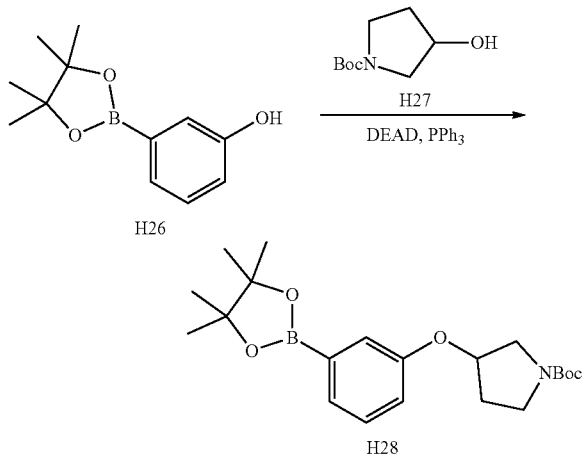

-continued

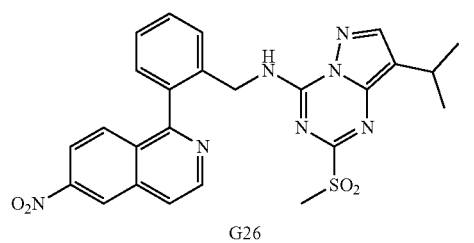

G26

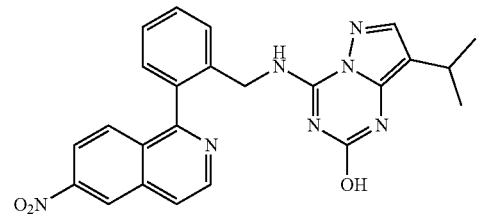

H29

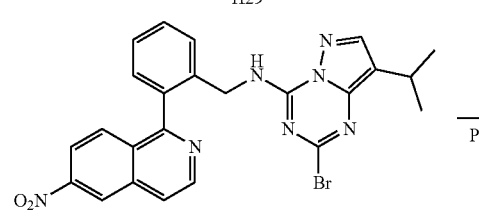

H30

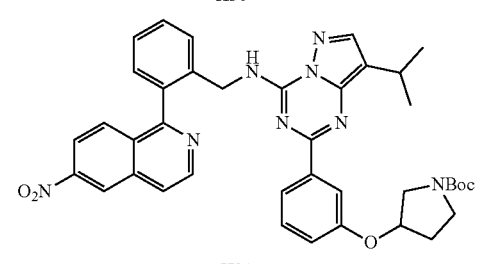

H31

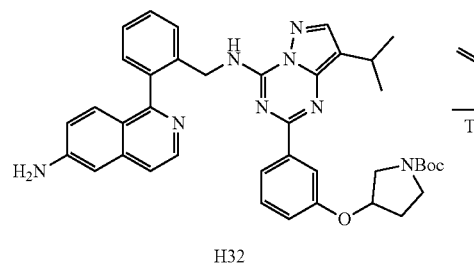

H32

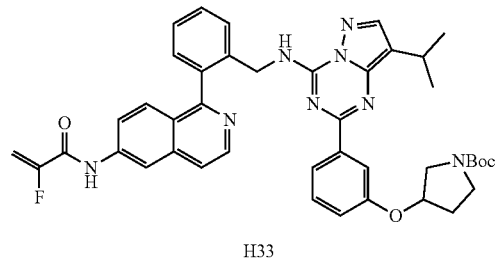

H33

-continued

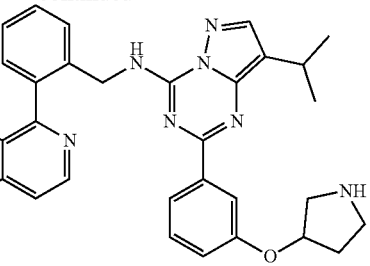

Compound 87

Procedure for Synthesis of H28

To a solution of compound H26 (500 mg, 2.27 mmol), compound H27 (638 mg, 3.41 mmol) and PPh₃ (893 mg, 3.41 mmol) in THF (10 mL) was added DIAD (689 mg, 3.41 mmol, 662 u) at 0° C. The resulting mixture was stirred at 15° C. for 24 hr to give yellow solution. TLC showed most of the starting material consumed. The reaction mixture was quenched by addition H₂O (30 mL) and extracted with EtOAc (30 mL×2). The combined organic layers were washed with brine (10 mL×2), dried over Na₂SO₄, filtered and concentrated under reduced pressure to give a residue. The residue was purified by column chromatography to give compound H28 (570 mg) as yellow oil.

Procedure for Synthesis of H29

To a mixture of compound G26 (1 g, 1.93 mmol) in dioxane (10 mL) and H₂O (10 mL) was added NaOH (309 mg, 7.73 mmol) and the mixture was stirred at 50° C. for 12 hours to give a yellow mixture. LCMS showed the desired product was observed. The mixture was concentrated under reduced pressure and adjusted to pH=3-4 and the mixture was filtered, and collected the white solid to afford compound H29 (620 mg) as a yellow solid.

Procedure for Synthesis of H30

To a mixture of compound H29 (500 mg, 1.10 mmol) in toluene (10 mL) were added POBr₃ (944 mg, 3.29 mmol, 334 uL) and N,N-diethylaniline (16.3 mg, 109 umol, 17.56 uL) at 15° C., the mixture was stirred at 100° C. for 3 hours to give a yellow mixture. LCMS showed the desired product was observed. The mixture was concentrated under pressure to give the crude product. The crude product was triturated with (PE/EA=3/1) at 15° C. for 30 min to afford compound H30 (330 mg) as a black brown solid.

Procedure for Synthesis of H31

To a mixture of compound H30 (330 mg, 636 umol) and compound H28 (247 mg, 636 umol) in dioxane (5 mL) and H₂O (2 mL) were added Na₂CO₃ (134 mg, 1.27 mmol, 2 eq) and Pd(dppf)Cl₂ (46.58 mg, 63.66 umol) and the mixture was stirred at 80° C. for 16 hours under N₂ to give a black mixture. LCMS showed the desired product was observed. The mixture was partitioned between EtOAc (15 ml) and water (10 mL). The aqueous phase was extracted with EtOAc (10 mL×2). The combined organic extract was washed with brine (10 mL), dried over Na₂SO₄, filtered, concentrated under reduced pressure to give crude product. The crude product was purified by combi flash (PE/EA=1/1) to afford compound H31 (50 mg) as a red solid.

Procedure for Synthesis of H32

The compound H31 (50 mg) was followed the same procedure of compound B7 to obtain 43 mg of compound H32 as a yellow powder.

Procedure for Synthesis of H33

The compound H32 (11.5 mg) was followed the same procedure of compound G31 to obtain 10 mg of compound H33 as a yellow powder.

Procedure for Synthesis of Compound 87

The compound H32 (10 mg) was followed the same procedure of compound A7 to obtain 3 mg of compound 87 as a yellow powder.

REFERENCES

D. B. Bregman, R. G. Pestell and V. J. Kidd. Cell cycle regulation and RNA polymerase II. *Front Biosci.* 2000 February; 1(5): D244-57.

D. Desai, H. C. Wessling, R. P. Fisher, and D. O. Morgan. Effects of phosphorylation by CAK on cyclin binding by $CDCl_2$ and CDK2. *Mol. Cell Biol.* 1995 January; 15(1): 345-350.

S. Akhtar, M. Heidemann, J. R. Tietjen, D. W. Zhang, R. D. Chapman, D. Eick, and A. Z. Ansari. TFIIH Kinase Places Bivalent Marks on the Carboxy-Terminal Domain of RNA Polymerase II. *Mol. Cell.* 2009 May; 15; 34(3):387-93.

S. Larochelle, R. Amat, K. G. Cutter, M. Sank), C. Zhang, J. J. Allen, K. M. Shokat, D. L. Bentley and R. P. Fisher. Cyclin-dependent kinase control of the initiation-to-elongation switch of RNA polymerase II. *Nat. Struct. Mol. Biol.* 2012 November; 19(11):1108-15.

G. I. Shapiro. Cyclin-Dependent Kinase Pathways as Targets for Cancer Treatment. *J. Clin. Oncol.* 2006 April; 10; 24(11):1770-83.

G. Lolli and L. N. Johnson. CAK-Cyclin-dependent Activating Kinase: a key kinase in cell cycle control and a target for drugs? *Cell Cycle.* 2005 April; 4(4):572-7.

T. I. Lee and R. A. Young. Transcriptional Regulation and its misregulation in Disease. *Cell.* 2013 March; 14; 152(6): 1237-51.

S. Nekhai, M. Zhou, A. Fernandez, W. S. Lane, Ned J. C. Lamb, J. Brady, A. Kumar. *Biochem. J.* 2002 June; 15; 364(Pt 3):649-57.

Y. K. Kim, C. F. Bourgeois, R. Pearson, M. Tyagi, M. J. West, J. Wong, S. Y. Wu, C. M. Chiang, and J. Karn. Recruitment of TFIIH to the HIV LTR is a rate-limiting step in the emergence of HIV from latency. *EMBO. J.* 2006 August; 9; 25(15): 3596-3604.

A. J. Kapasi and D. H. Spector. Inhibition of the Cyclin-Dependent Kinases at the Beginning of Human Cytomegalovirus Infection Specifically Alters the Levels and Localization of the RNA Polymerase II Carboxyl-Terminal Domain Kinases cdk9 and cdk7 at the Viral Transcriptosome. *J. Virol.* 2008 January; 82(1): 394-407.

Eickhoff et al, Pyrazolo-triazine derivatives as selective cyclin-dependent kinase inhibitors. PCT WO2013/128028A1

TABLE 1

Enzymatic activity of CDKs (1, 2, 5 and 7) and selectivity of CDK7

| # cpds | CDK1 | CDK2 | CDK5 | CDK7 | CDK1/CDK7* | CDK2/CDK7** | CDK5/CDK7*** |
|---|---|---|---|---|---|---|---|
| 1 | C | B | B | A | B | B | C |
| 2 | B | B | B | A | B | B | C |
| 3 | B | B | A | A | C | C | C |
| 5 | C | B | B | A | B | B | C |
| 6 | C | C | B | A | A | A | C |
| 7 | C | C | C | A | A | A | B |
| 8 | C | C | B | A | A | B | B |
| 10 | C | B | B | A | B | B | C |
| 11 | C | C | C | A | A | A | A |
| 12 | C | C | B | A | A | B | C |
| 14 | C | C | B | A | A | B | B |
| 15 | C | B | B | A | A | B | B |
| 16 | C | B | B | A | B | B | C |
| 18 | C | B | B | A | A | B | B |
| 19 | B | A | A | A | C | C | C |
| 20 | C | C | B | A | B | A | B |
| 21 | C | C | B | A | A | B | B |
| 22 | C | B | B | A | A | B | C |
| 23 | C | C | B | A | B | C | C |
| 24 | B | B | B | A | B | C | C |
| 25 | B | B | A | A | B | C | C |
| 26 | C | C | C | A | A | A | A |
| 27 | C | C | C | A | B | B | B |
| 28 | C | C | C | B | B | B | B |
| 29 | C | C | C | B | B | B | B |
| 30 | C | C | C | B | B | B | B |
| 31 | C | C | C | A | A | A | A |
| 32 | C | C | C | A | A | A | A |
| 33 | C | C | C | B | B | B | B |
| 34 | C | C | C | A | A | A | A |
| 35 | C | C | C | A | B | B | B |
| 36 | C | C | C | A | A | A | A |
| 37 | C | C | C | B | B | B | B |
| 38 | C | C | C | B | B | B | B |
| 39 | C | C | C | A | A | A | B |
| 40 | C | C | C | A | A | A | B |
| 41 | C | C | C | A | B | B | B |
| 42 | C | C | C | B | B | B | B |
| 43 | C | C | C | B | B | B | B |
| 44 | C | C | C | A | A | A | A |

TABLE 1-continued

Enzymatic activity of CDKs (1, 2, 5 and 7) and selectivity of CDK7

| # cpds | CDK1 | CDK2 | CDK5 | CDK7 | CDK1/CDK7* | CDK2/CDK7** | CDK5/CDK7*** |
|---|---|---|---|---|---|---|---|
| 45 | C | C | C | A | A | A | A |
| 46 | C | C | C | A | A | A | A |
| 47 | C | C | C | A | A | A | B |
| 48 | C | C | C | A | A | A | A |
| 49 | C | C | C | A | A | A | A |
| 50 | C | C | C | A | A | A | A |
| 51 | C | C | C | A | A | A | A |
| 52 | C | C | C | A | A | A | A |
| 53 | C | C | C | A | A | A | A |
| 54 | C | C | C | A | A | A | A |
| 55 | C | C | C | A | A | A | B |
| 56 | C | C | C | A | A | A | A |
| 57 | C | C | C | A | A | A | A |
| 58 | C | C | C | A | A | A | A |
| 59 | C | C | C | A | A | A | A |
| 60 | C | C | C | A | A | A | A |
| 61 | C | C | C | A | A | A | A |
| 62 | C | C | C | A | A | A | A |
| 63 | C | C | C | A | A | A | A |
| 64 | C | C | C | A | A | A | A |
| 65 | C | C | C | A | A | A | A |
| 66 | C | C | C | A | A | A | A |
| 67 | C | C | C | A | A | A | A |
| 68 | C | C | C | A | A | A | A |
| 69 | C | C | C | A | B | B | B |
| 70 | C | C | C | A | A | A | A |
| 71 | C | C | C | A | B | B | B |
| 72 | C | C | C | A | A | A | A |
| 73 | C | C | C | A | A | A | B |
| 74 | C | C | B | A | B | B | B |
| 75 | C | C | C | B | B | B | B |
| 76 | C | C | C | A | A | A | A |
| 77 | C | C | C | A | A | A | A |
| 78 | C | C | C | A | A | A | B |
| 79 | C | C | C | A | A | A | A |
| 80 | C | C | C | A | A | A | A |
| 81 | C | C | C | B | B | B | B |
| 82 | C | C | C | A | A | A | A |
| 83 | C | C | C | A | A | A | A |
| 84 | C | C | C | B | B | B | B |
| 85 | C | C | C | B | B | B | B |
| 86 | C | C | C | C | C | C | C |
| 87 | C | C | C | A | A | A | A |
| 88 | C | C | C | B | B | B | B |

Activity range: A indicates $IC_{50} \leq 100$ nM, B indicates $100 < IC_{50} \leq 1,000$ nM, C indicates $IC_{50} > 1,000$ nM
*CDK1/CDK7: Selectivity of CDK7 inhibition over CDK1 inhibition [fold]
**CDK2/CDK7: Selectivity of CDK7 inhibition over CDK2 inhibition [fold]
***CDK5/CDK7: Selectivity of CDK7 inhibition over CDK5 inhibition [fold]
Selectivity range: A indicates [fold] >500, B indicates $50 < $ [fold] $\leq 500$, C indicates [fold] $\leq 50$

TABLE 2

H460 viability assay

| # cpds | $IC_{50}$ |
|---|---|
| 1 | B |
| 2 | A |
| 3 | A |
| 5 | A |
| 6 | A |
| 7 | A |
| 8 | A |
| 9 | B |
| 10 | A |
| 11 | A |
| 12 | A |
| 13 | A |
| 14 | A |
| 15 | A |
| 16 | A |
| 18 | A |
| 19 | B |
| 20 | A |
| 21 | B |
| 22 | B |
| 23 | B |
| 24 | B |
| 25 | A |
| 26 | A |
| 27 | A |

Activity range: A indicates $IC_{50} \leq 1$ uM, B indicates $1 < IC_{50} \leq 10$ uM, C indicates $IC_{50} > 10$ uM

TABLE 3

| MV4-11 viability assay | |
|---|---|
| # cpds | IC$_{50}$ |
| 3 | A |
| 11 | A |
| 20 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | B |
| 71 | A |
| 72 | A |
| 73 | A |
| 74 | A |
| 75 | A |
| 76 | A |
| 77 | A |
| 78 | A |
| 79 | A |

Activity range: A indicates IC$_{50}$ ≤ 1 uM, B indicates 1 < IC$_{50}$ ≤ 10 uM, C indicates IC$_{50}$ > 10 uM

TABLE 4

| A2780 viability assay | |
|---|---|
| # cpds | IC$_{50}$ |
| 3 | A |
| 11 | A |
| 20 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | B |
| 59 | A |
| 60 | A |
| 61 | A |
| 62 | A |
| 63 | B |
| 64 | A |
| 65 | A |
| 66 | A |
| 67 | A |
| 68 | A |
| 69 | A |
| 70 | B |
| 71 | A |
| 72 | A |
| 73 | B |
| 74 | A |
| 75 | A |
| 76 | A |
| 77 | B |

Activity range: A indicates IC$_{50}$ ≤ 1 uM, B indicates 1 < IC$_{50}$ ≤ 10 uM, C indicates IC$_{50}$ > 10 uM

TABLE 5

| OVCAR-3 viability assay | |
|---|---|
| # cpds | IC$_{50}$ |
| 3 | A |
| 11 | A |
| 20 | A |
| 25 | A |
| 26 | A |
| 27 | A |
| 28 | A |
| 29 | A |
| 30 | A |
| 31 | A |
| 32 | A |
| 33 | A |
| 34 | A |
| 35 | A |
| 36 | A |
| 37 | A |

TABLE 5-continued

OVCAR-3 viability assay

| # cpds | IC$_{50}$ |
|---|---|
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | B |
| 59 | A |

TABLE 5-continued

OVCAR-3 viability assay

| # cpds | IC$_{50}$ |
|---|---|
| 60 | A |
| 61 | A |
| 62 | A |
| 63 | B |
| 64 | A |
| 65 | A |
| 66 | A |
| 67 | A |
| 68 | A |
| 69 | A |
| 70 | B |
| 71 | A |
| 72 | A |
| 73 | B |
| 74 | A |
| 75 | A |
| 76 | A |
| 77 | B |

Activity range: A indicates IC$_{50}$ ≤ 1 uM, B indicates 1 < IC$_{50}$ ≤ 10 uM, C indicates IC$_{50}$ > 10 uM

TABLE 6

Summarized compounds 1-88 in terms of their structures and corresponding characteristics

| #cpds | Structure | Characterization Data |
|---|---|---|
| 1 | (structure) | white powder; $^1$H-NMR (DMSO-d6, 400 MHz): δ 10.28 (1H, brs), 10.25 (1H, brs), 8.86 (1H, brs), 8.13 (1H, s), 7.88 (1H, d, J = 8.0 Hz), 7.80 (1H, s), 7.72 (1H, s), 7.65 (1H, d, J = 7.6 Hz), 7.60 (1H, d, J = 7.6 Hz), 7.44 (1H, t, J = 8.0 Hz), 7.28 (1H, t, J = 7.6 Hz), 7.12 (1H, d, J = 7.2 Hz), 6.75 (1H, td, J = 15.6, 6.0 Hz,), 6.28 (1H, d, J = 15.6 Hz), 4.59 (2H, s), 4.42-4.54 (2H, m), 3.06 (2H, d, J = 5.2 Hz), 2.85-2.98 (3H, m), 2.65-2.75 (1H, m), 2.18 (6H, s), 1.64-1.76 (2H, m), 1.23 (6H, d, J = 7.2 Hz), 1.03-1.15 (2H, m); LCMS: 95.8%, MS (ESI): m/z 611.3[M + H]+. |
| 2 | (structure) | white powder; $^1$H-NMR (DMSO-d6, 400 MHz): δ 10.12 (1H, brs), 8.85 (1H, brs), 7.70 (1H, s), 7.36-7.42 (2H, m), 7.24-7.36 (2H, m), 7.17 (1H, d, J = 7.6 Hz), 7.07 (1H, s), 6.90 (1H, dd, J = 8.0, 1.6 Hz), 6.63-6.74 (2H, m), 6.21 (1H, d, J = 15.2 Hz), 4.55 (2H, s), 4.39-4.50 (2H, m), 2.99-3.08 (2H, m), 2.81-2.97 (3H, m), 2.66-2.77 (1H, m), 2.16 (6H, s), 1.61-1.76 (2H, m), 1.22 (6H, d, J = 7.2 Hz), 0.99-1.13 (2H, m); LCMS: 100%, MS (ESI): m/z 584.2[M + H]+. |

TABLE 6-continued

Summarized compounds 1-88 in terms of their structures and corresponding characteristics

| #cpds | Structure | Characterization Data |
|---|---|---|
| 3 | 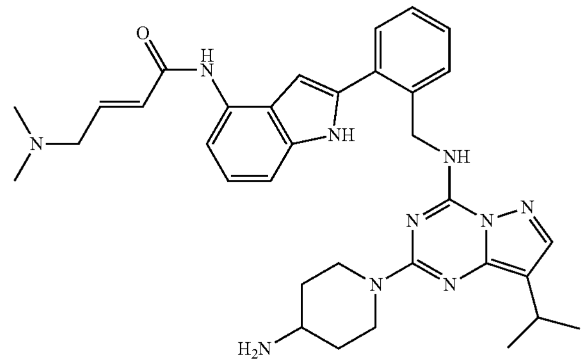 [SMILES: CC(C)c1cnn2c(NCc3ccccc3-c3cc4c(NC(=O)/C=C/CN(C)C)cccc4[nH]3)nc(N3CCC(N)CC3)nc12] | White powder; $^1$H-NMR (DMSO-d6, 400 MHz): δ 8.65 (1H, brs), 7.89 (1H, brs), 7.62 (1H, s), 7.48-7.59 (3H, m), 7.31-7.43 (2H, m), 7.16-7.22 (1H, m), 7.09-7.15 (1H, m), 6.95-7.06 (1H, m), 6.61 (1H, t, J = 5.6 Hz), 6.56 (1H, s), 6.21 (1H, d, J = 15.2 Hz), 4.83 (2H, d, J = 5.2 Hz), 4.55-4.65 (2H, m), 3.10-3.20 (2H, m), 2.98-3.08 (1H, m), 2.80-2.89 (3H, m), 2.30 (6H, s), 1.77-1.79 (2H, m), 1.28-1.32 (8H, m); LCMS: 100%, MS (ESI): m/z 629.4[M + Na]$^+$ |
| 4 | 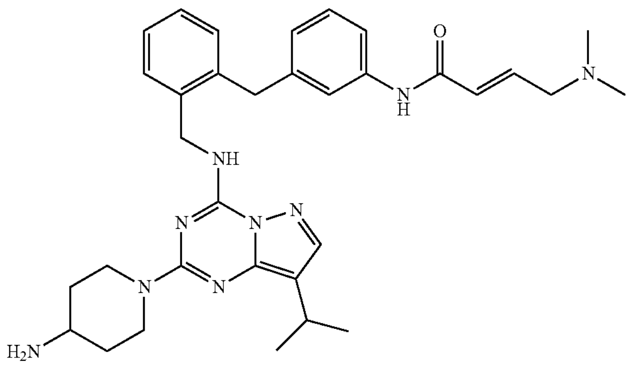 [SMILES: CC(C)c1cnn2c(NCc3ccccc3Cc3cccc(NC(=O)/C=C/CN(C)C)c3)nc(N3CCC(N)CC3)nc12] | white powder; $^1$H-NMR (CDCl3, 400 MHz): δ 7.56 (1H, s), 7.42-7.48 (2H, m), 7.26-7.32 (1H, m), 7.17-7.24 (1H, m), 7.14 (1H, brs), 7.07-7.12 (1H, m), 6.88-6.98 (2H, m), 6.60-6.70 (2H, m), 6.07 (1H, d, J = 15.2 Hz), 4.77 (2H, d, J = 6.0 Hz), 4.68-4.76 (2H, m), 3.09 (2H, d, J = 5.6 Hz), 2.96-3.04 (1H, m), 2.86-2.96 (3H, m), 2.26 (6H, s), 1.76-1.90 (2H, m), 1.23-1.34 (8H, m); LCMS: 100%, MS (ESI): m/z 584.4[M + H]+. |
| 5 | 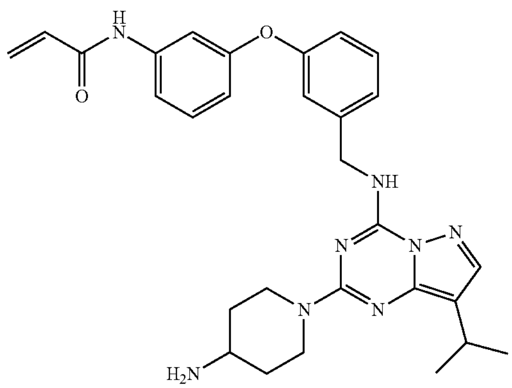 [SMILES: C=CC(=O)Nc1cccc(Oc2cccc(CNc3nc(N4CCC(N)CC4)nc4c(C(C)C)cnn34)c2)c1] | white powder; $^1$H-NMR (CDCl3, 400 MHz): δ 7.79 (1H, brs), 7.60 (1H, s), 7.40-7.50 (1H, m), 7.26-7.33 (2H, m), 7.19 (1H, s), 7.05-7.12 (2H, m), 6.93 (1H, d, J = 7.6 Hz), 6.75 (1H, d, J = 7.6 Hz), 6.71 (1H, brs), 6.41 (1H, d, J = 16.4 Hz), 6.24-6.34 (1H, m), 5.74 (1H, d, J = 10.0 Hz), 4.62-4.75 (4H, m), 2.96-3.06 (1H, m), 2.83-2.95 (3H, m), 1.80-1.84 (2H, m), 1.21-1.33 (8H, m); LCMS: 100%, MS (ESI): m/z 527.3[M + H]+. |
| 6 | 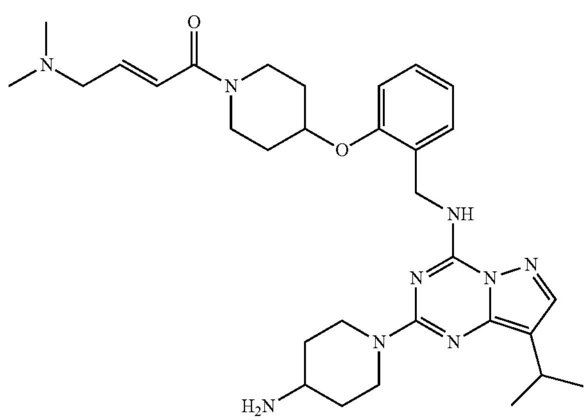 [SMILES: CC(C)c1cnn2c(NCc3ccccc3OC3CCN(C(=O)/C=C/CN(C)C)CC3)nc(N3CCC(N)CC3)nc12] | white powder; $^1$H-NMR (DMSO-d6, 400 MHz): δ 7.56 (1H, s), 7.33 (1H, d, J = 8.0 Hz), 7.24-7.28 (1H, m), 6.92 (1H, d, J = 6.8 Hz), 6.80-6.88 (2H, m), 6.63 (1H, t, J = 4.8 Hz), 6.53 (1H, d, J = 16.0 Hz), 4.76-4.83 (2H, m), 4.63-4.70 (2H, m), 3.65-3.80 (3H, m), 3.53-3.56 (1H, m), 3.21-3.25 (2H, m), 3.09-3.14 (1H, m), 2.91-3.03 (3H, m), 2.35 (6H, s), 1.94-1.97 (2H, m), 1.86-1.90 (4H, m), 1.45-1.48 (2H, m), 1.27 (6H, d, J = 7.2 Hz); LCMS: 100%, MS (ESI): m/z 576.3[M + H]+. |

TABLE 6-continued

Summarized compounds 1-88 in terms of their structures and corresponding characteristics

| #cpds | Structure | Characterization Data |
|---|---|---|
| 7 | 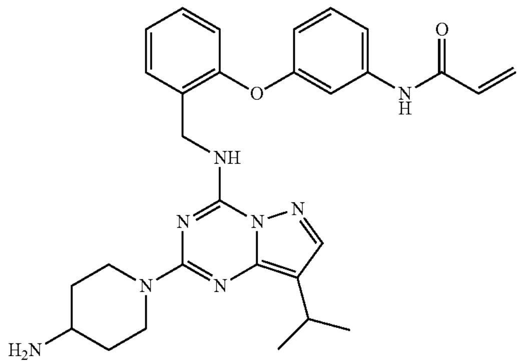 [SMILES: C=CC(=O)Nc1cccc(Oc2ccccc2CNc2nc(N3CCC(N)CC3)nc3c(C(C)C)cnn23)c1] | white powder; $^1$H-NMR (CDCl3, 400 MHz): δ 7.49 (1H, s), 7.38-7.40 (2H, m), 7.14-7.22 (3H, m), 7.04-7.06 (2H, m), 6.87 (1H, d, J = 8.0 Hz), 6.58-6.59 (1H, m), 6.53 (1H, t, J = 4.8 Hz), 6.33-6.37 (1H, d, J = 16.8 Hz), 6.12-6.14 (1H, m), 5.69 (1H, d, J = 10.8 Hz), 4.64-4.71 (4H, m), 2.82-2.95 (4H, m), 1.79-1.82 (2H, m), 1.19-1.27 (8H, m); LCMS: 91.6%, MS (ESI): m/z 527.3[M + H]+. |
| 8 | 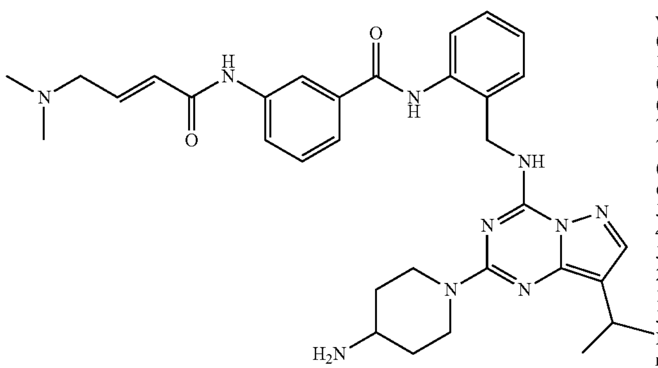 [SMILES: CC(C)c1cnn2c(NCc3ccccc3NC(=O)c3cccc(NC(=O)/C=C/CN(C)C)c3)nc(N3CCC(N)CC3)nc12] | white powder; $^1$H-NMR (DMSO-d6, 400 MHz): δ 10.26-10.27 (1H, s), 10.12-10.14 (1H, s), 8.85-8.69 (1H, brs), 8.21 (1H, s), 7.92 (1H, d, J = 8.0 Hz), 7.72 (1H, s), 7.65-7.68 (1H, m), 7.37-7.49 (3H, m), 7.27-7.31 (1H, m), 7.19-7.23 (1H, m), 6.73-6.76 (1H, m), 6.28 (1H, d, J = 15.6 Hz), 4.63 (2H, s), 4.42-4.47 (2H, m), 3.06 (2H, d, J = 5.2 Hz), 2.82-2.94 (3H, m), 2.70-2.77 (1H, m), 2.17 (6H, s), 1.64-1.69 (2H, m), 1.22 (6H, d, J = 7.2 Hz), 1.02-1.11 (2H, m); LCMS: 100.0%, MS (ESI): m/z 611.3[M + H]+. |
| 9 | 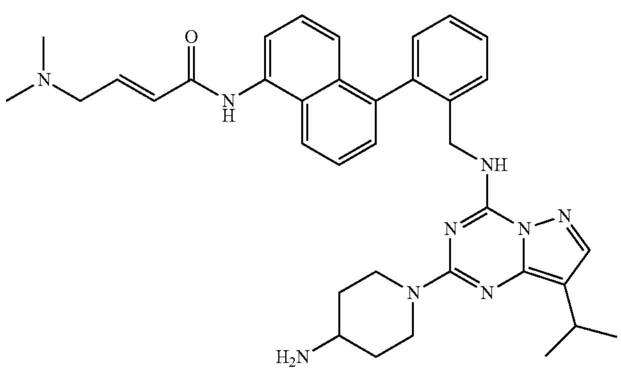 [SMILES: CC(C)c1cnn2c(NCc3ccccc3-c3cccc4c(NC(=O)/C=C/CN(C)C)cccc34)nc(N3CCC(N)CC3)nc12] | white powder; 1H-NMR (CDCl3, 400 MHz): δ 8.47-8.49 (2H, s), 7.97-7.99 (1H, m), 7.61-7.63 (1H, m), 7.55-7.58 (1H, m), 7.52 (1H, s), 7.38-7.49 (4H, m), 7.22-7.25 (1H, m), 7.04-7.11 (1H, m), 6.63-6.65 (1H, m), 6.35-6.40 (1H, m), 4.72-4.77 (1H, m), 4.78-4.55 (2H, m), 4.26-4.30 (1H, m), 3.19-3.21 (2H, m), 2.92-3.02 (2H, m), 2.76-2.83 (2H, m), 2.35 (6H, s), 1.79-7.82 (2H, m), 1.14-1.29 (8H, m); LCMS: 95.3%, MS (ESI): m/z 619.4[M + H]+. |
| 10 | 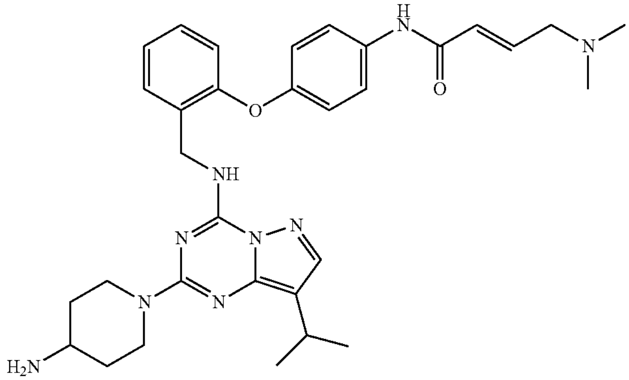 [SMILES: CC(C)c1cnn2c(NCc3ccccc3Oc3ccc(NC(=O)/C=C/CN(C)C)cc3)nc(N3CCC(N)CC3)nc12] | white powder; $^1$H-NMR (CDCl3, 400 MHz): δ 7.60 (1H, s), 7.44-7.53 (4H, m), 7.22-7.26 (1H, m), 7.08 (1H, t, J = 7.6 Hz), 6.93-7.00 (3H, m), 6.86 (1H, d, J = 7.6 Hz), 6.71 (1H, t, J = 6.2 Hz), 6.13 (1H, d, J = 15.6 Hz), 4.79 (2H, d, J = 6.4 Hz), 4.71-4.75 (2H, m), 3.12-3.15 (2H, m), 2.99-3.06 (1H, m), 2.89-2.96 (3H, m), 2.30 (6H, s), 1.86-1.89 (2H, m), 1.24-1.33 (8H, m); LCMS: 100.0%, MS (ESI): m/z 584.4[M + H]+. |

TABLE 6-continued

Summarized compounds 1-88 in terms of their structures and corresponding characteristics

| #cpds | Structure | Characterization Data |
|---|---|---|
| 11 | 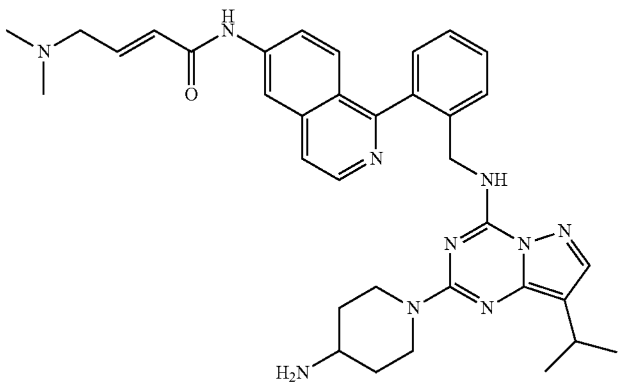 | white powder; $^1$H-NMR (DMSO-d6, 400 MHz): δ 10.51 (1H, brs), 8.44-8.50 (3H, m), 7.75 (1H, d, J = 5.6 Hz), 7.64 (1H, s), 7.55-7.60 (1H, m), 7.46-7.53 (3H, m), 7.42 (1H, t, J = 8.0 Hz), 7.33 (1H, d, J = 7.2 Hz), 6.78-6.85 (1H, m), 6.36 (1H, d, J = 15.2 Hz), 4.25-4.43 (4H, m), 3.08 (2H, d, J = 5.2 Hz), 2.72-2.86 (4H, m), 2.19 (6H, s), 1.60-1.70 (2H, m), 1.19 (6H, d, J = 7.2 Hz), 1.05-1.10 (2H, m); LCMS: 98.9%, MS (ESI): m/z 619.4[M + H]+. |
| 12 | 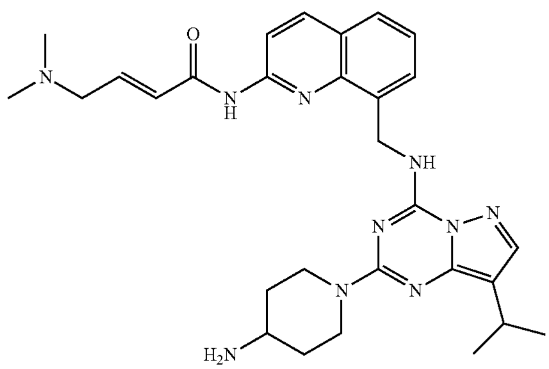 [SMILES: CC(C)c1cnn2c(NCc3cccc4ccc(NC(=O)/C=C/CN(C)C)nc34)nc(N3CCC(N)CC3)nc12] | white powder; $^1$H-NMR (CDCl3, 400 MHz): δ 9.36 (1H, brs), 8.51 (1H, d, J = 9.2 Hz), 8.14-8.17 (2H, m), 7.70 (1H, d, J = 6.8 Hz), 7.66 (1H, d, J = 6.8 Hz), 7.60 (1H, s), 7.34-7.38 (1H, m), 7.02-7.11 (1H, m), 6.32 (1H, d, J = 16.0 Hz), 5.16 (2H, d, J = 6.0 Hz), 4.78-4.84 (2H, m), 3.18 (2H, d, J = 6.4 Hz), 2.94-3.03 (4H, m), 2.33 (6H, s), 1.92-1.97 (2H, m), 1.30-1.45 (2H, m), 1.25 (6H, d, J = 6.8 Hz); LCMS: 95.9%, MS (ESI): m/z 565.3[M + Na]+. |
| 13 | 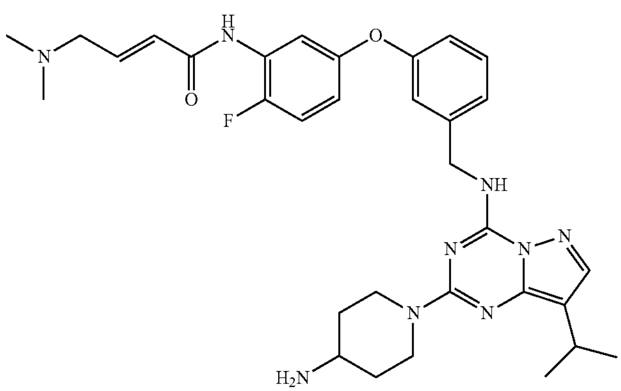 [SMILES: CC(C)c1cnn2c(NCc3cccc(Oc4ccc(F)c(NC(=O)/C=C/CN(C)C)c4)c3)nc(N3CCC(N)CC3)nc12] | white powder; $^1$HNMR (DMSO-d$_6$, 400 MHz): δ 9.93 (1H, brs), 8.89 (1H, brs), 7.81-7.83 (1H, m), 7.72 (1H, s), 7.23-7.31 (2H, m), 7.15 (1H, d, J = 8.0 Hz), 7.06 (1H, s), 6.86 (1H, dd, J = 7.6, 2.0 Hz), 6.69-6.75 (2H, m), 6.46 (1H, d, J = 15.6), 4.50-4.55 (4H, m), 3.03 (2H, d, J = 4.8 Hz) 2.84-2.93 (4H, m), 2.16 (6H, s), 1.75-1.80 (2H, m), 1.18-1.23 (8H, m); LCMS: 100%, MS (ESI): m/z 624.3[M + Na]$^+$. |
| 14 | 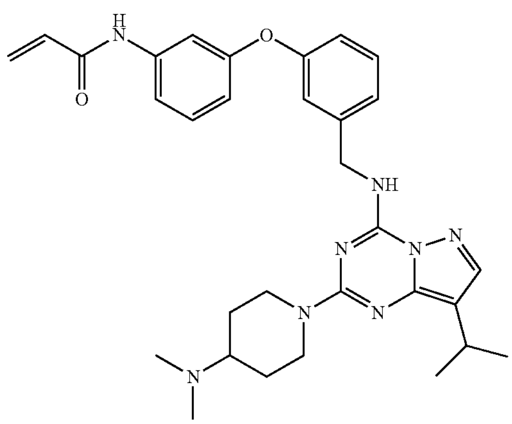 [SMILES: C=CC(=O)Nc1cccc(Oc2cccc(CNc3nc(N4CCC(N(C)C)CC4)nc4c(C(C)C)cnn34)c2)c1] | yellow powder; $^1$H-NMR (CDCl3, 400 MHz): δ 7.74 (1H, brs), 7.60 (1H, s), 7.41 (1H, d, J = 8.0 Hz), 7.23-7.31 (3H, m), 7.05-7.13 (2H, m), 6.93 (1H, dd, J = 8.4, 1.6 Hz), 6.75 (1H, dd, J = 8.4, 1.6 Hz), 6.69 (1H, t, J = 5.6 Hz), 6.42 (1H, dd, J = 16.8, 1.6 Hz), 6.21-6.31 (1H, m), 5.75 (1H, d, J = 10.4), 4.78-4.88 (2H, m), 4.68 (2H, d, J = 6.0 Hz), 2.98-3.09 (1H, m), 2.72-2.85 (2H, m), 2.39-2.49 (1H, m), 2.31 (6H, s), 1.82-1.88 (2H, m), 1.34-1.47 (2H, m), 1.28 (6H, d, J = 6.8 Hz); LCMS: 94.2%, MS (ESI): m/z 55.3[M + H]$^+$. |

TABLE 6-continued

Summarized compounds 1-88 in terms of their structures and corresponding characteristics

| #cpds | Structure | Characterization Data |
|---|---|---|
| 15 | 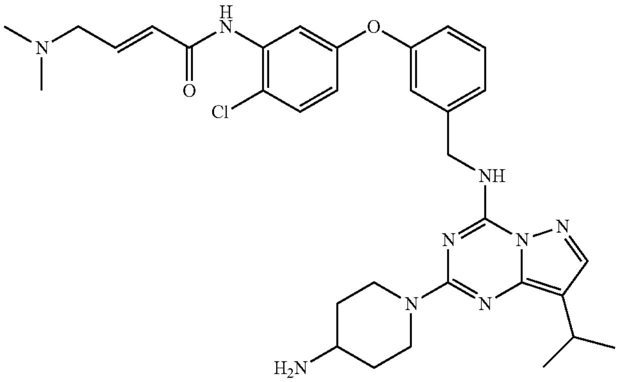 | yellow powder; $^1$H-NMR (CDCl3, 400 MHz): δ 8.18 (1H, s), 7.80 (1H, brs), 7.62 (1H, s), 7.27-7.32 (2H, m), 7.07-7.11 (2H, m), 6.92-7.05 (2H, m), 6.69-6.74 (2H, m), 6.24 (1H, d, J = 15.2 Hz), 4.67-4.76 (4H, m), 3.20-3.21 (2H, m), 3.01-3.04 (2H, m), 2.88-2.94 (2H, m), 2.33 (6H, s), 1.98-2.01 (2H, m), 1.36-1.45 (2H, m), 1.28 (6H, d, J = 6.8 Hz); LCMS: 95.4%, MS (ESI): m/z 618.3[M + H]$^+$. |
| 16 | 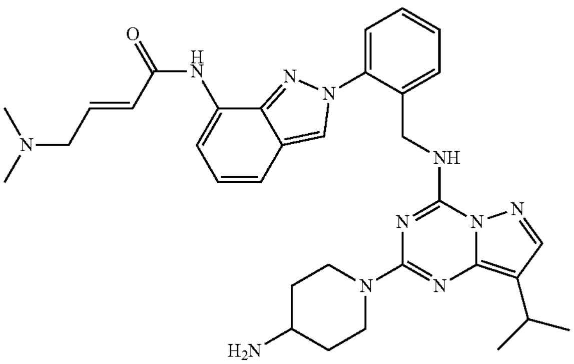 [SMILES: CC(C)c1cnn2c(NCc3ccccc3-n3cc4cccc(NC(=O)/C=C/CN(C)C)c4n3)nc(N3CCC(N)CC3)nc12] | yellowpowder; $^1$H-NMR (CDCl3, 400 MHz): δ 9.22 (1H brs), 8.59 (1H, t, J = 5.8 Hz), 8.42 (1H, d, J = 7.6 Hz), 8.19 (1H, s), 7.70 (1H, s), 7.66 (1H, d, J = 6.8 Hz), 7.40-7.47 (4H, m), 7.16-7.20 (1H, m), 7.04-7.08 (1H, m), 6.61 (1H, d, J = 15.2 Hz), 4.83-4.88 (2H, m), 4.58 (2H, d, J = 6.0 Hz), 3.38-3.40 (1H, m), 3.27 (2H, d, J = 6.4 Hz), 2.98-3.05 (3H, m), 2.56 (6H, s), 2.21-2.38 (2H, m), 1.65-1.68 (2H, m), 1.25-1.29 (8H, m); LCMS: 95.6%, MS (ESI): m/z 608.3[M + H]$^+$. |
| 17 | 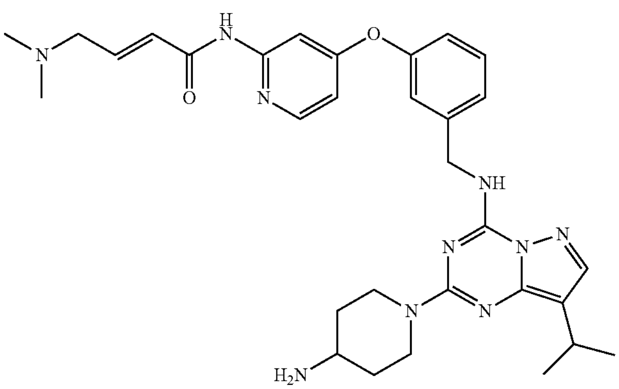 [SMILES: CC(C)c1cnn2c(NCc3cccc(Oc4ccnc(NC(=O)/C=C/CN(C)C)c4)c3)nc(N3CCC(N)CC3)nc12] | white powder; $^1$H-NMR (DMSO-d$_6$, 400 MHz): δ 11.13 (1H, brs), 10.76 (1H, brs), 9.08 (1H, brs), 8.24 (1H, d, J = 6.0 Hz), 8.00-8.22 (3H, m), 7.79 (1H, s), 7.73 (1H, s), 7.43 (1H, d, J = 8.0 Hz), 7.33 (1H, d, J = 7.2 Hz), 7.23 (1H, s), 7.05-7.15 (1H, m), 6.80-6.90 (1H, m), 6.73 (1H, d, J = 3.6 Hz), 6.56 (1H, d, J = 16.0 Hz), 4.55-4.70 (4H, m), 3.85-3.95 (2H, m), 2.85-3.00 (4H, m), 2.74 (6H, d, J = 3.6 Hz), 1.85-2.00 (2H, m), 1.30-1.50 (2H, m), 1.22 (6H, d, J = 6.4 Hz); LCMS: 100%, MS (ESI): m/z 607.3 [M + Na]$^+$ |
| 18 | 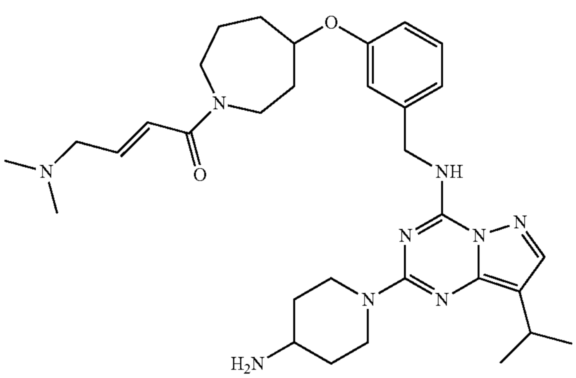 [SMILES: CC(C)c1cnn2c(NCc3cccc(OC4CCCN(C(=O)/C=C/CN(C)C)CC4)c3)nc(N3CCC(N)CC3)nc12] | Racemic mixture; white powder; $^1$H-NMR (CDCl3, 400 MHz): δ 7.61 (1H, s), 7.24 (1H, t, J = 7.8 Hz), 6.88-6.96 (3H, m), 6.78-6.81 (1H, m), 6.60-6.65 (1H, m), 6.40-6.45 (1H, m), 4.69-4.76 (4H, m), 4.48-4.51 (1H, m), 3.83-3.90 (1H, m), 3.43-3.72 (3H, m), 2.90-3.11 (6H, m), 2.27 (6H, d, J = 5.6 Hz), 1.99-2.08 (4H, m), 1.73-1.91 (4H, m), 1.25-1.37 (8H, m); LCMS: 94.9%, MS (ESI): m/z 612.5[M + Na]$^+$. |

TABLE 6-continued

Summarized compounds 1-88 in terms of their structures and corresponding characteristics

| #cpds | Structure | Characterization Data |
|---|---|---|
| 19 | 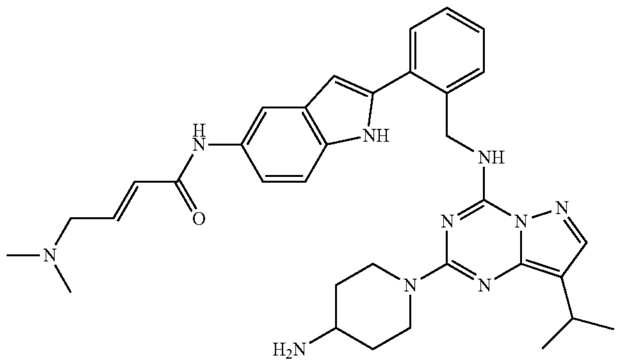 [SMILES: CC(C)c1cnn2c(NCc3ccccc3-c3cc4cc(NC(=O)/C=C/CN(C)C)ccc4[nH]3)nc(N3CCC(N)CC3)nc12] | white powder; $^1$H-NMR (DMSO-d$_6$, 400 MHz): δ 8.72 (1H, s), 7.87 (1H, s), 7.58 (2H, s), 7.46-7.54 (2H, m), 7.33-7.40 (2H, m), 7.18-7.26 (2H, m), 6.90-7.01 (1H, m), 6.64 (1H, brs), 6.54 (1H, s), 6.13 (1H, d, J = 15.6 Hz), 4.82 (2H, s), 4.55-4.65 (2H, m), 3.11 (2H, d, J = 5.2 Hz), 2.98-3.05 (1H, m), 2.79-2.88 (3H, m), 2.28 (6H, s), 1.70-1.80 (2H, m), 1.29 (8H, d, J = 6.8 Hz); LCMS: 100%, MS (ESI): m/z 629.2 [M + Na]$^+$ |
| 20 | 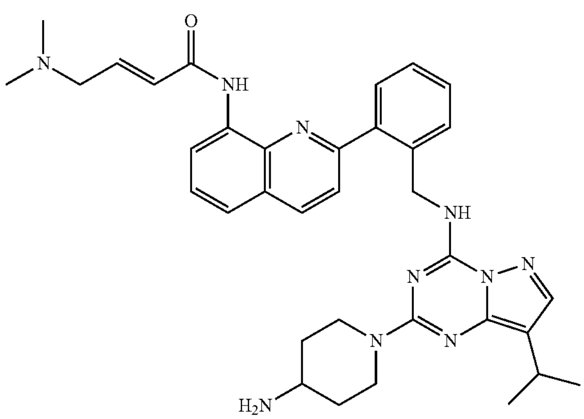 [SMILES: CC(C)c1cnn2c(NCc3ccccc3-c3ccc4cccc(NC(=O)/C=C/CN(C)C)c4n3)nc(N3CCC(N)CC3)nc12] | yellow powder; $^1$H NMR (DMSO-d$_6$, 400 MHz): δ 10.08 (1H, brs), 8.89 (1H, t, J = 5.6 Hz), 8.69 (1H, d, J = 7.6 Hz), 8.50 (1H, d, J = 8.4 Hz), 7.88 (1H, d, J = 8.4 Hz), 7.60-7.85 (7H, m), 7.43-7.49 (2H, m), 6.73-6.80 (1H, m), 6.50 (1H, d, J = 16.0 Hz), 5.04 (2H, d, J = 6.4 Hz), 4.30-4.33 (2H, m), 3.11-3.17 (1H, m), 3.00 (2H, d, J = 6.4 Hz), 2.83-2.92 (1H, m), 2.62-2.67 (2H, m), 2.11 (6H, s), 1.71-1.75 (2H, m), 1.07-1.27 (8H, m); LCMS: 100%, MS (ESI): m/z 619.4[M + H]$^+$. |
| 21 | 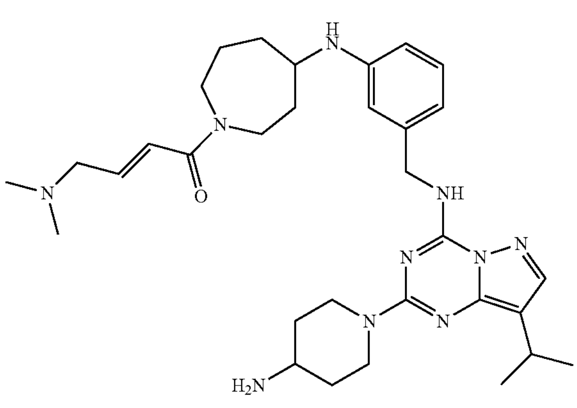 [SMILES: CC(C)c1cnn2c(NCc3cccc(NC4CCCN(C(=O)/C=C/CN(C)C)CC4)c3)nc(N3CCC(N)CC3)nc12] | Racemic mixture; white powder; $^1$H-NMR (CDCl3, 400 MHz): δ 7.60 (1H, s), 7.12 (1H, t, J = 7.2 Hz), 6.82-6.93 (1H, m), 6.64-6.69 (1H, m), 6.60-6.63 (1H, m), 6.40-6.52 (3H, m), 4.70-4.80 (2H, m), 4.56-4.70 (2H, m), 3.37-3.83 (6H, m), 2.89-3.16 (6H, m), 2.25-2.31 (6H, m), 1.93-2.01 (3H, m), 1.59-1.76 (2H, m), 1.39-1.48 (2H, m), 1.23-1.33 (8H, m); LCMS: 100%, MS (ESI): m/z 611.5[M + Na]$^+$. |

TABLE 6-continued

Summarized compounds 1-88 in terms of their structures and corresponding characteristics

| #cpds | Structure | Characterization Data |
|---|---|---|
| 22 | 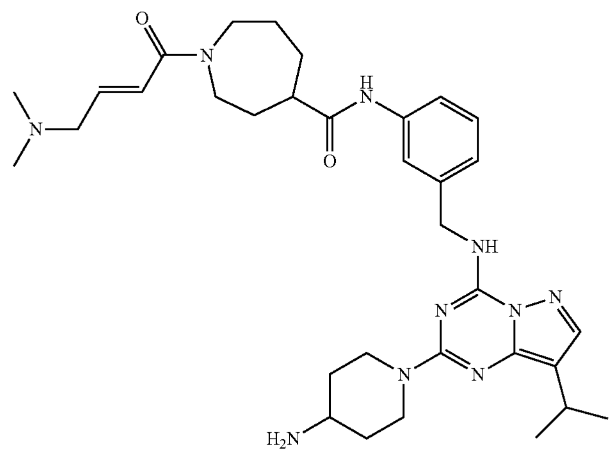 [SMILES: CC(C)c1cnn2c(NCc3cccc(NC(=O)C4CCCN(C(=O)/C=C/CN(C)C)CC4)c3)nc(N3CCC(N)CC3)nc12] | Racemic mixture; white powder; $^1$H-NMR (DMSO-$d_6$, 400 MHz): δ 7.89 (1H, brs), 7.59 (1H, s), 7.42-7.56 (2H, m), 7.21-7.26 (1H, m), 7.06 (1H, t, J = 6.0 Hz), 6.83-6.92 (1H, m), 6.65-6.75 (1H, m), 6.40 (1H, d, J =15.6 Hz), 4.65-4.77 (4H, m), 3.86-4.03 (1H, m), 3.75-3.85 (1H, m), 3.63 (1H, t, J = 5.6 Hz), 3.42-3.53 (1H, m), 3.18-3.36 (1H, m), 2.88-3.12 (6H, m), 2.32-2.46 (1H, m), 2.20-2.30 (7H, m), 1.83-1.92 (2H, m), 1.54-1.82 (2H, m), 1.19-1.40 (10H, m); LCMS: 100%, MS (ESI): m/z 617.5[M + H]$^+$. |
| 23 | 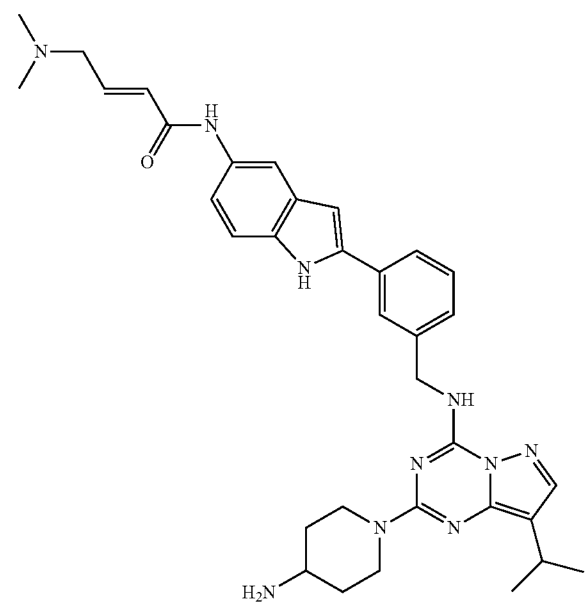 [SMILES: CC(C)c1cnn2c(NCc3cccc(-c4cc5cc(NC(=O)/C=C/CN(C)C)ccc5[nH]4)c3)nc(N3CCC(N)CC3)nc12] | white powder; $^1$H NMR (DMSO-$d_6$, 400 MHz): δ 11.52 (1H, brs), 9.98 (1H, brs), 9.01 (1H, t, J = 5.4 Hz), 8.00 (1H, s), 7.91 (1H, s), 7.77 (1H, s), 7.73 (1H, d, J = 7.2 Hz), 7.39 (1H, t, J = 8.0 Hz), 7.31-7.34 (2H, m), 7.26 (1H, d, J = 8.0 Hz), 6.83 (1H, s), 6.67-6.73 (1H, m), 6.33 (1H, d, J = 15.2 Hz), 4.63-4.67 (4H, m), 3.13-3.19 (3H, m), 2.86-2.94 (3H, m), 2.26 (6H, s), 1.85-1.91 (2H, m), 1.29-1.36 (2H, m), 1.23 (6H, d, J = 6.8 Hz); LCMS: 100%, MS (ESI): m/z 607.3[M + H]$^+$. |
| 24 | 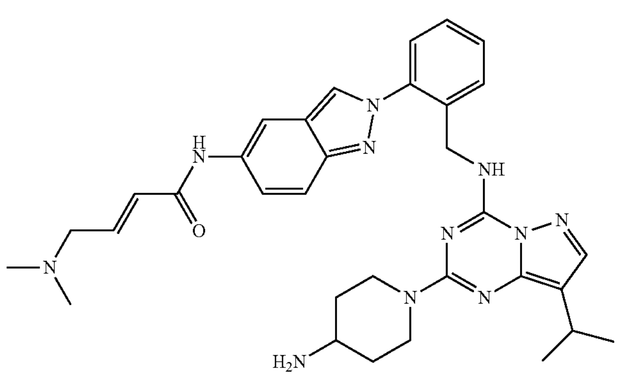 [SMILES: CC(C)c1cnn2c(NCc3ccccc3-n3cc4cc(NC(=O)/C=C/CN(C)C)ccc4n3)nc(N3CCC(N)CC3)nc12] | brown powder; $^1$H-NMR (DMSO-$d_6$, 400 MHz): δ 10.2 (1 2.72-2.83 (2H, m), 2.17-2.35 (6H, m), 1.81-1.90 (2H, m), 1.14-1.34 (8H, m); LCMS: 96.5%, MS (ESI): m/z = 608.3 [M + H]$^+$. |

TABLE 6-continued

Summarized compounds 1-88 in terms of their structures and corresponding characteristics

| #cpds | Structure | Characterization Data |
|---|---|---|
| 25 | 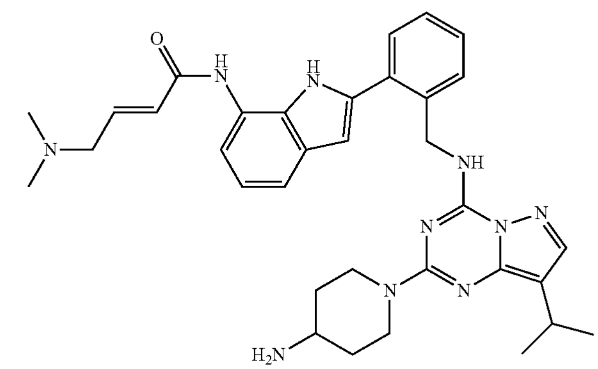 [SMILES: CC(C)c1cnn2c(NCc3ccccc3-c3cc4cccc(NC(=O)/C=C/CN(C)C)c4[nH]3)nc(N3CCC(N)CC3)nc12] | white powder; $^1$H-NMR (CDCl3, 400 MHz): δ 10.44 (1H, brs), 7.61 (1H, brs), 7.54-7.63 (3H, m), 7.48 (1H, d, J = 7.6 Hz), 7.32-7.41 (2H, m), 6.93-7.07 (2H, m), 6.79 (1H, d, J = 7.2 Hz), 6.57-6.68 (2H, m), 6.21 (1H, d, J = 14.8 Hz), 4.90 (2H, d, J = 5.6 Hz), 4.58-4.68 (2H, m), 3.12 (2H, d, J = 5.6 Hz), 3.98-3.06 (1H, m), 2.80-2.91 (3H, m), 2.29 (6H, s), 1.74-1.84 (2H, m), 1.29 (6H, d, J = 6.8 Hz), 1.20-1.26 (2H, m); LCMS: 100%, MS (ESI): m/z 629.3[M + Na]$^+$. |
| 26 | 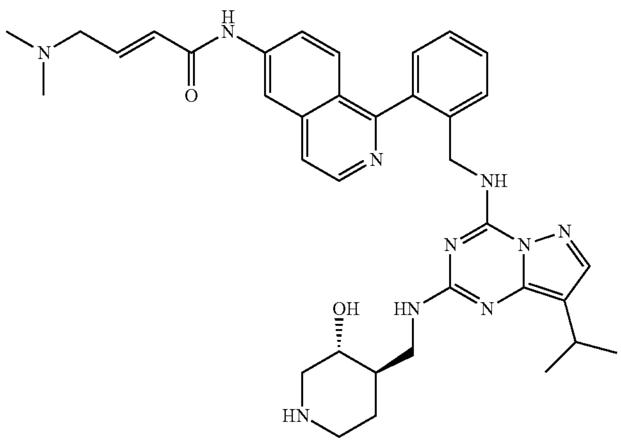 [SMILES: CC(C)c1cnn2c(NCc3ccccc3-c3nccc4cc(NC(=O)/C=C/CN(C)C)ccc34)nc(NC[C@H]3CCNC[C@@H]3O)nc12] | (3R, 4R); pale-yellow powder; $^1$H NMR (400 MHz, DMSO-d$_6$): δ 10.91-11.17 (2H, m), 9.03 (1H, br s), 8.82 (1H, br s), 8.38-8.58 (3H, m), 7.79-7.89 (1H, m), 7.70-7.77 (1H, m), 7.62-7.67 (1H, m), 7.50-7.57 (2H, m), 7.42-7.49 (1H, m), 7.37 (1H, br d, J = 7.2 Hz), 6.85-6.98 (1H, m), 6.63 (1H, d, J = 15.6 Hz), 5.67-5.96 (1H, 1H), 4.33-4.50 (2H, m), 3.96 (2H, d, J = 6.8 Hz), 3.42-3.57 (2H, m), 2.97-3.25 (3H, m), 2.81-2.90 (1H, m), 2.77 (6H, s), 2.58-2.69 (1H, m), 1.39-1.90 (3H, m), 1.19 (6H, br d, J = 6.4 Hz); LCMS: 100%, MS (ESI): m/z 649.3[M + H]$^+$ |
| 27 | 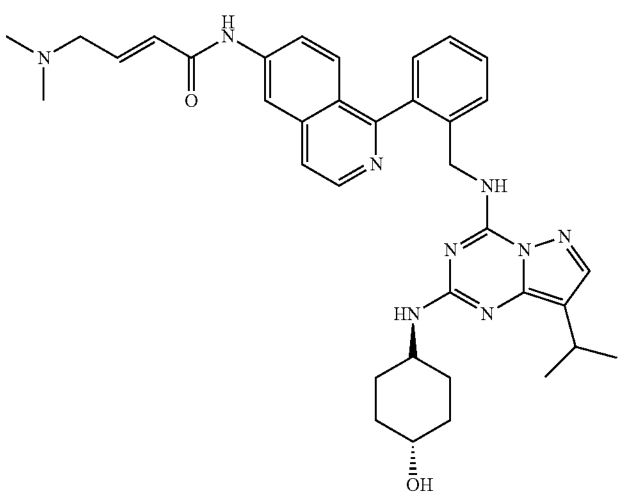 | (1R, 4R); yellow powder; $^1$H-NMR (400 MHz, CD$_3$OD): δ 8.67 (1H, s), 8.42 (1H, br d, J = 6.4 Hz), 8.24 (1H, br d, J = 6.4 Hz), 7.84-7.93 (2H, m), 7.78 (1H, d, J = 9.2 Hz), 7.68 (1H, br s), 7.62 (3H, m), 6.95-7.10 (1H, m), 6.72 (1 H, br d, J = 15.2 Hz), 4.70-5.10 (2H, m), 4.07 (2H, br d, J = 6.8 Hz) 3.47-3.65 (2H, m), 2.91-3.01 (6H, m), 2.77-2.87 (1H, m), 1.87-2.10 (3H, m), 1.65-1.72 (1H, m), 1.30-1.51 (4H, m), 1.12-1.23 (6H, m); LCMS: 100%, MS (ESI): m/z 634.3[M + H]$^+$. |

TABLE 6-continued

Summarized compounds 1-88 in terms of their structures and corresponding characteristics

| #cpds | Structure | Characterization Data |
|---|---|---|
| 28 | 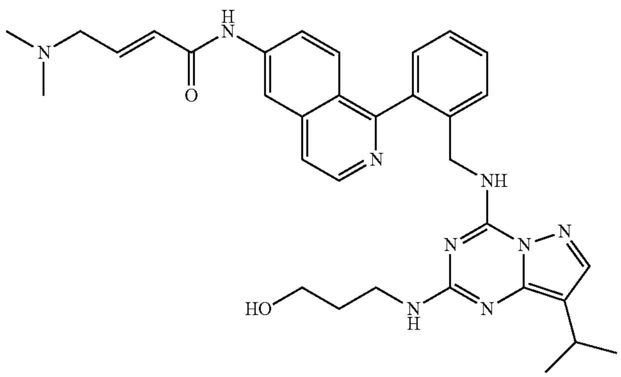 [SMILES: CC(C)c1cnn2c(NCc3ccccc3-c3nccc4cc(NC(=O)/C=C/CN(C)C)ccc34)nc(NCCCO)nc12] | yellow powder; $^1$H NMR (400 MHz, CD$_3$OD): δ 8.42 (1H, s), 8.37 (1H, d, J = 6.0 Hz), 7.68-7.77 (2H, m), 7.61-7.67 (1H, m), 7.46-7.60 (4H, m), 7.40 (1H, d, J = 7.6 Hz), 6.92-7.02 (1H, m), 6.64 (1 H, d, J = 15.2 Hz), 5.01-5.04 (1H, m), 4.39-4.43 (1H, m), 4.06 (2H, d, J = 6.4 Hz), 3.65 (2H, t, J = 6.0 Hz), 3.33-3.41 (2H, m), 2.97 (6H, s), 2.82-2.91 (1H, m), 1.74-1.80 (2H, m), 1.15-1.25 (6H, m); LCMS: 100%, MS (ESI): m/z 594.3[M + H]$^+$. |
| 29 | 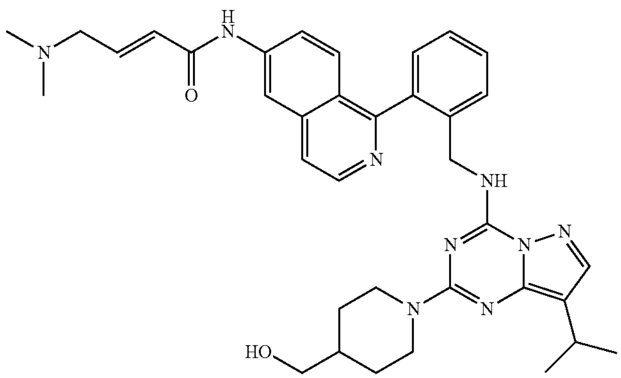 [SMILES: CC(C)c1cnn2c(NCc3ccccc3-c3nccc4cc(NC(=O)/C=C/CN(C)C)ccc34)nc(N3CCC(CO)CC3)nc12] | yellow solid; $^1$H-NMR (400 MHz, CD$_3$OD): δ 8.66 (1H, s), 6.42-6.44 (1H, m), 8.21-8.23 (1H, m), 7.80-7.87 (3H, m), 7.59-7.71 (4H, m), 7.00-7.07 (1H, m), 6.74-6.78 (1H, d, J = 15.6 Hz), 4.95-5.02 (1H, m), 4.71-4.81 (1H, m), 4.31-3.41 (2H, m), 4.08 (2H, d, J = 7.2 Hz), 3.46-3.47 (2H, m), 3.08-3.13 (2H, m), 2.96-2.97 (6H, m), 1.85-1.97 (2H, m), 1.29-1.38 (2H, m), 1.16-1.19 (6H, m); LCMS: 100.0%, MS (ESI): 634.3 m/z [(M + H)]$^+$. |
| 30 | 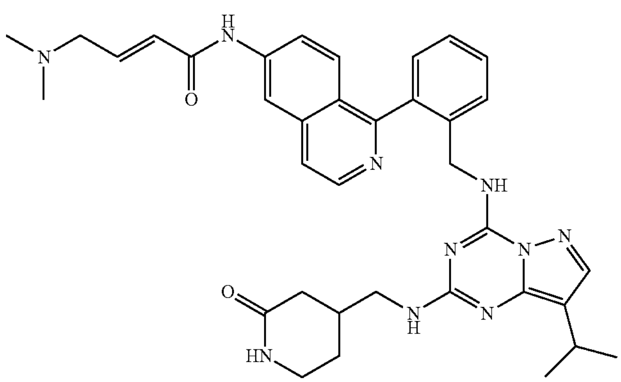 [SMILES: CC(C)c1cnn2c(NCc3ccccc3-c3nccc4cc(NC(=O)/C=C/CN(C)C)ccc34)nc(NCC3CCNC(=O)C3)nc12] | Racemic mixture; off-white powder; $^1$H NMR (400 MHz, CD$_3$OD): δ 8.27-8.42 (2H, m) 7.25-7.75 (8H, m), 6.91-7.07 (1H, m), 6.33 (1H, d, J = 15.2 Hz), 4.80-4.87 (1H, m), 4.60-4.67 (2H, m), 4.28-4.37 (1H, m), 3.47-3.56 (1H, m), 3.26 (2H, d, J = 6.4 Hz), 3.05-3.13 (1H, m), 2.85-2.92 (1H, m), 2.45-2.54 (2H, m), 2.36 (6H, s), 2.01-2.11 (1H, m), 1.65-1.75 (2H, m), 1.15-1.26 (6H, m); LCMS: 95.9%, MS (ESI): m/z 324.2 [M/2 + H]$^+$. |
| 31 | 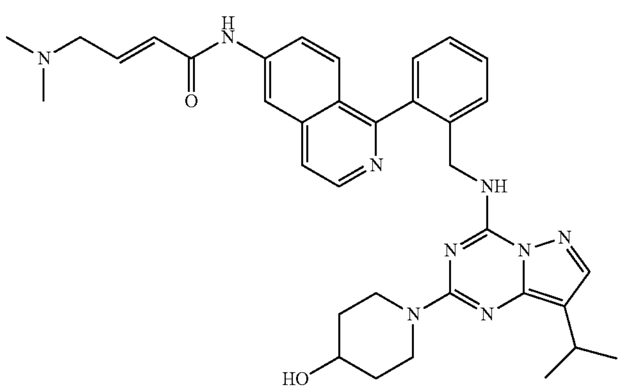 [SMILES: CC(C)c1cnn2c(NCc3ccccc3-c3nccc4cc(NC(=O)/C=C/CN(C)C)ccc34)nc(N3CCC(O)CC3)nc12] | light yellow powder; $^1$H NMR (400 MHz, CD$_3$OD): δ 8.32 (1H, d, J = 6.0 Hz), 8.29 (1H, s), 7.63-7.68 (1H, m), 7.53-7.61 (2H, m), 7.49 (1H, t, J = 6.8 Hz), 7.36-7.40 (2H, m), 7.31-7.35 (2H, m), 6.91-7.00 (1H, m), 6.38-6.42 (1H, m), 4.34-4.38 (1H, m), 4.13-4.25 (2H, m), 3.74-3.82 (1H, m), 3.49 (2H, d, J = 6.8 Hz), 2.98-3.13 (2H, m), 2.85 (1H, m), 2.53 (6H, s), 1.81 (2H, m), 1.23-1.45(3H, m), 1.19 (6H, d, J = 6.8 Hz); LCMS: 100%, MS (ESI): m/z 620.2 [M + H]$^+$. |

TABLE 6-continued

Summarized compounds 1-88 in terms of their structures and corresponding characteristics

| #cpds | Structure | Characterization Data |
|---|---|---|
| 32 | 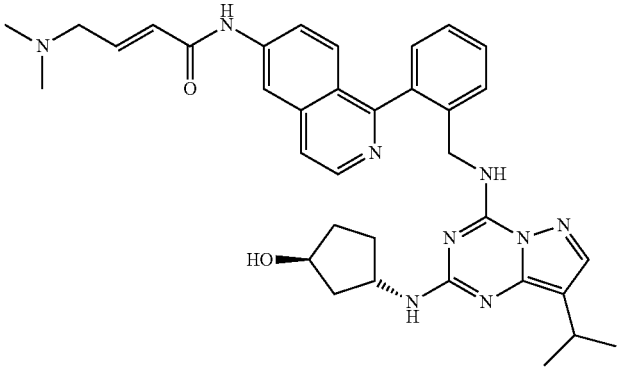 | (1S, 3S); light yellow solid; $^1$H-NMR (MeOD, 400 MHz): δ 8.69-8.71 (1H, m), 8.42-8.45 (1H, m), 8.25-8.27 (1H, m), 7.80-7.88 (3H, m), 7.58-7.72 (4H, m), 6.99-7.07 (1H, m), 6.73 (1H, d, J =15.2 Hz), 5.01-5.06 (1H, m), 4.91-4.94 (1H, m), 4.71-4.78 (1H, m), 4.39-4.44 (1H, m), 4.26-4.29 (1H, m), 4.07(2H, d, J = 7.2 Hz), 2.96 (6H, s), 2.84-2.88 (1H, m), 2.06-2.32 (2H, m), 1.95-1.99 (1H, m), 1.61-1.80 (3H, m), 1.18-1.21 (6H, m); LCMS: 99.7%, MS (ESI): 620.2 m/z [M + H]$^+$. |
| 33 | 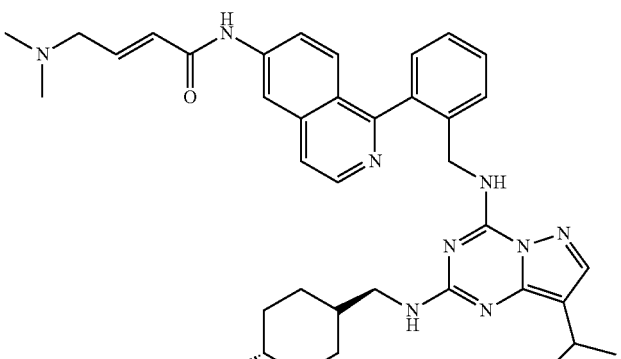 | (1R, 4R); white powder; 1H NMR (CD$_3$OD, 400 MHz): δ 8.66 (1H, d, J = 2.0 Hz), 8.43 (1H, d, J = 6.8 Hz), 8.23 (1H, d, J = 6.8 Hz), 7.76-7.88 (3H, m), 7.66-7.74 (1H, m), 7.55-7.63 (3H, m), 6.97-7.08 (1H, m), 6.71 (1H, d, J = 15.6 Hz), 4.89-4.90 (2H, m), 4.07 (2H, d, J = 6.4 Hz), 3.45-3.54 (1H, m), 3.17-3.26 (1H, m), 3.04 (1H, m), 2.96 (6H, s), 2.84 (1H, m), 1.88-2.05 (2H, m), 1.67-1.83 (2H, m), 1.36-1.49 (1H, m), 1.28-1.35 (1H, m), 1.14-1.21 (7H, m), 0.84-1.11 (2H, m); LCMS: 99.7%, MS (ESI): m/z 648.2 [M + H]$^+$; HPLC (254 nm): 100%. |
| 34 | 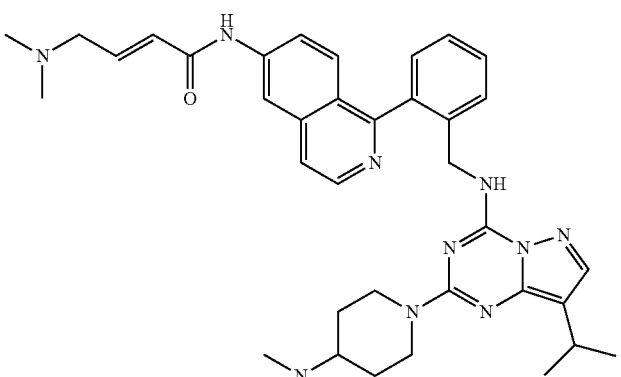 | yellow powder; $^1$H NMR (400 MHz, CD$_3$OD): δ 8.67 (1H, s), 8.38-8.45 (1H, br s), 8.18-8.26 (1H, m), 7.78-7.88 (3H, m), 7.55-7.73 (4H, m), 6.97-7.08 (1H, m), 6.74 (1H, d, J = 15.2 Hz), 4.95-5.03 (1H, m), 4.66-4.76 (1H, m), 4.48-4.59 (2H, m), 4.07 (2H, d, J = 6.8 Hz), 3.39-3.54 (1H, m), 3.03-3.24 (3H, m), 2.96 (6H, s), 2.76 (3H, s), 2.14-2.31 (2H, m), 1.46-1.80 (2H, m), 1.19 (6H, d, J = 6.8 Hz); LCMS: 99.7%, MS (ESI): m/z 633.3 [M + H]$^+$ |
| 35 | 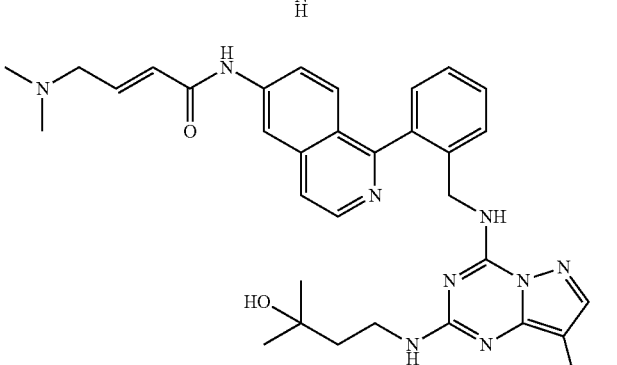 | light yellow solid; $^1$H-NMR (CD$_3$OD, 400 MHz): δ 8.69 (1H, s), 8.44 (1H, d, J = 6.4 Hz), 8.23 (1H, d, J = 6.8 Hz), 7.81-7.87 (3H, m), 7.68-7.72 (2H, m), 7.59-7.60 (2H, m), 6.99-7.07 (1H, m), 6.73 (1H, d, J = 15.2 Hz), 5.04-5.08 (1H, m), 4.70-4.74 (1H, m), 4.07 (2H, d, J = 6.4 Hz), 3.41-3.44 (2H, m), 2.96 (6H, s), 2.82-2.86 (1H, m), 1.69-1.73 (2H, m), 1.28 (6H, s), 1.21 (6H, d, J = 6.8 Hz); LCMS: 98.2%, MS (ESI): 622.3 m/z [(M + H)]$^+$. |

TABLE 6-continued

Summarized compounds 1-88 in terms of their structures and corresponding characteristics

| #cpds | Structure | Characterization Data |
|---|---|---|
| 36 | 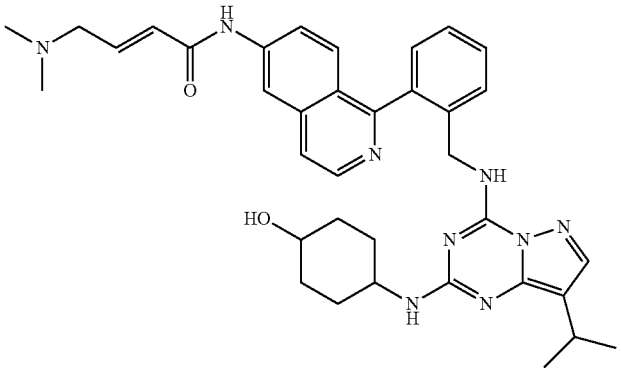 [SMILES: CC(C)c1cnn2c(NCc3ccccc3-c3nccc4cc(NC(=O)/C=C/CN(C)C)ccc34)nc(NC3CCC(O)CC3)nc12] | White solid; $^1$H NMR (400 MHz, DMSO-d$_6$): δ 11.24-11.45 (2H, m), 9.42-9.66 (1H, m), 8.61-8.66 (1H, m), 8.41-8.47 (1H, m), 8.18-8.23 (1H, m), 7.72-7.75 (2H, m), 7.67-7.69 (1H, m), 7.54-7.60 (1H, m), 7.41-7.52 (2H, m), 6.91-7.01 (1H, m), 6.65 (1 H, m), 4.74-4.83 (1H, m), 4.50-4.61 (1H, m), 3.95-4.02 (2H, m), 2.72-2.81 (6H, m), 1.76-1.91 (1H, m), 1.44-1.68 (5H, m), 1.21-1.38 (2H, m), 1.10-1.16 (6H, m); LCMS: 100%, MS (ESI): m/z 634.3 [M + H]$^+$. |
| 37 | 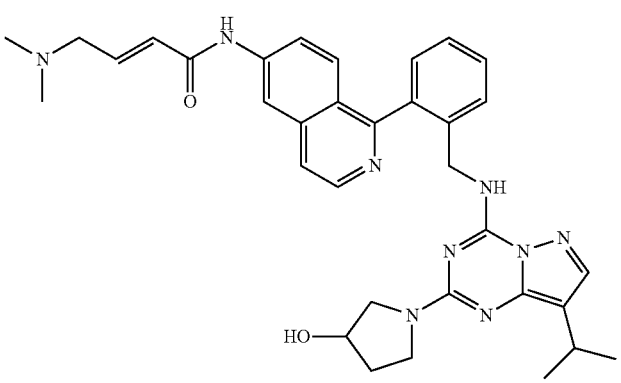 [SMILES: CC(C)c1cnn2c(NCc3ccccc3-c3nccc4cc(NC(=O)/C=C/CN(C)C)ccc34)nc(N3CCC(O)C3)nc12] | Racemic mixture; off-white powder; $^1$H NMR (400 MHz, CD$_3$OD): δ 8.64-8.70 (1H, m), 8.40-8.51 (1H, m), 8.17-8.28 (1H, m), 7.81-7.92 (3H, m), 7.68-7.75 (2H, m), 7.58-7.66 (2H, m), 7.01-7.09 (1H, m), 6.77 (1H, d, J = 15.2 Hz), 5.11-5.20 (1H, m), 4.53-4.72 (2H, m), 4.09 (2H, d, J = 7.2 Hz), 3.38-3.86 (4H, m), 3.08-3.21 (1H, m), 2.93 (6H, s), 2.03-2.32 (2H, m), 1.14-1.26 (6H, m); HPLC: 100%, MS (ESI): m/z 606.2 [M + H]$^+$ |
| 38 | 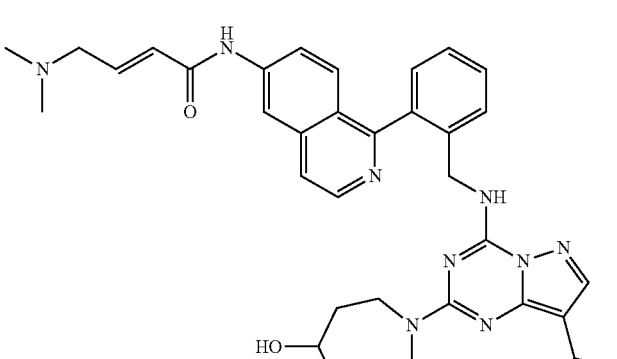 | Racemic mixture; light yellow solid; $^1$H-NMR (MeOD, 400 MHz): δ 8.67 (1H, s), 8.41-8.43 (1H, m), 8.18-8.23 (1H, m), 7.80-7.87 (3H, m), 7.59-7.68 (4H, m), 6.99-7.07 (1H, m), 6.74 (1H, d, J = 15.2 Hz), 4.95-4.99 (1H, m), 4.72-4.81 (1H, m), 4.07 (2H, d, J = 7.2 Hz), 3.42-3.93 (4H, m), 3.09-3.14 (1H, m), 2.96 (6H, s), 2.07-2.22 (1H, m), 1.43-1.98 (5H, m), 1.16-1.19 (6H, m); LCMS: 99.8%, MS (ESI): 634.2 m/z [(M + H)]$^+$ |
| 39 | 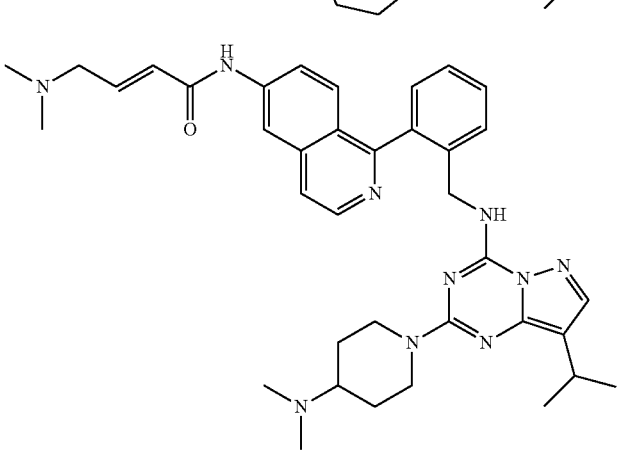 | Light yellow solid; $^1$H NMR (400 MHz, CD$_3$OD): δ 8.68 (1H, s), 8.42 (1H, d, J = 6.0 Hz), 8.21 (1H, d, J = 6.4 Hz), 7.82-7.89 (3H, m), 7.65-7.75 (2H, m), 7.59-7.64 (2H, m), 7.00-7.11 (1H, m), 6.74 (1H, d, J = 15.6 Hz), 4.98-5.07 (1H, m), 4.68-4.75 (1H, m), 4.54-4.62 (2H, m), 4.07 (2H, d, J = 6.8 Hz), 3.59-3.69 (1H, m), 3.08-3.28 (3H, m), 2.98 (6H, s), 2.94 (6H, s), 2.21-2.29 (2H, m), 1.72-1.87 (2H, m), 1.29-1.33 (2H, m), 1.19-1.24 (6H, m); LCMS: 97.9%, MS (ESI): m/z 647.3 [M + H]$^+$ |

TABLE 6-continued

Summarized compounds 1-88 in terms of their structures and corresponding characteristics

| #cpds | Structure | Characterization Data |
|---|---|---|
| 40 | 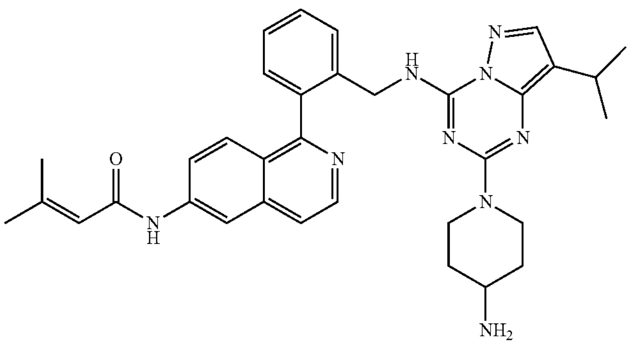 [SMILES: CC(C)=CC(=O)Nc1ccc2c(-c3ccccc3CNc3nc(N4CCC(N)CC4)nc4c(C(C)C)cnn34)nccc2c1] | yellow powder; $^1$H NMR (400 MHz, CD$_3$OD): δ 8.58 (1H, s), 8.38 (1H, s), 8.10-8.19 (1H, m), 7.80-7.90 (2H, m), 7.66-7.74 (2H, m), 7.52-7.63 (3H, m), 6.02 (1H, s), 5.00-5.09 (1H, m), 4.65-4.72 (1H, m), 4.48-4.56 (2H, m), 3.46-3.59 (1H, m), 2.97-3.23 (3H, m), 2.33 (3H, s), 2.10-2.22 (2H, m), 2.01 (3H, s), 1.47-1.76 (2H, m), 1.21 (6H, d, J = 6.8 Hz); HPLC: 96.1%, MS (ESI): m/z 590.2[M + H]$^+$ |
| 41 | 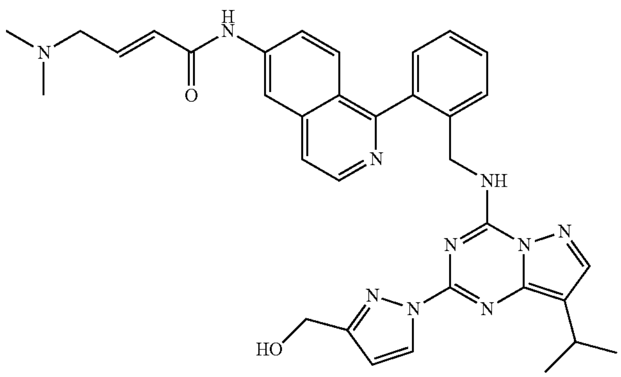 [SMILES: CC(C)c1cnn2c(NCc3ccccc3-c3nccc4cc(NC(=O)/C=C/CN(C)C)ccc34)nc(-n3ccc(CO)n3)nc12] | Yellow powder; $^1$H NMR (CD$_3$OD, 400 MHz): δ 8.51 (1H, s), 8.37 (1H, d, J = 2.8 Hz), 8.11 (1H, d, J = 6.8 Hz), 7.77-7.89 (4H, m), 7.62-7.71 (3H, m), 7.57 (1H, d, J = 6.8 Hz), 6.97-7.05 (1H, m), 6.58-6.63 (2H, m), 5.03-5.10 (1H, m), 4.76-4.81 (1H, m), 4.74 (2H, s), 4.09 (2H, d, J = 7.2 Hz), 3.08-3.17 (1H, m), 2.99 (6H, s), 1.29-1.34 (6H, m); LCMS: 99.2%, MS (ESI): 617.2 m/z [M + H]$^+$ |
| 42 | 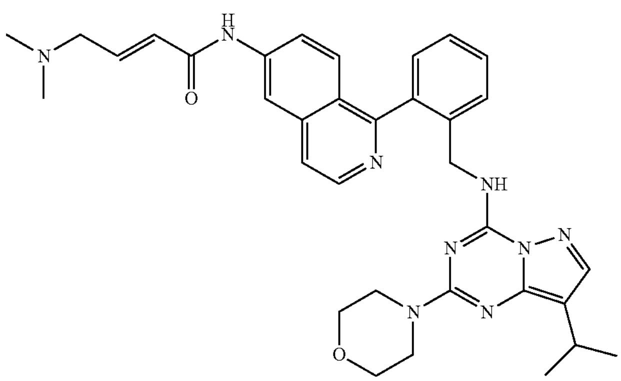 [SMILES: CC(C)c1cnn2c(NCc3ccccc3-c3nccc4cc(NC(=O)/C=C/CN(C)C)ccc34)nc(N3CCOCC3)nc12] | off-white powder; $^1$H NMR (400 MHz, CD$_3$OD): δ 8.65 (1H, d, J = 1.6 Hz), 8.41 (1H, d, J = 6.8 Hz), 8.21 (1H, d, J = 6.4 Hz), 7.77-7.89 (3H, m), 7.55-7.73 (4H, m), 6.97-7.12 (1H, m), 6.75 (1 H, d, J = 15.2 Hz), 4.97-5.03 (1H, m), 4.69-4.76 (1H, m), 4.07 (2H, d, J = 6.8 Hz), 3.66-3.85 (8H, m), 3.04-3.16 (1H, m), 2.96 (6 H, s), 1.16-1.21 (6H, m); HPLC: 99.4%, MS (ESI): m/z 606.2 [M + H]$^+$ |
| 43 | 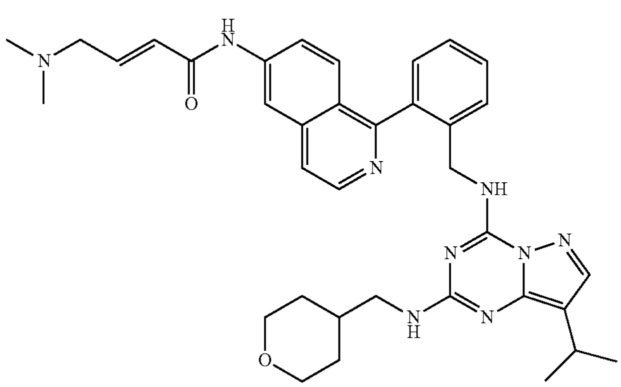 [SMILES: CC(C)c1cnn2c(NCc3ccccc3-c3nccc4cc(NC(=O)/C=C/CN(C)C)ccc34)nc(NCC3CCOCC3)nc12] | White powder; $^1$H NMR (CD$_3$OD, 400 MHz): δ 8.70 (1H, s), 8.46 (1H, d, J = 7.2 Hz), 8.22-8.28 (1H, m), 7.82-7.89 (3H, m), 7.57-7.76 (4H, m), 7.00-7.09 (1H, m), 6.71 (1H, d, J = 15.2 Hz), 4.96-5.02 (1H, m), 4.75-4.83 (1H, m), 4.08 (2H, d, J = 6.4 Hz), 3.84-4.01 (2H, m), 3.32-3.39 (2H, m), 3.23-3.28 (1H, m), 3.06-3.21 (1H, m), 2.98 (6H, s), 2.83-2.88 (1H, m), 1.73-1.80 (1H, m), 1.55-1.64 (2H, m), 1.25-1.32 (1H, m), 1.18-1.24 (6H, m); LCMS: 100%, MS (ESI): m/z 634.2[M + H]$^+$ |

TABLE 6-continued

Summarized compounds 1-88 in terms of their structures and corresponding characteristics

| #cpds | Structure | Characterization Data |
|---|---|---|
| 44 | 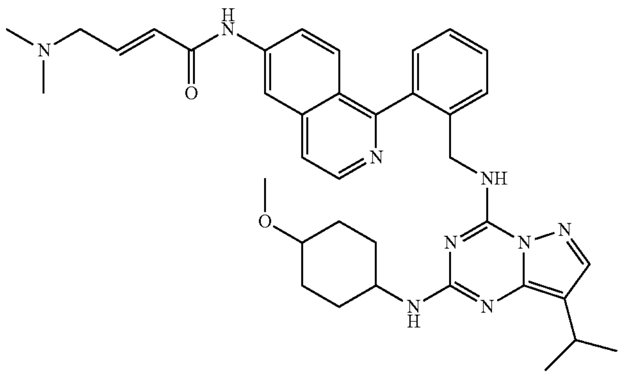 [SMILES: COC1CCC(Nc2nc(NCc3ccccc3-c3nccc4cc(NC(=O)/C=C/CN(C)C)ccc34)n3ncc(C(C)C)c3n2)CC1] | Light yellow solid; $^1$H-NMR (CD$_3$OD, 400 MHz): δ 8.88-6.89 (1H, m), 8.41-8.43 (1H, m), 8.26-8.28 (1H, m), 7.78-7.88 (3H, m), 7.67-7.71 (1H, m), 7.55-7.60 (3H, m), 6.99-7.07 (1H, m), 6.71 (1H, d, J = 15.2 Hz), 4.95-4.99 (1H, m), 4.78-4.82 (1H, m), 4.07 (2H, d, J = 7.2 Hz), 3.52-3.57 (1H, m), 3.40 (3H, s), 3.22-3.28 (1H, m), 2.96 (6H, s), 2.80-2.87 (1H, m), 2.03-2.17 (3H, m), 1.71-1.73 (1H, m), 1.27-1.48 (4H, m), 1.16-1.19 (6H, m); LCMS: 100.0%, MS (ESI): 648.3 m/z [(M + H)]$^+$ |
| 45 | 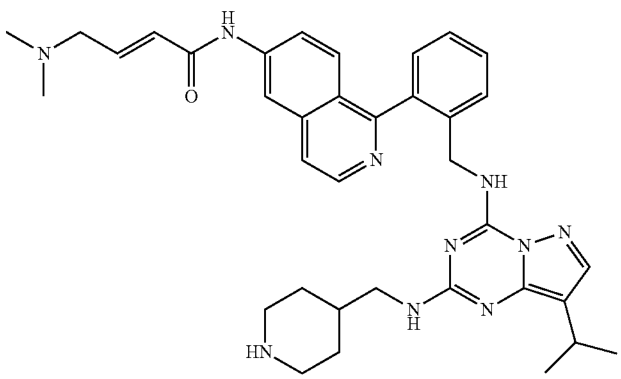 | Light yellow solid; $^1$H-NMR (CD$_3$OD, 400 MHz): δ 8.68 (1H, s), 8.45 (1H, d, J = 6.4 Hz), 8.23 (1H, d, J = 6.8 Hz), 7.82-7.83 (3H, m), 7.68-7.72 (1H, m), 7.59-7.65 (3H, m), 6.99-7.05 (1H, m), 6.72 (1H, d, J = 15.2 Hz), 5.04-5.08 (1H, m), 4.77-4.81 (1H, m), 4.07 (2H, d, J = 6.8 Hz), 3.37-3.48 (3H, m), 3.18-3.27 (1H, m), 2.96-3.02 (8H, m), 2.83-2.88 (1H, m), 1.93-1.96 (m, 3H), 1.49-1.55 (2H, m), 1.18-1.21 (6H, m); LCMS: 100.0%, MS (ESI): 633.3 m/z [(M + H)]$^+$ |
| 46 | 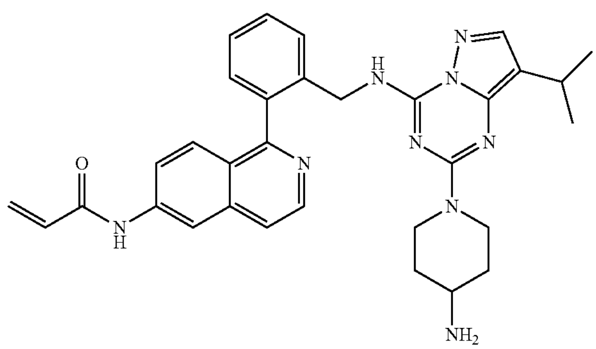 [SMILES: C=CC(=O)Nc1ccc2c(-c3ccccc3CNc3nc(N4CCC(N)CC4)nc4c(C(C)C)cnn34)nccc2c1] | off-white powder; $^1$H NMR (400 MHz, CD$_3$OD): δ 8.59 (1 H, d, J = 2.0 Hz), 8.38 (1H, d, J = 6.4 Hz), 8.16 (1H, d, J = 6.4 Hz), 7.79-7.88 (2H, m), 7.66-7.78 (2H, m), 7.57-7.62 (2H, m), 7.53 (1H, s), 6.51-6.58 (2H, m), 5.94 (1H, dd, J = 8.0, 3.6 Hz), 4.98-5.09 (1H, m), 4.65-4.74 (1H, m), 4.49-4.57 (2H, m), 3.43-3.54 (1H, m), 2.95-3.21 (3H, m), 2.04-2.21 (2H, m), 1.44-1.76 (2H, m), 1.20 (6H, d, J = 6.8 Hz); HPLC: 100%, MS (ESI): m/z 562.2[M + H]$^+$. |
| 47 | 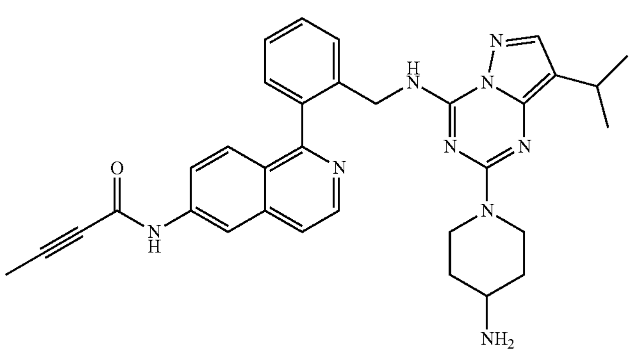 [SMILES: CC#CC(=O)Nc1ccc2c(-c3ccccc3CNc3nc(N4CCC(N)CC4)nc4c(C(C)C)cnn34)nccc2c1] | Light yellow powder; $^1$H NMR (CD$_3$OD, 400 MHz): δ 8.43 (1H, s), 8.39 (1H, d, J = 6.4 Hz), 8.17 (1H, d, J = 6.4 Hz), 7.78-7.84 (2H, m), 7.62-7.71 (2H, m), 7.56-7.62 (2H, m), 7.55 (1H, s), 4.91-5.05 (1H, m), 4.63-4.71 (1H, m), 4.47-4.551 (2H, m), 3.43-3.56 (1H, m), 3.10-3.29 (2H, m), 3.00-3.08 (1H, m), 2.02-2.21 (5H, m), 1.63-1.76 (1H, m), 1.51-1.59 (1H, m), 1.21-1.27 (6H, m); LCMS: 96.8%, MS (ESI): m/z 574.2 [M + H]$^+$ |

TABLE 6-continued

Summarized compounds 1-88 in terms of their structures and corresponding characteristics

| #cpds | Structure | Characterization Data |
|---|---|---|
| 48 | 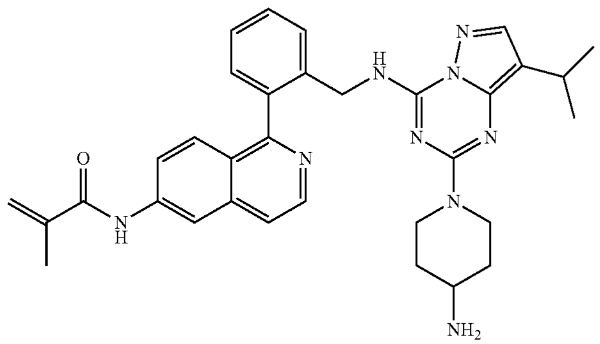 [SMILES: C=C(C)C(=O)Nc1ccc2c(-c3ccccc3CNc3nc(N4CCC(N)CC4)nc4c(C(C)C)cnn34)nccc2c1] | Pale yellow powder; ¹H NMR (CD₃OD, 400 MHz): δ 8.55 (1H, d, J = 2.0 Hz), 8.37-8.42 (1H, m), 8.20 (1H, d, J = 6.4 Hz), 7.77-7.92 (3H, m), 7.64-7.72 (1H, m), 7.54-7.62 (3H, m), 5.98 (1H, s), 5.71 (1H, d, J = 1.2 Hz), 4.99-5.07 (1H, m), 4.67-4.73 (1H, m), 4.47-4.54 (1H, m), 3.44-3.56 (1H, m), 3.17-3.24 (1H, m), 3.03-3.09 (1H, m), 2.08-2.21 (2H, m), 2.06 (3H, s), 1.64-1.78 (1H, m), 1.55-1.60 (1H, m), 1.16-1.21 (6H, m); LCMS: 100%, MS (ESI): m/z 576.2 [M + H]⁺ |
| 49 | 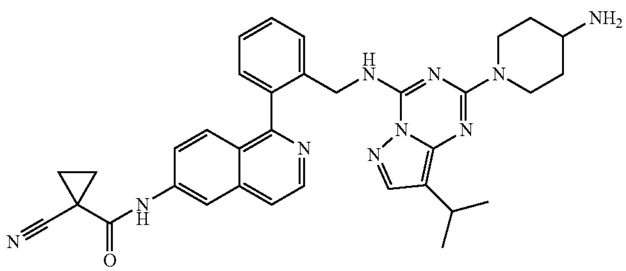 [SMILES: CC(C)c1cnn2c(NCc3ccccc3-c3nccc4cc(NC(=O)C5(C#N)CC5)ccc34)nc(N3CCC(N)CC3)nc12] | White powder; ¹H NMR (CD₃OD, 400 MHz): δ 8.48 (1H, d, J = 1.6 Hz), 8.40 (1H, d, J = 6.8 Hz), 8.19 (1H, d, J = 6.8 Hz), 7.80-7.89 (3H, m), 7.63-7.72 (2H, m), 7.55-7.62 (2H, m), 4.98-5.07 (1H, m), 4.68-4.75 (1H, m), 4.51-4.57 (2H, m), 3.46-3.52 (1H, m), 3.13-3.23 (2H, m), 3.04-3.09 (1H, m), 2.08-2.17 (2H, m), 1.74-1.87 (4H, m), 1.55-1.72 (2H, m), 1.23-1.28 (6H, m); LCMS: 99.8%, MS (ESI):601.2 m/z [M + H]⁺ |
| 50 | 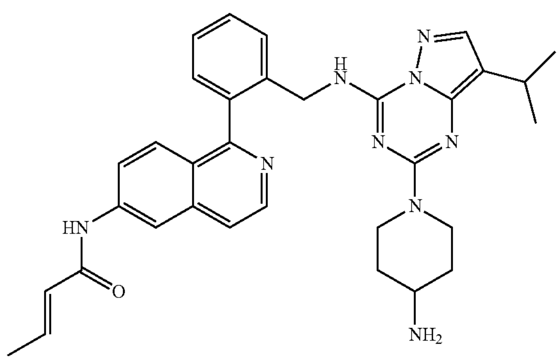 [SMILES: C/C=C/C(=O)Nc1ccc2c(-c3ccccc3CNc3nc(N4CCC(N)CC4)nc4c(C(C)C)cnn34)nccc2c1] | Yellow powder; ¹H NMR (CD₃OD, 400 MHz): δ 8.57 (1H, d, J = 2.0 Hz), 8.41 (1H, d, J = 6.4 Hz), 8.19 (1H, d, J = 6.8 Hz), 7.73-7.88 (3H, m), 7.66-7.71 (1H, m), 7.56-7.62 (3H, m), 7.06-7.17 (1H, m), 6.25 (1H, dd, J = 14.8, 2.0 Hz), 4.99-5.06 (1H, m), 4.66-4.73 (1H, m), 4.45-4.52 (2H, m), 3.47-3.58 (1H, m), 3.18-3.38 (2H, m, overlap with CD₃OD signal), 3.0-3.09 (1H, m), 2.10-2.19 (2H, m), 1.98 (3H, dd, J = 6.8, 1.6 Hz), 1.65-1.80 (1H, m), 1.49-1.64 (1H, m), 1.18 (6H, d, J = 6.8 Hz); LCMS: 100%, MS (ESI): m/z 576.3 [M + H]⁺ |
| 51 | 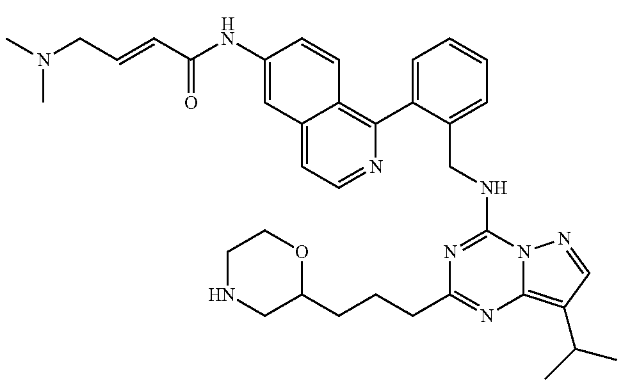 [SMILES: CC(C)c1cnn2c(NCc3ccccc3-c3nccc4cc(NC(=O)/C=C/CN(C)C)ccc34)nc(CCCC3CNCCO3)nc12] | Racemic mixture; off-white powder; ¹H NMR (400 MHz, CD₃OD): δ 8.71 (1H, s), 8.48 (1H, d, J = 6.4 Hz), 8.27 (1H, d, J = 6.0 Hz), 7.81-7.92 (3H, m), 7.56-7.75 (4H, m), 7.00-7.13 (1H, m), 6.77 (1H, d, J = 15.2 Hz), 5.06-5.14 (1H, m), 4.72-4.79 (1H, m), 4.06-4.21 (3H, m), 3.86-3.97 (2H, m), 3.43-3.59 (2H, m), 3.25-3.33 (3H, m), 3.14-3.26 (1H, m), 2.98 (6H, s), 2.83-2.94 (1H, m), 1.57-1.82 (2H, m), 1.21 (6H, d, J = 6.4 Hz); HPLC: 100%, MS (ESI): m/z 649.3 [M + H]⁺ |

TABLE 6-continued

Summarized compounds 1-88 in terms of their structures and corresponding characteristics

| #cpds | Structure | Characterization Data |
|---|---|---|
| 52 | 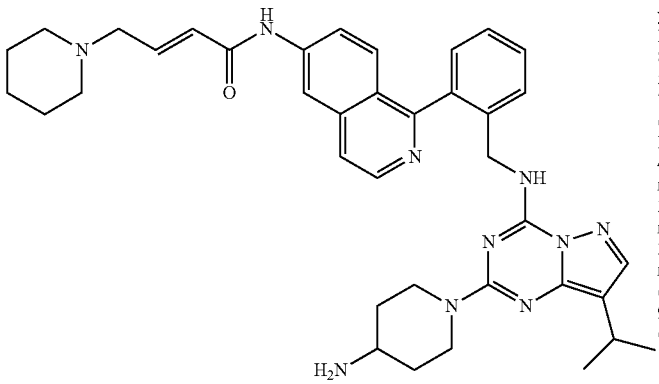 [SMILES: CC(C)c1cnn2c(NCc3ccccc3-c3nccc4cc(NC(=O)/C=C/CN5CCCCC5)ccc34)nc(N3CCC(N)CC3)nc12] | yellow powder; $^1$H NMR (400 MHz, CD$_3$OD): δ 8.69 (1H, s), 8.47 (1H, s), 8.26 (1H, d, J = 5.2 Hz), 7.80-7.93 (3H, m), 7.56-7.76 (4H, m), 7.02-7.14 (1H, m), 6.76 (1H, d, J = 14.8 Hz), 5.08-5.18 (1H, m), 4.69-4.78 (1H, m), 4.47-4.56 (2H, m), 4.03-4.08 (2H, m), 3.48-3.68 (5H, m), 2.94-3.18 (3H, m), 2.11-2.23 (2H, m), 2.00-2.07 (2H, m), 1.80-1.92 (4H, m), 1.51-1.67 (2H, m), 1.20 (6H, d, J = 6.0 Hz); HPLC: 97.1%, MS (ESI): m/z 659.3 [M + H]$^+$ |
| 53 | 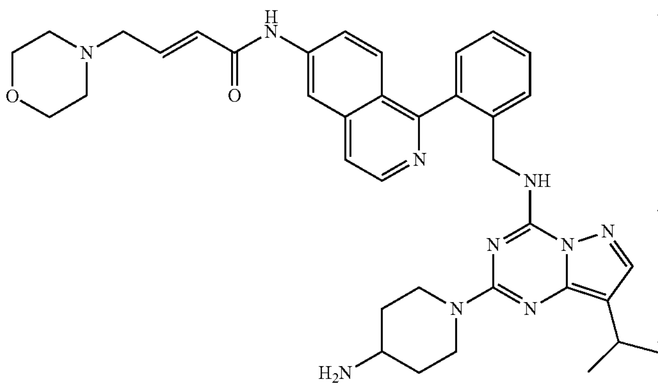 [SMILES: CC(C)c1cnn2c(NCc3ccccc3-c3nccc4cc(NC(=O)/C=C/CN5CCOCC5)ccc34)nc(N3CCC(N)CC3)nc12] | yellow powder; $^1$H NMR (400 MHz, CD$_3$OD): δ 8.69 (1H, s), 8.45 (1H, d, J = 5.2 Hz), 8.25 (1H, d, J = 6.4 Hz), 7.81-7.96 (3H, m), 7.59-7.76 (4H, m), 7.02-7.17 (1H, m), 6.79 (1H, d, J = 15.2 Hz), 5.01-5.08 (1H, m), 4.73-4.78 (1H, m), 4.48-4.55 (2H, m), 4.05-4.21 (4H, m), 3.79-3.92 (2H, m), 3.48-3.63 (4H, m), 3.12-3.28 4H, m), 2.11-2.27 (2H, m), 1.56-1.85 (2H, m), 1.20 (6H, d, J = 6.0 Hz); HPLC: 100%, MS (ESI): m/z 661.3[M + H]$^+$ |
| 54 | 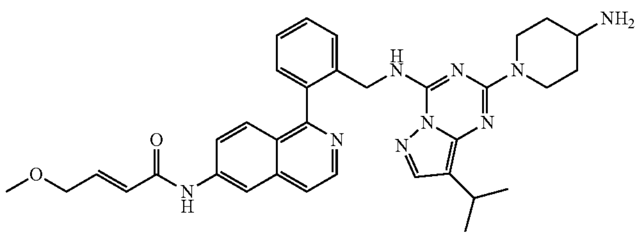 [SMILES: COC/C=C/C(=O)Nc1ccc2c(-c3ccccc3CNc3nc(N4CCC(N)CC4)nc4c(C(C)C)cnn34)nccc2c1] | off-white powder; $^1$H NMR (CD$_3$OD, 400 MHz): δ 8.56 (1H, s), 8.31-8.36 (1H, m), 8.08-8.13 (1H, m), 7.77-7.90 (2H, m), 7.42-7.75 (5H, m), 7.06-7.13 (1H, m), 6.46 (1H, d, J = 15.2 Hz), 4.64-4.71 (1H, m), 4.52-4.58 (2H, m), 4.14-4.23 (2H, m), 3.44-3.53 (4H, m), 2.87-3.19 (3H, m), 2.04-2.13 (2H, m), 1.29-1.72 (3H, m), 1.20 (6H, d, J = 6.8 Hz); LCMS: 99.8%, MS (ESI): 606.2 m/z[M + H]+ |
| 55 | 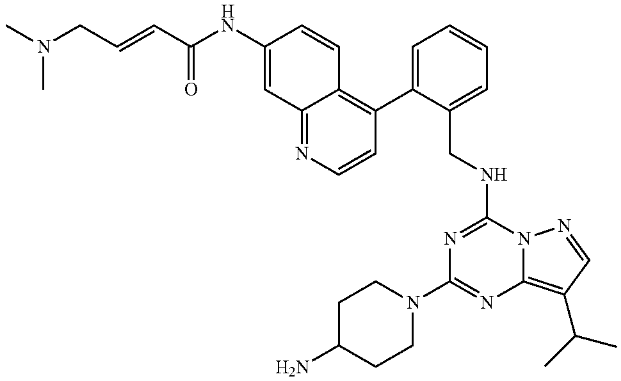 [SMILES: CC(C)c1cnn2c(NCc3ccccc3-c3ccnc4cc(NC(=O)/C=C/CN(C)C)ccc34)nc(N3CCC(N)CC3)nc12] | yellow powder; $^1$H NMR (400 MHz, DMSO-d$_6$): δ ppm 10.95 (1H, brs) 8.87 (1H, d, J = 4.8 Hz), 8.65-8.72 (1H, m), 8.64 (1H, s), 8.13 (2H, brs), 7.65-7.75 (2H, m), 7.39-7.57 (3H, m), 7.24-7.38 (3H, m), 6.82-6.95 (1H, m), 6.62 (1H, d, J = 14.8 Hz), 4.18-4.48 (4H, m), 3.76-3.88 (2H, m), 3.19-3.26 (1H, m), 2.83-2.94 (1H, m), 2.55-2.76 (9H, m), 1.86 (2H, m), 1.28-1.39 (2H, m), 1.20 (6H, d, J = 6.8 Hz); LCMS: 100%, MS (ESI): m/z 619.3 [M + H]$^+$ |

TABLE 6-continued

Summarized compounds 1-88 in terms of their structures and corresponding characteristics

| #cpds | Structure | Characterization Data |
|---|---|---|
| 56 | 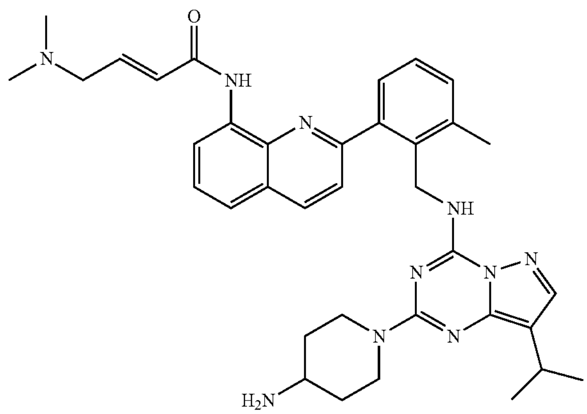 [SMILES: Cc1cccc(-c2ccc3cccc(NC(=O)/C=C/CN(C)C)c3n2)c1CNc1nc(N2CCC(N)CC2)nc2c(C(C)C)cnn12] | yellow solid; $^1$H-NMR (CD$_3$OD, 400 MHz): δ 8.70-8.72 (1H, m), 8.29-8.33 (1H, m), 7.78 (1H, s), 7.61-7.72 (3H, m), 7.42-7.48 (2H, m), 7.32-7.34 (1H, m), 6.86-6.92 (1H, m), 6.72-6.75 (1H, m), 4.32-4.36 (2H, m), 4.03 (2H, d, J = 7.2 Hz), 3.45-3.49 (1H, m), 3.02-3.15 (3H, m), 2.94 (6H, s), 2.61 (3H, s), 2.09-2.12 (2H, m), 1.55-1.61 (2H, m), 1.26 (6H, d, J = 6.8 Hz); LCMS: 100.0%, MS (ESI): 633.3 m/z [(M + H)]$^+$ |
| 57 | 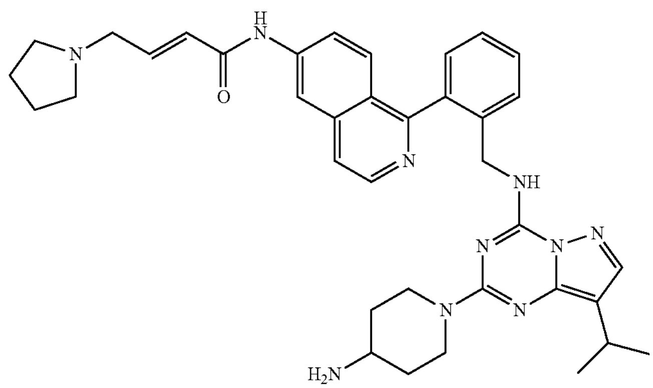 [SMILES: CC(C)c1cnn2c(NCc3ccccc3-c3nccc4cc(NC(=O)/C=C/CN5CCCC5)ccc34)nc(N3CCC(N)CC3)nc12] | off-white powder; $^1$H NMR (400 MHz, CD$_3$OD): δ 8.63 (1H, s), 8.32-8.37 (1H, m), 8.14 (1H, d, J = 6.4 Hz), 7.80-7.87 (2H, m), 7.72-7.76 (1H, m), 7.68 (1H, t, J = 8.0 Hz), 7.54-7.63 (2H, m), 7.48 (1H, s), 6.96-7.15 (1H, m), 6.72 (1H, d, J = 15.20 Hz), 4.66-4.73 (2H, m), 4.53-4.59 (2H, m), 4.16 (2H, d, J = 6.8 Hz), 3.69-3.74 (2H, m), 3.42-3.53 (1H, m), 2.93-3.25 (5H, m), 2.03-2.32 (6H, m), 1.43-1.69 (2H, m), 1.20 (6H, d, J = 7.2 Hz); HPLC: 100%, MS (ESI): m/z 645.3[M + H]$^+$ |
| 58 | 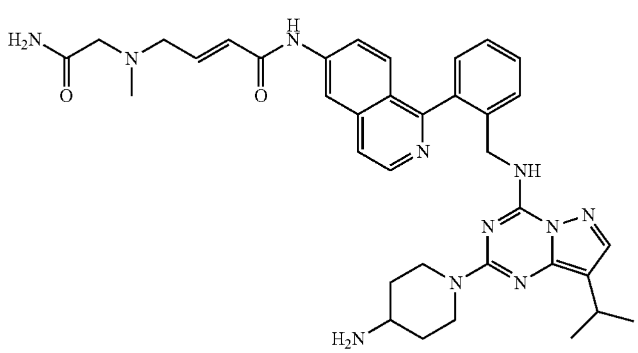 [SMILES: CC(C)c1cnn2c(NCc3ccccc3-c3nccc4cc(NC(=O)/C=C/CN(C)CC(N)=O)ccc34)nc(N3CCC(N)CC3)nc12] | yellow powder; $^1$H NMR (400 MHz, CD$_3$OD): δ 8.63 (1H, s), 8.37 (1H, d, J = 6.4 Hz), 8.16 (1H, d, J = 6.2 Hz), 7.73-7.88 (3H, m), 7.50-7.71 (4H, m), 6.95-7.08 (1H, m), 6.72 (1H, d, J = 15.2 Hz), 4.95-5.03 (1H, m), 4.65-4.71 (1H, m), 4.46-4.54 (2H, m), 3.99-4.19 (4H, m), 3.42-3.50 (1H, m), 3.10-3.17 (2H, m), 2.91-3.07 (4H, m), 2.05-2.13 (2H, m), 1.43-1.74 (2H, m), 1.16 (6H, d, J = 6.8 Hz); HPLC: 100%, MS (ESI): m/z 662.3[M + H]$^+$ |
| 59 | 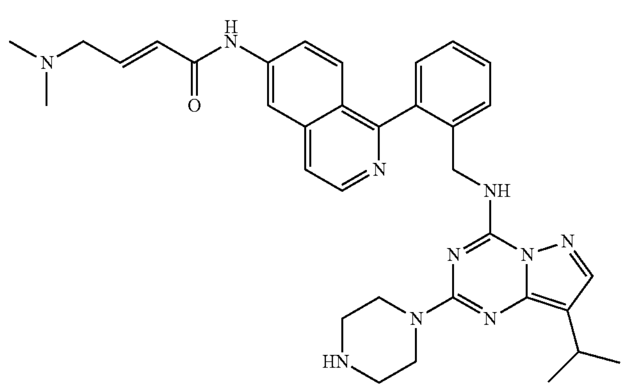 | pale yellow powder; $^1$H NMR (CD$_3$OD, 400 MHz): δ 8.61 (1H, d, J = 1.6 Hz), 8.33 (1H, d, J = 6.8 Hz), 8.11 (1H, d, J = 6.4 Hz), 7.77-7.85 (2H, m), 7.72-7.76 (1H, m), 7.64-7.70 (1H, m), 7.54-7.63 (2H, m), 7.48 (1H, s), 6.97-7.07 (1H, m), 6.72 (1H, d, J = 15.2 Hz), 4.96-5.03 (2H, m), 4.67-4.74 (1H, m), 4.05-4.09 (2H, m), 3.91-4.00 (4H, m), 3.26-3.32 (4H, m), 2.94-2.99 (7H, m), 1.20 (6H, d, J = 7.2 Hz); LCMS: 100%, MS (ESI): m/z 605.6 [M + H]$^+$ |

TABLE 6-continued

Summarized compounds 1-88 in terms of their structures and corresponding characteristics

| #cpds | Structure | Characterization Data |
|---|---|---|
| 60 | 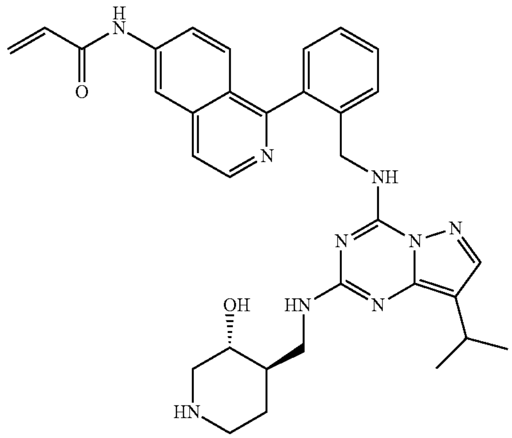 [SMILES: C=CC(=O)Nc1ccc2c(-c3ccccc3CNc3nc(NC[C@H]4CCNC[C@@H]4O)nc4c(C(C)C)cnn34)nccc2c1] | (3R, 4R); off-white powder; $^1$H NMR (400 MHz, CD$^3$OD): δ 8.54 (1H, s), 8.33-8.37 (1H, m), 8.06-8.12 (1H, m), 7.67-7.78 (2H, m), 7.51-7.64 (3H, m), 7.44-7.50 (2H, m), 6.38-6.44 (2H, m), 5.80-5.86 (1H, m), 4.94-5.05 (2H, m), 4.52-4.72 (2H, m), 3.49-3.75 (2H, m), 3.32-3.38 (1H, m), 2.64-2.95 (3H, m), 1.85-2.01 (1H, m), 1.71-1.79 (1H, m), 1.42-1.50 (1H, m), 1.09 (6H, d, J = 6.8 Hz); HPLC: 97.5%, MS (ESI): m/z 592.3 [M + H]$^+$ |
| 61 | 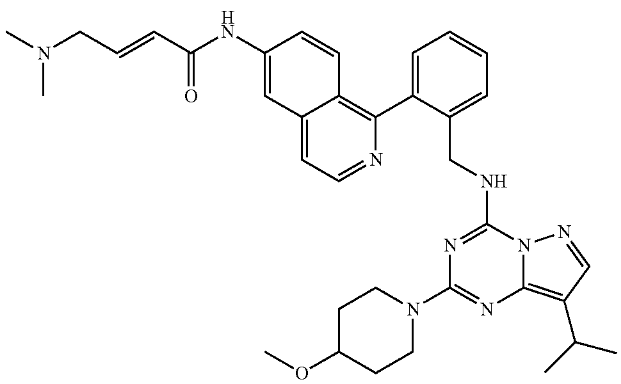 [SMILES: COC1CCN(c2nc(NCc3ccccc3-c3nccc4cc(NC(=O)/C=C/CN(C)C)ccc34)n3ncc(C(C)C)c3n2)CC1] | pale yellow powder; $^1$H NMR (400 MHz, CD$_3$OD): δ 8.64 (1H, s), 8.37 (1H, d, J = 6.8 Hz), 8.16 (1H, d, J = 6.8 Hz), 7.76-7.86 (3H, m), 7.65-7.70 (1H, m), 7.54-7.64 (3H, m), 6.98-7.07 (1H, m), 6.72 (1H, d, J = 15.2 Hz), 4.95-5.01 (1H, m), 4.81-4.87 (1H, m), 4.68-4.74 (1H, m), 4.07 (2H, d, J = 7.2 Hz), 3.85-3.99 (2H, m), 3.52-3.64 (3H, m), 3.40 (3H, s), 3.00-3.09 (1H, m), 2.96 (6H, s), 2.91 (1H, s), 1.83-2.05 (3H, m), 1.57-1.69 (2H, m), 1.15-1.20 (6H, m); LCMS: 99.4%, MS (ESI): m/z 634.3 [M + H]$^+$ |
| 62 | 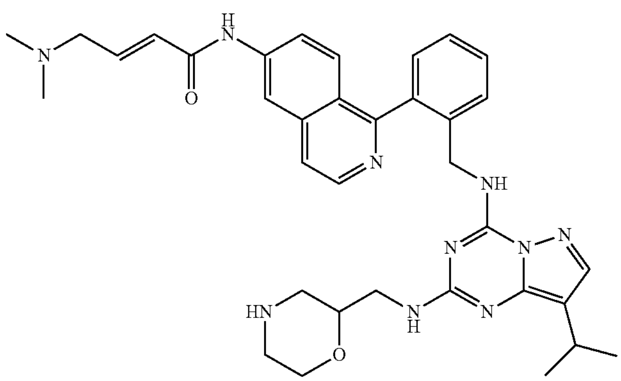 [SMILES: CC(C)c1cnn2c(NCc3ccccc3-c3nccc4cc(NC(=O)/C=C/CN(C)C)ccc34)nc(NCC3CNCCO3)nc12] | Racemic mixture; yellow solid; $^1$H -NMR (CD$_3$OD, 400 MHz): δ 8.65-8.69 (1H, m), 8.43-8.47 (1H, m), 8.18-8.24 (1H, m), 7.78-7.88 (3H, m), 7.65-7.72 (2H, m), 7.57-7.61 (2H, m), 6.98-7.06 (1H, m), 6.73 (1H, d, J = 15.2 Hz), 4.99-5.11 (2H, m), 4.70-4.81 (1H, m), 3.84-4.12 (5H, m), 3.38-3.65 (3H, m), 2.81-3.24 (9H, m), 1.16-1.22 (6H, m); LCMS: 100%, MS (ESI): 657.2 m/z [M + Na]$^+$ |
| 63 | 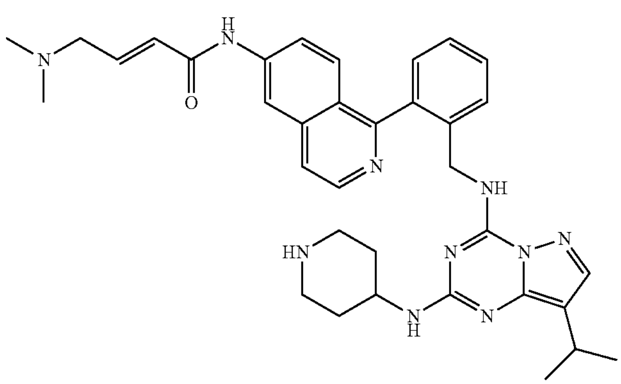 [SMILES: CC(C)c1cnn2c(NCc3ccccc3-c3nccc4cc(NC(=O)/C=C/CN(C)C)ccc34)nc(NC3CCNCC3)nc12] | yellow powder; $^1$H NMR (CD$_3$OD, 400 MHz): δ 8.63 (1H, s), 8.39-8.45 (1H, m), 8.11-8.17 (1H, m), 7.50-7.91 (7H, m), 6.96-7.13 (1H, m), 6.72 (1H, d, J = 15.4 Hz), 5.09-5.16 (1H, m), 3.97-4.16 (3H, m), 3.37-3.62 (3H, m), 3.12-3.27 (1H, m), 2.77-3.05 (8H, m), 2.24-2.31 (1H, m), 1.68-2.05 (3H, m), 1.12-1.29 (6H, m); LCMS: 100%, MS (ESI): 619.3 m/z [M + H]$^+$ |

TABLE 6-continued

Summarized compounds 1-88 in terms of their structures and corresponding characteristics

| #cpds | Structure | Characterization Data |
|---|---|---|
| 64 | 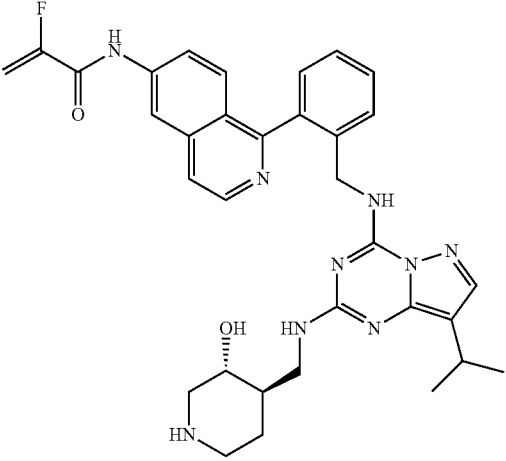 [SMILES: C=C(F)C(=O)Nc1ccc2c(-c3ccccc3CNc3nc(NC[C@H]4CCNC[C@@H]4O)nc4c(C(C)C)cnn34)nccc2c1] | (3R, 4R); yellow solid; $^1$H-NMR (CD$_3$OD, 400 MHz): δ 8.64-8.68 (1H, m), 8.51 (1H, dd, J = 6.4, 3.2 Hz), 8.27-8.31 (1H, m), 7.81-7.92 (3H, m), 7.65-7.72 (2H, m), 7.57-7.62 (2H, m), 5.87 (1H, dd, J = 46.0, 3.6 Hz), 5.46 (1H, dd, J = 14.8, 3.6 Hz), 5.06-5.13 (1H, m), 4.65-4.75 (1H, m), 3.69-3.76 (1H, m), 3.54-3.62 (1H, m), 3.34-3.47 (3H, m), 2.78-3.01 (3H, m), 1.98-2.05 (1H, m), 1.81-1.92 (1H, m), 1.53-1.65 (1H, m), 1.20 (6H, d, J = 6.8 Hz); LCMS: 99.4%, MS (ESI): 610.2 m/z [M + H]$^+$ |
| 65 | 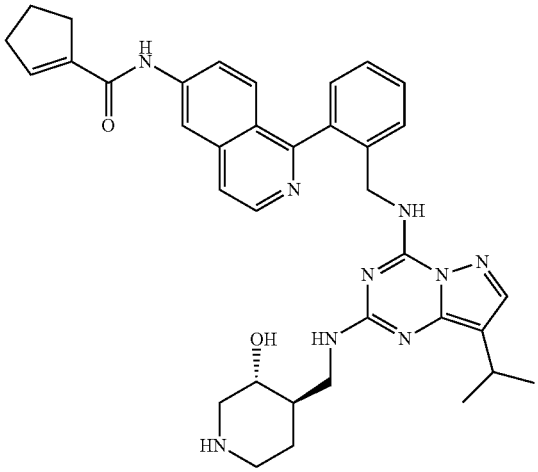 [SMILES: CC(C)c1cnn2c(NCc3ccccc3-c3nccc4cc(NC(=O)C5=CCCC5)ccc34)nc(NC[C@H]3CCNC[C@@H]3O)nc12] | (3R, 4R); yellow solid; $^1$H-NMR (CD$_3$OD, 400 MHz): δ 8.58-8.61 (1H, m), 8.44 (1H, dd, J = 6.4, 2.4 Hz), 8.17-8.22 (1H, m), 7.79-7.91 (3H, m), 7.56-7.72 (4H, m), 6.92 (1H, d, J = 2.0 Hz), 5.05-5.13 (1H, m), 4.68-4.75 (1H, m), 3.69-3.76 (1H, m), 3.37-3.59 (4H, m), 2.60-3.01 (7H, m), 1.96-2.07 (3H, m), 1.79-1.88 (1H, m), 1.52-1.63 (1H, m), 1.18 (6H, d, J = 6.8 Hz); LCMS: 98.3%, MS (ESI): 632.2 m/z [M + H]$^+$ |
| 66 | 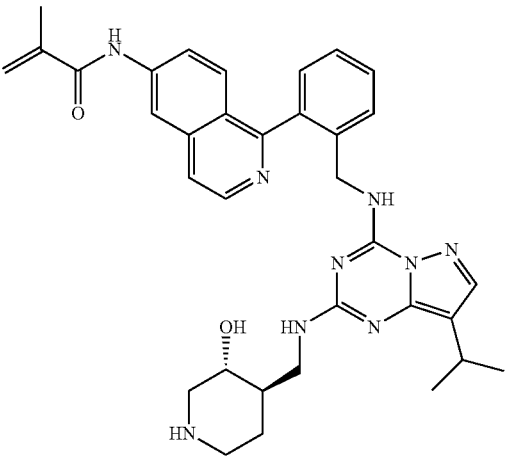 [SMILES: C=C(C)C(=O)Nc1ccc2c(-c3ccccc3CNc3nc(NC[C@H]4CCNC[C@@H]4O)nc4c(C(C)C)cnn34)nccc2c1] | (3R, 4R); yellow solid; $^1$H-NMR (CD$_3$OD, 400 MHz): δ 8.52-8.59 (1H, m), 8.39-8.45 (1H, m), 8.04-8.13 (1H, m), 7.52-7.88 (7H, m), 5.94 (1H, s), 5.69 (1H, s), 5.08-5.17 (1H, m), 4.62-4.73 (1H, m), 3.34-3.76 (5H, m), 2.76-3.05 (3H, m), 1.52-2.10 (6H, m), 1.20 (6H, d, J = 6.8 Hz); LCMS: 98.9%, MS (ESI): 606.2 m/z [M + H]$^+$ |

TABLE 6-continued

Summarized compounds 1-88 in terms of their structures and corresponding characteristics

| #cpds | Structure | Characterization Data |
|---|---|---|
| 67 | 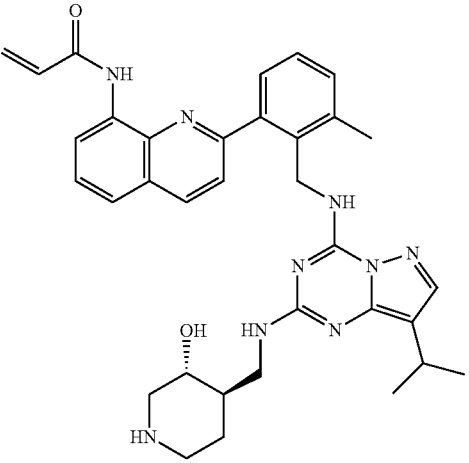 [SMILES: C=CC(=O)Nc1cccc2ccc(-c3cccc(C)c3CNc3nc(NC[C@H]4CCNC[C@@H]4O)nc4c(C(C)C)cnn34)nc12] | (3R, 4R); light yellow powder; $^1$H-NMR (CD$_3$OD, 400 MHz): δ 8.73 (1H, d, J = 8.0 Hz), 8.32 (1H, d, J = 8.8 Hz), 7.74 (1H, s), 7.59-7.69 (3H, m), 7.46-7.48 (2H, m), 7.35-7.37 (1H, m), 6.49-6.56 (1H, m), 6.32-6.36 (1H, m), 5.69-5.76 (1H, m), 4.91-4.95 (3H, m), 4.84-4.86 (1H, m), 3.60-3.66 (1H, m), 3.34-3.39 (1H, m), 3.25-3.28 (1H, m), 2.84-2.94 (2H, m), 2.69-2.75 (1H, m), 2.57 (3H, s), 1.88-1.94 (1H, m), 1.73-1.77 (1H, m), 1.43-1.47 (1H, m), 1.26 (6H, d, J = 6.8 Hz); LCMS: 100.0%, MS (ESI): 606.3 m/z [(M + H)]$^+$ |
| 68 | 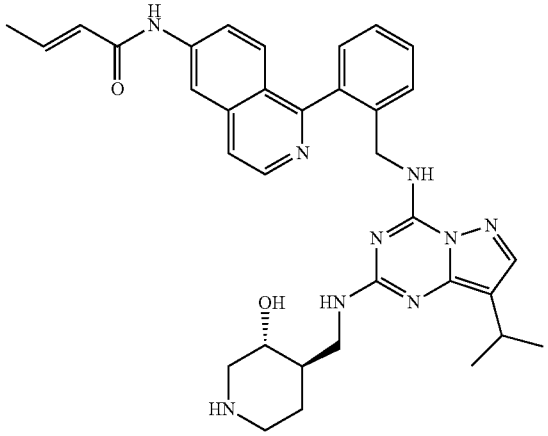 [SMILES: C/C=C/C(=O)Nc1ccc2c(-c3ccccc3CNc3nc(NC[C@H]4CCNC[C@@H]4O)nc4c(C(C)C)cnn34)nccc2c1] | (3R, 4R); yellow solid; $^1$H-NMR (CD$_3$OD, 400 MHz): δ 8.59-8.63 (1H, m), 8.42-8.47 (1H, m), 8.17-8.22 (1H, m), 7.55-7.73 (7H, m), 7.06-7.12 (1H, m), 6.22 (1H, d, J = 15.2 Hz), 5.05-5.12 (1H, m), 4.64-4.75 (1H, m), 3.69-3.76 (1H, m), 3.30-3.58 (4H, m), 2.89-3.01 (1H, m), 2.75-2.84 (2H, m), 1.95-2.04 (4H, m), 1.80-1.91 (1H, m), 1.52-1.63 (1H, m), 1.18 (6H, d, J = 6.8 Hz); LCMS: 100%, MS (ESI): 606.3 m/z [M + H]$^+$ |
| 69 | 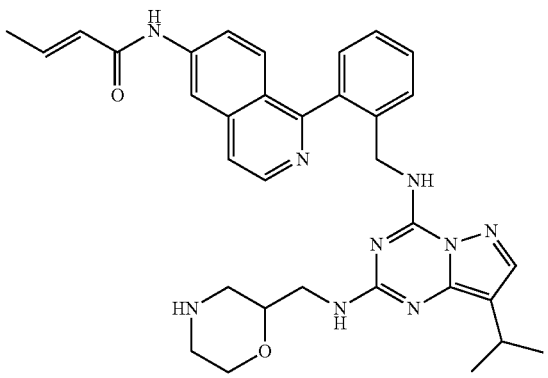 [SMILES: C/C=C/C(=O)Nc1ccc2c(-c3ccccc3CNc3nc(NCC4CNCCO4)nc4c(C(C)C)cnn34)nccc2c1] | Racemic mixture; yellow solid; $^1$H-NMR (CD$_3$OD, 400 MHz): δ 8.54-8.61 (1H, m), 8.42 (1H, d, J = 6.8 Hz), 8.14-8.18 (1H, m), 7.55-7.87 (7H, m), 7.06-7.14 (1H, m), 6.22 (1H, d, J = 15.2 Hz), 5.03-5.13 (1H, m), 4.67-4.72 (1H, m), 3.81-4.15 (3H, m), 3.34-3.61 (3H, m), 2.79-3.25 (3H, m), 1.97 (3H, d, J = 6.8 Hz), 1.16-1.21 (6H, m); LCMS: 100%, MS (ESI): 592.3 m/z [M + H]$^+$ |

TABLE 6-continued

Summarized compounds 1-88 in terms of their structures and corresponding characteristics

| #cpds | Structure | Characterization Data |
|---|---|---|
| 70 | 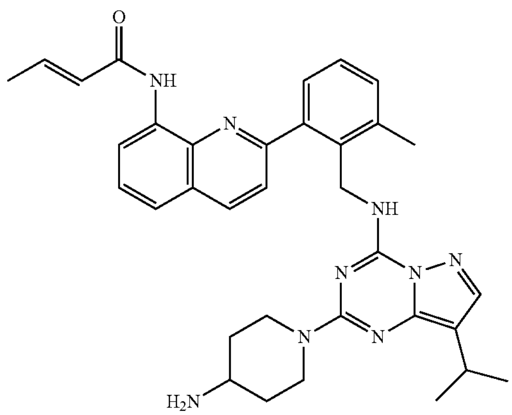 | Yellow powder; $^1$H-NMR (CD$_3$OD, 400 MHz): δ 8.54 (1H, d, J = 7.6 Hz), 8.45 (1H, d, J = 8.8 Hz), 7.65-7.77 (4H, m), 7.45-7.52 (2H, m), 7.35-7.37 (1H, m), 6.91-6.97 (1H, m), 6.22 (1H, d, J = 14.8 Hz), 4.93-4.94 (2H, m), 3.64-3.65 (1H, m), 3.32-3.36 (2H, m), 3.26-3.28 (2H, m), 2.85-2.92 (2H, m), 2.74-2.77 (1H, m), 2.62 (3H, s), 1.87-1.95 (3H, m), 1.70-1.77 (1H, m), 1.44-1.52 (1H, m), 1.25 (6H, d, J = 6.8 Hz), 0.85-0.91 (1H, m); LCMS: 98.5%, MS (ESI): 620.2 m/z [(M + H)]$^+$ |
| 71 | 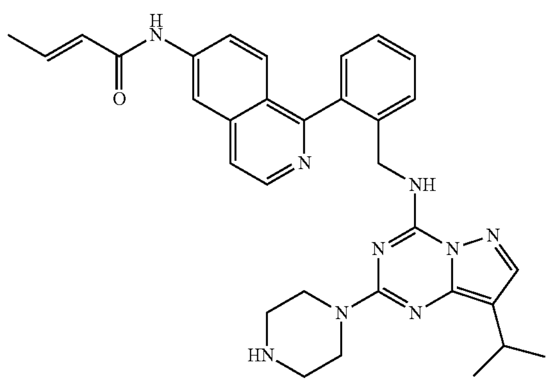 [SMILES: C/C=C/C(=O)Nc1ccc2c(-c3ccccc3CNc3nc(N4CCNCC4)nc4c(C(C)C)cnn34)nccc2c1] | yellow solid; $^1$H-NMR (CD$_3$OD, 400 MHz): δ 8.57 (1H, d, J = 2.0 Hz), 8.38 (1H, d, J = 6.8 Hz), 8.16 (1H, d, J = 6.8 Hz), 7.79-7.86 (2H, m), 7.66-7.74 (2H, m), 7.57-7.62 (3H, m), 7.07-7.14 (1H, m), 6.25 (1H, dd, J = 15.2, 1.6 Hz), 5.01-5.05 (1H, m), 4.68-4.72 (1H, m), 4.01-4.05 (4H, m), 3.33-3.36 (4H, m), 3.00-3.07 (1H, m), 1.98 (3H, dd, J = 6.8, 1.6 Hz), 1.20 (6H, dd, J = 6.8, 1.6 Hz); LCMS: 100.0%, MS (ESI): 562.2 m/z [(M + H)]$^+$ |
| 72 | 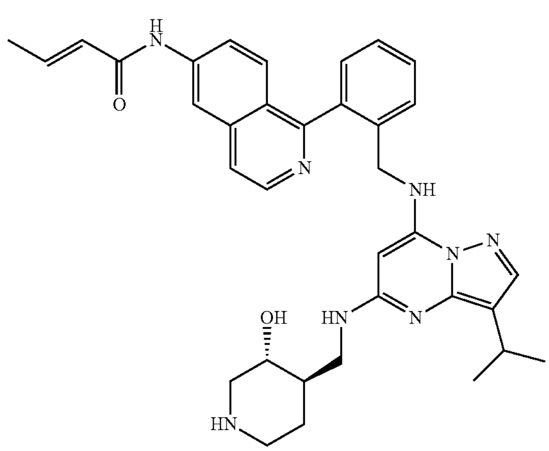 [SMILES: C/C=C/C(=O)Nc1ccc2c(-c3ccccc3CNc3cc(NC[C@H]4CCNC[C@@H]4O)nc4c(C(C)C)cnn34)nccc2c1] | (3R, 4R); yellow powder; $^1$H-NMR (CD$_3$OD, 400 MHz): δ 8.46-8.52 (1H, m), 8.36-8.38 (1H, m), 8.05-8.08 (1H, m), 7.78-7.87 (2H, m), 7.65-7.69 (2H, m), 7.49-7.55 (3H, m), 7.05-7.12 (1H, m), 6.24 (1H, dd, J = 15.2, 1.2 Hz), 4.99-5.03 (1H, m), 4.65-4.72 (1H, m), 3.67-3.73 (1H, m), 3.38-3.48 (4H, m), 2.98-3.05 (1H, m), 2.81-2.91 (2H, m), 2.4-2.09 (1H, m), 1.97 (3H, dd, J = 6.8, 1.2 Hz), 1.81-1.86 (1H, m), 1.62-1.68 (1H, m), 1.17-1.22 (6H, m); LCMS: 99.4%, MS (ESI):605.3 m/z [(M + H)]$^+$ |

TABLE 6-continued

Summarized compounds 1-88 in terms of their structures and corresponding characteristics

| #cpds | Structure | Characterization Data |
|---|---|---|
| 73 | 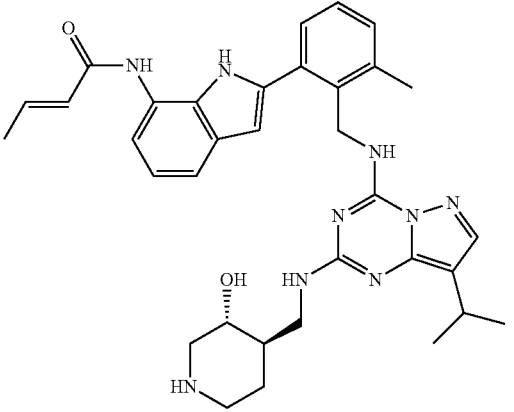 [SMILES: C/C=C/C(=O)Nc1cccc2cc(-c3cccc(C)c3CNc3nc(NC[C@H]4CCNC[C@@H]4O)nc4c(C(C)C)cnn34)[nH]c12] | (3R, 4R); off-white powder; $^1$H NMR (CD$_3$OD, 400 MHz): δ 7.85 (1H, s), 7.36-7.45 (3H, m), 7.34 (1H, d, J = 8.0 Hz), 7.19 (1H, d, J = 7.6 Hz), 6.97-7.05 (1H, m), 6.60-6.74 (1H, m), 6.17 (1H, d, J = 15.2 Hz), 4.93-4.97 (2H, m), 3.55-3.61 (1H, m), 3.45-3.54 (1H, m), 3.35-3.43 (1H, m), 3.23-3.27 (1H, m), 3.03-3.09 (1H, m), 2.94-3.01 (1H, m), 2.57-2.68 (2H, m), 2.54 (3H, s), 1.88 (3H, d, J = 6.4 Hz), 1.64-1.84 (2H, m), 1.34-1.45 (1H, m), 1.30 (6H, d, J = 6.8 Hz); LCMS: 100%, MS (ESI): m/z 608.3 [M + H]$^+$ |
| 74 | 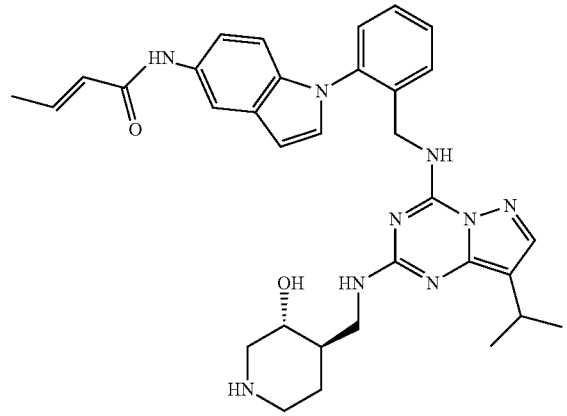 [SMILES: C/C=C/C(=O)Nc1ccc2c(ccn2-c2ccccc2CNc2nc(NC[C@H]3CCNC[C@@H]3O)nc3c(C(C)C)cnn23)c1] | (3R, 4R); white powder; $^1$H NMR (CD$_3$OD, 400 MHz): δ 7.93 (1H, s), 7.68-7.84 (2H, m), 7.59 (2H, m), 7.36 (1H, d, J = 7.2 Hz), 7.23-7.30 (1H, m), 6.89-7.04 (2H, m), 6.77-6.83 (1H, m), 6.48-6.56 (1H, m), 6.18 (1H, d, J = 14.8 Hz), 4.51-4.69 (2H, m), 3.60-3.69 (2H, m), 3.41-3.52 (1H, m), 3.13-3.19 (1H, m), 2.70-3.02 (4H, m), 1.89-1.99 (4H, m), 1.74-1.82 (1H, m), 1.41-1.57 (1H, m), 1.20-1.34 (6H, m); LCMS: 99.9%, MS (ESI): 594.2 m/z [M + H]$^+$ |
| 75 | 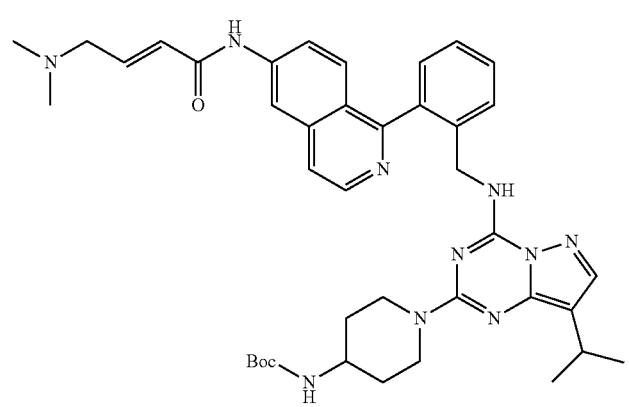 [SMILES: CC(C)c1cnn2c(NCc3ccccc3-c3nccc4cc(NC(=O)/C=C/CN(C)C)ccc34)nc(N3CCC(NC(=O)OC(C)(C)C)CC3)nc12] | white powder; $^1$H NMR (400 MHz, CDCl$_3$): δ 8.33-8.57 (3H, m), 7.53-7.65 (4H, m), 7.34-7.48 (4H, m), 6.95-7.12 (2H, m), 6.29-6.52 (1H, m), 4.69-4.88 (1H, m), 4.38-4.59 (3H, m), 4.17-4.36 (1H, m), 3.54-3.73 (1H, m), 3.25-3.40 (2H, m), 2.83-3.05 (3H, m), 2.48 (6H, s), 1.85-2.0 (2H, m), 1.46 (9H, s), 1.24-1.26 (8H, m); LCMS: 100%, MS (ESI): m/z 719.3 [M + H]$^+$ |

TABLE 6-continued

Summarized compounds 1-88 in terms of their structures and corresponding characteristics

| #cpds | Structure | Characterization Data |
|---|---|---|
| 76 | 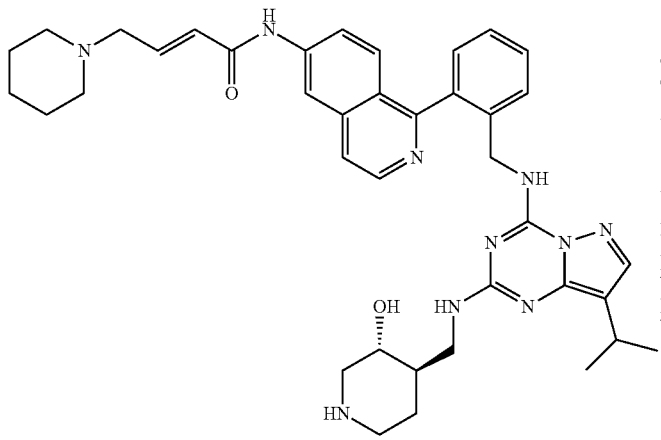 [SMILES: CC(C)c1cnn2c(NCc3ccccc3-c3nccc4cc(NC(=O)/C=C/CN5CCCCC5)ccc34)nc(NC[C@H]3CCNC[C@@H]3O)nc12] | (3R, 4R); Yellow solid; $^1$H-NMR (CD$_3$OD, 400 MHz): δ 8.66-8.70 (1H, m), 8.45 (1H, dd, J = 6.8, 2.4 Hz), 8.19-8.24 (1H, m), 7.80-7.88 (3H, m), 7.64-7.71 (2H, m), 7.56-7.61 (2H, m), 7.01-7.08 (1H, m), 6.70 (1H, d, J = 15.2 Hz), 5.02-5.07 (1H, m), 4.69-4.79 (1H, m), 4.02 (2H, d, J = 7.2 Hz), 3.70-3.76 (1H, m), 3.53-3.60 (3H, m), 3.31-3.46 (3H, m), 2.76-3.07 (5H, m), 1.96-2.03 (3H, m), 1.78-1.91 (4H, m), 1.51-1.62 (2H, m), 1.19 (6H, d, J = 7.2 Hz); LCMS: 100%, MS (ESI): 689.3 m/z [M + H]$^+$. |
| 77 | 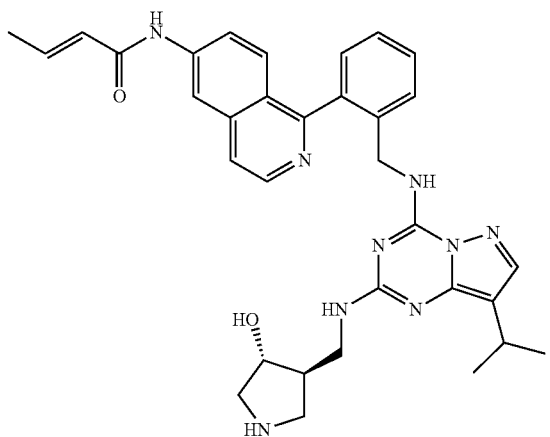 [SMILES: C/C=C/C(=O)Nc1ccc2c(-c3ccccc3CNc3nc(NC[C@H]4CNC[C@@H]4O)nc4c(C(C)C)cnn34)nccc2c1] | Mixture of 2 trans isomer; yellow solid; $^1$H-NMR (CD$_3$OD, 400 MHz): δ 8.55-8.62 (1H, m), 8.41-8.46 (1H, m), 8.15-8.19 (1H, m), 7.56-7.87 (7H, m), 7.06-7.18 (1H, m), 6.21 (1H, d, J = 16.0 Hz), 5.09-5.21 (1H, m), 4.67-4.82 (2H, m), 4.26-4.35 (1H, m), 3.41-3.62 (3H, m), 3.12-3.21 (2H, m), 2.80-2.86 (1H, m), 2.38-2.59 (1H, m), 1.97 (3H, dd, J = 7.2, 1.6 Hz), 1.18 (6H, d, J = 6.8 Hz). LCMS: 100%, MS (ESI): 592.2 m/z [M + H]$^+$. |
| 78 | 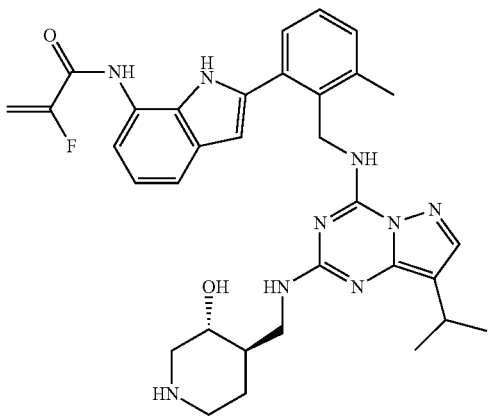 [SMILES: C=C(F)C(=O)Nc1cccc2cc(-c3cccc(C)c3CNc3nc(NC[C@H]4CCNC[C@@H]4O)nc4c(C(C)C)cnn34)[nH]c12] | (3R, 4R); gray powder; $^1$H NMR (MeOD, 400 MHz): δ ppm 7.85 1H, s), 7.34-7.48 (4H, m), 7.18 (1H, d, J = 7.6 Hz), 7.03-7.10 (1H, m), 6.49 (1H, s), 5.34-5.52 (1H, m), 5.21 (1H, dd, J = 15.2, 3.2 Hz), 4.92-4.95 (2H, m), 3.50-3.62 (2H, m), 3.37-3.45 (1H, m), 3.20-3.27 (1H, m), 2.93-3.05 (2H, m), 2.50-2.61 (5H, m), 1.67-1.83 (2 H, m), 1.33-1.42 (1H, m), 1.30 (6H, d, J = 6.8 Hz); LCMS: 100%, MS (ESI): m/z 612.3 [M + H]+ |

TABLE 6-continued

Summarized compounds 1-88 in terms of their structures and corresponding characteristics

| #cpds | Structure | Characterization Data |
|---|---|---|
| 79 | 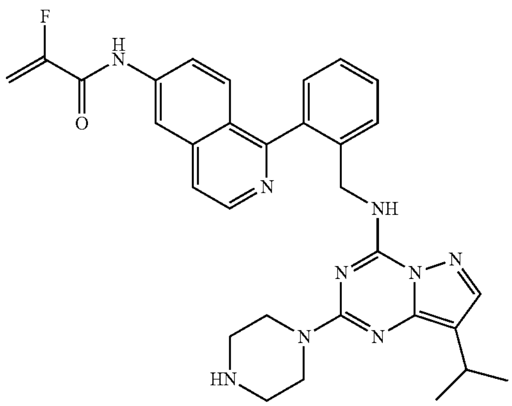 [SMILES: C=C(F)C(=O)Nc1ccc2c(-c3ccccc3CNc3nc(N4CCNCC4)nc4c(C(C)C)cnn34)nccc2c1] | Yellow solid; $^1$H-NMR (CD$_3$OD, 400 MHz): δ 8.56 (1H, d, J = 2.0 Hz), 8.36 (1H, d, J = 6.4 Hz), 8.15 (1H, d, J = 6.8 Hz), 7.76-7.83 (3H, m), 7.61-7.67 (1H, m), 7.53-7.60 (2H, m), 7.44 (1H, s), 5.85 (1H, dd, J = 46.0, 3.6 Hz), 5.44 (1H, dd, J = 15.2, 3.6 Hz), 5.00 (1H, d, J = 15.6 Hz), 4.63 (1H, d, J = 15.6 Hz), 3.89-4.00 (4H, m), 3.21-3.29 (4H, m, overlap with water signal), 2.87-2.95 (1H, m), 1.15-1.21 (6H, m); LCMS: 100%, MS (ESI): 566.2 m/z [M + H]$^+$ |
| 80 | 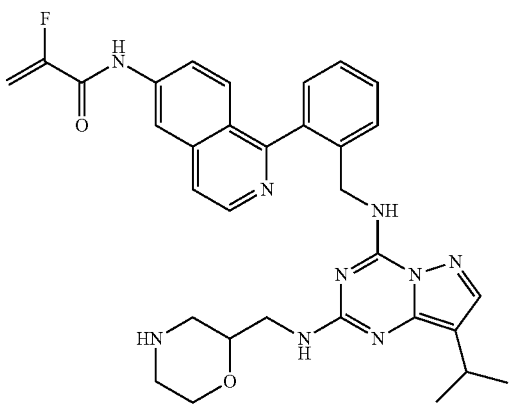 [SMILES: C=C(F)C(=O)Nc1ccc2c(-c3ccccc3CNc3nc(NCC4CNCCO4)nc4c(C(C)C)cnn34)nccc2c1] | Racemic mixture; Yellow solid; $^1$H-NMR (CD$_3$OD, 400 MHz): δ 8.62-8.65 (1H, m), 8.44-8.49 (1H, m), 8.20-8.24 (1H, m), 7.79-7.90 (3H, m), 7.65-7.71 (2H, m), 7.54-7.61 (2H, m), 5.85 (1H, dd, J = 46.4, 3.6 Hz), 5.44 (1H, dd, J = 14.8, 3.6 Hz), 5.03-5.13 (1H, m), 4.65-4.76 (1H, m), 3.81-4.12 (3H, m), 3.32-3.61 (3H, m), 2.78-3.21 (4H, m), 1.16-1.21 (6H, m); LCMS: 99.3%, MS (ESI): 596.2 m/z [M + H]$^+$ |
| 81 | 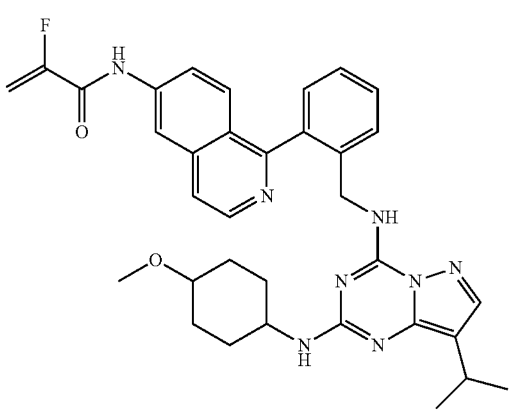 [SMILES: C=C(F)C(=O)Nc1ccc2c(-c3ccccc3CNc3nc(NC4CCC(OC)CC4)nc4c(C(C)C)cnn34)nccc2c1] | off-white powder; $^1$H NMR (400 MHz, CD$_3$OD): δ 8.56 (1H, s), 8.44 (1H, d, J = 6.8 Hz), 8.24 (1H, d, J = 6.4 Hz), 7.92-8.00 (1H, m), 7.81-7.91 (2H, m), 7.73 (1H, t, J = 7.2 Hz), 7.62 (1H, d, J = 7.6 Hz), 7.52-7.56 (1H, m), 7.46 (1H, s), 5.85 (1H, dd, J = 46.4, 4.0 Hz), 5.48 (1H, dd, J = 15.2, 4.0 Hz), 4.90-5.02 (2H, m), 4.73-4.83 (1H, m), 3.41 (3H, s), 3.23-3.32 (2H, m), 2.85-2.94 (1H, m), 1.99-2.24 (3H, m), 1.65-1.76 (1H, m), 1.30-1.55 (4H, m), 1.15-1.24 (6H, m); HPLC: 98.5% MS (ESI): m/z 608.2 [M + H]$^+$ |

TABLE 6-continued

Summarized compounds 1-88 in terms of their structures and corresponding characteristics

| #cpds | Structure | Characterization Data |
|---|---|---|
| 82 | 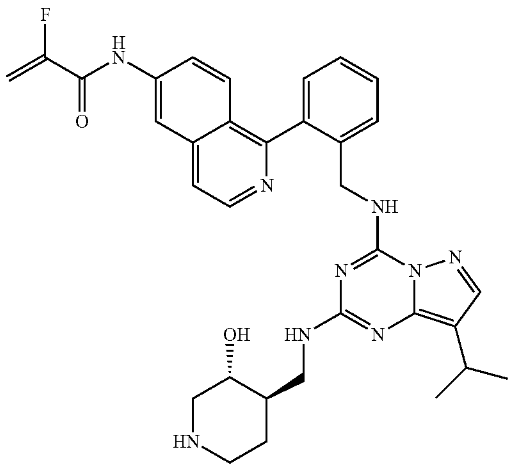 [SMILES: C=C(F)C(=O)Nc1ccc2c(-c3ccccc3CNc3nc(NC[C@H]4CCNC[C@@H]4O)nc4c(C(C)C)cnn34)nccc2c1] | (3R, 4R); light yellow solid; $^1$H-NMR (CD$_3$OD, 400 MHz): δ 8.52-8.60 (1H, m), 8.44 (1H, J = 6.8 Hz), 8.22-8.26 (1H, m), 7.81-7.92 (3H, m), 7.67-7.72 (1H, m), 7.56-7.63 (2H, m), 7.48 (1H, s), 5.87 (1H, dd, J = 46.0, 2.8 Hz), 5.46 (1H, dd, J = 15.2, 4.0 Hz), 5.07-5.12 (1H, m), 4.73-4.79 (1H, m), 3.69-3.75 (1H, m), 3.37-3.56 (4H, m), 2.99-3.12 (1H, m), 2.81-2.97 (1H, m), 2.06-2.12 (1H, m), 1.82-1.89 (1H, m), 1.64-1.73 (1H, m), 1.17-1.24 (6H, m); LCMS: 99.7%; MS (ESI): 609.2 m/z [(M + H)]$^+$ |
| 83 | 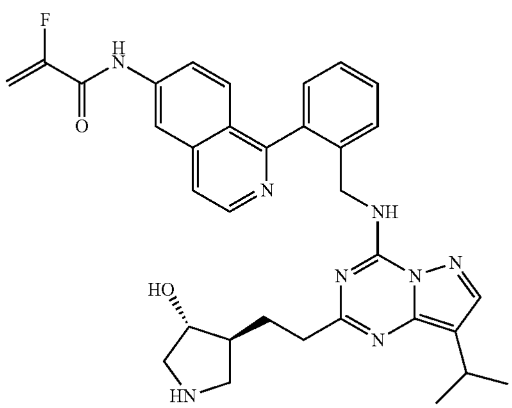 [SMILES: C=C(F)C(=O)Nc1ccc2c(-c3ccccc3CNc3nc(CC[C@H]4CNC[C@@H]4O)nc4c(C(C)C)cnn34)nccc2c1] | Mixture of 2 trans isomer; Yellow solid; $^1$H-NMR (CD$_3$OD, 400 MHz): δ 8.60-8.67 (1H, m), 8.48-8.52 (1H, m), 8.24-8.28 (1H, m), 7.81-7.93 (3H, m), 7.56-7.73 (4H, m), 5.85 (1H, dd, J = 46.0, 3.6 Hz), 5.44 (1H, dd, J = 14.8, 3.6 Hz), 5.09-5.22 (1H, m), 4.67-4.77 (1H, m), 4.36-4.35 (1H, m), 3.46-3.62 (3H, m), 3.10-3.21 (2H, m), 2.81-2.88 (1H, m), 2.41-2.62 (1H, m), 1.16-1.22 (6H, m); LCMS: 100%, MS (ESI): 596.2 m/z [M + H]$^+$ |
| 84 | 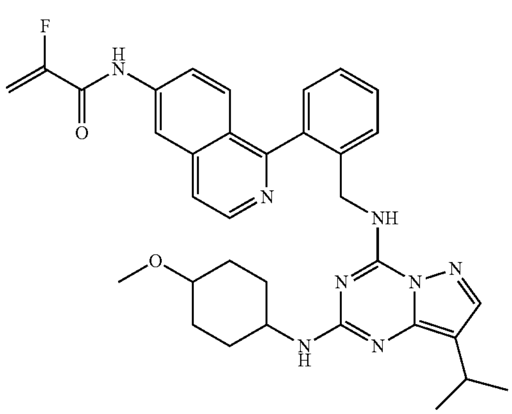 [SMILES: C=C(F)C(=O)Nc1ccc2c(-c3ccccc3CNc3nc(NC4CCC(OC)CC4)nc4c(C(C)C)cnn34)nccc2c1] | Yellow solid; $^1$H-NMR (CD$_3$OD, 400 MHz): δ 8.63 (1H, s), 8.43 (1H, d, J = 6.8 Hz), 8.29 (1H, d, J = 6.8 Hz), 7.82-7.92 (3H, m), 7.65-7.71 (1H, m), 7.57-7.62 (2H, m), 7.54 (1H, s), 5.85 (1H, dd, J = 46.4, 3.6 Hz), 5.45 (1H, dd, J = 14.8, 3.6 Hz), 4.92-4.99 (1H, m), 4.72-4.80 (1H, m), 3.51-3.58 (1H, m), 3.39 (3H, s), 3.22-3.31 (1H, m, overlap with CD$_3$OD signal), 2.76-2.83 (1H, m), 2.01-2.18 (3H, m), 1.69-1.73 (1H, m), 1.27-1.46 (4H, m), 1.15-1.21 (6H, m); LCMS: 100%, MS (ESI): 609.2 m/z [M + H]$^+$ |

TABLE 6-continued

Summarized compounds 1-88 in terms of their structures and corresponding characteristics

| #cpds | Structure | Characterization Data |
|---|---|---|
| 85 | 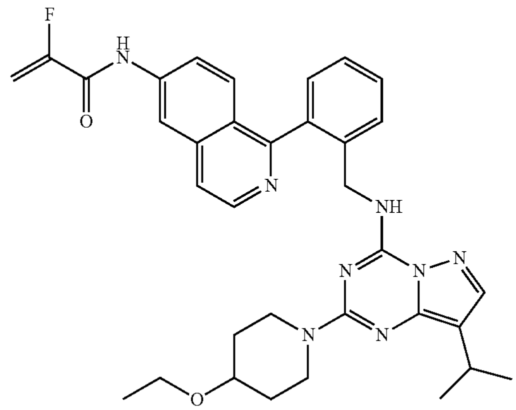 [SMILES: C=C(F)C(=O)Nc1ccc2c(-c3ccccc3CNc3nc(N4CCC(OCC)CC4)nc4c(C(C)C)cnn34)nccc2c1] | White powder; H NMR (CDCl$_3$, 400 MHz): δ 8.54 (1H, d, J = 5.6 Hz), 8.30 (1H, s), 8.04 (1H, brs), 7.59 (1H, d, J = 8.8 Hz), 7.55 (2H, d, J = 6.0 Hz), 7.44 (1H, s), 7.30-7.42 (3H, m), 7.25 (1H, d, J = 8.8 Hz), 6.92-6.96 (1H, m), 5.85 (1H, dd, J = 47.6, 3.6 Hz), 5.26 (1H, dd, J = 14.8, 3.6 Hz), 4.76-4.85 (1H, m), 4.12-4.31 (3H, m), 3.42-3.53 (3H, m), 3.09-3.18 (2H, m), 2.83-2.96 (1H, m), 1.80-1.87 (2H, m), 1.43-1.51 (2H, m, overlap with water signal), 1.15-1.21 (9H, m); LCMS: 98.8%, MS (ESI): m/z 609.3 [M + H]$^+$ |
| 86 | 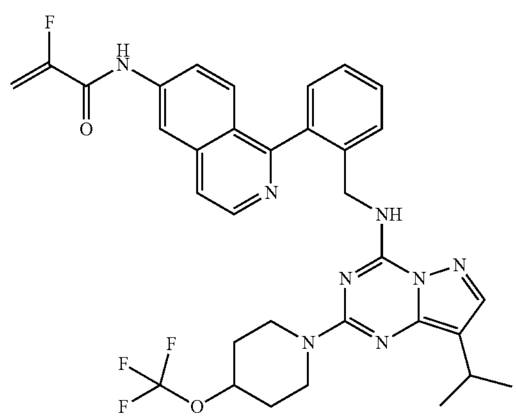 [SMILES: C=C(F)C(=O)Nc1ccc2c(-c3ccccc3CNc3nc(N4CCC(OC(F)(F)F)CC4)nc4c(C(C)C)cnn34)nccc2c1] | Off-white powder; $^1$H NMR (CDCl$_3$, 400 MHz): δ 8.62 (1H, d, J = 6.0 Hz), 8.41 (1H, s), 8.06-8.15 (1H, m), 7.61-7.75 (3H, m), 7.31-7.57 (5H, m), 7.02-7.23 (1H, m), 5.95 (1H, dd, J = 47.6, 3.2 Hz), 5.37 (1H, dd, J = 14.8, 3.2 Hz), 4.85-4.96 (1H, m), 4.46-4.54 (1H, m), 4.07-4.36 (2H, m), 3.47-3.60 (2H, m), 29.5-3.04 (1H, m), 1.92-2.05 (2H, m), 1.68-1.80 (2H, m), 1.27 (6H, d, J = 6.8 Hz); LCMS: 97.3%, MS (ESI): 649.1 m/z [M + H]+ |
| 87 | 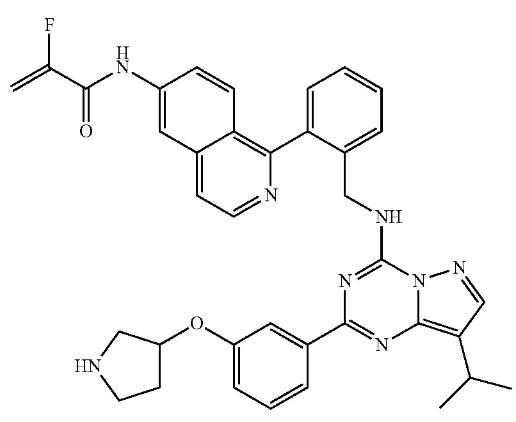 [SMILES: C=C(F)C(=O)Nc1ccc2c(-c3ccccc3CNc3nc(-c4cccc(OC5CCNC5)c4)nc4c(C(C)C)cnn34)nccc2c1] | Racemic mixture; off-white powder; $^1$H NMR (400 MHz, CD$_3$OD) δ 8.39 (1H, s), 7.97 (1H, d, J = 6.4 Hz), 7.83-7.92 (2H, m), 7.73-7.80 (4H, m), 7.61-7.72 (3H, m), 7.56 (1H, d, J = 7.6 Hz), 7.44 (1H, t, J = 8.0 Hz), 7.12-7.16 (1H, m), 5.85 (1H, dd, J = 40.0, 4.0 Hz), 5.79 (1H, dd, J = 14.8, 3.6 Hz), 5.35-5.38 (1H, m), 5.03-5.07 (1H, m), 3.64-3.69 (1H, m), 3.18-3.27 (2H, m), 3.11-3 .17 (1H, m), 2.41-2.48 (2H, m), 2.02-2.08 (1H, m), 1.58-1.64 (1H, m), 1.28-1.34 (6H, m); HPLC: 96.9% MS (ESI): m/z 643.2[M + H]$^+$ |

TABLE 6-continued

Summarized compounds 1-88 in terms of their structures and corresponding characteristics

| #cpds | Structure | Characterization Data |
|---|---|---|
| 88 | 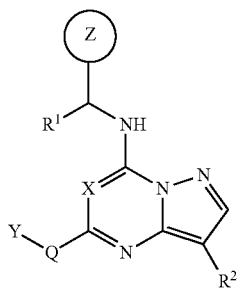 | Yellow powder; $^1$H NMR (CDCl$_3$, 400 MHz): δ 8.47 (1H, d, J = 6.0 Hz), 8.28 (1H, d, J = 1.2 Hz), 8.04-8.08 (1H, m), 7.59 (1H, d, J = 9.2 Hz), 7.52-7.57 (2H, m), 7.35-7.46 (3H, m), 7.26-7.34 (2H, m), 5.85 (1H, dd, J = 47.6, 3.6 Hz), 5.27 (1H, dd, J = 15.2, 3.6 Hz), 4.78-4.85 (1H, m), 4.08-4.24 (3H, m), 3.32-3.39 (4H, m), 3.19-3.30 (2H, m), 2.85-2.96 (1H, m), 1.79-1.84 (2H, m), 1.45-1.58 (2H, m, overlap with water signal), 1.17 (6H, d, J = 6.8 Hz); LCMS: 98%, MS (ESI): m/z 595.2 [M + H]$^+$ |

The invention claimed is:

1. A compound having Formula I:

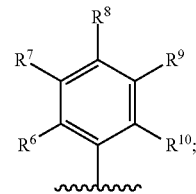

Formula I or a pharmaceutically acceptable salt or stereoisomer thereof, wherein:
X is CH or N;
R$^1$ is H;
R$^2$ is C$_1$-C$_6$ alkyl, C$_1$-C$_3$ haloalkyl, or C(O)CH$_3$;
Q is —C(O)—, —C(O)CH$_2$—, —C(O)NH—, —NH—, —NHCH$_2$—, —NHCH$_2$CH$_2$—, —NHC(O)—, —NHS(O)$_2$—, —O—, or —OCH$_2$—;
Y is C$_1$-C$_6$ alkyl, C$_3$-C$_6$ cycloalkyl, heterocyclyl, aryl, or heteroaryl;
  wherein the C$_1$-C$_6$ alkyl is substituted with one or two substituents independently selected from the group consisting of NR$^5$R$^5$, OR$^5$, heterocyclyl, aryl, and heteroaryl;
  wherein the C$_3$-C$_8$ cycloalkyl or heterocyclyl is optionally substituted with one or two substituents independently selected from the group consisting of R$^3$, R$^4$, and C(O)R$^5$; and
  wherein the aryl or heteroaryl is optionally substituted with one or two substituents independently selected from the group consisting of halogen, C$_1$-C$_6$ alkyl, C(O)R$^5$, NR$^5$R$^5$, OR$^5$, heterocyclyl, heteroaryl, and R$^3$;
each R$^3$ is independently H, halogen, C$_1$-C$_6$ alkyl, C(O)NH$_2$, NR$^5$R$^5$, NHC(O)R$^5$, OR$^5$, heterocyclyl, aryl, or heteroaryl, wherein each C$_1$-C$_6$ alkyl is optionally and independently substituted with one substituent selected from the group consisting of NH$_2$ and OH;
each R$^4$ is independently H, halogen, C$_1$-C$_6$ alkyl, NR$^5$R$^5$, OR$^5$, =O, heterocyclyl, aryl, or heteroaryl, wherein each C$_1$-C$_6$ alkyl is optionally and independently substituted with one substituent selected from the group consisting of NH$_2$ and OH;
each R$^5$ is independently H, C$_1$-C$_6$ alkyl, C$_1$-C$_3$ haloalkyl, C$_3$-C$_6$ cycloalkyl, heterocyclyl, or heteroaryl;
  wherein each heterocyclyl and heteroaryl is optionally and independently substituted with one or two substituents independently selected from the group consisting of halogen, C$_1$-C$_6$ alkyl, NR$^{11}$R$^{11}$, and OR$^{11}$; and
  wherein each C$_1$-C$_6$ alkyl substituent of each heterocyclyl and heteroaryl is optionally and independently substituted with one substituent selected from the group consisting of NH$_2$ and OH;
each R$^{11}$ is independently H, C$_1$-C$_6$ alkyl, C$_3$-C$_{10}$ cycloalkyl, or W;
Z is:

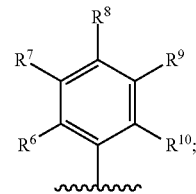

(i) R$^6$ is a ring selected from the following Group B:

Group B

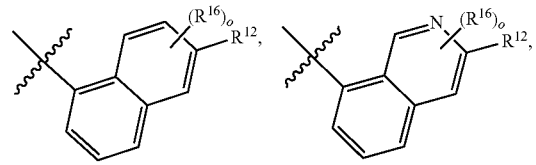

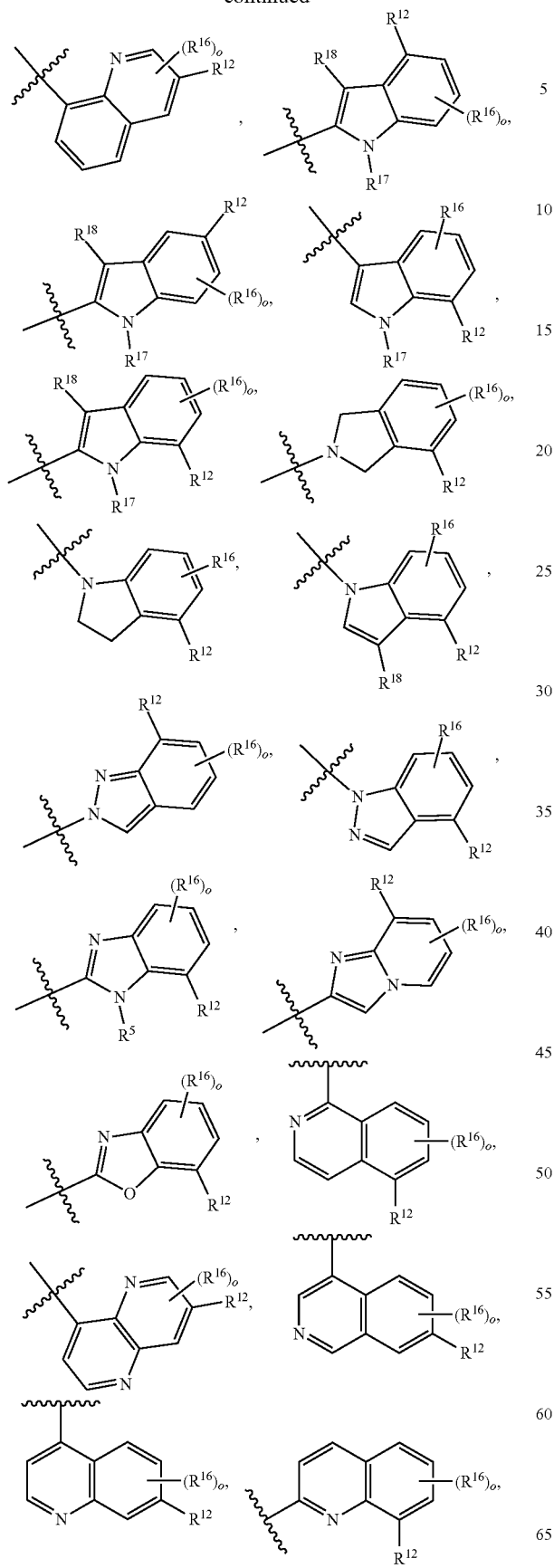
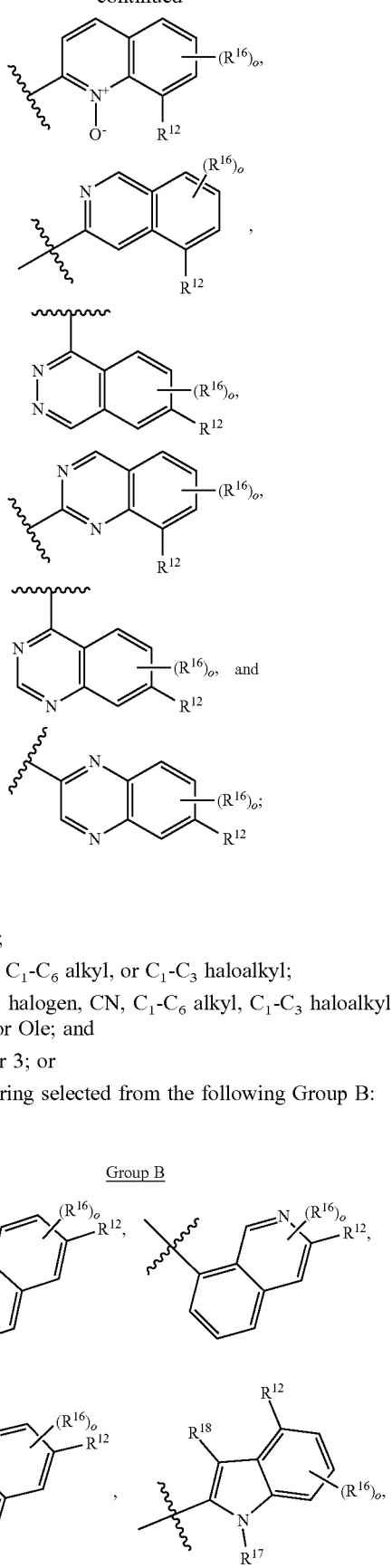
R[12] is H;
R[16] is W;
R[17] is H, $C_1$-$C_6$ alkyl, or $C_1$-$C_3$ haloalkyl;
R[18] is H, halogen, CN, $C_1$-$C_6$ alkyl, $C_1$-$C_3$ haloalkyl, $NH_2$, or Ole; and
is 1, 2, or 3; or
(ii) R[6] is a ring selected from the following Group B:
Group B -continued
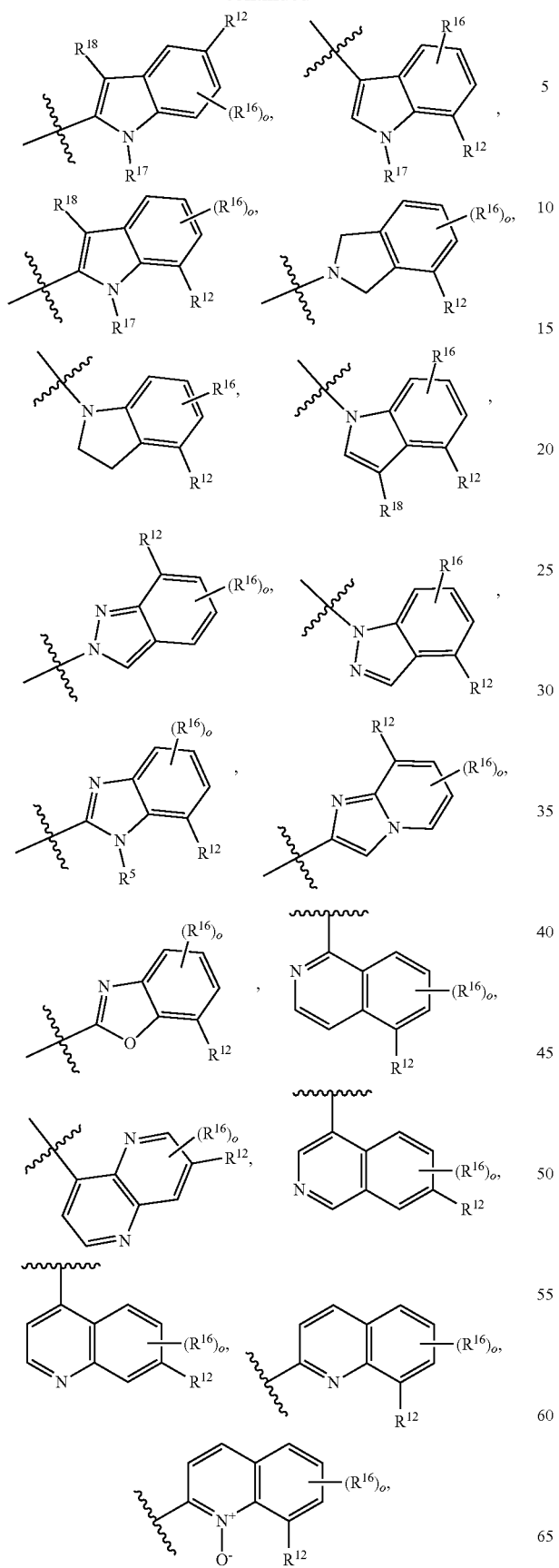
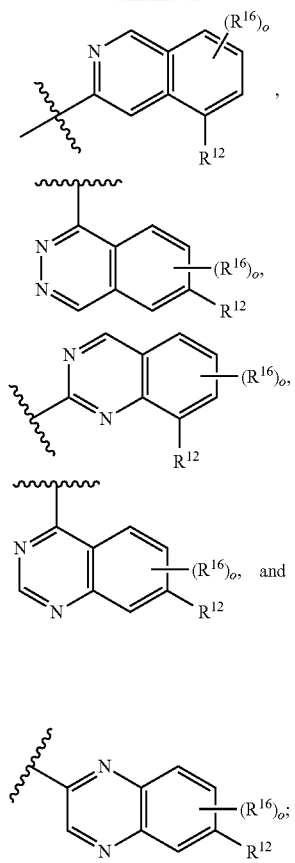
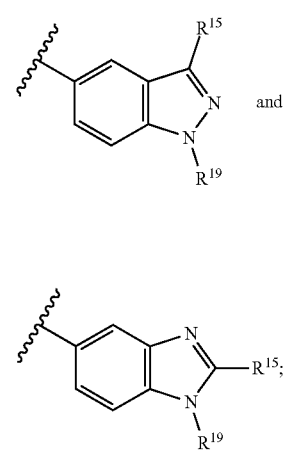
$R^{12}$ is W;
$R^{16}$ is H, halogen, CN, $C_1$-$C_6$ alkyl, $C_1$-$C_3$ haloalkyl, $NH_2$, or OW;
$R^{17}$ is H, $C_1$-$C_6$ alkyl, or $C_1$-$C_3$ haloalkyl;
$R^{18}$ is H, halogen, CN, $C_1$-$C_6$ alkyl, $C_1$-$C_3$ haloalkyl, $NH_2$, or OW; and
is 1, 2, or 3; or
(iii) $R^6$ is a ring selected from the following Group B:
Group B and
R¹⁵ is W; or
(iv) R⁶ is a ring selected from the following Group B:

Group B

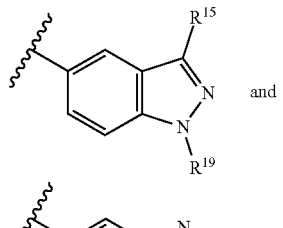

and
R¹⁵ is H; and
R¹⁹ is W; or
(v) R⁶ is a ring selected from the following Group B:

Group B

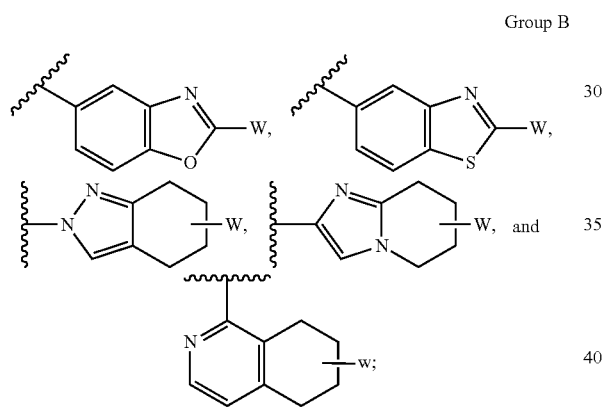

R⁷ is H;
R⁸ is H, halogen, CN, $C_1$-$C_6$ alkyl, $C_1$-$C_3$ haloalkyl, or OR⁵, wherein the $C_1$-$C_6$ alkyl is optionally substituted with one substituent selected from the group consisting of NHR⁵ and OR⁵;
R⁹ is H, halogen, CN, $C_1$-$C_6$ alkyl, $C_1$-$C_3$ haloalkyl, or OR⁵, wherein the $C_1$-$C_6$ alkyl is optionally substituted with one substituent selected from the group consisting of NHR⁵ and OR⁵;
R¹⁰ is H, halogen, CN, $C_1$-$C_6$ alkyl, $C_1$-$C_3$ haloalkyl, or OR⁵, wherein the $C_1$-$C_6$ alkyl is optionally substituted with one substituent selected from the group consisting of NHR⁵ and OR⁵;
W is a structure selected from the following Group C:

Group C

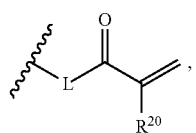 (c-1)

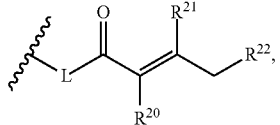 (c-2)

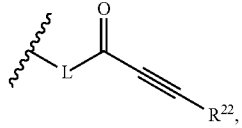 (c-3)

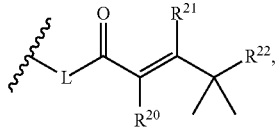 (c-4)

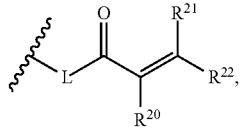 (c-5)

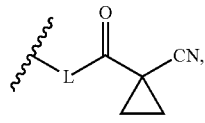 (c-6)

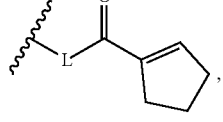 (c-7)

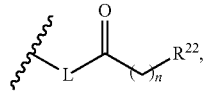 (c-8)

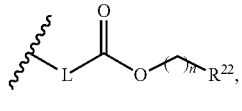 (c-9)

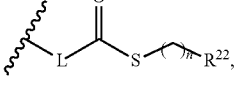 (c-10)

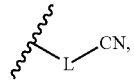 (c-11)

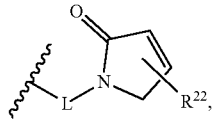 (c-12)

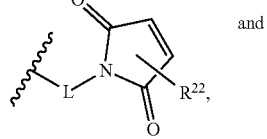 and (c-13)

-continued

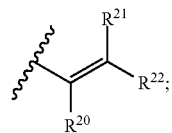
(c-14)

each L is independently absent, —NH—, or —O—;
each $R^{20}$ is independently H, halogen, CN, $C_1$-$C_6$ alkyl, $C_1$-$C_3$ haloalkyl, $OR^5$, or heterocyclyl;
each $R^{21}$ is independently H, halogen, CN, $C_1$-$C_6$ alkyl, $C_1$-$C_3$ haloalkyl, $OR^5$, or heterocyclyl;
each $R^{22}$ is independently H, halogen, CN, $C_1$-$C_6$ alkyl, $NR^5R^5$, $NR^{19}R^{20}$, $NR^{19}CH_2C(O)NH_2$, $OR^5$, $C_3$-$C_{10}$ cycloalkyl, or heterocyclyl, wherein each $R^{19}$ is independently H, $C_1$-$C_6$ alkyl, $C_3$-$C_{10}$ cycloalkyl, or W; and
each n is independently 1, 2, or 3.

2. The compound according to claim 1, wherein the compound has Formula Ia:

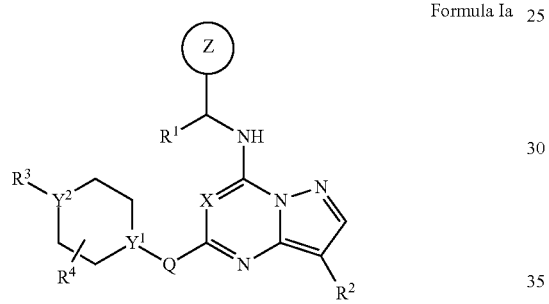
Formula Ia or a pharmaceutically acceptable salt or stereoisomer thereof,
wherein:
Q is —C(O)—, —C(O)CH$_2$—, —NH—, —NHCH$_2$—, —NHC(O)—, —NHS(O)$_2$—, —O—, or —OCH$_2$—;
$Y^1$ is CH, COH, or N;
$Y^2$ is CH, COH, or N;
$R^3$ is H, halogen, $C_1$-$C_6$ alkyl, C(O)NH$_2$, $NR^5R^5$, NHC(O)$R^5$, or OH, wherein the $C_1$-$C_6$ alkyl is optionally substituted with one substituent selected from the group consisting of NH$_2$ and OH;
each $R^4$ is independently H, halogen, $C_1$-$C_6$ alkyl, NH$_2$, or $OR^5$, wherein each $C_1$-$C_6$ alkyl is optionally and independently substituted with one substituent selected from the group consisting of NH$_2$ and OH;
each $R^5$ is independently H, $C_1$-$C_6$ alkyl, or $C_1$-$C_3$ haloalkyl;
W is a structure selected from the following Group C:

Group C

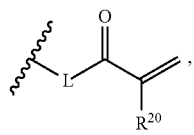
(c-1)

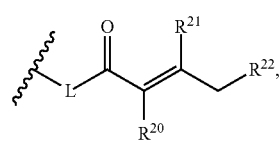
(c-2)

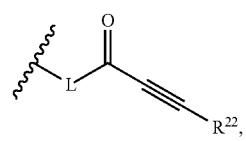
(c-3)

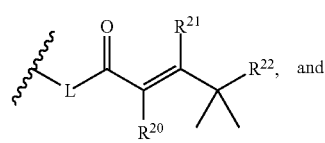
(c-4)

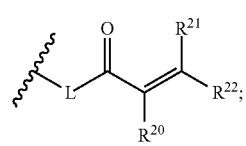
(c-5)

and
$R^{22}$ is H, halogen, CN, $C_1$-$C_6$ alkyl, $NR^5R^5$, $NR^{19}R^{20}$, $OR^5$, $C_3$-$C_{10}$ cycloalkyl, or heterocyclyl.

3. The compound according to claim 1, wherein the compound has Formula II:

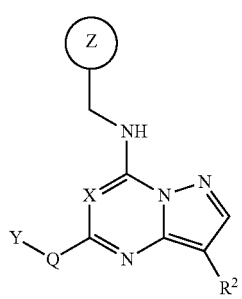
Formula II or a pharmaceutically acceptable salt or stereoisomer thereof,
wherein:
Q is —C(O)—, —C(O)CH$_2$—, —C(O)NH—, —NH—, —NHCH$_2$—, —NHC(O)—, —NHS(O)$_2$—, —O—, or —OCH$_2$—.

4. The compound according to claim 1, wherein the compound has Formula III:

Formula III

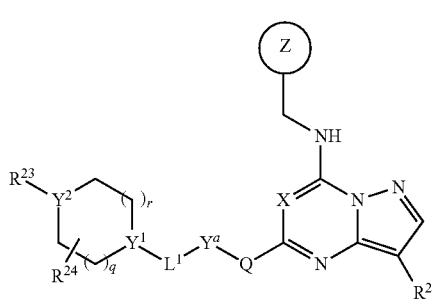

or a pharmaceutically acceptable salt or stereoisomer thereof,
wherein:
Q is —C(O)—, —C(O)CH$_2$—, —C(O)NH—, —NH—, —NHCH$_2$—, —NHCH$_2$CH$_2$—, —NHC(O)—, —NHS(O)$_2$—, —O—, or —OCH$_2$—;
Y$^a$ is absent;
L$^1$ is absent;
Y$^1$ is CH, COH, or N;
Y$^2$ is CH, COH, or N;
R$^{23}$ is H, halogen, C$_1$-C$_6$ alkyl, C(O)NH$_2$, NR$^5$R$^5$, NHC(O)R$^5$, OR$^5$, heterocyclyl, aryl, or heteroaryl, wherein the C$_1$-C$_6$ alkyl is optionally substituted with one substituent selected from the group consisting of NH$_2$ and OH;
each R$^{24}$ is independently H, halogen, C$_1$-C$_6$ alkyl, NR$^5$R$^5$, OR$^5$, =O, heterocyclyl, aryl, or heteroaryl, wherein each C$_1$-C$_6$ alkyl is optionally and independently substituted with one substituent selected from the group consisting of NH$_2$ and OH;
q is 0, 1, or 2; and
r is 0, 1, 2, or 3.

5. The compound according to claim 1, wherein the compound has Formula IV:

Formula IV

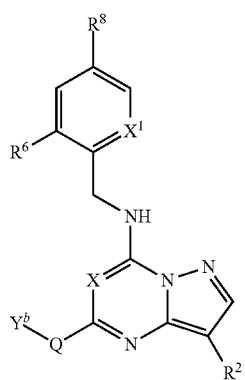

or a pharmaceutically acceptable salt or stereoisomer thereof,
wherein:
X$^1$ is CR$^{10}$;
R$^{10}$ is H, halogen, CN, C$_1$-C$_6$ alkyl, C$_1$-C$_3$ haloalkyl, or OR$^5$, wherein the C$_1$-C$_6$ alkyl is optionally substituted with one substituent selected from the group consisting of NHR$^5$ and OR$^5$;
Y$^b$ is a ring selected from the following Group F:

Group F

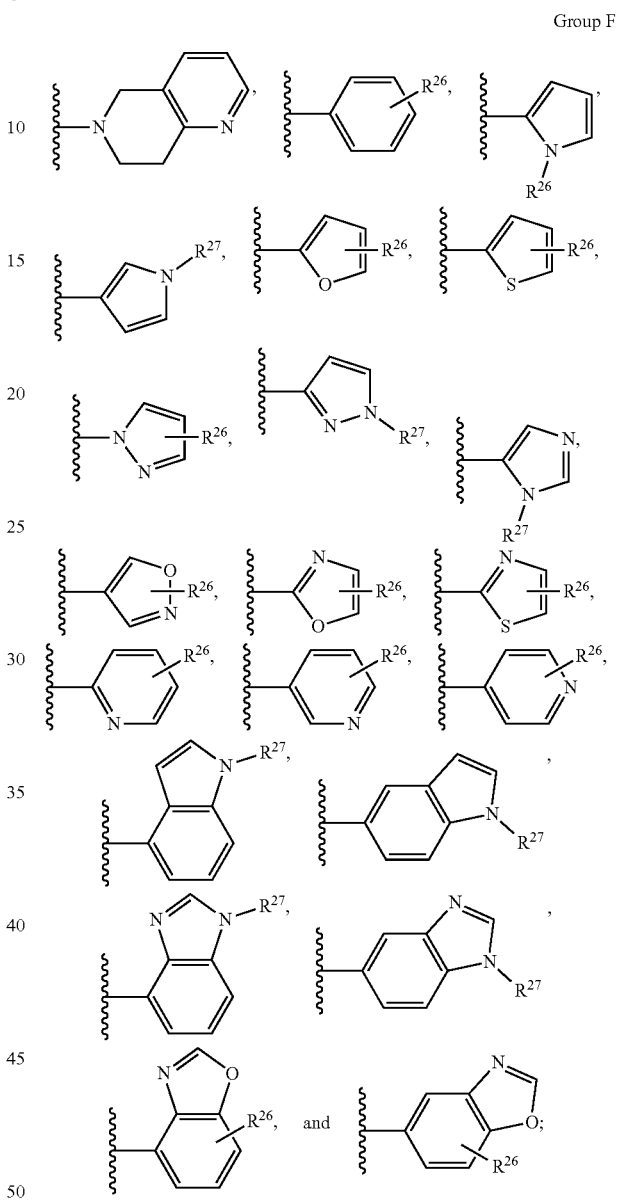

each R$^{26}$ is independently H, halogen, C$_1$-C$_6$ alkyl, C(O)NH$_2$, NR$^5$R$^5$, NHC(O)R$^5$, OR$^5$, heterocyclyl, aryl, or heteroaryl, wherein each C$_1$-C$_6$ alkyl is optionally and independently substituted with one substituent selected from the group consisting of NH$_2$ and OH; and
each R$^{27}$ is independently H, halogen, C$_1$-C$_6$ alkyl, C(O)NH$_2$, NR$^5$R$^5$, NHC(O)R$^5$, OR$^5$, heterocyclyl, aryl, or heteroaryl, wherein each C$_1$-C$_6$ alkyl is optionally and independently substituted with one substituent selected from the group consisting of NH$_2$ and OH.

6. The compound according to claim 1, or a pharmaceutically acceptable salt or stereoisomer thereof, wherein R$^2$ is C$_1$-C$_6$ alkyl.

7. The compound according to claim 1, or a pharmaceutically acceptable salt or stereoisomer thereof, wherein exactly one of the following applies:
(i) $R^{12}$ is W; or
(ii) $R^{15}$ is W; or
(iii) $R^{16}$ is W; or
(iv) $R^{19}$ is W.

8. The compound according to claim 1, or a pharmaceutically acceptable salt or stereoisomer thereof, wherein: Z is:

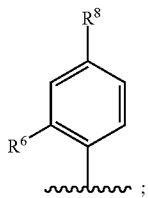

and
$R^8$ is halogen, CN, $C_1$-$C_6$ alkyl, $C_1$-$C_3$ haloalkyl, or $OR^5$, wherein the $C_1$-$C_6$ alkyl is optionally substituted with one substituent selected from the group consisting of $NHR^5$ and $OR^5$.

9. The compound according to claim 1, or a pharmaceutically acceptable salt or stereoisomer thereof, wherein Z is:

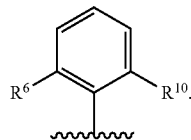

10. The compound according to claim 1, or a pharmaceutically acceptable salt or stereoisomer thereof, wherein Z is:

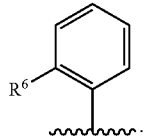

11. A pharmaceutical composition comprising at least one pharmaceutically acceptable carrier, excipient, and/or diluent together with a compound according to claim 1, or a pharmaceutically acceptable salt or stereoisomer thereof, as an active ingredient.

12. A method for inhibiting cyclin-dependent kinase (CDK) activity in a subject, wherein the method comprises administering to the subject in need thereof a therapeutically effective amount of a compound according to claim 1, or a pharmaceutically acceptable salt or stereoisomer thereof.

13. The method according to claim 12, wherein the subject has a disease selected from the group consisting of an autoimmune disease, an immunological disease, an infectious disease, an inflammatory disease, and a proliferative disease.

14. The method according to claim 13, wherein the autoimmune disease or immunological disease is selected from the group consisting of acquired immunodeficiency syndrome (AIDS), alopecia, anaphylaxis, an antibody deficiency state, asthma, ataxia-telangiectasia, atopic dermatitis, an autoimmune disease, a cell mediated immunodeficiency, chronic aggressive hepatitis, chronic obstructive pulmonary disease, Crohn's disease, dermatomyositis, diabetes, DiGeorge syndrome, a drug allergy, eczema, a food allergy, Goodpasture syndrome (GPS), Hashimoto's disease, hyper IgE syndrome (HIES), an immune mediated cancer, immune mediated glomerulonephritis, inflammatory bowel disease, lupus erythematosus, a manifestation of an allergic disease, myasthenia gravis (MG), multiple sclerosis (MS), an occupational allergy, osteoporosis, pemphigus, pernicious anemia, phakogene uveitis, psoriasis, a primary immunodeficiency, primary biliary cirrhosis, a recurrent infection, a rejection of a transplanted organ, a rejection of a transplanted tissue, a rheumatic disease, rhinitis, scleroderma, a severe anaphylactic reaction, a severe combined immunodeficiency, sinusitis, sympathetic ophthalmia, ulcerative colitis, Werlhof's disease, a white cell defect, and Wiskott-Aldrich syndrome (WAS).

15. The method according to claim 14, wherein the autoimmune disease is autoimmune hemolytic anemia or autoimmune thyroid disease.

16. The method according to claim 14, wherein the diabetes is immune-mediated diabetes or type 1 diabetes mellitus.

17. The method according to claim 14, wherein the lupus erythematosus is systemic lupus erythematosus (SLE).

18. The method according to claim 14, wherein the pemphigus is pemphigus vulgaris.

19. The method according to claim 14, wherein the rheumatic disease is rheumatoid arthritis (RA).

20. The method according to claim 13, wherein the infectious disease is an opportunistic disease.

21. The method according to claim 13, wherein the infectious disease is selected from the group consisting of acquired immunodeficiency syndrome (AIDS), an adenovirus infection, alveolar hydatid disease (AHD), amoebiasis, angiostrongyliasis, anisakiasis, anthrax, aphthae epizooticae, babesiosis, balantidiasis, a *baylisascaris* infection, *bilharzia* (schistosomiasis), a *Blastocystis hominis* infection, lyme borreliosis, botulism, brainerd diarrhea, brucellosis, bovine spongiform encephalopathy (BSE), candidiasis, capillariasis, chronic fatigue syndrome (CFS), Chagas disease, chickenpox, a *Chlamydia pneumoniae* infection, cholera, Creutzfeldt-Jakob disease (CJD), clonorchiasis, cutaneous larva migrans (CLM), coccidioidomycosis, conjunctivitis, coxsackievirus A16 (cox A16), cryptococcal disease, cryptosporidiosis, cyclosporiasis, a cytomegalovirus infection, Dengue fever, a *dipylidium caninum* infection, ebola hemorrhagic fever (EHF), alveolar echinococcosis (AE), encephalitis, an *Entamoeba coli* infection, an *Entamoeba dispar* infection, an *Entamoeba hartmanni* infection, an *Entamoeba polecki* infection, an enterovirus infection (polio/non-polio), an Epstein Barr virus infection, an *Escherichia coli* infection, a foodborne infection, fungal dermatitis, a fungal infection, gastroenteritis, a Group A streptococcal disease, a Group B streptococcal disease, Hansen's disease (leprosy), hantavirus pulmonary syndrome, head lice infestation (pediculosis), a *Elicobacter pylori* infection, a hematologic disease, a hendra virus infection, hepatitis B virus (HBV), hepatitis C virus (HCV), herpes zoster (shingles), a human immunodeficiency virus (HIV) infection, human ehrlichiosis, a human parainfluenza virus infection, influenza, isosporiasis, Lassa fever, leishmaniasis, malaria, Marburg hemorrhagic fever, measles, meningitis, a *Mycobacterium avium* complex (MAC) infection, a *naegleria* infection, neurocysticercosis, a nosocomial infection, a nonpathogenic intestinal amebae infection, onchocerciasis, opisthorchiasis, a papilloma virus infection, a parvovirus infection, pertussis, a pinworm infection, a plague, *pneumocystis* pneumonia (PCP), a polyomavirus infection, Q fever, rabies, a respiratory syncytial virus (RSV) infection, rheumatic fever, Rift Valley fever, a rotavirus infection, a roundworms infection, *salmonellosis*, scabies, shigellosis, sleeping sickness, smallpox, a streptococcal infection, a tapeworm infection, tetanus, toxic shock syndrome, tuberculosis duodenum, a varicella-zoster virus infection, a *vibrio parahaemolyticus* infection, *vibrio* septicemia, viral hemorrhagic fever, a wart, a waterborne infectious disease, West Nile fever, and yellow fever.

22. The method according to claim 21, wherein the leishmaniasis is visceral leishmaniasis (VL).

23. The method according to claim 13, wherein one or more of the following applies to the inflammatory disease:
    (1) the inflammatory disease is caused by an allergic agent, an autoimmune agent, an idiopathic agent, an irritative agent, a metabolic agent, or a traumatic agent; or
    (2) the inflammatory disease is caused by a bacteria, a fungus, a parasite, a prion, or a virus; or
    (3) the inflammatory disease is induced by a bacteria, a fungus, a parasite, a prion, or a virus; or
    (4) the inflammatory disease is initiated by a bacteria, a fungus, a parasite, a prion, or a virus; or
    (5) the inflammatory disease is enhanced by a bacteria, a fungus, a parasite, a prion, or a virus.

24. The method according to claim 13, wherein the inflammatory disease is selected from the group consisting of an inflammatory disease of the blood vessels, inflammatory bowel disease, an inflammatory disease of the central nervous system (CNS), an inflammatory disease of the larynx, an inflammatory disease of the middle ear, an inflammatory rheumatic disease, an inflammatory disease of the skin, and uveitis.

25. The method according to claim 24, wherein the inflammatory disease of the blood vessels, inflammatory bowel disease, inflammatory disease of the central nervous system (CNS), inflammatory disease of the larynx, inflammatory disease of the middle ear, inflammatory rheumatic disease, inflammatory disease of the skin, or uveitis is selected from the group consisting of abscessation, *acanthamoeba* infection, acne vulgaris, actinomycosis, acute inflammatory dermatoses, an acute laryngeal infection of an adult, acute multifocal placoid pigment epitheliopathy, acute (thermal) injury, acute retinal necrosis, acute suppurative otitis media, an algal disorder, allergic contact dermatitis, amyloidosis angioedema, ankylosing spondylitis, aspergillosis, atopic dermatitis, an autoantibody in vasculitis, a bacterial disorder, Behcet's disease (BD), birdshot choroidopathy, Borna disease, brucellosis, bullous myringitis, bursitis, candidiasis, canine distemper encephalomyelitis, canine hemorrhagic fever, canine herpes virus encephalomyelitis, cholesteatoma, chronic granulomatous disease (CGD), chronic inflammatory dermatoses, chronic relapsing encephalomyelitis, chronic suppurative otitis media, common upper respiratory infection, Crohn's disease, cryptococcal disease, dermatomyositis, diphtheria, discoid lupus erythematosus (DLE), drug-induced vasculitis, a drug reaction, encephalitozoonosis, eosinophilic meningoencephalitis, epiglottitis, erythema multiforme (EM), feline leukemia virus, feline immunodeficiency virus, feline infectious peritonitis, feline polioencephalitis, feline spongiform encephalopathy, fibromyalgia, gastroesophageal (laryngopharyngeal) reflux disease, giant cell arteritis, glanders, Gilchrist's disease, glaucomatocyclitic crisis, gonorrhea, granular myringitis, granuloma, granulomatous meningoencephalitis (GME), herpes simplex, histoplasmosis, a hypersensitivity reaction, an idiopathic disease, an idiopathic inflammatory disorder, an immune and idiopathic disorder, an infection of the immunocompromised host, infectious canine hepatitis, inhalation laryngitis, interstitial nephritis, irritant contact dermatitis, juvenile rheumatoid arthritis, Kawasaki's disease, La Crosse virus encephalitis, laryngotracheobronchitis, leishmaniasis, leprosy, leptospirosis, leukemia, lichen planus, lupus, lymphoma, meningitis, meningoencephalitis in greyhounds, miscellaneous meningoencephalitis, microscopic polyangiitis, multifocal choroiditis, multifocal distemper encephalomyelitis in mature animals, multiple sclerosis, muscle tension dysphonia (MTD), a mycotic (fungal) disease, necrotizing encephalitis, neosporosis, ocular cicatricial pemphigoid (OCP), old dog encephalitis, onchocerciasis, parasitic encephalomyelitis, a parasitic infection, parvovirus encephalitis, pediatric laryngitis, pollution and inhalant allergy, polymyositis, post-vaccinal canine distemper encephalitis, a prion protein induced disease, protothecosis, protozoal encephalitis-encephalomyelitis, pseudorabies, psoriasis, psoriatic arthritis, pug dog encephalitis, radiation injury, radiation laryngitis, radionecrosis, relapsing polychondritis, Reiter's syndrome, retinitis pigmentosa, retinoblastoma, rheumatoid arthritis, rhinoscleroma, a Rickettsial disorder, Rocky Mountain spotted fever, salmon poisoning disease (SPD), sarcocystosis, sarcoidosis, schistosomiasis, scleroderma, serpiginous choroiditis, shaker dog disease, Sjogren's syndrome, spasmodic croup, a spirochetal disease, spongiotic dermatitis, sporotrichosis, steroid responsive meningitis-arteritis, Stevens-Johnson syndrome (SJS, EM major), sympathetic ophthalmia, syngamosis, systemic vasculitis in sarcoidosis, Takayasu's arteritis, tendinitis (tendonitis), thromboangiitis obliterans (Buerger disease), tick-borne encephalitis in dogs, toxic epidermal necrolysis (TEN), toxocariasis, toxoplasmosis, trauma, trichinosis, trypanosomiasis, tuberculosis, tularemia, ulcerative colitis, urticaria (hives), vasculitis, a viral disorder, vitiligo, vocal abuse, vocal-cord hemorrhage, Vogt-Koyanagi-Harada syndrome (VKH), Wegener's granulomatosis, and Whipple's disease.

26. The method according to claim 25, wherein the abscessation is a laryngeal abscess.

27. The method according to claim 25, wherein the bacterial disorder is bacterial laryngitis or bacterial meningitis.

28. The method according to claim 25, wherein the canine distemper encephalomyelitis is canine distemper encephalomyelitis in an immature animal.

29. The method according to claim 25, wherein the meningitis is miscellaneous meningitis.

30. The method according to claim 25, wherein the mycotic (fungal) disease is a mycotic (fungal) disease of the central nervous system (CNS).

31. The method according to claim 25, wherein the spirochetal disease is syphilis.

32. The method according to claim 25, wherein the trauma is traumatic laryngitis.

33. The method according to claim 25, wherein the uveitis is selected from the group consisting of Fuchs heterochromic uveitis, lens-induced uveitis, and pars planitis.

34. The method according to claim 25, wherein the vasculitis is selected from the group consisting of vasculitis of the central nervous system (CNS), vasculitis in the idiopathic inflammatory myopathies, vasculitis secondary to a bacterial infection, vasculitis secondary to a fungal infection, vasculitis secondary to a parasitic infection, vasculitis and malignancy, and vasculitis and rheumatoid arthritis.

35. The method according to claim 25, wherein the viral disorder is viral laryngitis.

36. The method according to claim 13, wherein the proliferative disease is a cancer selected from the group consisting of acoustic neurinoma, adenocarcinoma, ampullary carcinoma, anal carcinoma, astrocytoma, basal cell carcinoma, bladder cancer, bone cancer, brain metastases, brain stem glioma, a brain tumor (glioma), breast carcinoma, bronchial adenoma, bronchial carcinoma, cancer of the central nervous system, canine mammary carcinoma, a carcinoid, carcinoma unknown primary tumor (CUP-syndrome), cervical cancer, cervical carcinoma, a cervical tumor, cholangiocarcinoma, colon carcinoma, colorectal cancer, colorectal carcinoma, corpus cancer, a craniopharyngioma, a Desmoid tumor, ductal carcinoma in situ, endometrial carcinoma, an ear tumor, ependymoma, an epithelial cancer type, esophageal cancer, esophageal carcinoma, estrogen dependent breast cancer, estrogen independent breast cancer, a Ewing tumor, an eye tumor, an eyelid tumor, feline mammary carcinoma, fibroblastic sarcoma, gallbladder cancer, gallbladder carcinoma, gastric cancer, a gastrointestinal tumor, a germ cell tumor, glioblastoma, a gynecologic tumor, a head and neck tumor (a tumor of the ear, nose, and throat area), hemangiopericytoma, hemangiosarcoma, a hematologic tumor, hepatocellular carcinoma, a hypophysis tumor, hypothalamic glioma, invasive ductal carcinoma, invasive lobular carcinoma, Kaposi's sarcoma, kidney cancer, laryngeal cancer, leiomyosarcoma (LMS), leukemia, liver cancer, liver metastases, lobular carcinoma in situ, lung cancer, lymph sarcoma, lymphoma, malignant fibrous histiocytoma, malignant histiocytosis, malignant neoplasia, a mast cell tumor, medulloblastoma, melanoma, a meningioma, mesothelioma, mixed hepatocellular cholangiocarcinoma, mycosis fungoide, nasal cancer, nephroblastoma, neurinoma, neuroblastoma, a neuroectodermal tumor, non-small-cell lung carcinoma, a nose tumor, oligodendroglioma, oral cancer (cancer in the mouth area and on the lips), osteolytic carcinoma, osteoplastic carcinoma, an osteosarcoma, ovarian cancer, ovarian carcinoma, pancreatic cancer, pancreatic carcinoma, a pelvis tumor, penile cancer, pharyngeal cancer, a pineal tumor, plasmacytoma, pleuropulmonary blastoma, prostate cancer, rectal cancer, rectal carcinoma, renal cell carcinoma, retinoblastoma, rhabdomyosarcoma, salivary gland cancer, sarcoma of the uterus, skin cancer, small-cell lung carcinoma, small intestine cancer, a small intestinal tumor, a soft tissue tumor, a soft tissue sarcoma, squamous cell cancer, squamous cell carcinoma, stomach cancer, testicular cancer, a throat tumor, thymoma, thyroid carcinoma, tongue cancer, tube carcinoma, a ureter tumor, urethral cancer, a urologic tumor, urothelial carcinoma, uterine cancer, vaginal cancer, vulva cancer, and wart appearance.

37. The method according to claim 36, wherein the adenocarcinoma is anal gland adenocarcinoma.

38. The method according to claim 36, wherein the astrocytoma is cerebellar astrocytoma or cerebral astrocytoma.

39. The method according to claim 36, wherein the gastrointestinal tumor is a malignant tumor of the gastrointestinal tract.

40. The method according to claim 36, wherein the kidney cancer is hereditary papillary renal cancer or sporadic papillary renal cancer.

41. The method according to claim 36, wherein the leukemia is acute leukemia or hairy cell leukemia.

42. The method according to claim 36, wherein the lymphoma is selected from the group consisting of acquired immunodeficiency syndrome (AIDS)-related lymphoma, Burkitt's lymphoma, lymphoma of the central nervous system, cutaneous T-cell lymphoma, Hodgkin's lymphoma, non-Hodgkin's lymphoma, and T-cell lymphoma.

43. The method according to claim 36, wherein the melanoma is selected from the group consisting of choroidal melanoma, intraocular melanoma, malignant melanoma, and oral melanoma.

44. The method according to claim 36, wherein the oral cancer (cancer in the mouth area and on the lips) is oral cavity cancer.

45. The method according to claim 36, wherein the pharyngeal cancer is selected from the group consisting of hypopharyngeal cancer, nasopharyngeal cancer, and oropharyngeal cancer.

46. The method according to claim 17, wherein the skin cancer is selected from the group consisting of Merkel cell skin cancer, non-melanoma skin cancer, and skin cancer of the testis.

47. A compound selected from the group consisting of:

| # compound | structure |
| --- | --- |
| 3 | 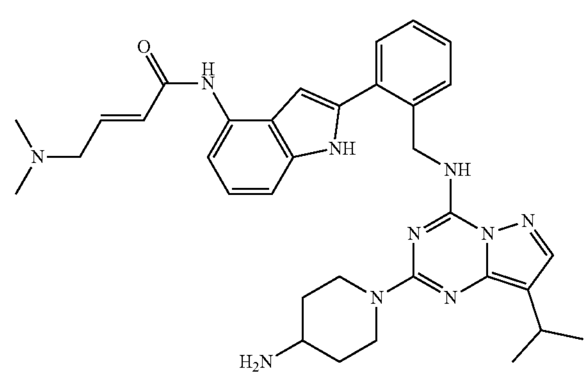 [SMILES: CC(C)c1cnn2c(NCc3ccccc3-c3cc4c(NC(=O)/C=C/CN(C)C)cccc4[nH]3)nc(N3CCC(N)CC3)nc12] |

-continued
| # compound | structure |
|---|---|
| 9 | 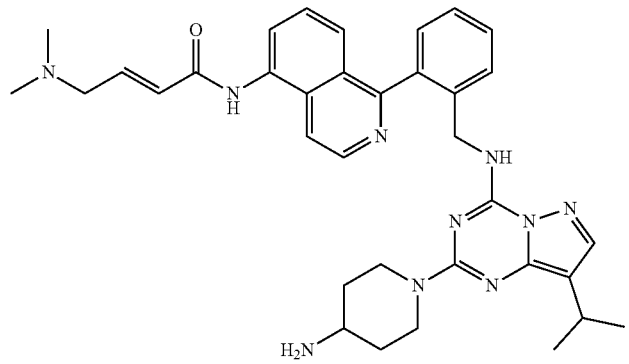 [SMILES: CC(C)c1cnn2c(NCc3ccccc3-c3nccc4c(NC(=O)/C=C/CN(C)C)cccc34)nc(N3CCC(N)CC3)nc12] |
| 11 | 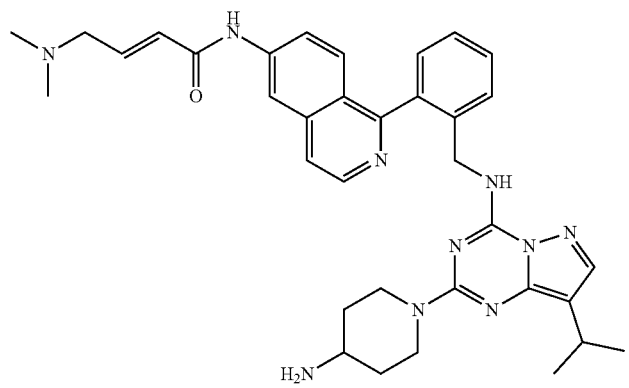 |
| 16 | 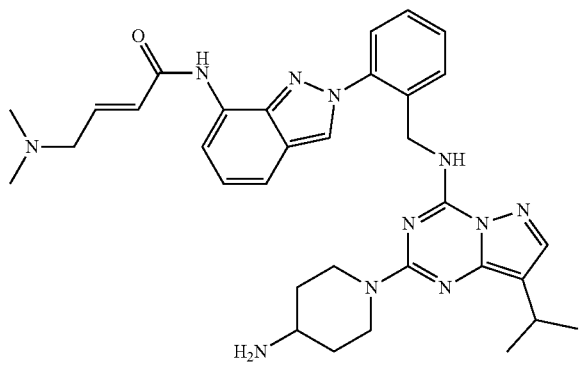 [SMILES: CC(C)c1cnn2c(NCc3ccccc3-n3cc4cccc(NC(=O)/C=C/CN(C)C)c4n3)nc(N3CCC(N)CC3)nc12] |
| 19 | 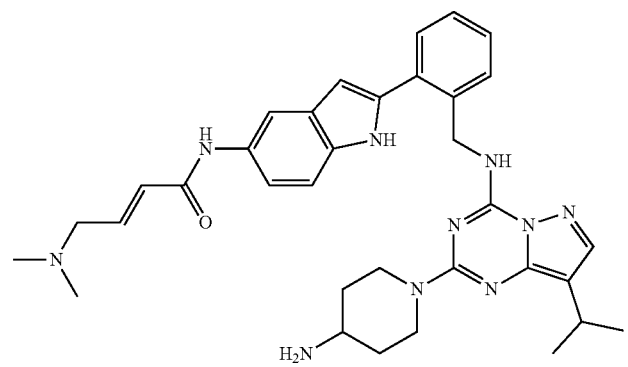 [SMILES: CC(C)c1cnn2c(NCc3ccccc3-c3cc4cc(NC(=O)/C=C/CN(C)C)ccc4[nH]3)nc(N3CCC(N)CC3)nc12] |

| # compound | structure |
|---|---|
| 20 | 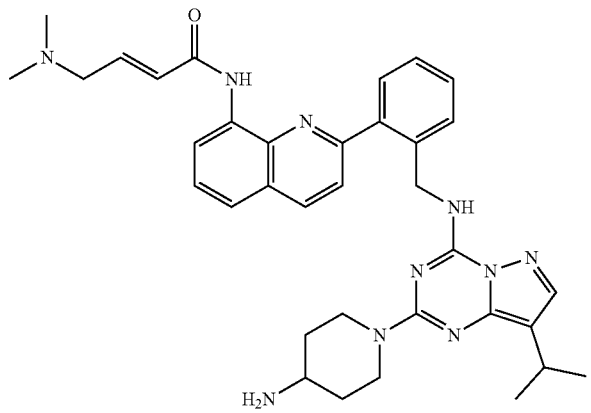 [SMILES: CC(C)c1cnn2c(NCc3ccccc3-c3ccc4cccc(NC(=O)/C=C/CN(C)C)c4n3)nc(N3CCC(N)CC3)nc12] |
| 24 | 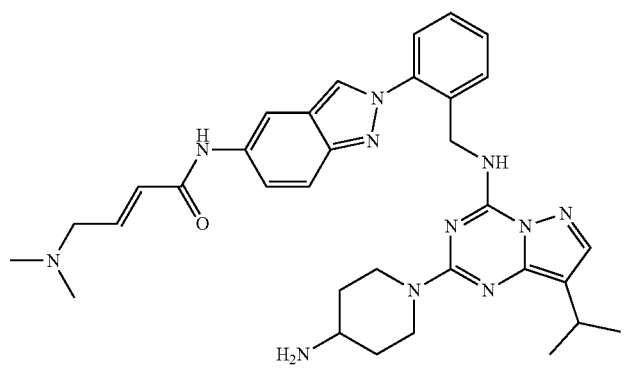 [SMILES: CC(C)c1cnn2c(NCc3ccccc3-n3cc4cc(NC(=O)/C=C/CN(C)C)ccc4n3)nc(N3CCC(N)CC3)nc12] |
| 25 | 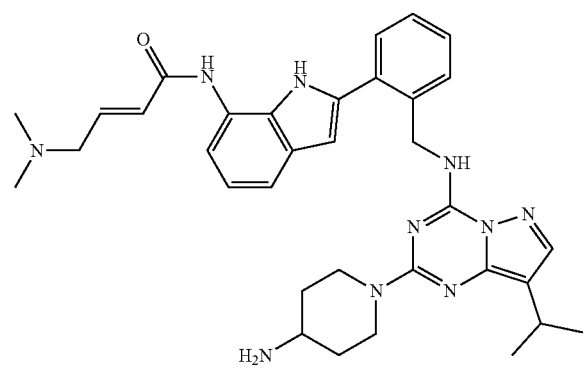 [SMILES: CC(C)c1cnn2c(NCc3ccccc3-c3cc4cccc(NC(=O)/C=C/CN(C)C)c4[nH]3)nc(N3CCC(N)CC3)nc12] |
| 26 | 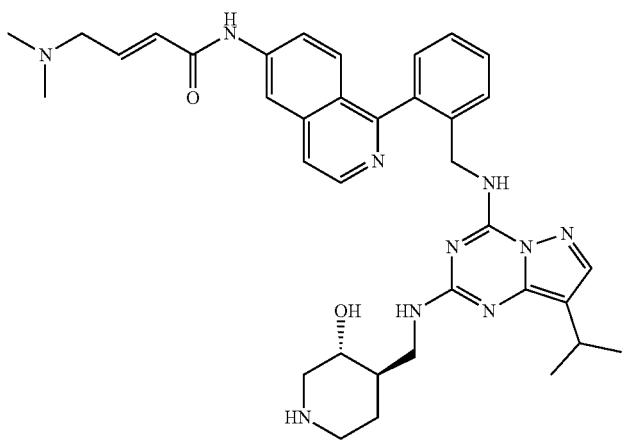 [SMILES: CC(C)c1cnn2c(NCc3ccccc3-c3nccc4cc(NC(=O)/C=C/CN(C)C)ccc34)nc(NC[C@H]3CCNC[C@@H]3O)nc12] |

-continued
| # compound | structure |
|---|---|
| 27 | 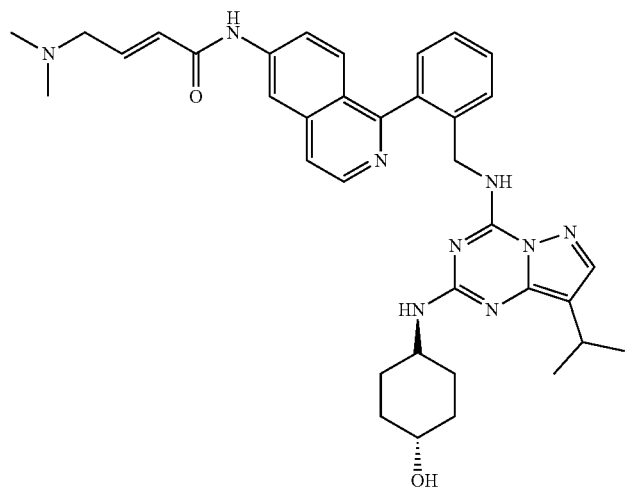 |
| 28 | 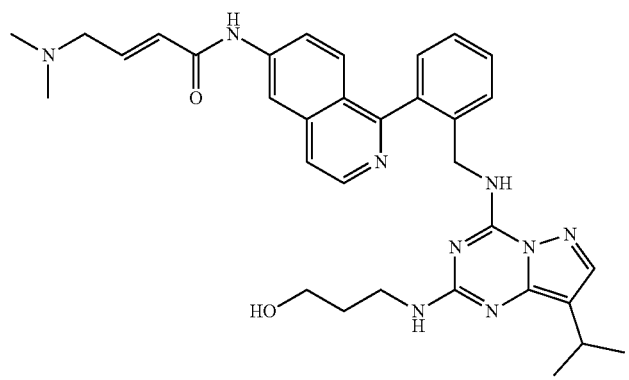 [SMILES: CC(C)c1cnn2c(NCc3ccccc3-c3nccc4cc(NC(=O)/C=C/CN(C)C)ccc34)nc(NCCCO)nc12] |
| 29 | 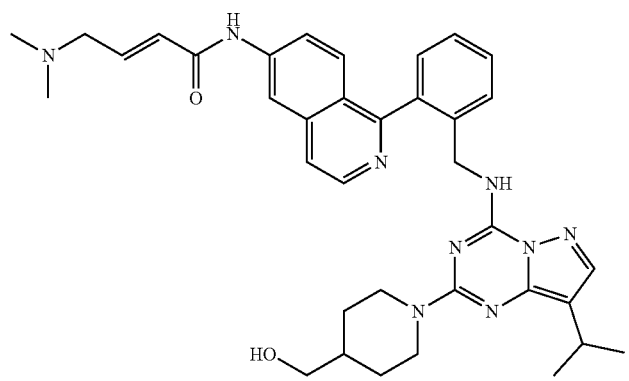 [SMILES: CC(C)c1cnn2c(NCc3ccccc3-c3nccc4cc(NC(=O)/C=C/CN(C)C)ccc34)nc(N3CCC(CO)CC3)nc12] |
| 30 | 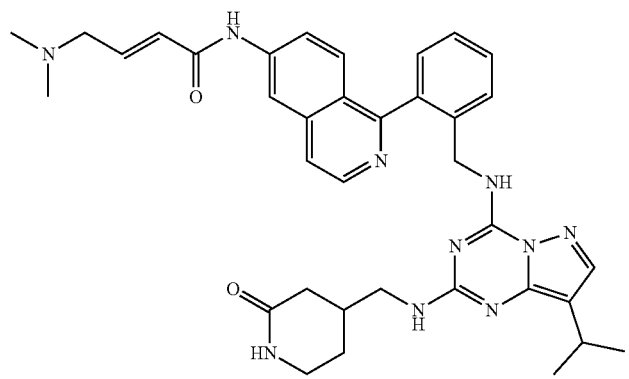 [SMILES: CC(C)c1cnn2c(NCc3ccccc3-c3nccc4cc(NC(=O)/C=C/CN(C)C)ccc34)nc(NCC3CCNC(=O)C3)nc12] |

-continued
| # compound | structure |
|---|---|
| 31 | 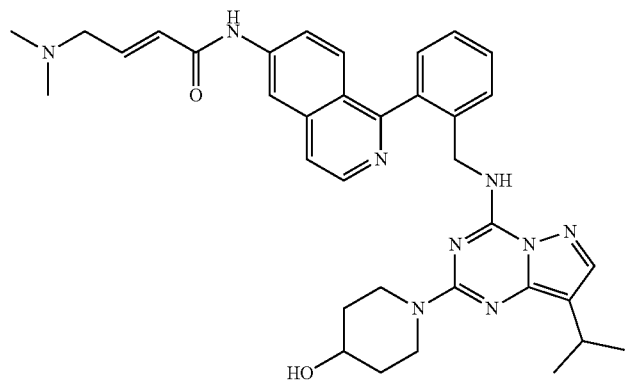 [SMILES: CC(C)c1cnn2c(NCc3ccccc3-c3nccc4cc(NC(=O)/C=C/CN(C)C)ccc34)nc(N3CCC(O)CC3)nc12] |
| 32 | 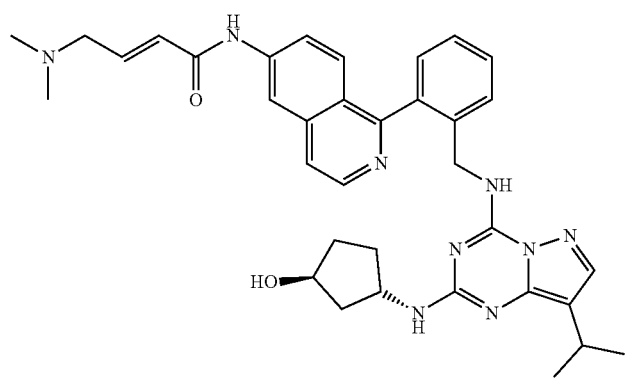 |
| 33 | 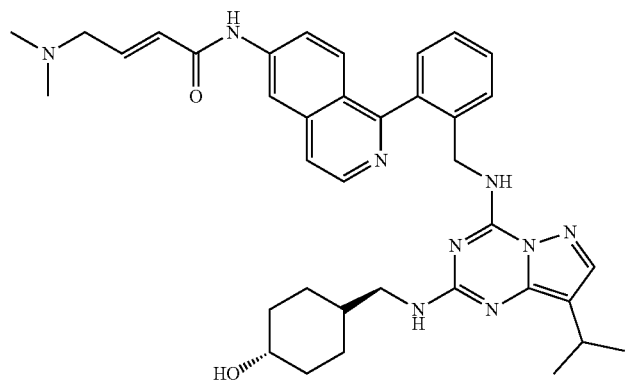 |
| 34 | 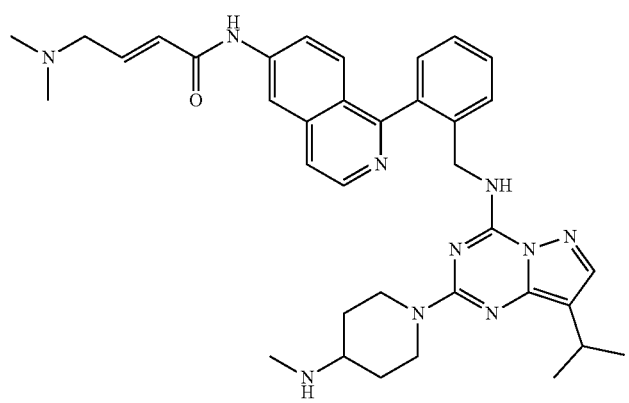 [SMILES: CNC1CCN(c2nc(NCc3ccccc3-c3nccc4cc(NC(=O)/C=C/CN(C)C)ccc34)n3ncc(C(C)C)c3n2)CC1] |

-continued
| # compound | structure |
|---|---|
| 35 | 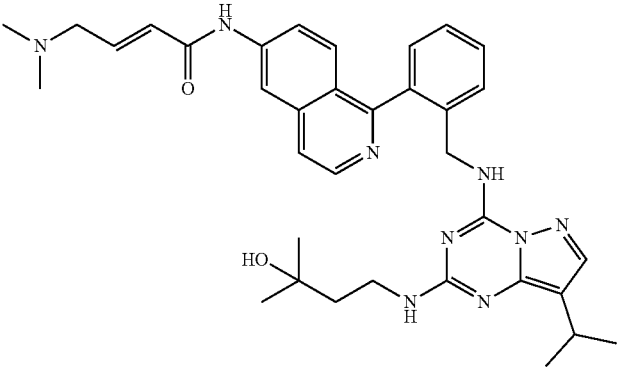 [SMILES: CC(C)c1cnn2c(NCc3ccccc3-c3nccc4cc(NC(=O)/C=C/CN(C)C)ccc34)nc(NCCC(C)(C)O)nc12] |
| 36 | 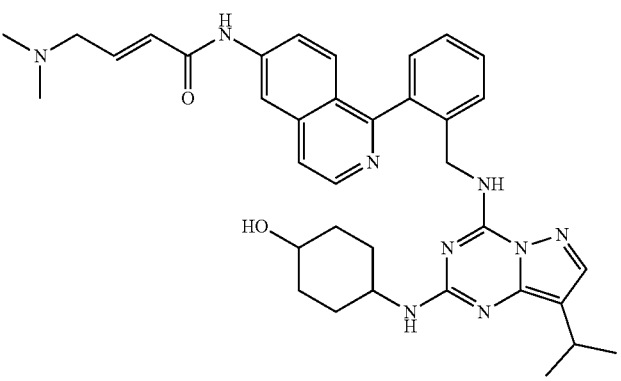 [SMILES: CC(C)c1cnn2c(NCc3ccccc3-c3nccc4cc(NC(=O)/C=C/CN(C)C)ccc34)nc(NC3CCC(O)CC3)nc12] |
| 37 | 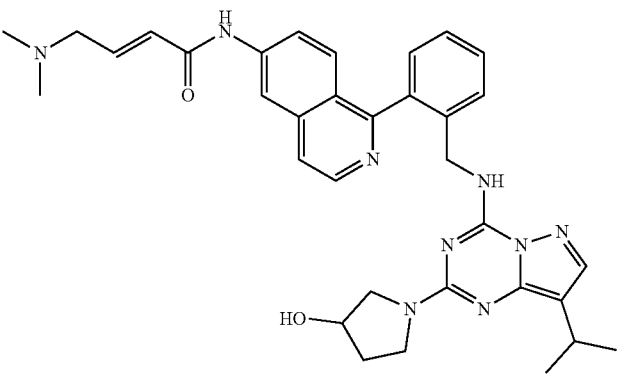 [SMILES: CC(C)c1cnn2c(NCc3ccccc3-c3nccc4cc(NC(=O)/C=C/CN(C)C)ccc34)nc(N3CCC(O)C3)nc12] |
| 38 | 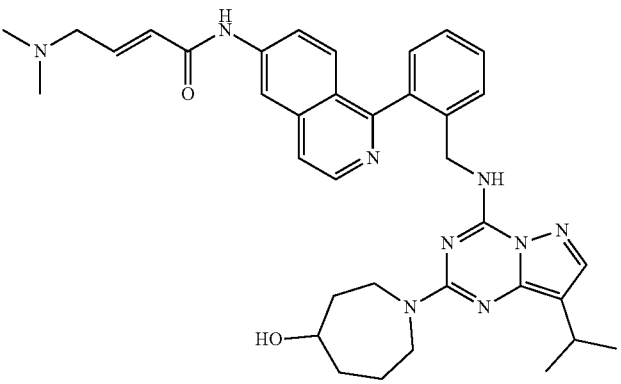 [SMILES: CC(C)c1cnn2c(NCc3ccccc3-c3nccc4cc(NC(=O)/C=C/CN(C)C)ccc34)nc(N3CCCC(O)CC3)nc12] |

| # compound | structure |
| --- | --- |
| 39 | 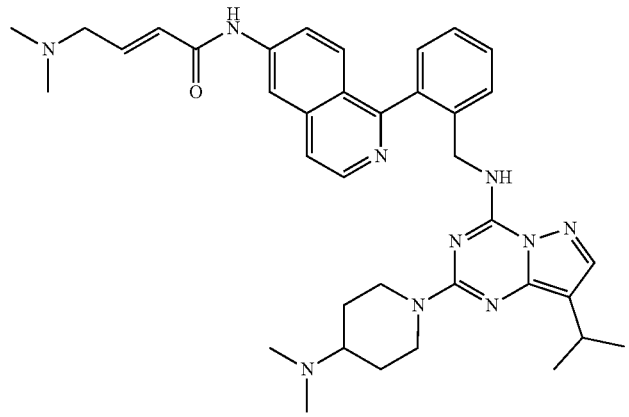 [SMILES: CC(C)c1cnn2c(NCc3ccccc3-c3nccc4cc(NC(=O)/C=C/CN(C)C)ccc34)nc(N3CCC(N(C)C)CC3)nc12] |
| 40 | 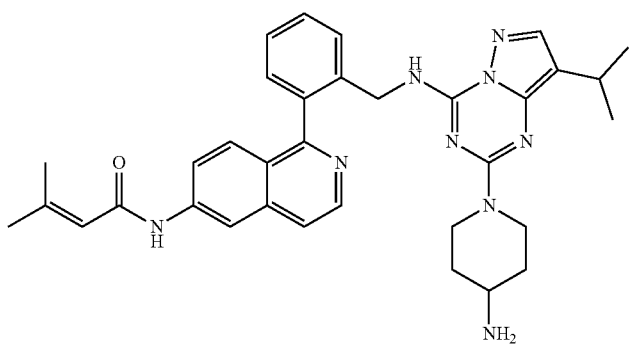 [SMILES: CC(C)=CC(=O)Nc1ccc2c(-c3ccccc3CNc3nc(N4CCC(N)CC4)nc4c(C(C)C)cnn34)nccc2c1] |
| 41 | 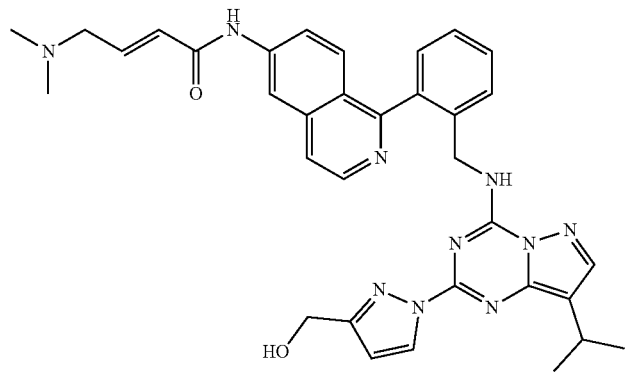 [SMILES: CC(C)c1cnn2c(NCc3ccccc3-c3nccc4cc(NC(=O)/C=C/CN(C)C)ccc34)nc(-n3ccc(CO)n3)nc12] |
| 42 | 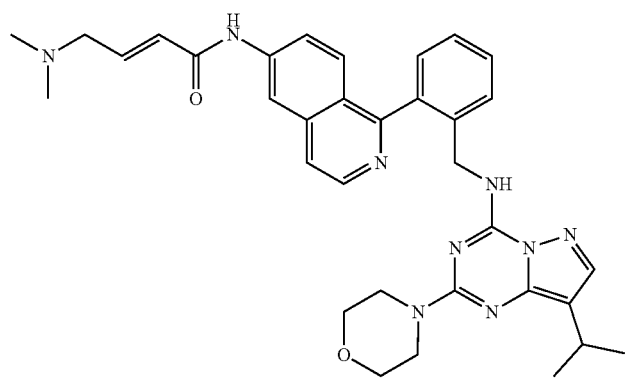 [SMILES: CC(C)c1cnn2c(NCc3ccccc3-c3nccc4cc(NC(=O)/C=C/CN(C)C)ccc34)nc(N3CCOCC3)nc12] |

-continued
| # compound | structure |
|---|---|
| 43 | 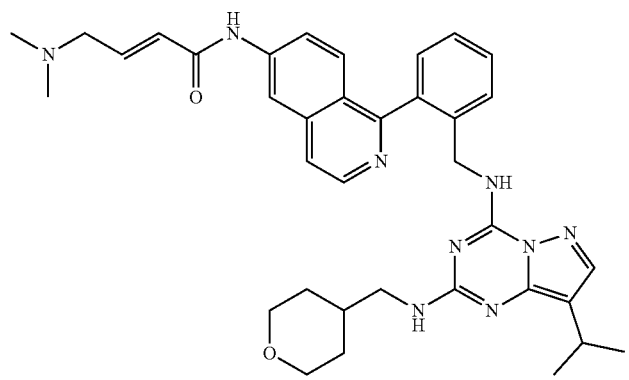 [SMILES: CC(C)c1cnn2c(NCc3ccccc3-c3nccc4cc(NC(=O)/C=C/CN(C)C)ccc34)nc(NCC3CCOCC3)nc12] |
| 44 | 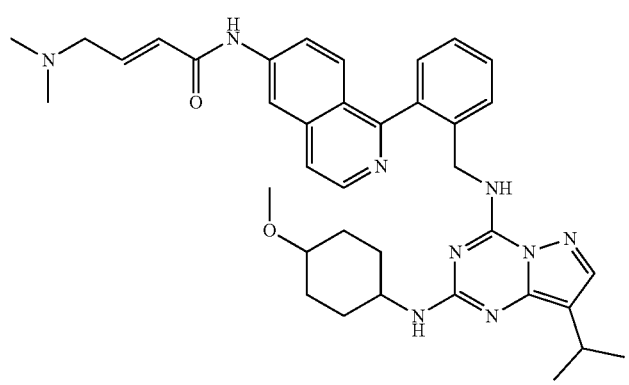 [SMILES: COC1CCC(Nc2nc(NCc3ccccc3-c3nccc4cc(NC(=O)/C=C/CN(C)C)ccc34)n3ncc(C(C)C)c3n2)CC1] |
| 45 | 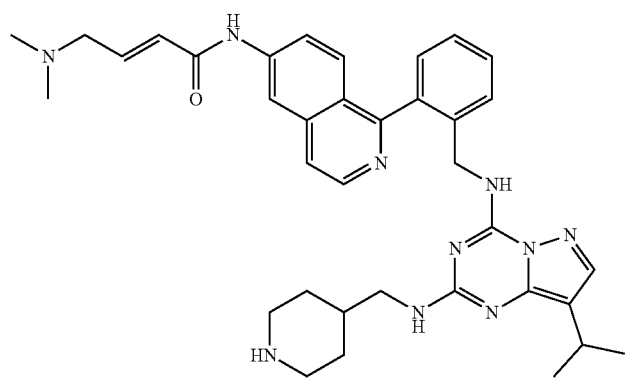 |
| 46 | 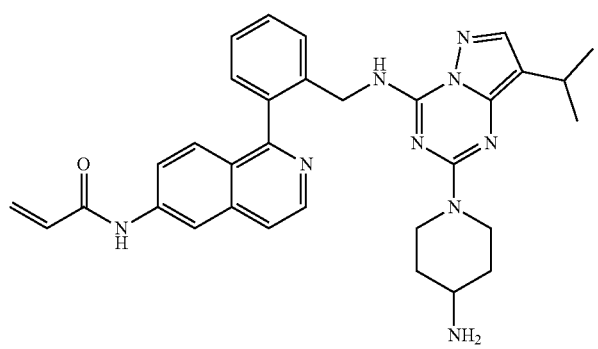 [SMILES: C=CC(=O)Nc1ccc2c(-c3ccccc3CNc3nc(N4CCC(N)CC4)nc4c(C(C)C)cnn34)nccc2c1] |

| # compound | structure |
|---|---|
| 47 | 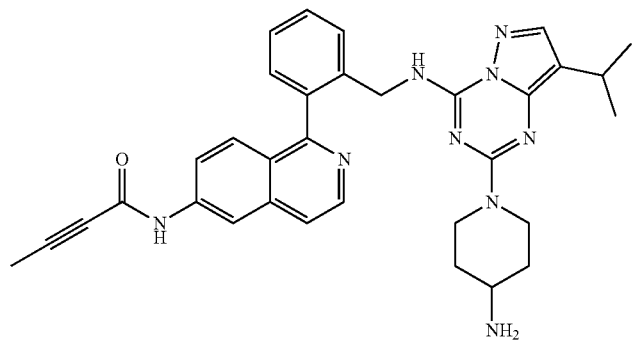 [SMILES: CC#CC(=O)Nc1ccc2c(-c3ccccc3CNc3nc(N4CCC(N)CC4)nc4c(C(C)C)cnn34)nccc2c1] |
| 48 | 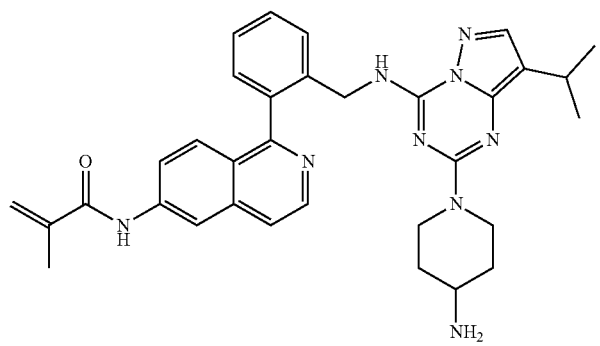 [SMILES: C=C(C)C(=O)Nc1ccc2c(-c3ccccc3CNc3nc(N4CCC(N)CC4)nc4c(C(C)C)cnn34)nccc2c1] |
| 49 | 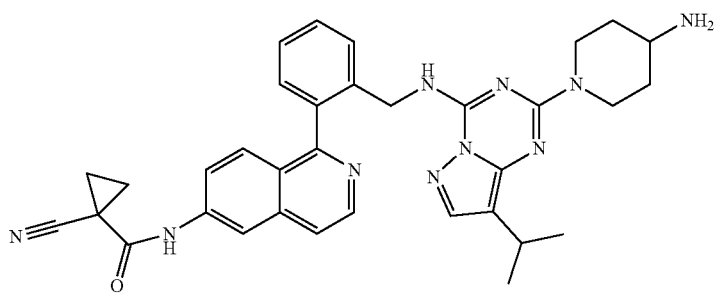 [SMILES: CC(C)c1cnn2c(NCc3ccccc3-c3nccc4cc(NC(=O)C5(C#N)CC5)ccc34)nc(N3CCC(N)CC3)nc12] |
| 50 | 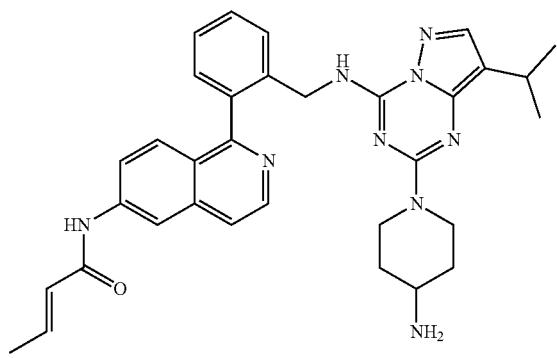 [SMILES: C/C=C/C(=O)Nc1ccc2c(-c3ccccc3CNc3nc(N4CCC(N)CC4)nc4c(C(C)C)cnn34)nccc2c1] |

-continued
| # compound | structure |
|---|---|
| 51 | 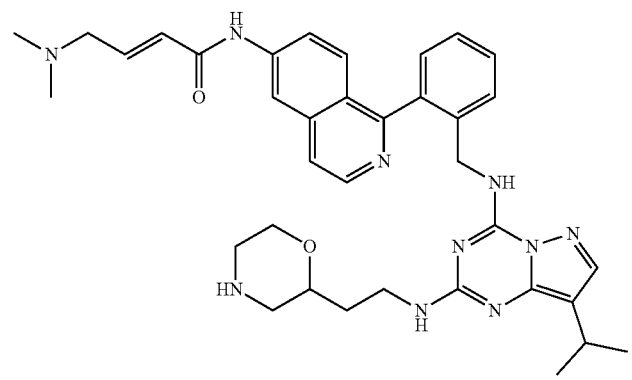 [SMILES: CC(C)c1cnn2c(NCc3ccccc3-c3nccc4cc(NC(=O)/C=C/CN(C)C)ccc34)nc(NCCC3CNCCO3)nc12] |
| 52 | 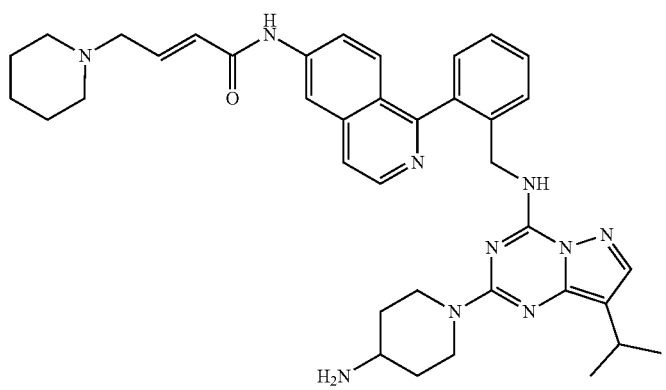 [SMILES: CC(C)c1cnn2c(NCc3ccccc3-c3nccc4cc(NC(=O)/C=C/CN5CCCCC5)ccc34)nc(N3CCC(N)CC3)nc12] |
| 53 | 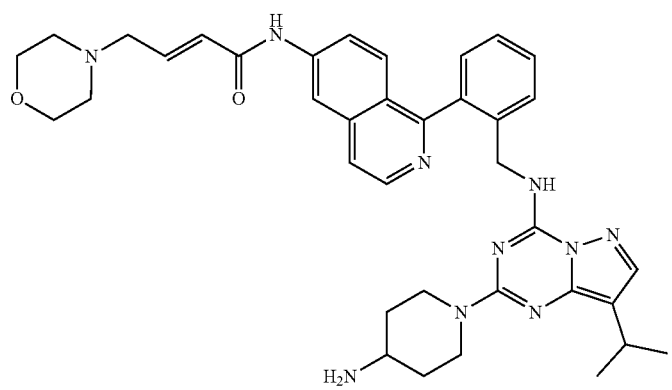 [SMILES: CC(C)c1cnn2c(NCc3ccccc3-c3nccc4cc(NC(=O)/C=C/CN5CCOCC5)ccc34)nc(N3CCC(N)CC3)nc12] |
| 54 | 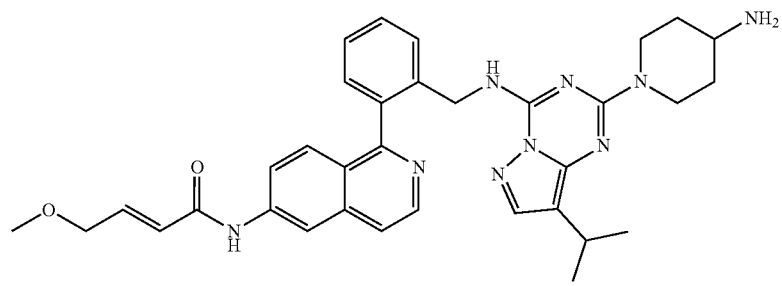 [SMILES: COC/C=C/C(=O)Nc1ccc2c(-c3ccccc3CNc3nc(N4CCC(N)CC4)nc4c(C(C)C)cnn34)nccc2c1] |

-continued

| # compound | structure |
|---|---|
| 55 | 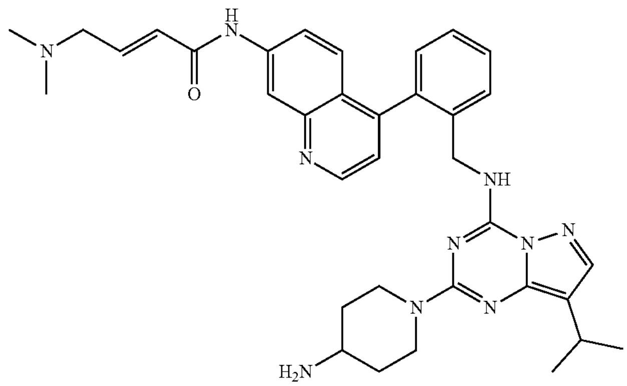 [SMILES: CC(C)c1cnn2c(NCc3ccccc3-c3ccnc4cc(NC(=O)/C=C/CN(C)C)ccc34)nc(N3CCC(N)CC3)nc12] |
| 56 | 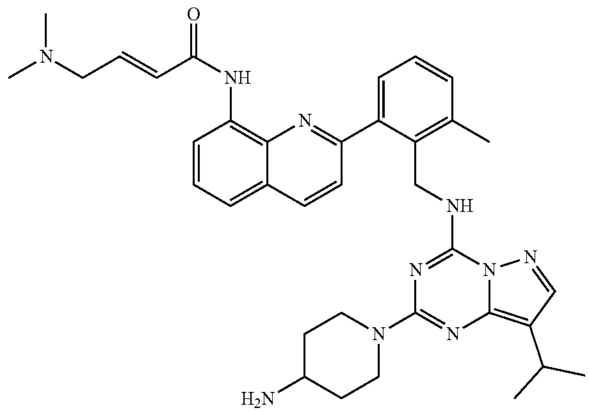 [SMILES: Cc1cccc(-c2ccc3cccc(NC(=O)/C=C/CN(C)C)c3n2)c1CNc1nc(N2CCC(N)CC2)nc2c(C(C)C)cnn12] |
| 57 | 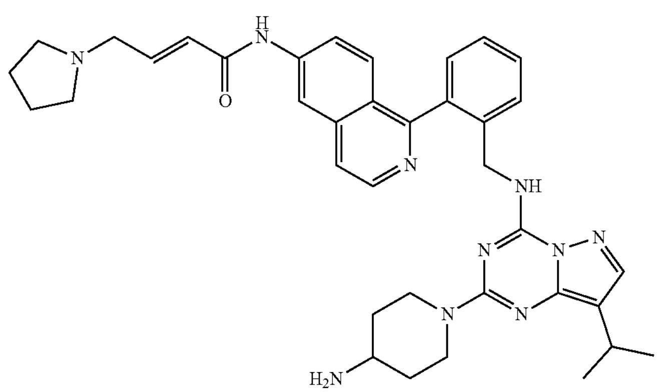 [SMILES: CC(C)c1cnn2c(NCc3ccccc3-c3nccc4cc(NC(=O)/C=C/CN5CCCC5)ccc34)nc(N3CCC(N)CC3)nc12] |
| 58 | 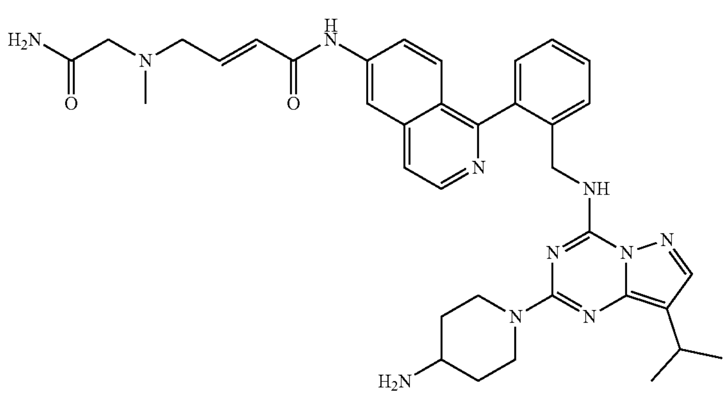 [SMILES: CC(C)c1cnn2c(NCc3ccccc3-c3nccc4cc(NC(=O)/C=C/CN(C)CC(N)=O)ccc34)nc(N3CCC(N)CC3)nc12] |

-continued
| # compound | structure |
|---|---|
| 59 | 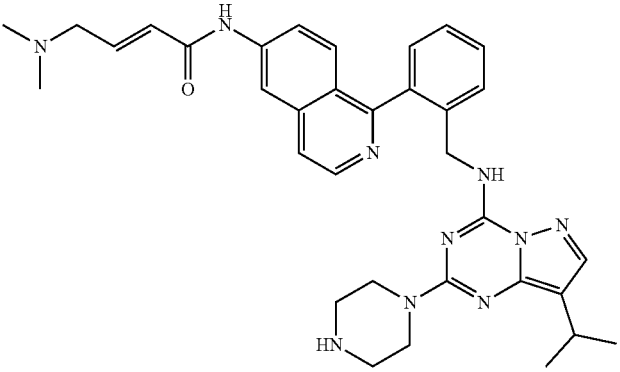 [SMILES: CC(C)c1cnn2c(NCc3ccccc3-c3nccc4cc(NC(=O)/C=C/CN(C)C)ccc34)nc(N3CCNCC3)nc12] |
| 60 | 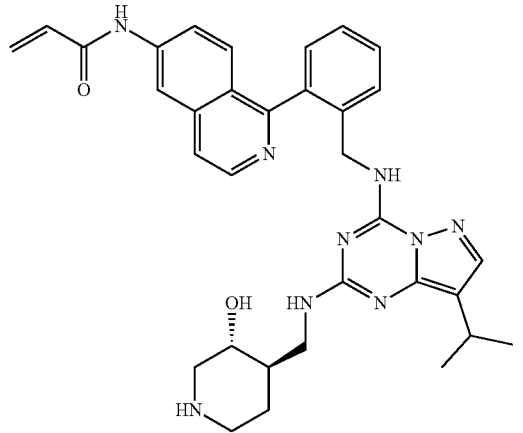 [SMILES: C=CC(=O)Nc1ccc2c(-c3ccccc3CNc3nc(NC[C@H]4CCNC[C@@H]4O)nc4c(C(C)C)cnn34)nccc2c1] |
| 61 | 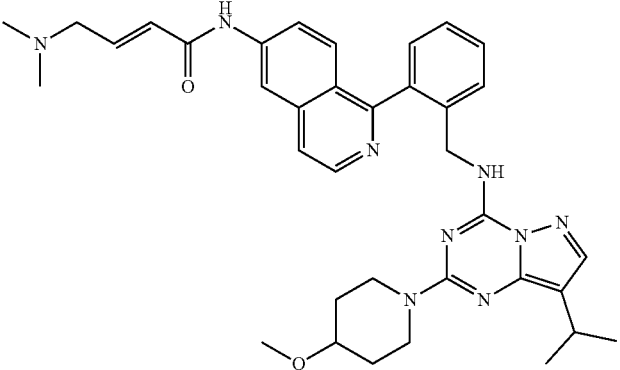 [SMILES: COC1CCN(c2nc(NCc3ccccc3-c3nccc4cc(NC(=O)/C=C/CN(C)C)ccc34)n3ncc(C(C)C)c3n2)CC1] |
| 62 | 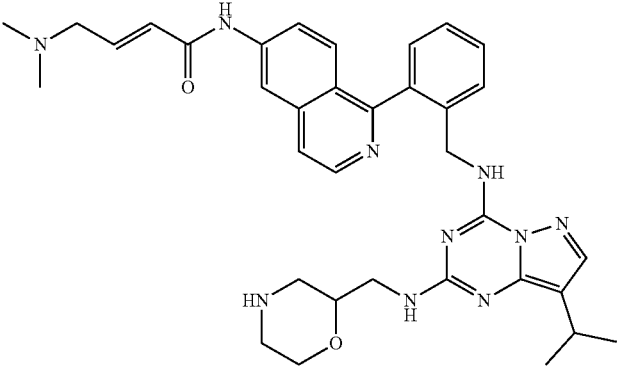 |

| # compound | structure |
|---|---|
| 63 | 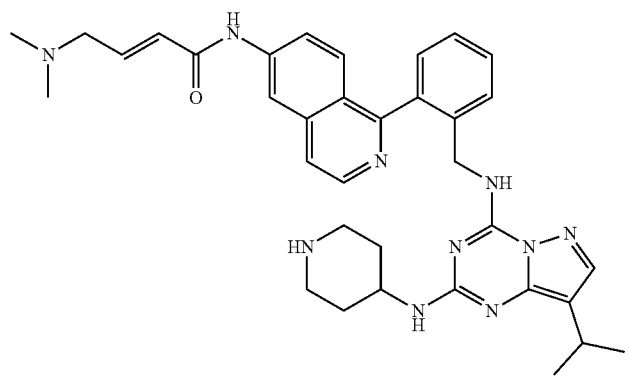 [SMILES: CC(C)c1cnn2c(NCc3ccccc3-c3nccc4cc(NC(=O)/C=C/CN(C)C)ccc34)nc(NC3CCNCC3)nc12] |
| 64 | 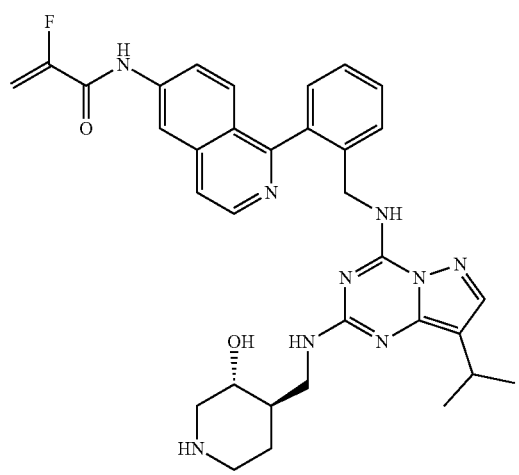 [SMILES: C=C(F)C(=O)Nc1ccc2c(-c3ccccc3CNc3nc(NC[C@H]4CCNC[C@@H]4O)nc4c(C(C)C)cnn34)nccc2c1] |
| 65 | 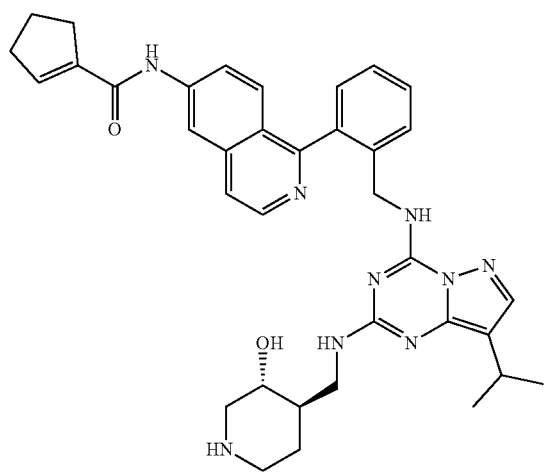 [SMILES: CC(C)c1cnn2c(NCc3ccccc3-c3nccc4cc(NC(=O)C5=CCCC5)ccc34)nc(NC[C@H]3CCNC[C@@H]3O)nc12] |

| # compound | structure |
|---|---|
| 66 | 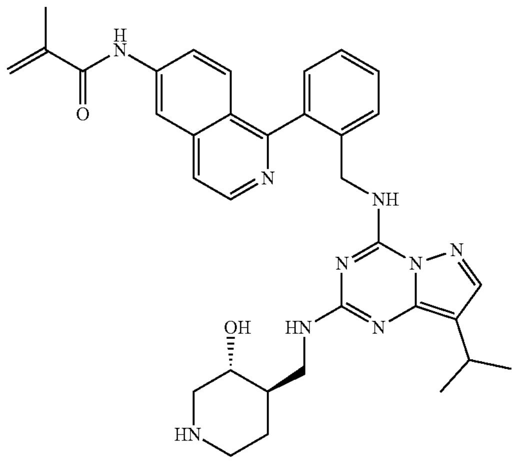 [SMILES: C=C(C)C(=O)Nc1ccc2c(-c3ccccc3CNc3nc(NC[C@H]4CCNC[C@@H]4O)nc4c(C(C)C)cnn34)nccc2c1] |
| 67 | 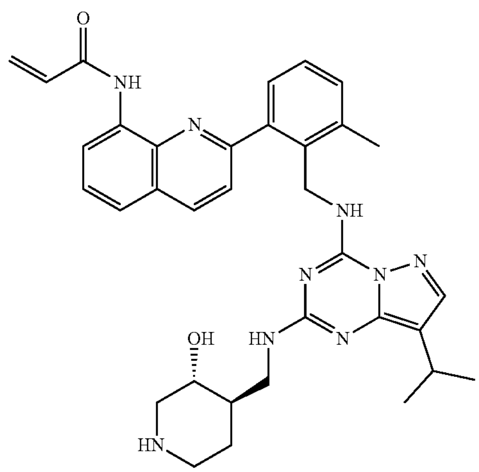 [SMILES: C=CC(=O)Nc1cccc2ccc(-c3cccc(C)c3CNc3nc(NC[C@H]4CCNC[C@@H]4O)nc4c(C(C)C)cnn34)nc12] |
| 68 | 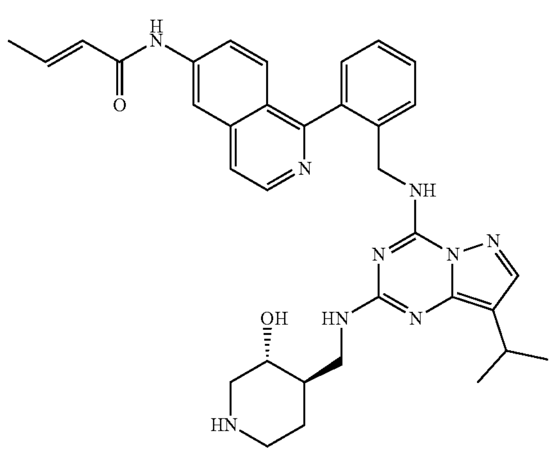 [SMILES: C/C=C/C(=O)Nc1ccc2c(-c3ccccc3CNc3nc(NC[C@H]4CCNC[C@@H]4O)nc4c(C(C)C)cnn34)nccc2c1] |

-continued
| # compound | structure |
|---|---|
| 69 | 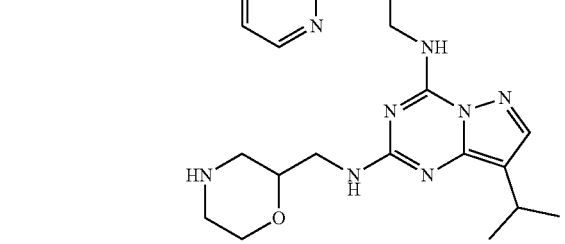 |
| 70 | 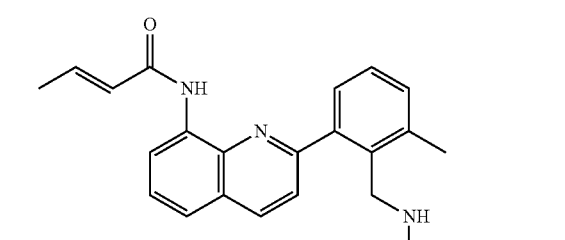 |
| 71 | 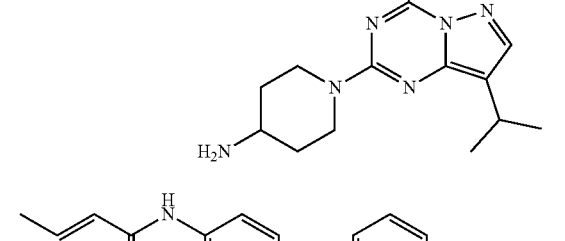 |
| 72 | 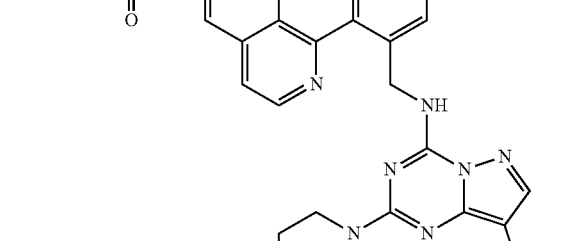 |

| # compound | structure |
|---|---|
| 73 | 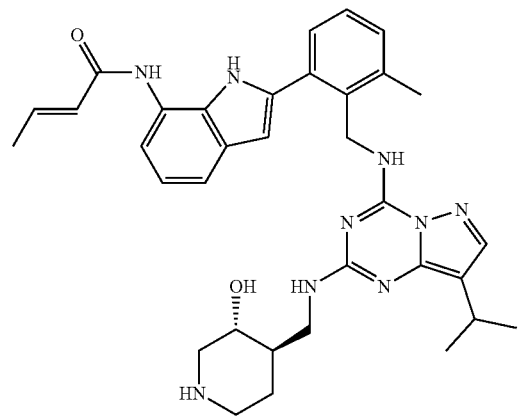 [SMILES: C/C=C/C(=O)Nc1cccc2cc(-c3cccc(C)c3CNc3nc(NC[C@H]4CCNC[C@@H]4O)nc4c(C(C)C)cnn34)[nH]c12] |
| 74 | 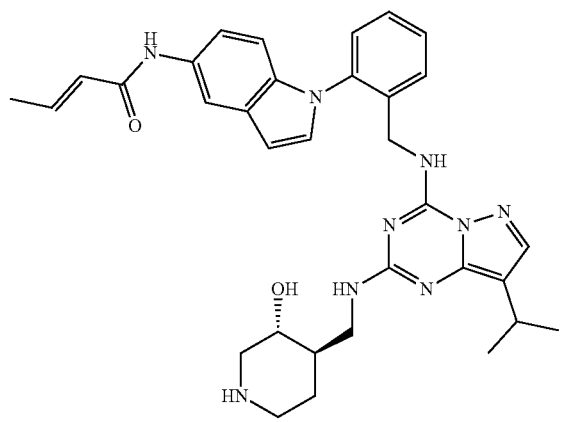 [SMILES: C/C=C/C(=O)Nc1ccc2c(ccn2-c2ccccc2CNc2nc(NC[C@H]3CCNC[C@@H]3O)nc3c(C(C)C)cnn23)c1] |
| 75 | 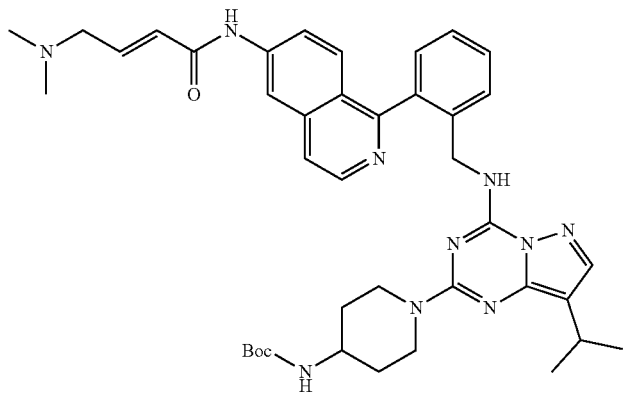 [SMILES: CC(C)c1cnn2c(NCc3ccccc3-c3nccc4cc(NC(=O)/C=C/CN(C)C)ccc34)nc(N3CCC(NC(=O)OC(C)(C)C)CC3)nc12] |

| # compound | structure |
|---|---|
| 76 | 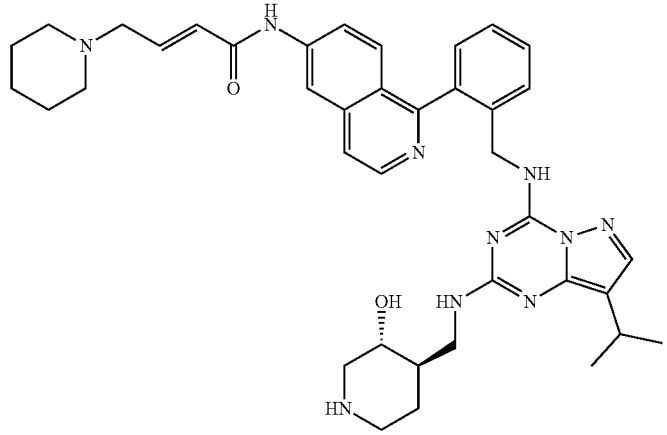 [SMILES: CC(C)c1cnn2c(NCc3ccccc3-c3nccc4cc(NC(=O)/C=C/CN5CCCCC5)ccc34)nc(NC[C@H]3CCNC[C@@H]3O)nc12] |
| 77 | 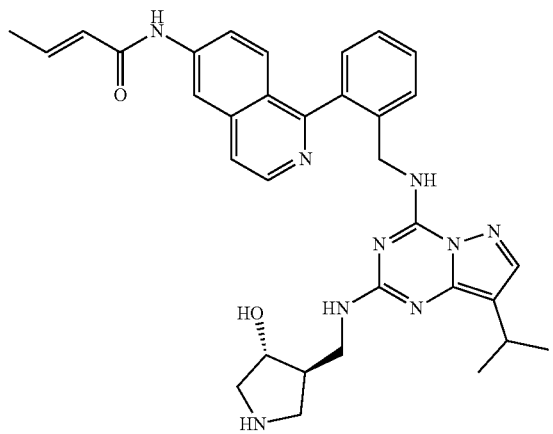 [SMILES: C/C=C/C(=O)Nc1ccc2c(-c3ccccc3CNc3nc(NC[C@H]4CNC[C@@H]4O)nc4c(C(C)C)cnn34)nccc2c1] |
| 78 | 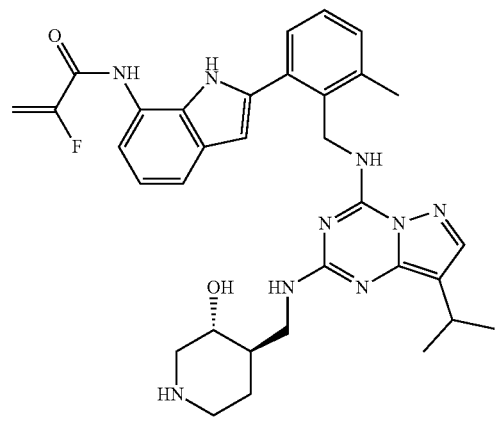 [SMILES: C=C(F)C(=O)Nc1cccc2cc(-c3cccc(C)c3CNc3nc(NC[C@H]4CCNC[C@@H]4O)nc4c(C(C)C)cnn34)[nH]c12] |

| # compound | structure |
|---|---|
| 79 | 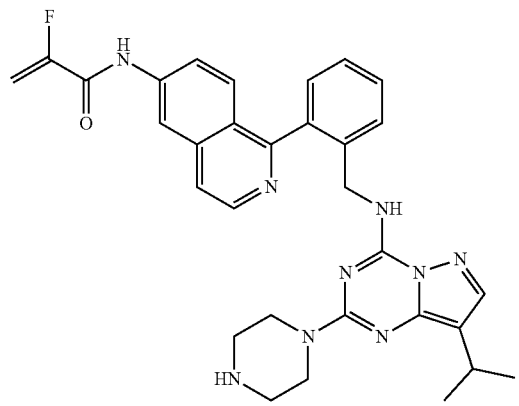 [SMILES: C=C(F)C(=O)Nc1ccc2c(-c3ccccc3CNc3nc(N4CCNCC4)nc4c(C(C)C)cnn34)nccc2c1] |
| 80 | 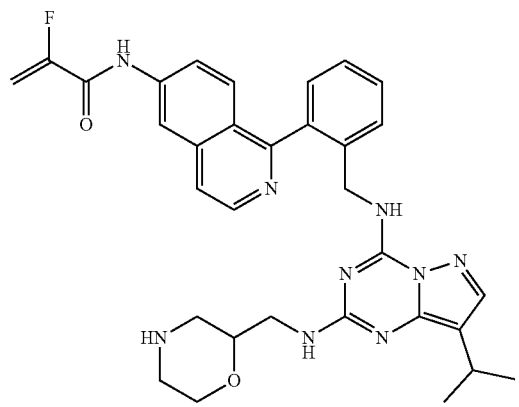 [SMILES: C=C(F)C(=O)Nc1ccc2c(-c3ccccc3CNc3nc(NCC4CNCCO4)nc4c(C(C)C)cnn34)nccc2c1] |
| 81 | 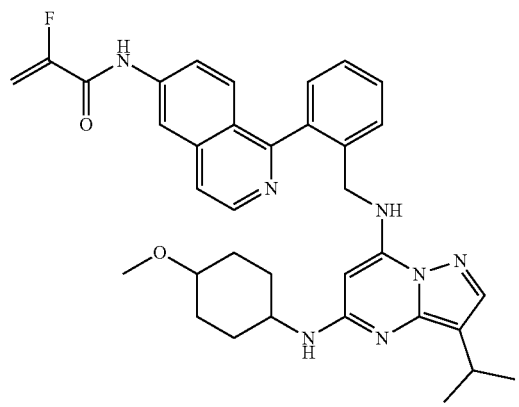 [SMILES: C=C(F)C(=O)Nc1ccc2c(-c3ccccc3CNc3cc(NC4CCC(OC)CC4)nc4c(C(C)C)cnn34)nccc2c1] |

| # compound | structure |
|---|---|
| 82 | 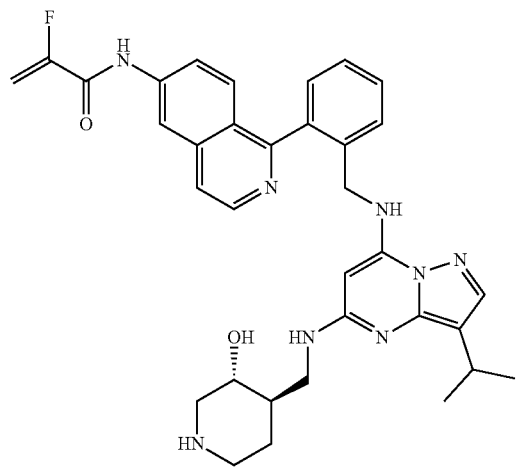 [SMILES: C=C(F)C(=O)Nc1ccc2c(-c3ccccc3CNc3cc(NC[C@H]4CCNC[C@@H]4O)nc4c(C(C)C)cnn34)nccc2c1] |
| 83 | 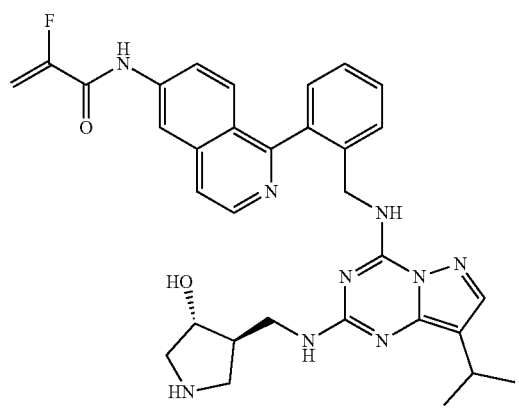 [SMILES: C=C(F)C(=O)Nc1ccc2c(-c3ccccc3CNc3nc(NC[C@H]4CNC[C@@H]4O)nc4c(C(C)C)cnn34)nccc2c1] |
| 84 | 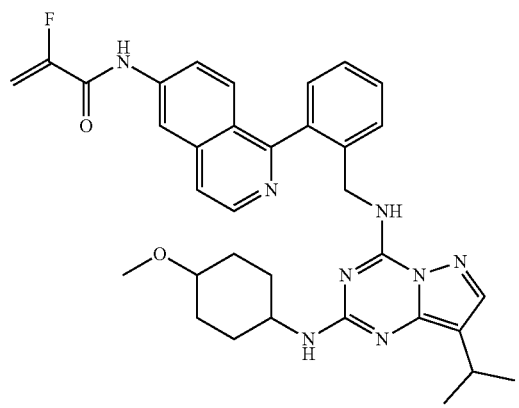 [SMILES: C=C(F)C(=O)Nc1ccc2c(-c3ccccc3CNc3nc(NC4CCC(OC)CC4)nc4c(C(C)C)cnn34)nccc2c1] |

| # compound | structure |
|---|---|
| 85 | 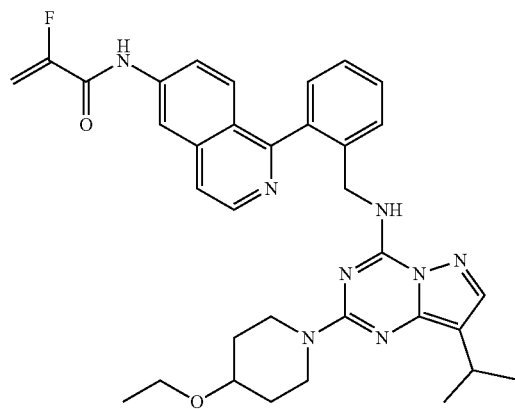 [SMILES: C=C(F)C(=O)Nc1ccc2c(-c3ccccc3CNc3nc(N4CCC(OCC)CC4)nc4c(C(C)C)cnn34)nccc2c1] |
| 86 | 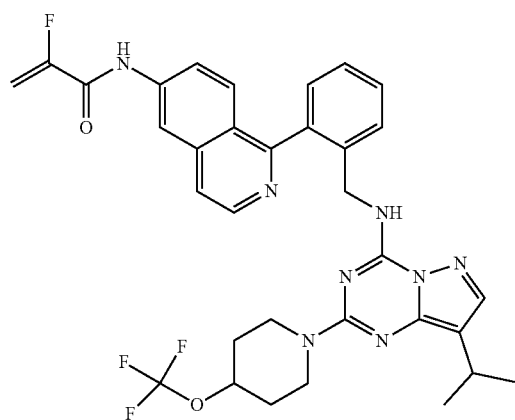 [SMILES: C=C(F)C(=O)Nc1ccc2c(-c3ccccc3CNc3nc(N4CCC(OC(F)(F)F)CC4)nc4c(C(C)C)cnn34)nccc2c1] |
| 87 | 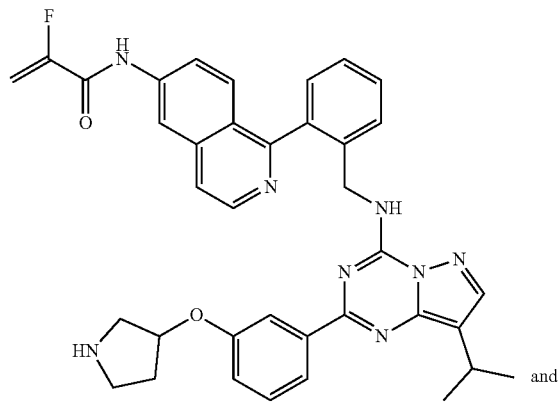 [SMILES: C=C(F)C(=O)Nc1ccc2c(-c3ccccc3CNc3nc(-c4cccc(OC5CCNC5)c4)nc4c(C(C)C)cnn34)nccc2c1] and |

| # compound | structure |
|---|---|
| 88 | 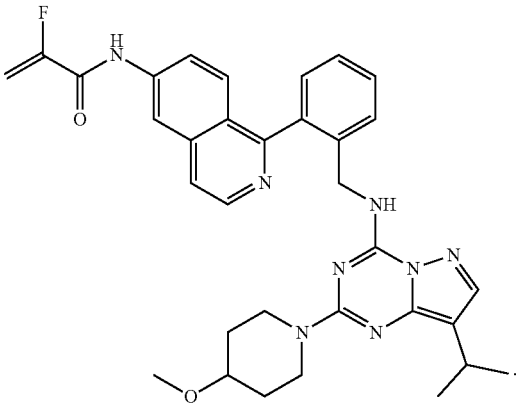 [SMILES: C=C(F)C(=O)Nc1ccc2c(-c3ccccc3CNc3nc(N4CCC(OC)CC4)nc4c(C(C)C)cnn34)nccc2c1] |
or a pharmaceutically acceptable salt thereof.